US008766001B2

(12) United States Patent
Pflumm et al.

(10) Patent No.: US 8,766,001 B2

(45) Date of Patent: *Jul. 1, 2014

(54) COMPOUNDS FOR ELECTRONIC DEVICES

(75) Inventors: Christof Pflumm, Frankfurt am Main (DE); Arne Buesing, Frankfurt am Main (DE); Amir Hossain Parham, Frankfurt am Main (DE); Rocco Fortte, Frankfurt am Main (DE); Holger Heil, Frankfurt am Main (DE); Philipp Stoessel, Frankfurt am Main (DE)

(73) Assignee: Merck Patent GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/993,352

(22) PCT Filed: Mar. 5, 2009

(86) PCT No.: PCT/EP2009/001554

§ 371 (c)(1), (2), (4) Date: Nov. 18, 2010

(87) PCT Pub. No.: WO2009/141026

PCT Pub. Date: Nov. 26, 2009

(65) Prior Publication Data

US 2011/0092701 A1 Apr. 21, 2011

(30) Foreign Application Priority Data

May 19, 2008 (DE) ......................... 10 2008 024 182

(51) Int. Cl.
*C07C 211/00* (2006.01)

(52) U.S. Cl.
USPC ................. 564/1; 544/37; 544/102; 544/348; 548/161; 548/202; 548/307.4; 548/483; 549/57; 549/68; 564/305

(58) Field of Classification Search
USPC ......... 544/37, 102, 348; 548/161, 202, 307.4, 548/483; 549/57, 68; 564/305
See application file for complete search history.

(56) References Cited

U.S. PATENT DOCUMENTS

| | | | |
|---|---|---|---|
| 4,539,507 | A | 9/1985 | VanSlyke et al. |
| 5,151,629 | A | 9/1992 | VanSlyke |
| 5,840,217 | A | 11/1998 | Lupo et al. |
| 6,458,909 | B1 | 10/2002 | Spreitzer et al. |
| 6,908,783 | B1 | 6/2005 | Kuehl et al. |
| 7,521,525 | B2 | 4/2009 | Sohn et al. |
| 7,701,131 | B2 | 4/2010 | Gerhard et al. |
| 2005/0040390 | A1 | 2/2005 | Pfeiffer et al. |
| 2006/0046092 | A1 | 3/2006 | Towns et al. |
| 2006/0063027 | A1 | 3/2006 | Vestweber et al. |
| 2008/0026135 | A1 | 1/2008 | Bentsen et al. |
| 2008/0145708 | A1 | 6/2008 | Heil et al. |
| 2008/0220285 | A1 | 9/2008 | Vestweber et al. |
| 2009/0066225 | A1 | 3/2009 | Kimura et al. |

FOREIGN PATENT DOCUMENTS

| | | | |
|---|---|---|---|
| CA | 2608765 | | * 11/2006 |
| EP | 0676461 | A2 | 10/1995 |
| EP | 1476881 | A2 | 11/2004 |
| EP | 1596445 | A1 | 11/2005 |
| EP | 1860097 | A1 | 11/2007 |
| KR | 10-2006-0025933 | A | 3/2006 |
| WO | WO-98/27136 | A1 | 6/1998 |
| WO | WO-2004/058911 | A2 | 7/2004 |
| WO | WO-2005/011013 | A1 | 2/2005 |
| WO | WO-2006/100896 | A1 | 9/2006 |
| WO | WO-2006/108497 | A1 | 10/2006 |
| WO | WO-2006/122630 | A1 | 11/2006 |

* cited by examiner

*Primary Examiner* — Douglas M Willis

(74) *Attorney, Agent, or Firm* — Drinker Biddle & Reath LLP

(57) ABSTRACT

The present invention relates to the improvement in organic electroluminescent devices by using compounds of the formula (1), (I)

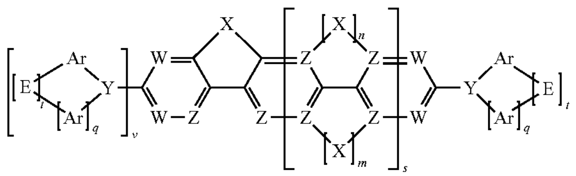

in particular as hole-injection or hole-transport materials in a hole-injection or hole-transport layer.

11 Claims, No Drawings

COMPOUNDS FOR ELECTRONIC DEVICES

RELATED APPLICATIONS

This application is a national stage application (under 35 U.S.C. §371) of PCT/EP2009/001554, filed Mar. 5, 2009, which claims benefit of German Application No. 10 2008 024 182.8, filed May 19, 2008.

The present invention describes novel compounds and the use thereof in electronic devices.

The general structure of organic electroluminescent devices is described, for example, in U.S. Pat. Nos. 4,539,507, 5,151,629, EP 0676461 and WO 98/27136. However, these devices still exhibit considerable problems which require urgent improvement:

1. The efficiency is still low, especially in the case of fluorescent OLEDs, and should be improved.
2. There is still a need for improvement in the operating lifetime, in particular in the case of blue emission.
3. The operating voltage is quite high, especially in the case of fluorescent OLEDs, and should therefore be reduced further in order to improve the power efficiency. This is of major importance, in particular, for mobile applications. Further improvements are desirable here, in particular in the case of charge-transport materials.
4. In the case of hole-transport materials in accordance with the prior art, the voltage is dependent on the layer thickness of the hole-transport layer. In practice, a relatively thick hole-transport layer would frequently be desirable. However, this is scarcely possible to achieve with materials in accordance with the prior art owing to the associated increase in voltage.
5. In the case of hole-transport materials in accordance with the prior art, there are frequently problems with processability since these materials crystallise out at the edge of the vapour-deposition source and thus clog the vapour-deposition source. Materials of this type can therefore only be employed in mass production with increased technical complexity.

The closest prior art for hole-injection and -transport materials are cis- and trans-indenofluorene derivatives which are substituted by one or two diarylamino groups, in accordance with WO 06/100896 and WO 06/122630. Although substituted indenofluorene derivatives are generally also included therein, only indenofluorenes having an unsubstituted indenofluorene skeleton are, however, explicitly disclosed. No examples having substituted indenofluorene structures are disclosed, and in particular the positions at which substituents lead to particularly good results and the substituents that result in improvements are not disclosed. It is merely disclosed that, in particular, the unsubstituted indenofluorenes are particularly preferred. However, it has been found that the latter result in high operating voltages on use in a hole-injection or hole-transport layer, meaning that Furthermore, there are frequently problems with materials of this type since they clog the vapour-deposition source due to crystallisation.

Surprisingly, it has now been found that indenofluorene derivatives having one or two diarylamino substituents which are substituted at certain positions of the indenofluorene skeleton have significant improvements here. Improvements are likewise achieved if individual C atoms at certain positions in the indenofluorene skeleton have been replaced by nitrogen. These compounds enable a reduction in the operating voltage at the same time as constantly good efficiency and lifetime compared with the corresponding unsubstituted compounds. The present invention therefore relates to these compounds and to the use thereof in OLEDs.

The invention therefore relates to compounds of the formula (1)

formula (1)

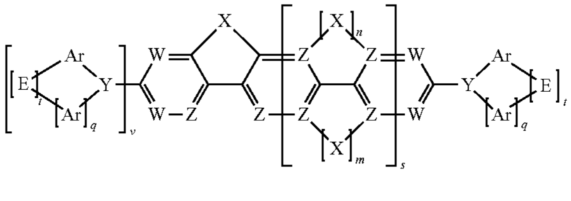

where the following applies to the symbols and indices used:

Y is on each occurrence, identically or differently, B, N, P, P═O, $PF_2$, C═O, O, S, S═O or $SO_2$;

Ar is on each occurrence, identically or differently, an aromatic or heteroaromatic ring system having 5 to 40 aromatic ring atoms, which may be substituted by one or more radicals $R^1$;

X is on each occurrence, identically or differently, a group selected from $B(R^1)$, $C(R^1)_2$, —$CR^1$═$CR^1$—, —$CR^1$═N—, $Si(R^1)_2$, C═O, C═$NR^1$, C═$C(R^1)_2$, O, S, $SO_2$, $N(R^1)$, P(═O)$R^1$ or a combination of two, three or four of these groups;

Z is C if a group X is bonded to the group Z, or is on each occurrence, identically or differently, CR or N if no group X is bonded to the group Z;

W is on each occurrence, identically or differently, CH or N;

R is on each occurrence, identically or differently, H, D, F, CN, $B(OR^2)_2$, $Si(R^2)_3$, $N(Ar)_2$, C(═O)Ar, P(═O)$Ar_2$, S(═O)Ar, S(═O)$_2$Ar, $CR^2$═$CR^2$Ar, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by —$R^2C$═$CR^2$—, $Si(R^2)_2$, C═O, C═S, C═$NR^2$, —O—, —S—, —COO— or —$CONR^2$— and where one or more H atoms may be replaced by F, Cl, Br, I, CN or $NO_2$, or an aromatic or heteroaromatic ring system having 5 to 40 aromatic ring atoms, which may be substituted by one or more non-aromatic radicals $R^1$, or an aryloxy or heteroaryloxy group having 5 to 40 aromatic ring atoms, which may be substituted by one or more non-aromatic radicals $R^1$, or a combination of these systems; two or more adjacent substituents R here may also form a mono- or polycyclic ring system with one another;

E is on each occurrence, identically or differently, a single bond, $N(R^1)$, O, S, $C(R^1)_2$, $C(R^1)_2$—$C(R^1)_2$, $Si(R^1)_2$ or $B(R^1)$;

$R^1$ is on each occurrence, identically or differently, H, D, F, Cl, Br, I, CN, $NO_2$, $B(OR^2)_2$, $Si(R^2)_3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by —$R^2C$═$CR^2$—, —C≡C—, $Si(R^2)_2$, $Ge(R^2)_2$, $Sn(R^2)_2$, C═O, C═S, C═Se, C═$NR^2$, —O—, —S—, —COO— or —$CONR^2$— and where one or more H atoms may be replaced by F, Cl, Br, I, CN or $NO_2$, or an aromatic or heteroaromatic ring system having 5 to 40 aromatic ring atoms, which may be substituted by one or more non-aromatic radicals $R^1$, or an aryloxy or heteroaryloxy group having 5 to 40 aromatic ring atoms, which may be substituted by one or more non-aromatic radicals $R^1$, or a combination of these systems; two or more substituents $R^1$ here may also form a mono- or polycyclic ring system with one another;

$R^2$ is on each occurrence, identically or differently, H or an aliphatic or aromatic hydrocarbon radical having 1 to 20 C atoms;

m, n are 0 or 1, with the proviso that m+n=1;

q is on each occurrence 1 if the corresponding central atom of the group Y is an element from main group 3 or 5 and is on each occurrence equal to 0 if the corresponding central atom of the group Y is an element from main group 4 or 6;

s is 1, 2 or 3;

t is on each occurrence, identically or differently, 0 or 1, where t=0 means that radicals $R^1$ are bonded instead of the group E; furthermore, t=0 if q=0;

v is 0 or 1, where, for v=0, hydrogen or a group R may be bonded instead of the group Y;

characterised in that at least one radical R represents a substituent other than H or D.

For the purposes of this invention, adjacent substituents are taken to mean substituents which are either bonded to the same atom, i.e., for example, the two substituents $R^1$ in a $C(R^1)_2$ group, or substituents which are bonded to directly adjacent atoms, i.e., for example, the two substituents R in a C(R)—C(R) group.

For the purposes of this invention, an aryl group or heteroaryl group is taken to mean an aromatic group or heteroaromatic group respectively having a common aromatic electron system, where an aryl group contains 6 to 24 C atoms and a heteroaryl group contains 2 to 24 C atoms and a total of at least 5 aromatic ring atoms. The heteroatoms are preferably selected from N, O and/or S. For the purposes of this invention, this can be a single homo- or heterocyclic ring, for example benzene, pyridine, thiophene, etc., or it can be a condensed aromatic ring system in which at least two aromatic or heteroaromatic rings, for example benzene rings, are fused to one another, i.e. are condensed onto one another by anellation, i.e. have at least one common edge and thus also a common aromatic system. This aryl or heteroaryl group may be substituted or unsubstituted; any substituents present may likewise form further ring systems. Thus, for example, systems such as naphthalene, anthracene, phenanthrene, pyrene, etc., are to be regarded as aryl groups for the purposes of this invention and quinoline, acridine, benzothiophene, carbazole, etc., are to be regarded as heteroaryl groups for the purposes of this invention, while, for example, biphenyl, fluorene, spirobifluorene, etc., are not aryl groups since separate aromatic electron systems are present here.

For the purposes of this invention, an aromatic ring system contains 6 to 40 C atoms in the ring system. For the purposes of this invention, a heteroaromatic ring system contains 2 to 40 C atoms and at least one heteroatom in the ring system, with the proviso that the total number of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but in which, in addition, a plurality of aryl or heteroaryl groups may be interrupted by a short, non-aromatic unit (less than 10% of the atoms other than H, preferably less than 5% of the atoms other than H), such as, for example, a C, N or O atom. Thus, for example, systems such as 9,9'-spirobifluorene, 9,9-diarylfluorene, triarylamine, diaryl ether, etc., are also to be regarded as aromatic ring systems for the purposes of this invention.

For the purposes of the present invention, a $C_1$- to $C_{40}$-alkyl group, in which individual H atoms or $CH_2$ groups may also be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl, 2,2,2-trifluoroethyl, ethenyl, propenyl, butenyl, pentenyl, cyclopentenyl, hexenyl, heptynyl, cyclohexenyl, heptenyl, cycloheptenyl, octenyl, cyclooctenyl, ethynyl, propynyl, butynyl, pentynyl, hexynyl or octynyl. A $C_1$ to $C_{40}$-alkoxy group is particularly preferably taken to mean methoxy, ethoxy, n-propoxy, i-propoxy, n-butoxy, i-butoxy, s-butoxy, t-butoxy or 2-methylbutoxy. A $C_2$-$C_{24}$-aryl or -heteroaryl group, which can be monovalent or divalent depending on the use, may in each case also be substituted by the above-mentioned radicals $R^1$ and may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine, benzothiadiazole. For the purposes of this invention, aromatic and heteroaromatic ring systems are taken to mean, in particular, biphenylene, terphenylene, fluorene, spirobifluorene, dihydrophenanthrene, tetrahydropyrene or cis- or trans-indenofluorene, in addition to the above-mentioned aryl and heteroaryl groups.

In a preferred embodiment of the invention, the symbol W stands for CH.

In a preferred embodiment of the invention, a maximum of two symbols Z in compounds of the formula (1) stand for N and the other symbols Z stand for C or CR. In a particularly preferred embodiment of the invention, either all symbols Z stand for C or CR or precisely two symbols Z stand for N and the other symbols Z stand for C or CR.

Preference is furthermore given to compounds of the formula (1) in which the symbol s=1 or s=2. Very particular preference is given to compounds where s=1.

Preferred embodiments of the invention are the compounds of the formulae (2) to (5)

formula (2)

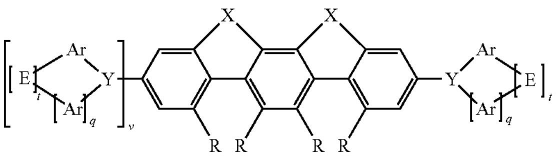

formula (3)

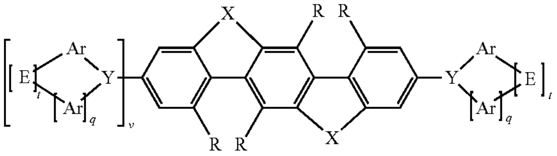

formula (4)

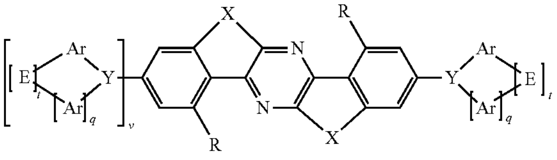

formula (5)

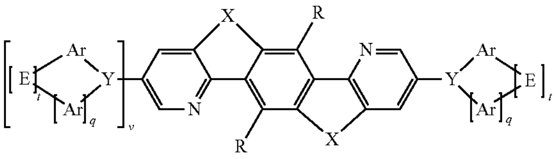

where the symbols and indices used have the meanings indicated above, and at least one group R in formulae (2), (3), (4) and (5) stands for a substituent other than hydrogen or deuterium.

Preference is given to compounds of the formulae (1) to (5) in which the symbol Y stands, identically or differently, for nitrogen, C═O, phosphorus or P═O, particularly preferably for nitrogen, C═O or P═O. Y very particularly preferably stands for nitrogen.

Preference is furthermore given to compounds of the formulae (1) to (5) in which the index v=1.

Preference is furthermore given to compounds of the formulae (1) to (5) in which the symbols Ar stand, identically or differently on each occurrence, for an aromatic or heteroaromatic ring system having 5 to 16 aromatic ring atoms, for a triarylamine or for spirobifluorene, each of which may be substituted by one or more radicals $R^1$, particularly preferably for an aromatic or heteroaromatic ring system selected from benzene, ortho-, meta- or para-biphenyl, fluorene, naphthalene, anthracene, phenanthrene, benzanthracene, pyridine, pyrene, thiophene, triphenylamine, diphenyl-1-naphthylamine, diphenyl-2-naphthylamine, phenyldi(1-naphthyl)amine and phenyldi(2-naphthyl)amine, each of which may be substituted by $R^1$. The symbols Ar very particularly preferably stand, identically or differently on each occurrence, for phenyl, 1-naphthyl or 2-naphthyl, each of which may be substituted by one or two radicals $R^1$.

Preference is furthermore given to compounds of the formulae (1) to (5) in which the index t=0 or in which the index t=1, and the corresponding symbol E stands for a single bond, $C(R^1)_2$, S or $N(R^1)$. Particular preference is given to compounds of the formulae (1) to (5) in which the index t=0 or in which the index t=1, and the corresponding symbol E stands for a single bond or $C(R^1)_2$.

Preference is furthermore given to compounds of the formulae (1) to (5) in which the symbol $R^1$ stands, identically or differently on each occurrence, for H, F, CN, a straight-chain alkyl group having 1 to 5 C atoms or a branched alkyl group having 3 to 5 C atoms, where in each case one or more non-adjacent $CH_2$ groups may be replaced by $—R^2C═CR^2—$, —O— or —S— and where one or more H atoms may be replaced by F, or a monovalent aryl or heteroaryl group having 5 to 16 aromatic ring atoms, which may be substituted by one or more non-aromatic radicals $R^1$, where two or more radicals $R^1$ may form a ring system with one another; $R^1$ particularly preferably stands for H, F, CN, methyl, tert-butyl, or a monovalent aryl or heteroaryl group having 4 to 6 C atoms, which may be substituted by one or more non-aromatic radicals $R^1$, where two aromatic radicals $R^1$ may form a ring system with one another.

$R^1$, if it is bonded to a group X, is furthermore preferably a straight-chain alkyl group having 1 to 10 C atoms or a branched or cyclic alkyl group having 3 to 10 C atoms, where in each case one or more non-adjacent $CH_2$ groups may be replaced by $—R^2C═CR^2—$, —O— or —S— and where one or more H atoms may be replaced by F, or a monovalent aryl or heteroaryl group having 5 to 16 aromatic ring atoms, which may be substituted by one or more non-aromatic radicals $R^1$; two adjacent radicals $R^1$ here may also form a ring system with one another. The radicals $R^1$ are particularly preferably selected from straight-chain alkyl groups having 1 to 4 C atoms or branched alkyl groups having 3 or 4 C atoms, in particular methyl groups, or phenyl groups; two or more radicals $R^1$ here may form a ring system with one another. If a plurality of radicals $R^1$ form a ring system with one another, a Spiro structure is thus formed. This may be preferred, in particular, if the radicals $R^1$ stand for phenyl groups.

In the compounds of the formulae (2), (3), (4) and (5), at least one substituent R is other than H or D. It is also possible here for a plurality of substituents R to be other than H or D. Preferably, two radicals R are other than H or D. Preferred structures of the formulae (2), (3), (4) and (5) are the structures of the formulae (6) to (11) depicted below.

formula (6)

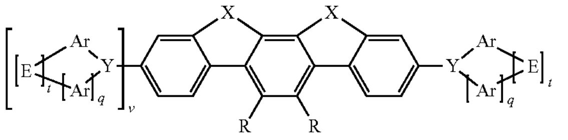

formula (7)

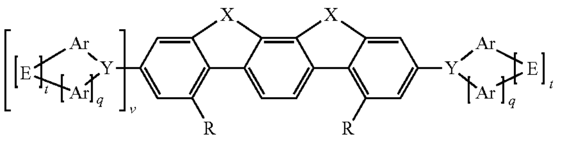

-continued formula (8)

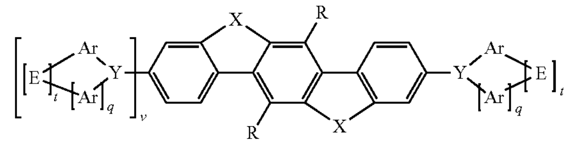

formula (9)

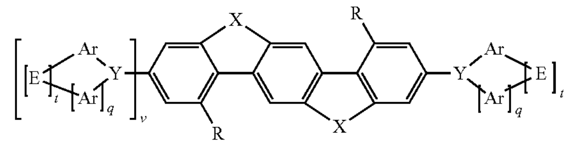

formula (10)

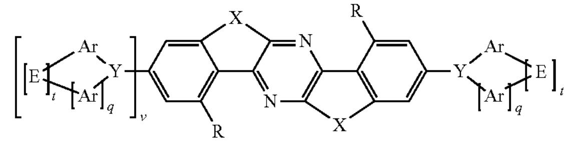

formula (11)

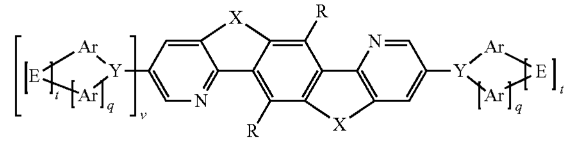

The symbols and indices here have the above-mentioned meanings, and the radicals R are other than hydrogen or deuterium.

Preferred radicals R other than hydrogen or deuterium are on each occurrence, identically or differently, a straight-chain alkyl group having 1 to 20 C atoms or a branched or cyclic alkyl group having 3 to 20 C atoms, each of which may be substituted by one or more radicals $R^2$, where one or more H atoms may be replaced by F, or an aromatic or heteroaromatic ring system having 5 to 20 aromatic ring atoms, which may be substituted by one or more non-aromatic radicals $R^1$, or a combination of these systems; two or more adjacent substituents R here may also form a mono- or polycyclic ring system with one another. Particularly preferred radicals R are on each occurrence, identically or differently, a straight-chain alkyl group having 1 to 10 C atoms or a branched or cyclic alkyl group having 3 to 10 C atoms, each of which may be substituted by one or more radicals $R^2$. Very particularly preferred alkyl groups are methyl, ethyl, n-propyl, i-propyl, n-butyl, i-butyl, s-butyl, t-butyl, 2-butyl, 2-methylbutyl, n-pentyl, s-pentyl, tert-penyl, 2-pentyl, 3-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl or 3-(3,7-dimethyl)octyl. If the alkyl groups are chiral, they can either be used as enantiomerically pure group or diastereomerically pure group or as a mixture of the enantiomers, in particular as the racemate, or a mixture of the diastereomers. In particular for compounds which are vapour-deposited from the gas phase during device manufacture, the alkyl group is very particularly preferably methyl.

Preference is furthermore given to compounds of the formulae (1) to (11) in which the symbols X are on each occurrence, identically or differently, selected from $C(R^1)_2$, $C(=C(R^1)_2)$, C=O, $C=NR^1$, O, S, $SO_2$ or $N(R^1)$. Very particular preference is given to compounds of the formulae (1) to (11) in which the symbols X on each occurrence, identically or differently, are selected from $C(R^1)_2$, $N(R^1)$ and S, very particularly preferably $C(R^1)_2$.

Very particular preference is therefore given to compounds of the formulae (6a) to (11a)

formula (6a)

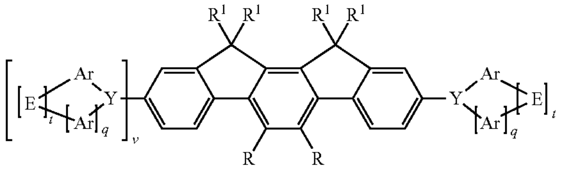

formula (7a)

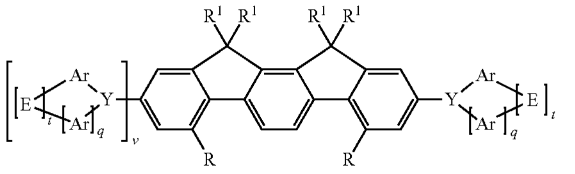

formula (8a)

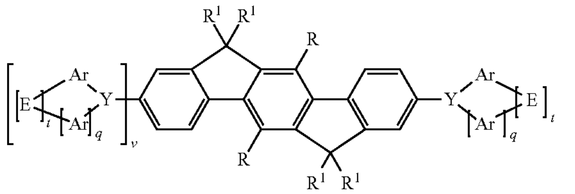

formula (9a)

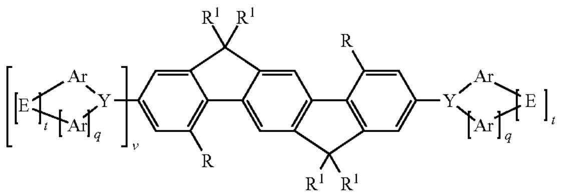

formula (10a)

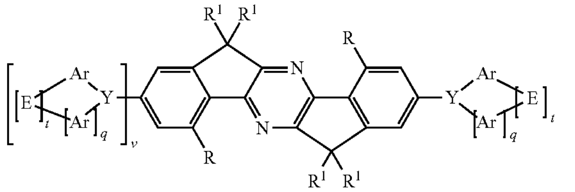

formula (11a)

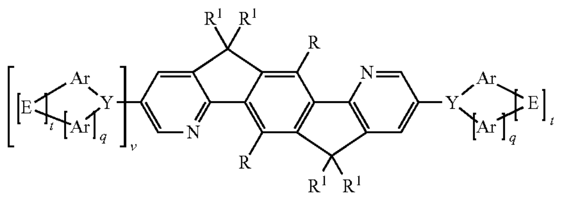

where the symbols and indices used have the above-mentioned meanings and R is other than hydrogen and other than deuterium.

Preference is furthermore given to compounds of the formulae (1) to (11) or (6a) to (11a) in which the symbols Y are selected identically. Very particular preference is given to compounds in which, if present, both groups E are additionally selected identically.

In the statements above, the preferred embodiments of the symbols and indices used are indicated in each case. Particular preference is given to compounds of the formulae (1) to (11) or (6a) to (11a) in which the preferred embodiments indicated above are combined with one another.

Examples of preferred compounds of the formula (1) are structures (1) to (320) depicted below.

(1)

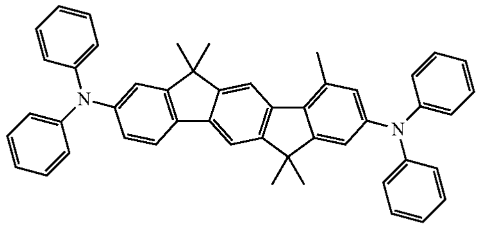

(2)

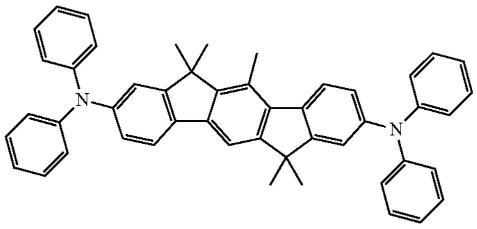

(3)

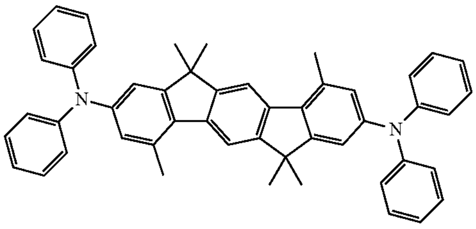

(4)

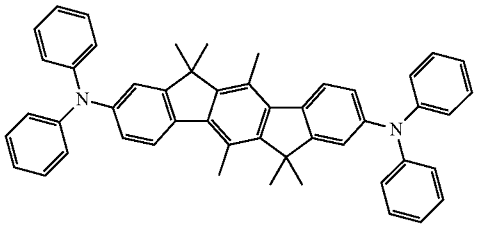

(5)

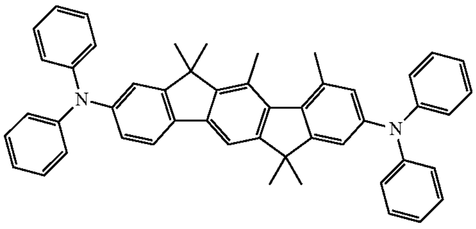

(6)

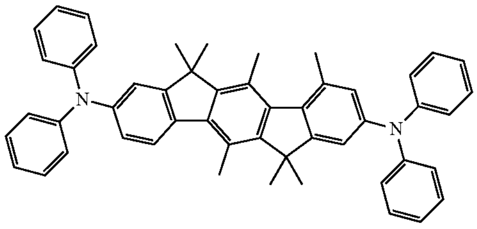

(7)

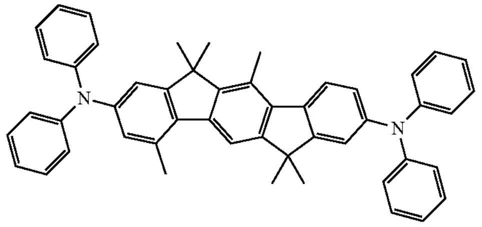

(8)

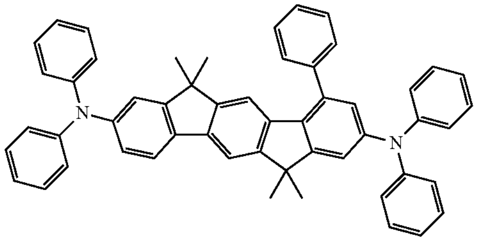

(9)

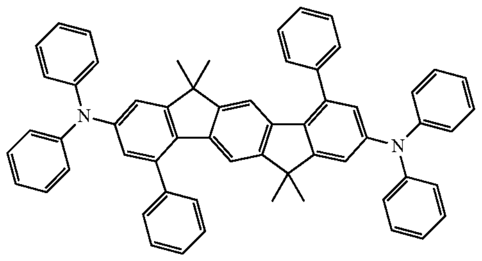

(10)

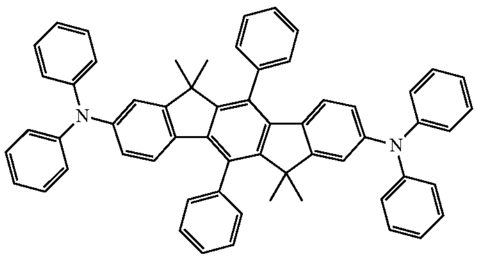

-continued
(11)
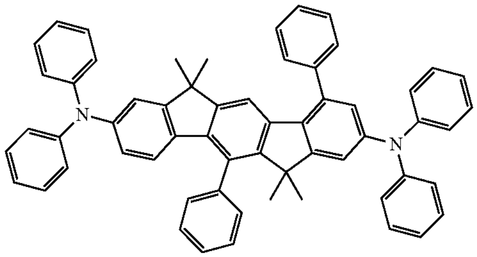
(12)
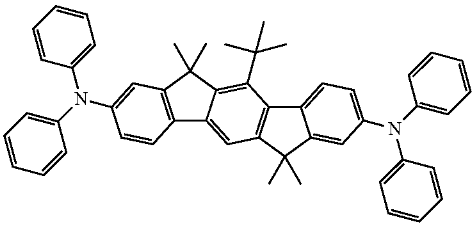
(13)
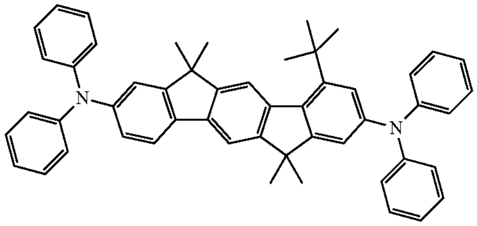
(14)
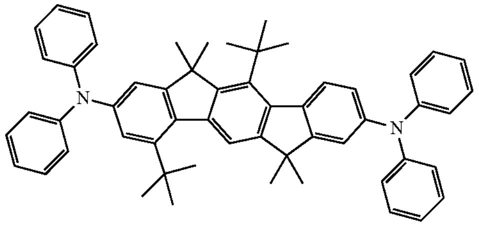
(15)
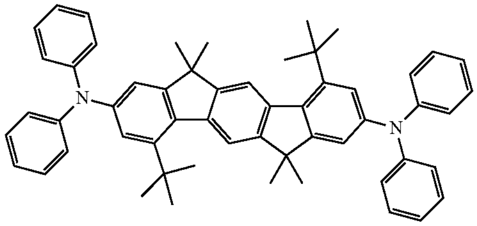
(16)
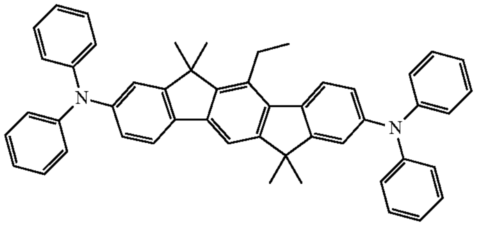
(17)
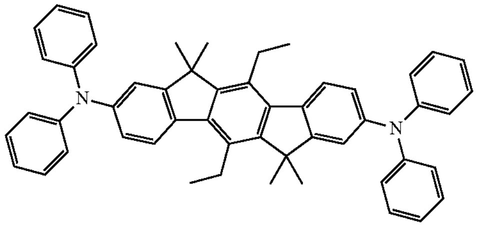
(18)
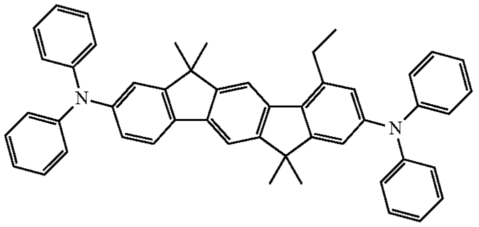
(19)
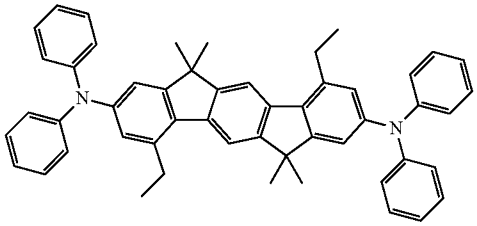
(20)
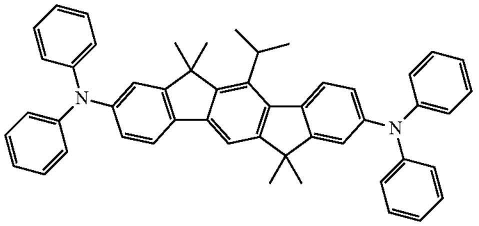
(21)
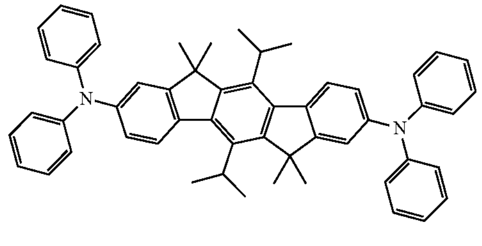
(22)
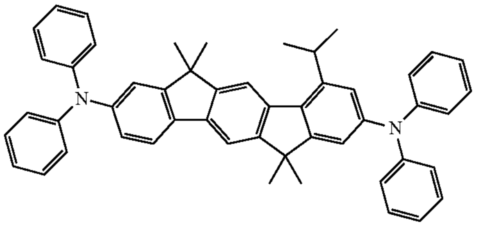

-continued
(23)
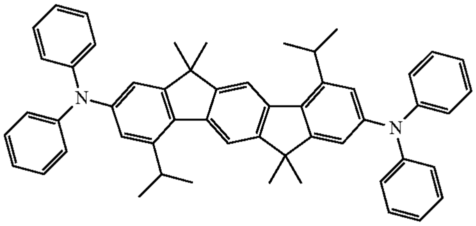
(24)
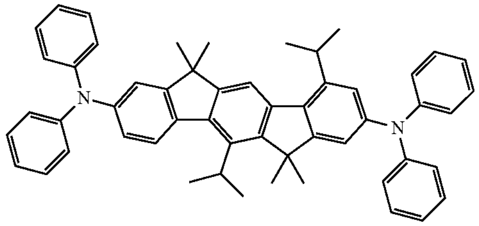
(25)
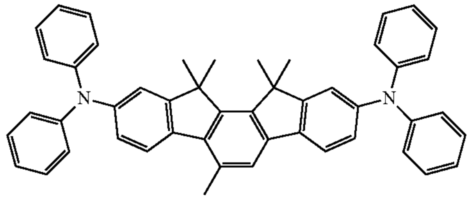
(26)
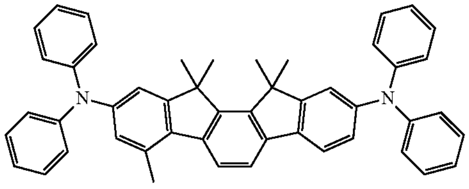
(27)
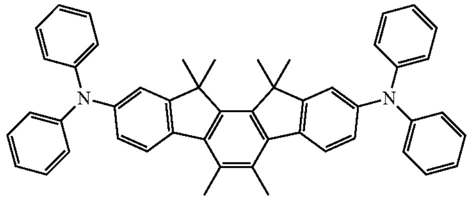
(28)
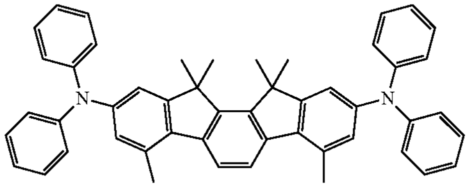
(29)
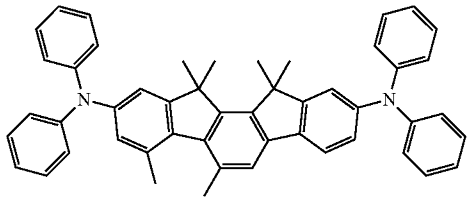
(30)
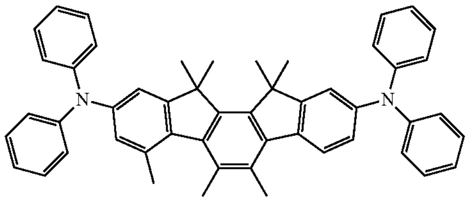
(31)
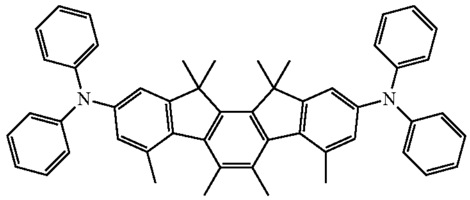
(32)
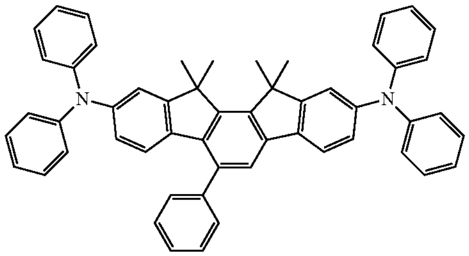
(33)
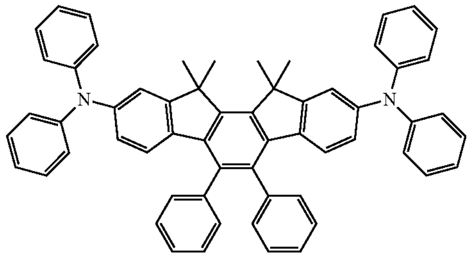
(34)
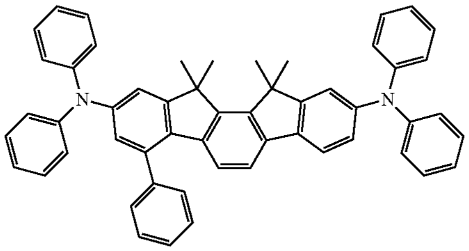

-continued
(35)
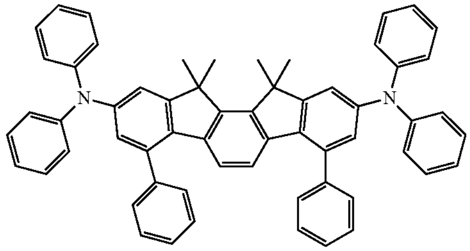
(36)
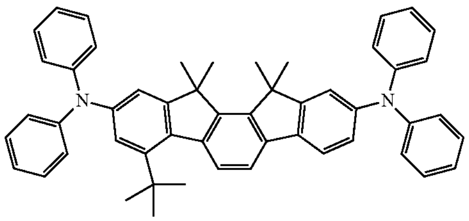
(37)
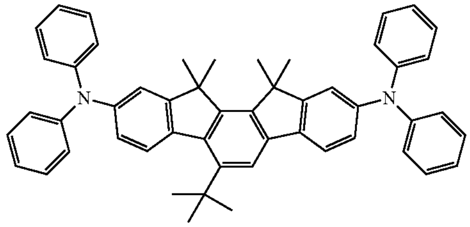
(38)
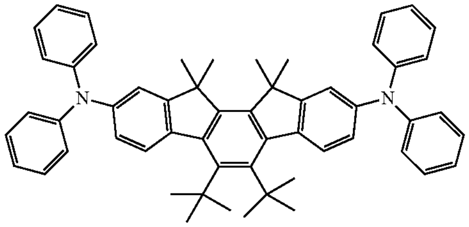
(39)
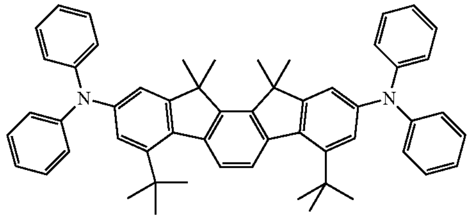
(40)
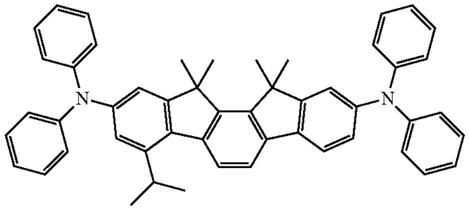
(41)
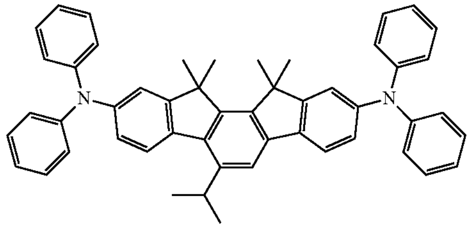
(42)
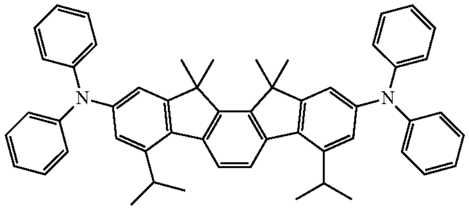
(43)
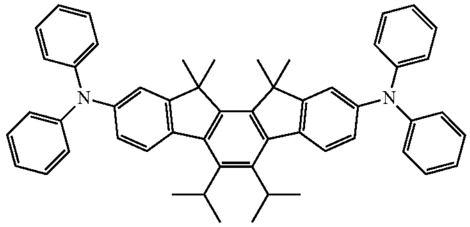
(44)
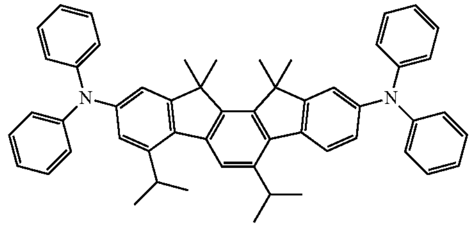
(45)
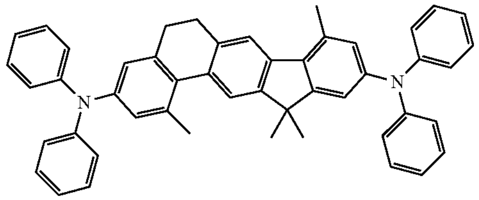
(46)
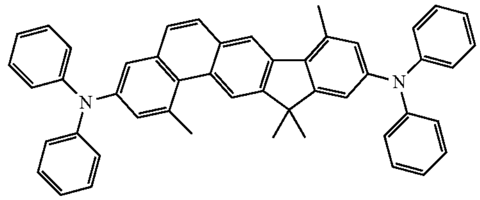

-continued
(47)
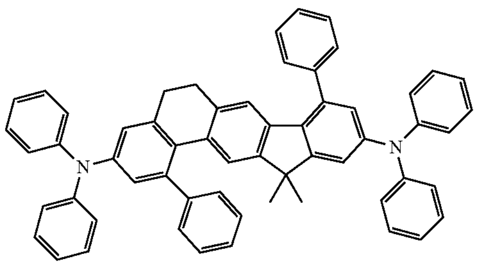
(48)
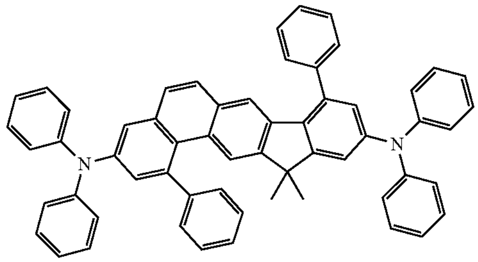
(49)
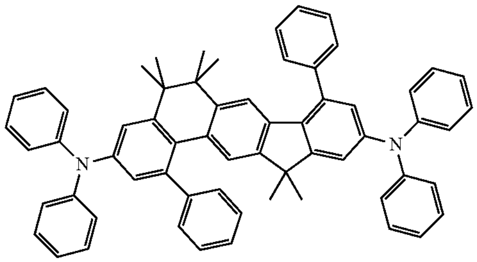
(50)
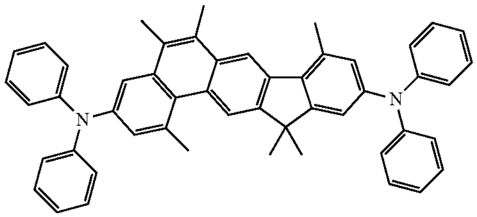
(51)
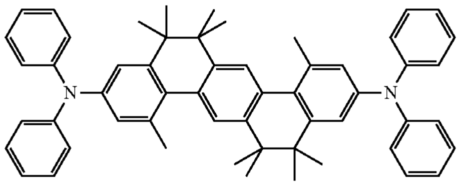
(52)
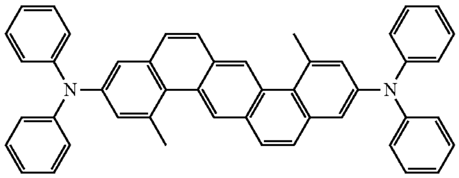
(53)
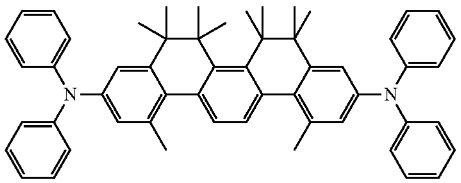
(54)
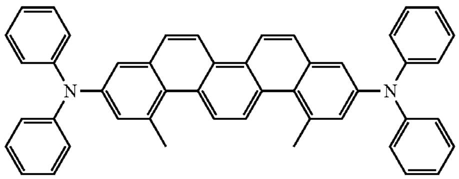
(55)
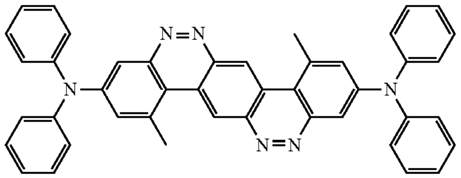
(56)
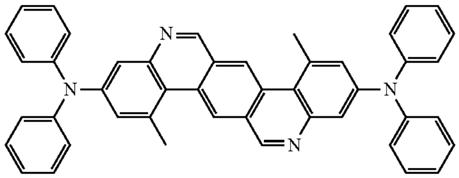
(57)
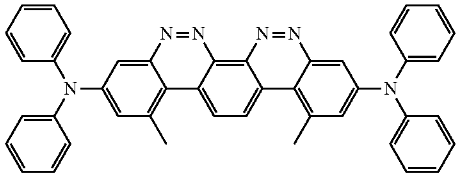
(58)
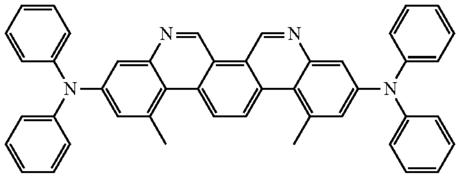
(59)
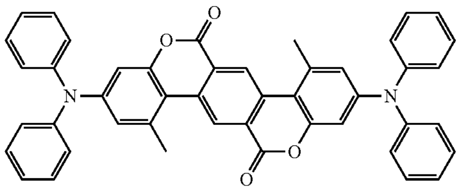
(60)
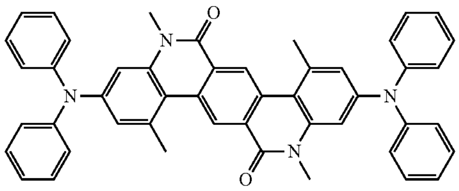

-continued
(61)
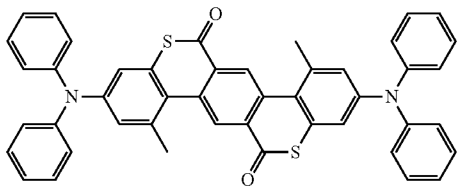
(62)
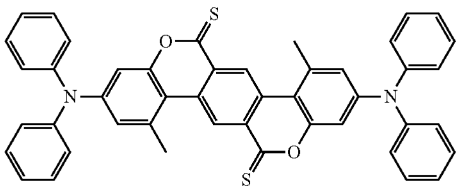
(63)
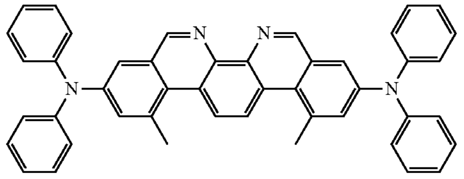
(64)
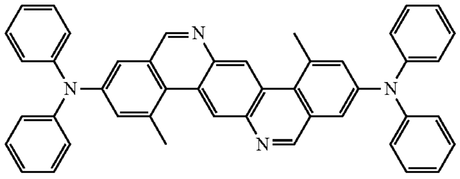
(65)
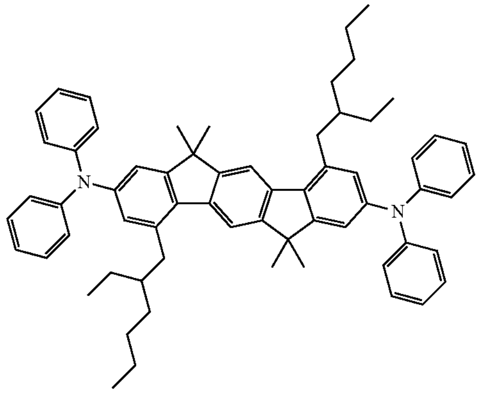
(66)
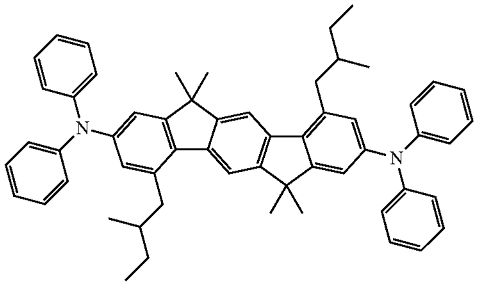
(67)
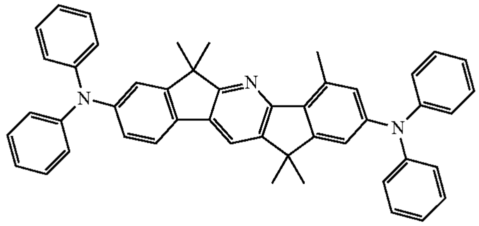
(68)
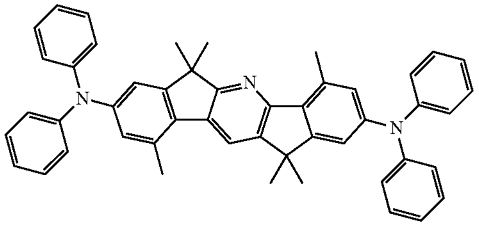
(69)
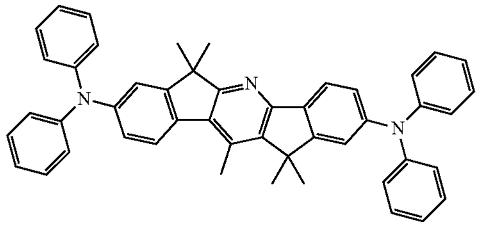
(70)
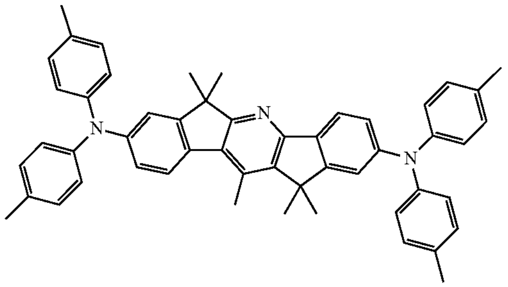
(71)
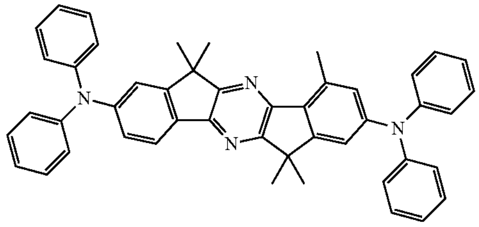
(72)
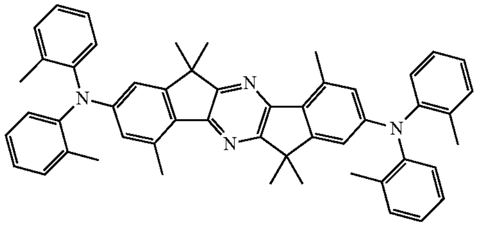

-continued
(73)
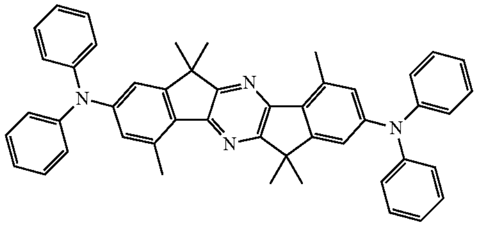
(74)
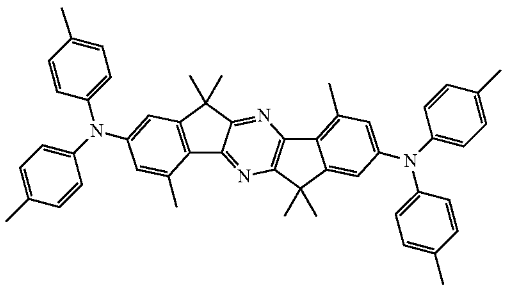
(75)
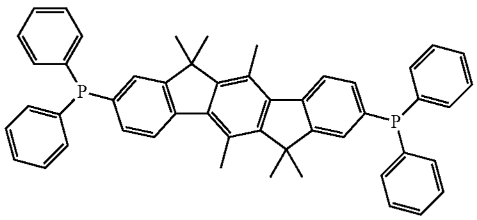
(76)
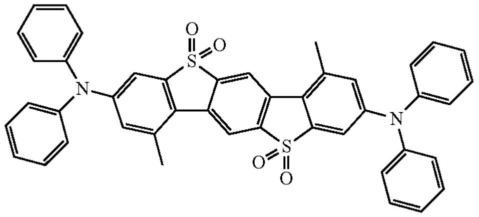
(77)
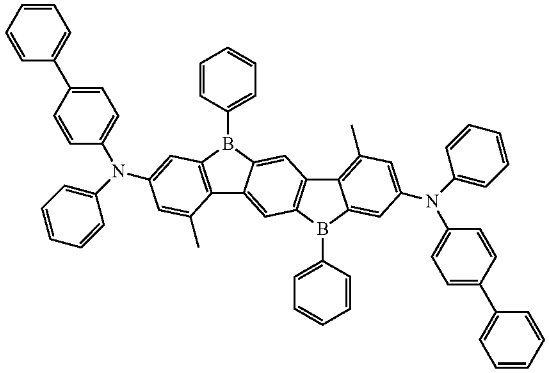
(78)
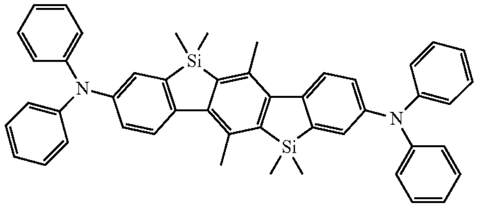
(79)
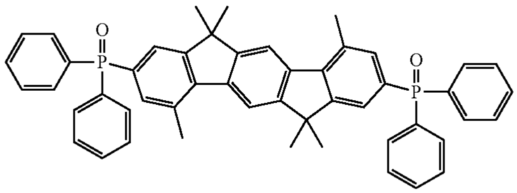
(80)
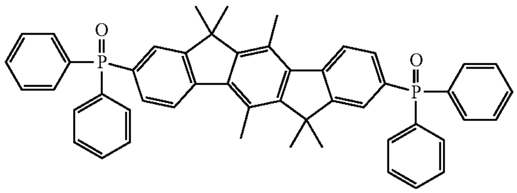
(81)
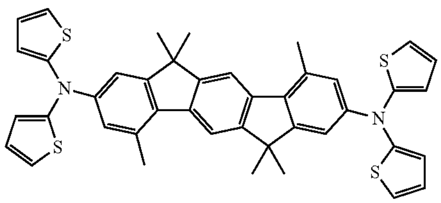
(82)
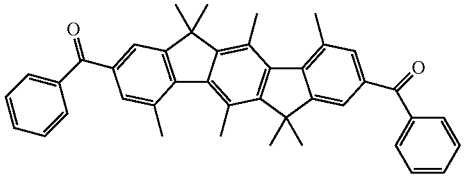
(83)
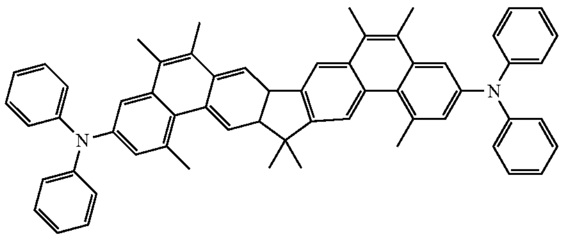
(84)
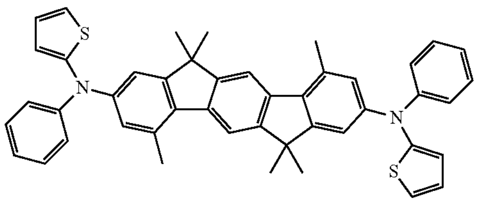

-continued
(85)
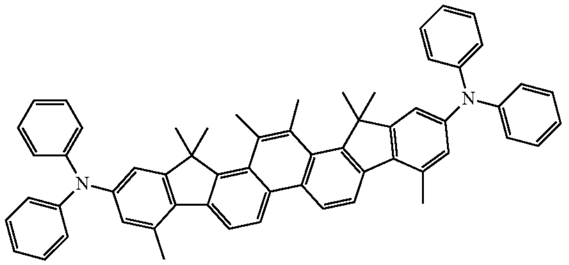
(86)
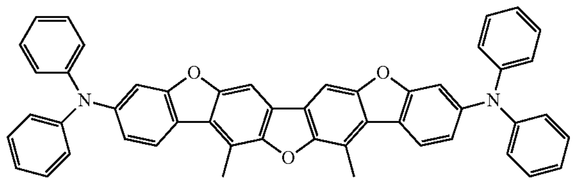
(87)
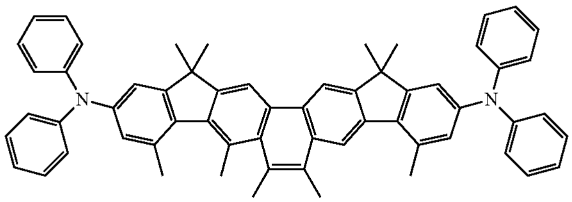
(88)
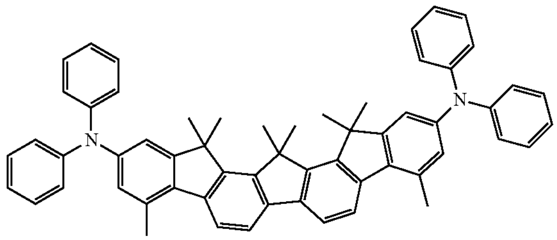
(89)
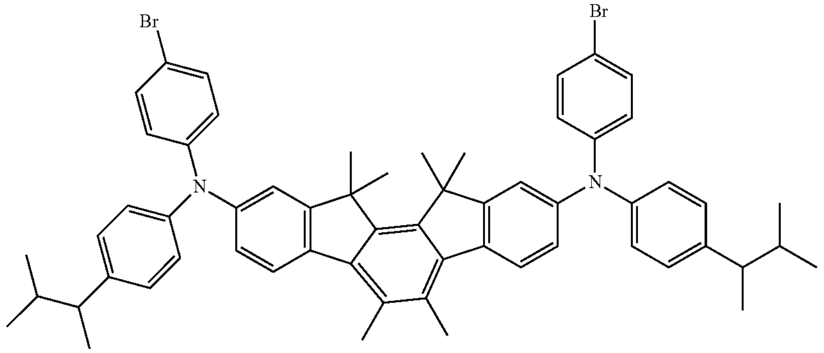
(90)
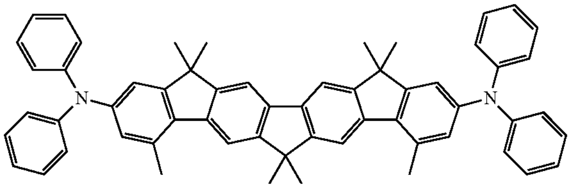
(91)
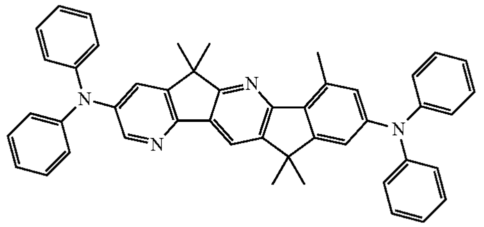
(92)
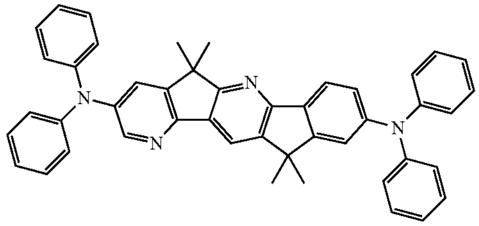
(93)
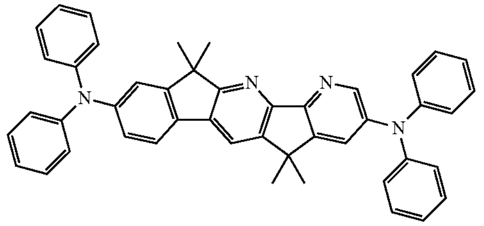
(94)
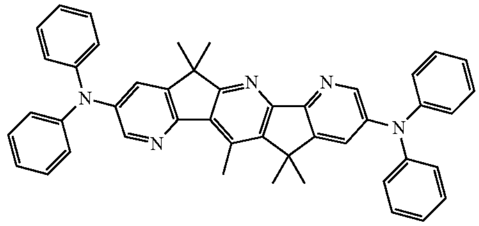
(95)
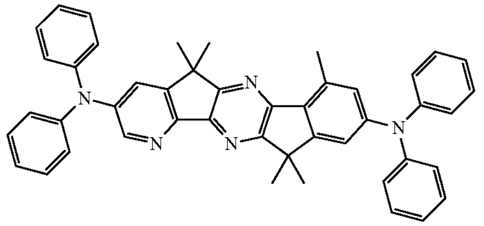

-continued
(96)
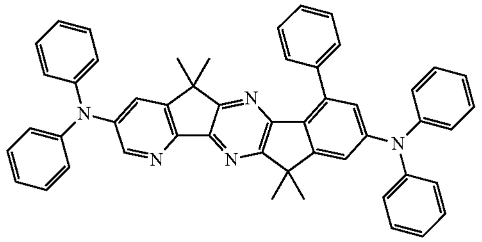
(97)
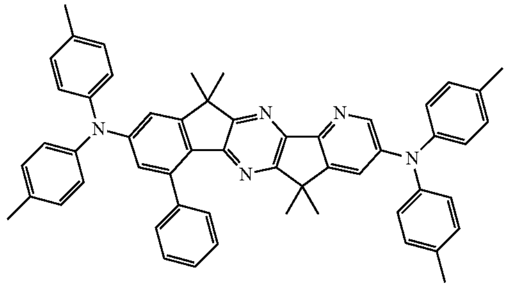
(98)
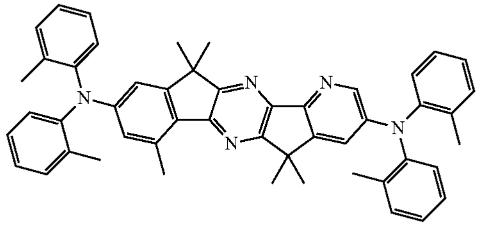
(99)
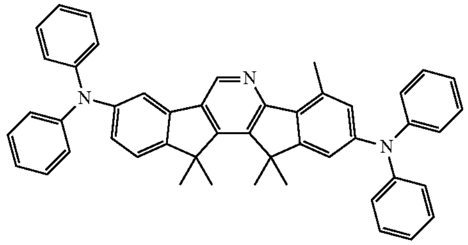
(100)
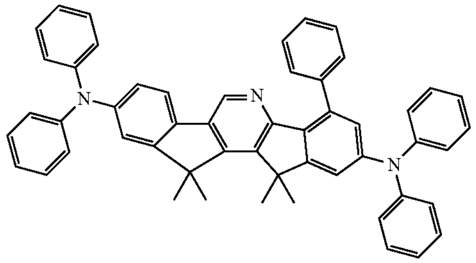
(101)
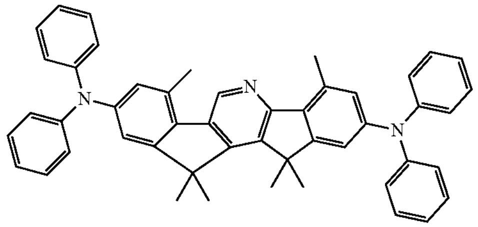
(102)
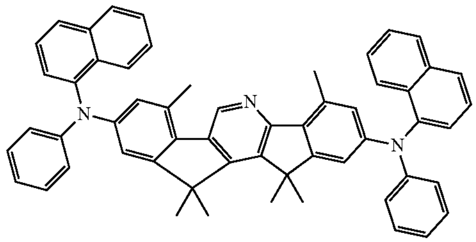
(103)
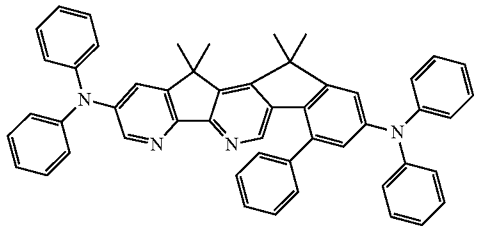
(104)
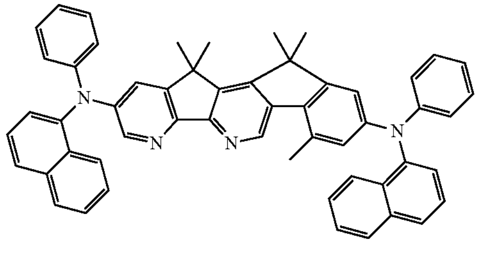
(105)
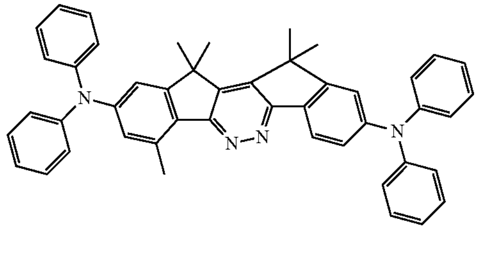

-continued
(106)
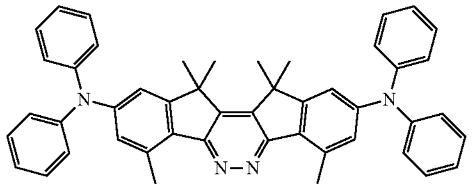
(107)
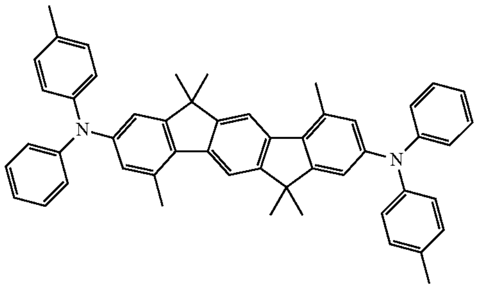
(108)
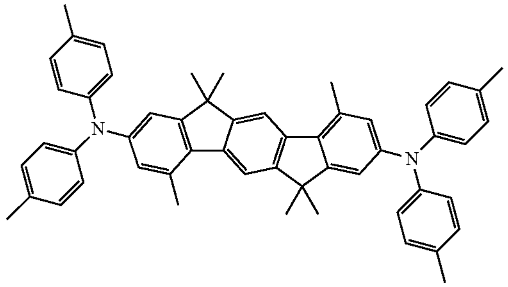
(109)
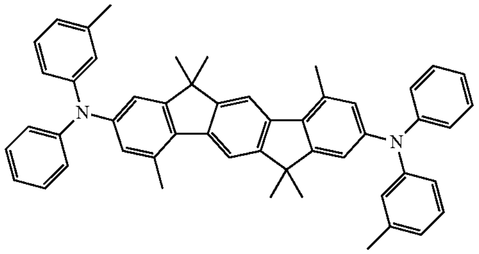
(110)
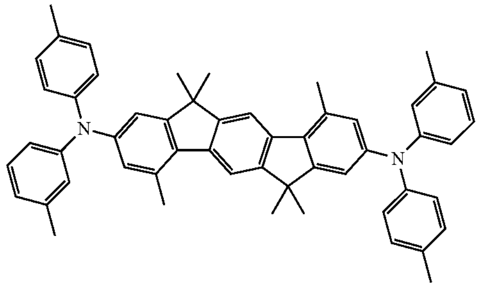
(111)
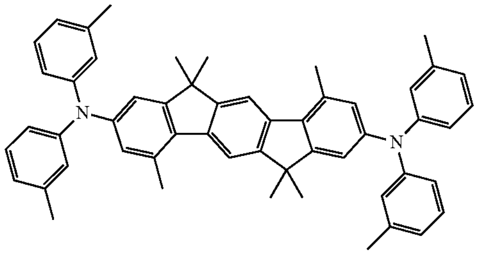
(112)
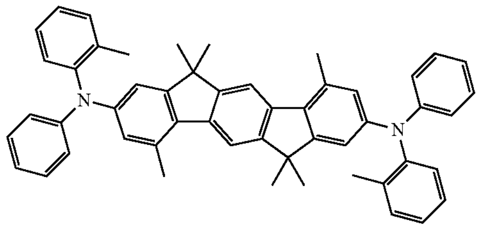
(113)
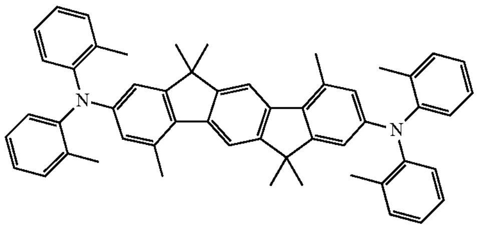
(114)
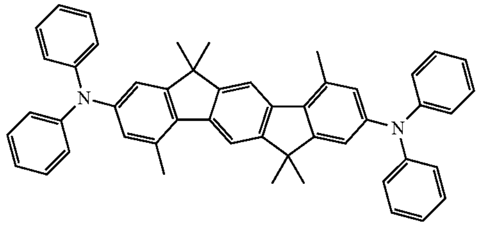
(115)
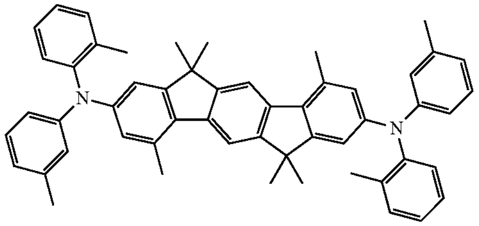

-continued
(116)
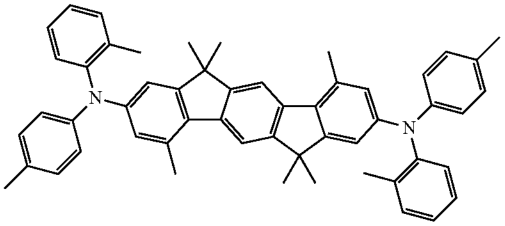
(117)
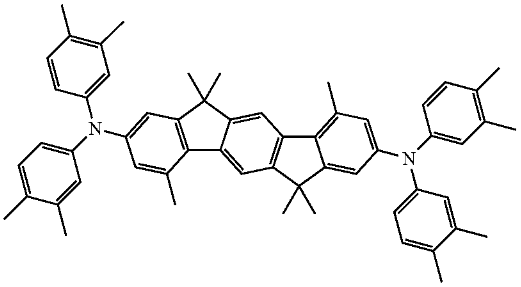
(118)
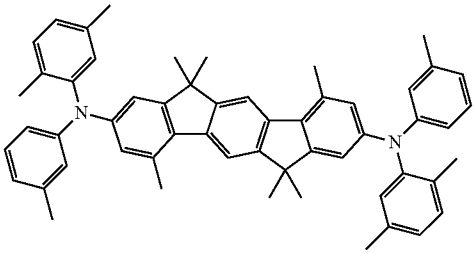
(119)
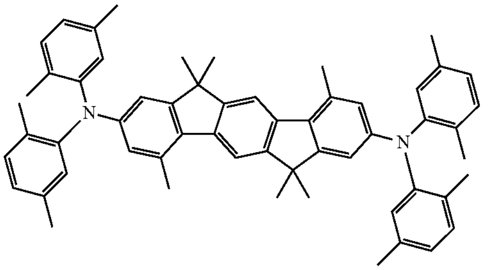
(120)
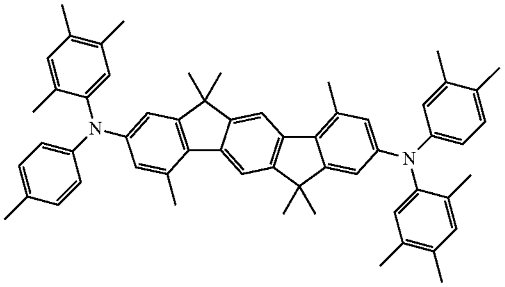
(121)
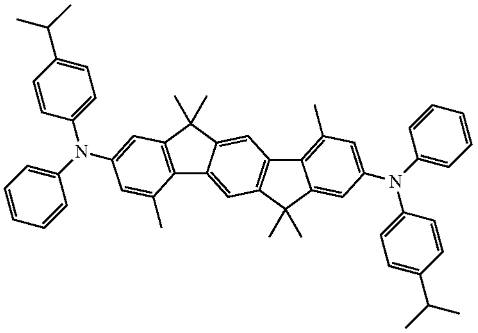
(122)
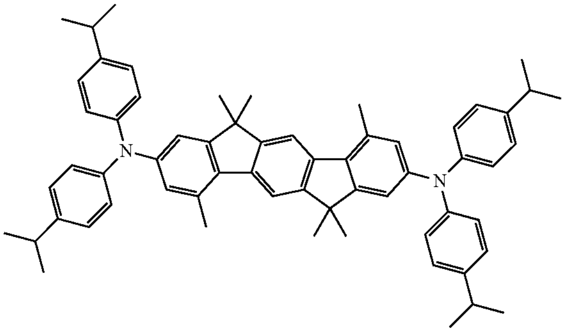
(123)
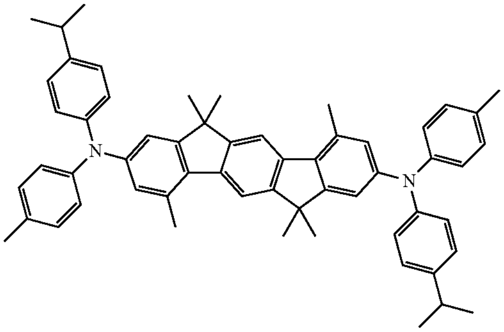
(124)
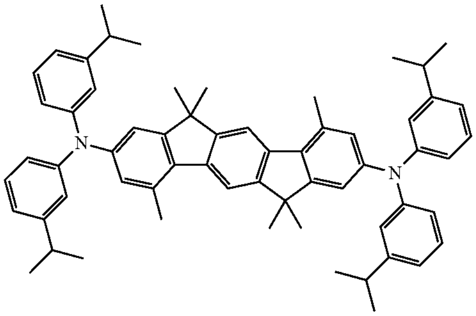
(125)
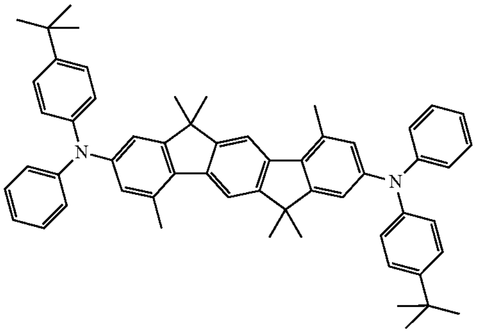

-continued
(126)
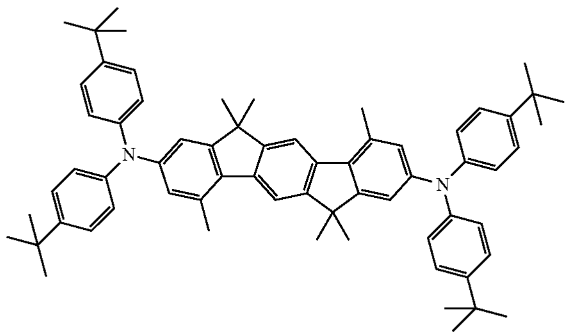
(127)
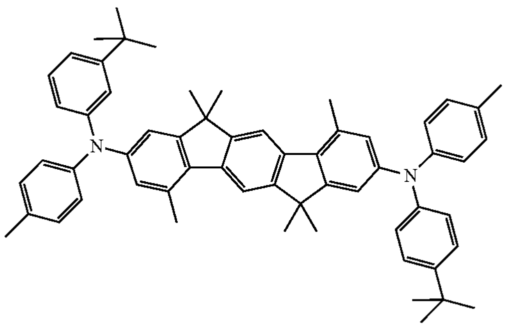
(128)
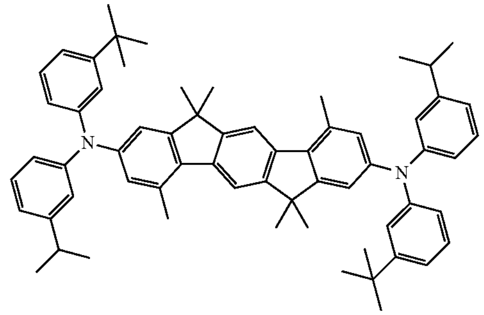
(129)
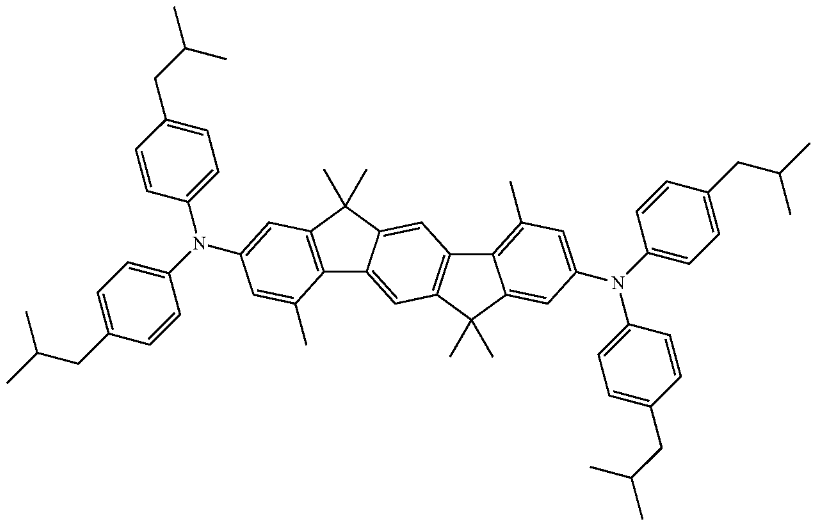
(130)
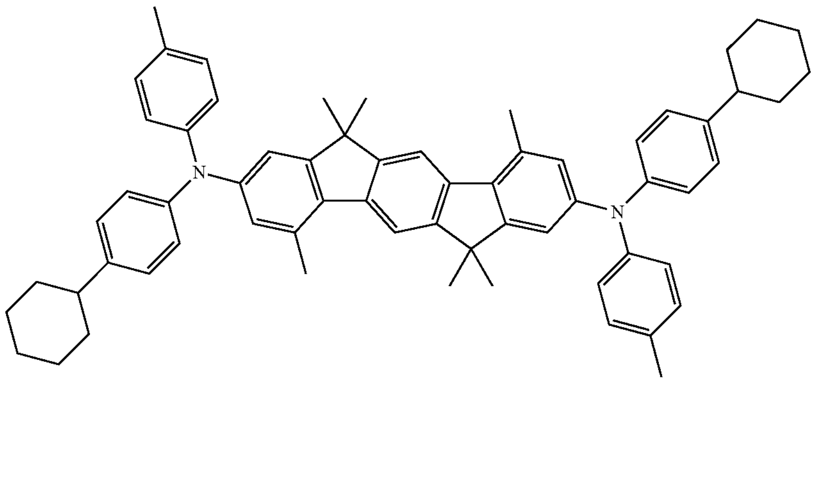

-continued
(131)
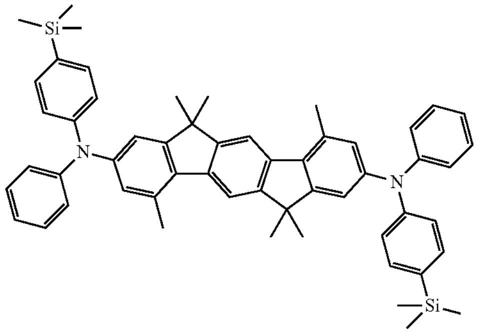
(132)
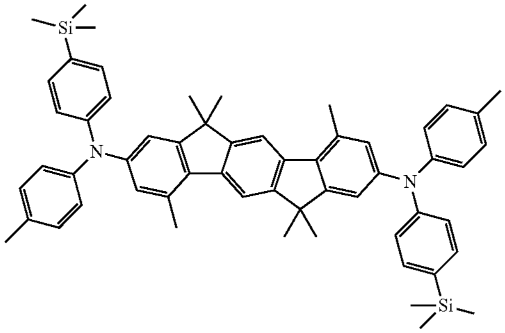
(133)
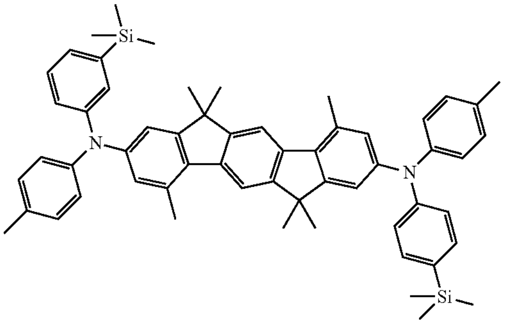
(134)
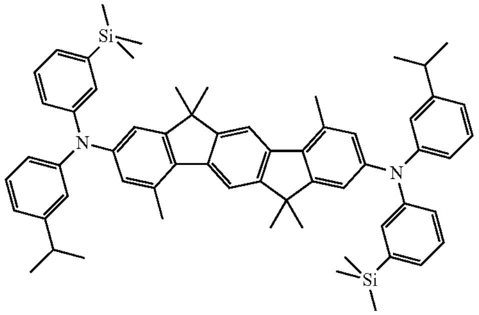
(135)
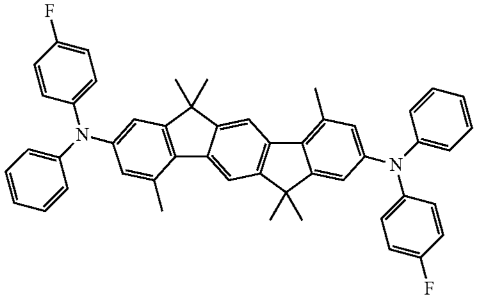
(136)
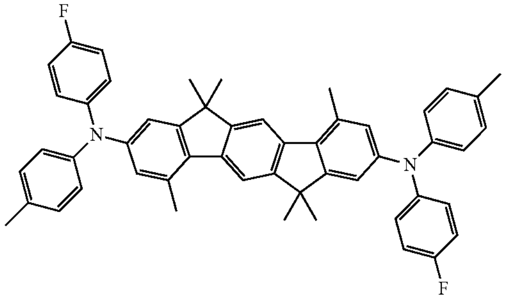
(137)
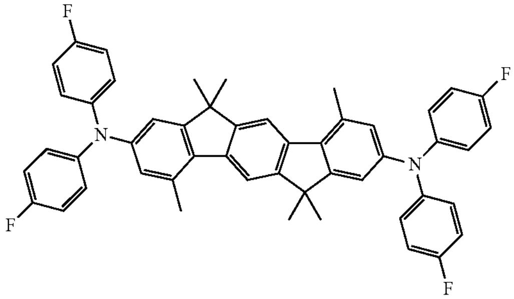
(138)
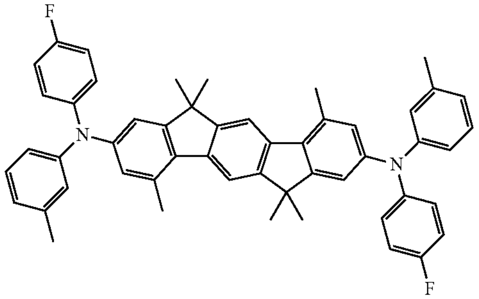
(139)
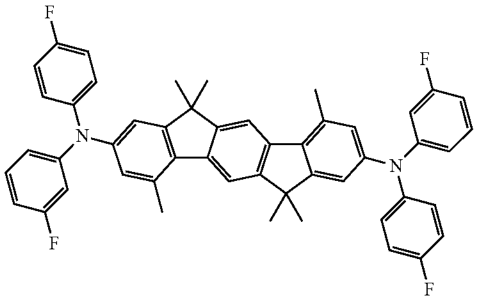
(140)
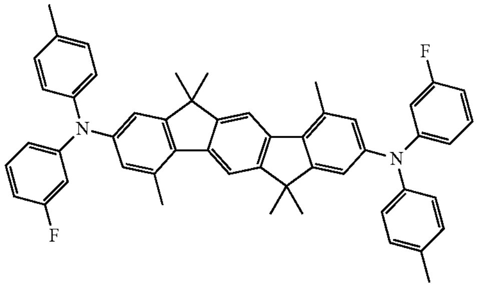

-continued
(141)
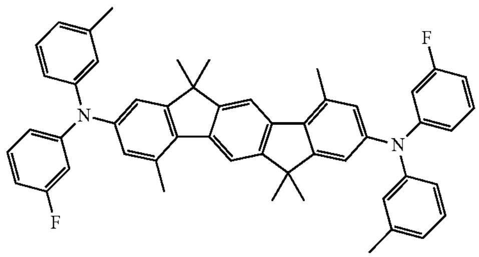
(142)
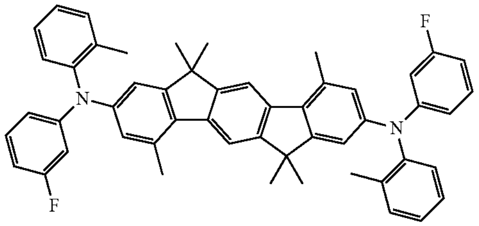
(143)
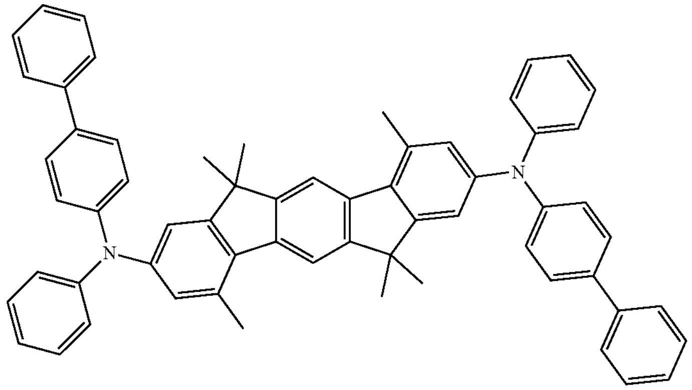
(144)
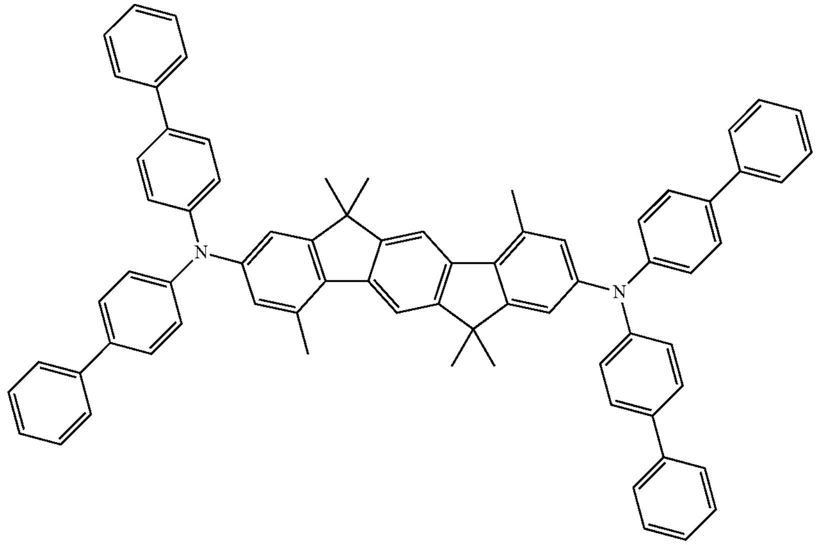
(145)
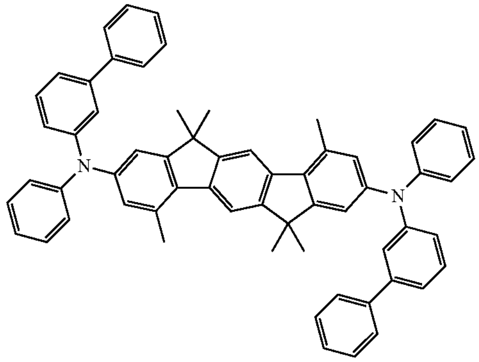
(146)
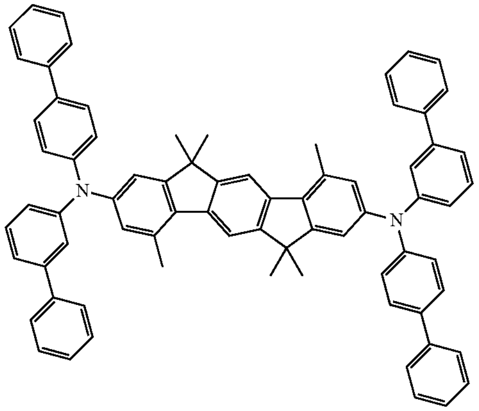

-continued
(147)
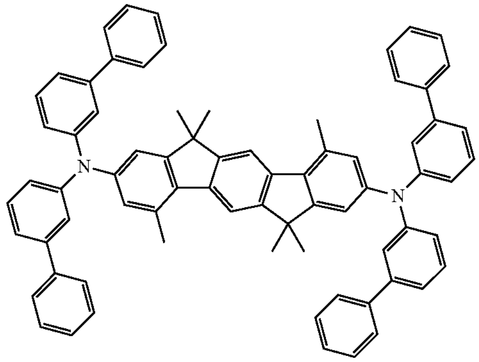
(148)
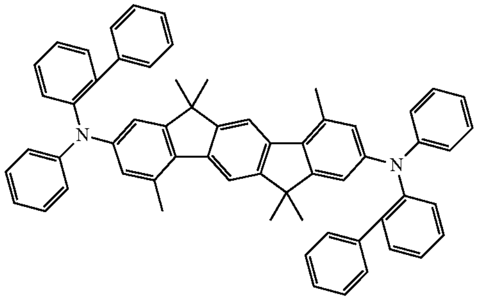
(149)
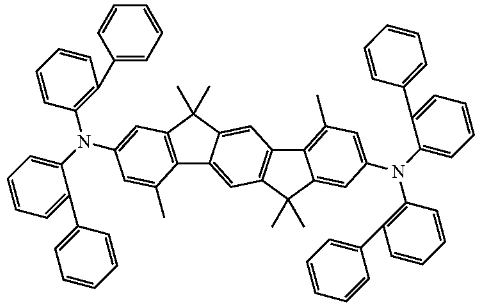
(150)
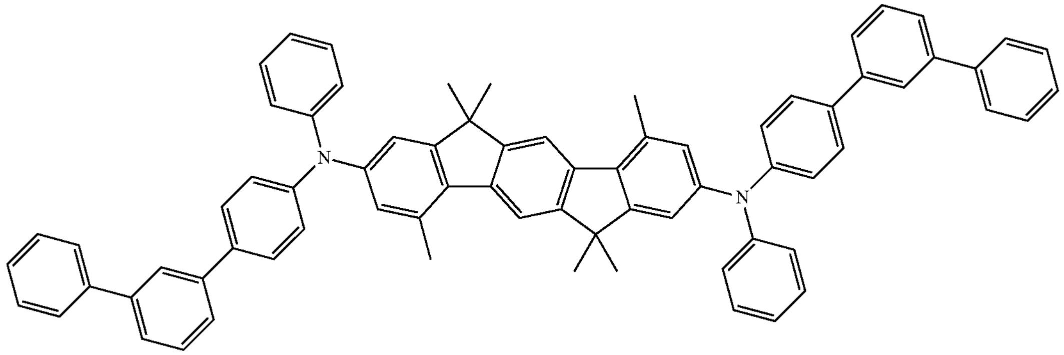
(151)
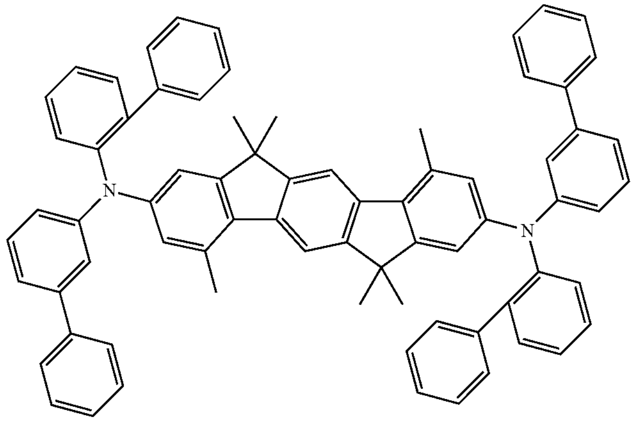

-continued
(152)
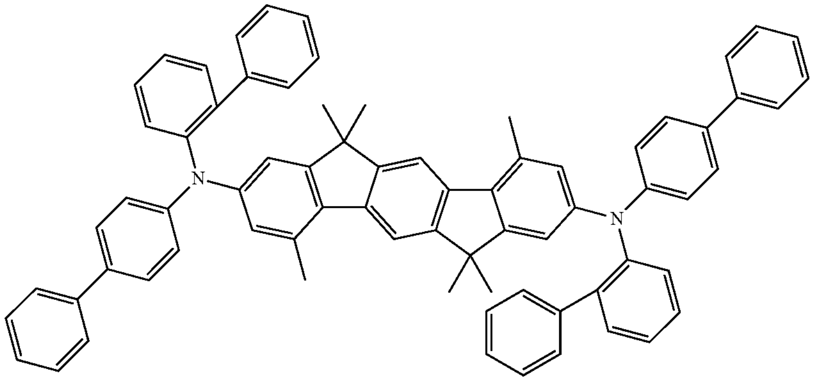
(153)
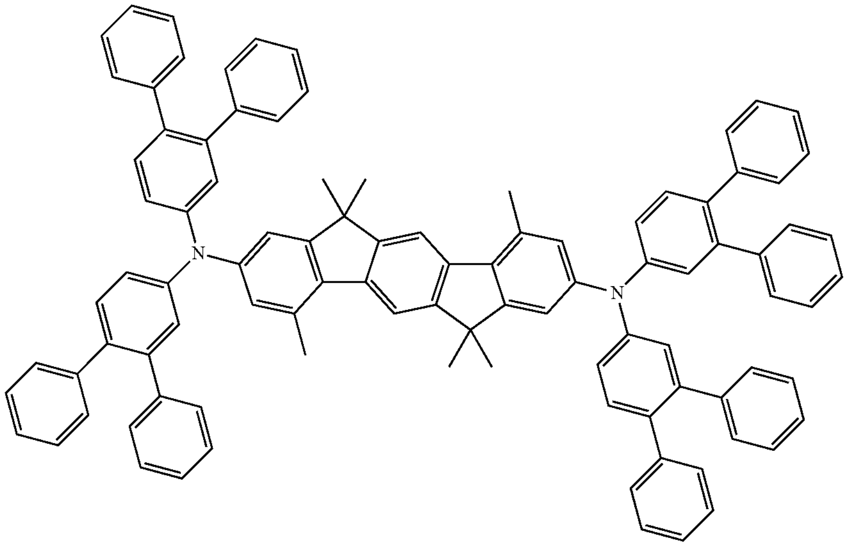
(154)
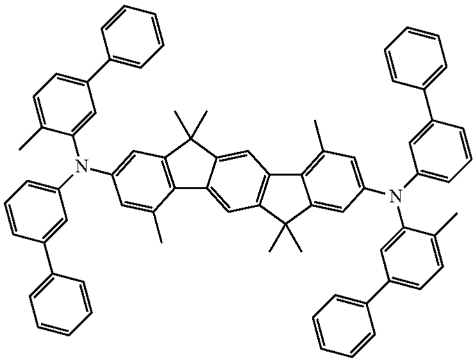
(155)
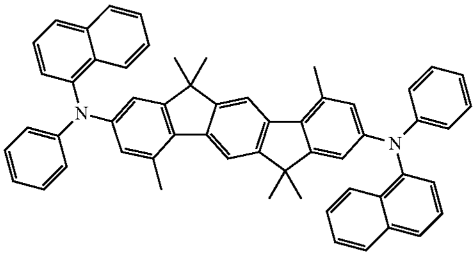

-continued
(156)
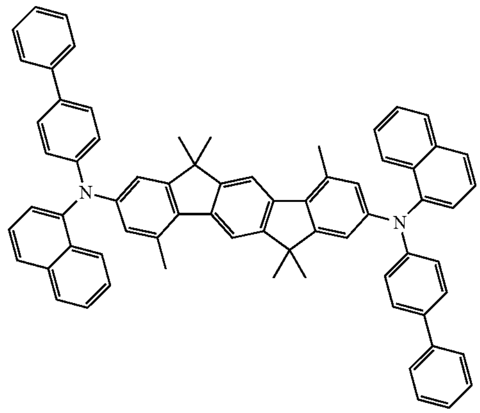
(157)
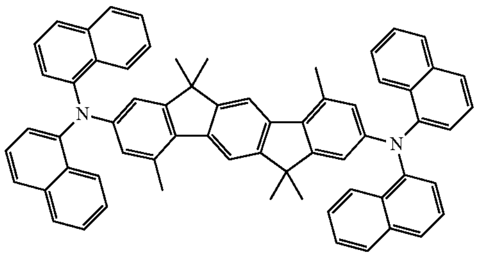
(158)
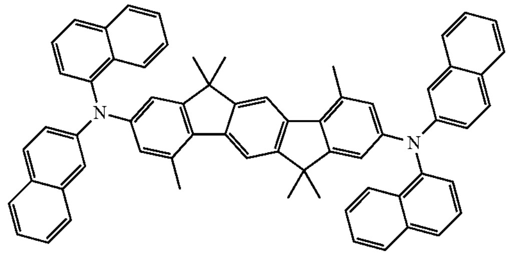
(159)
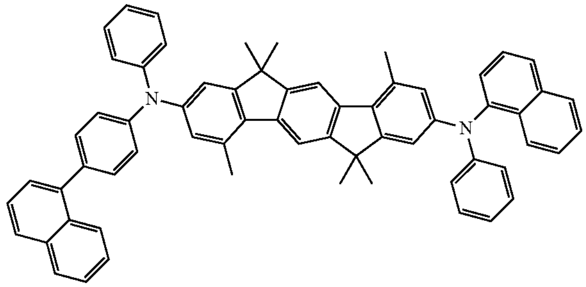
(160)
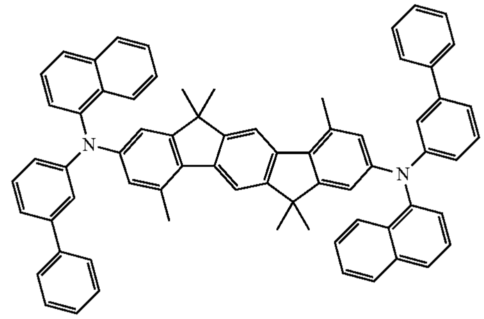
(161)
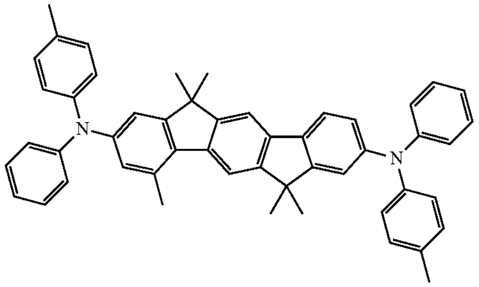
(162)
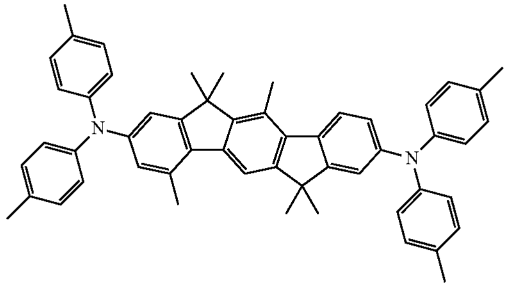
(163)
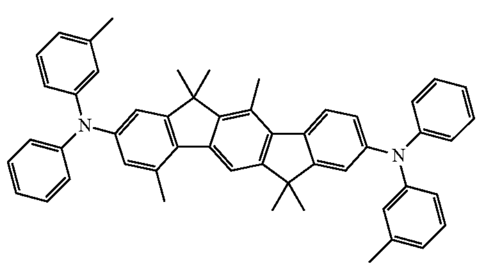
(164)
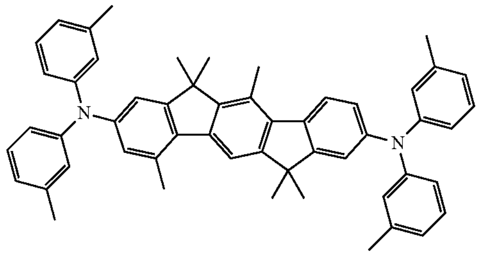
(165)
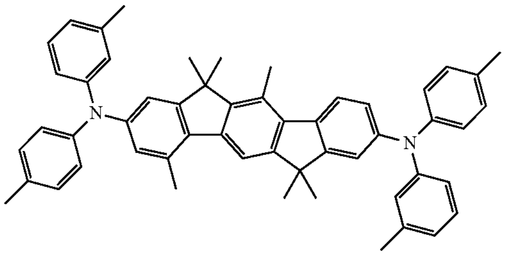

-continued
(166)
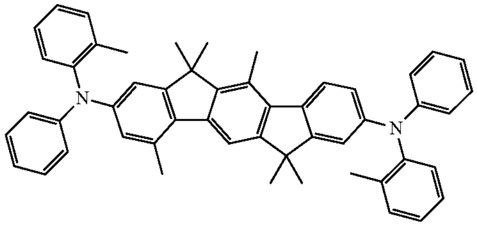
(167)
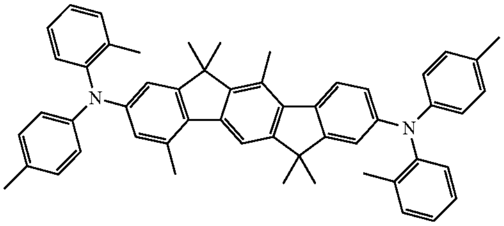
(168)
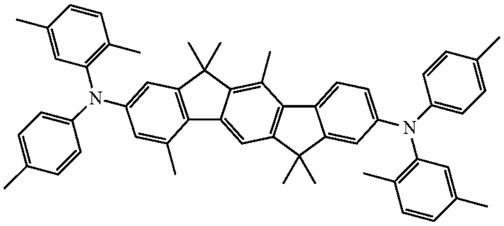
(169)
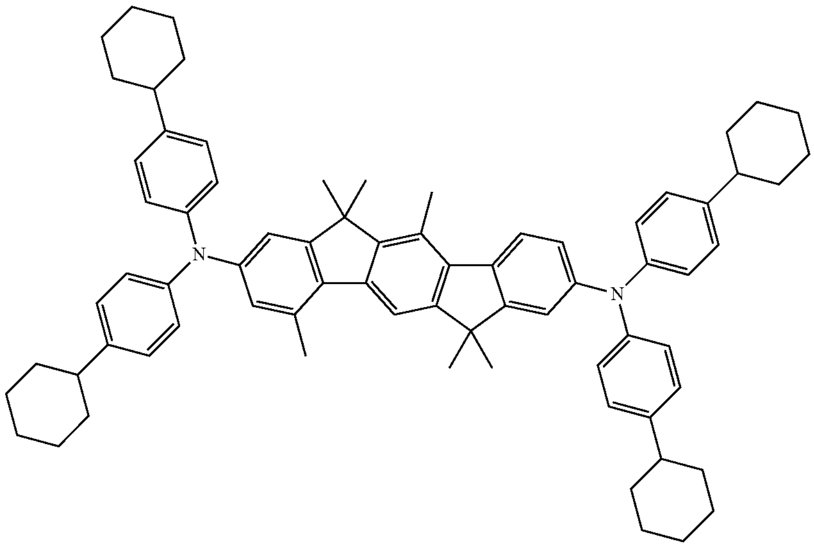
(170)
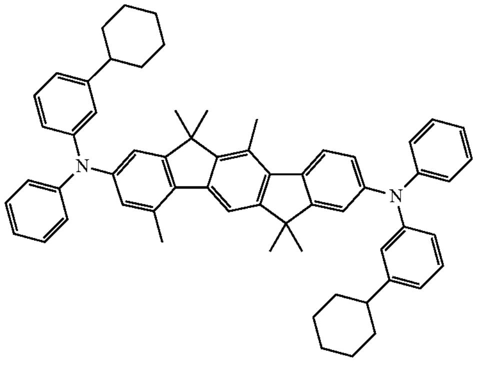
(171)
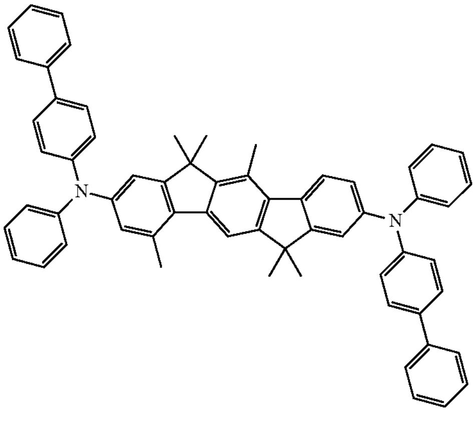

-continued
(172)
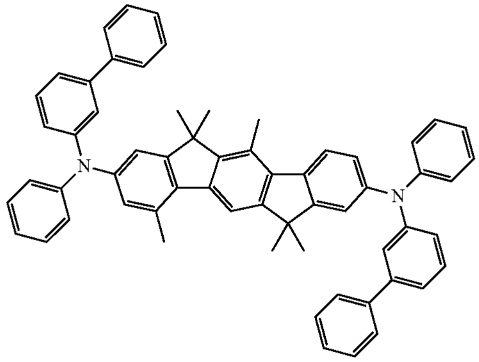
(173)
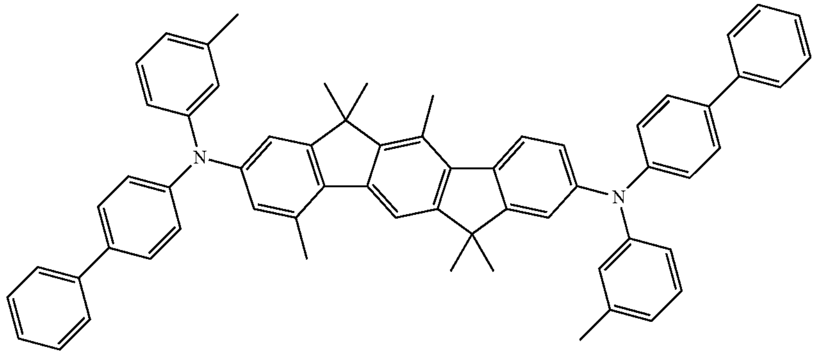
(174)
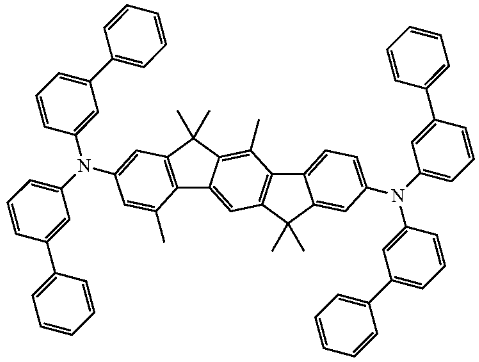
(175)
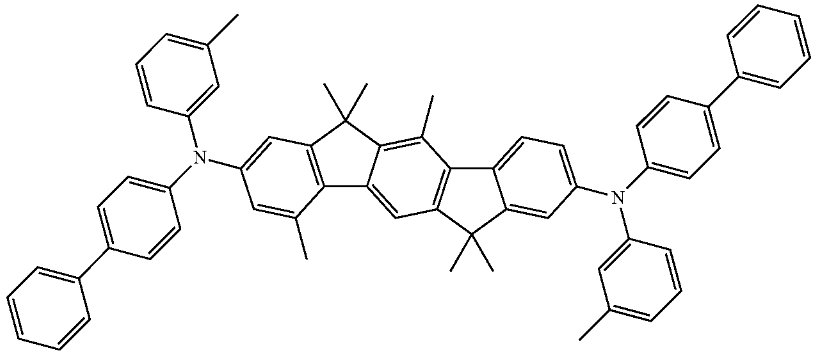

-continued
(176)
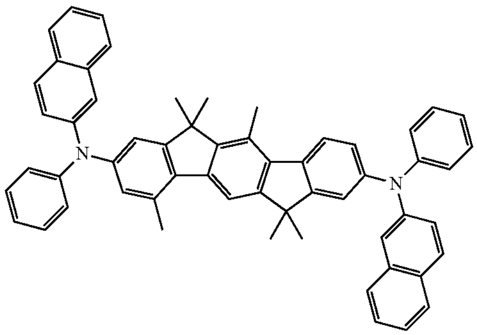
(177)
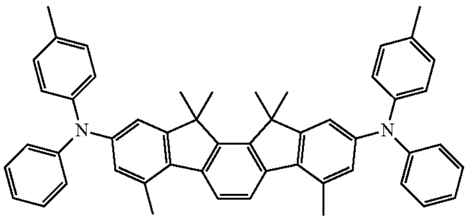
(178)
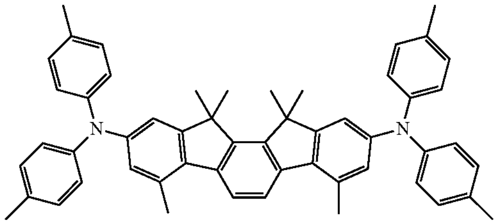
(179)
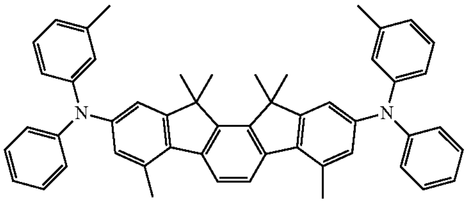
(180)
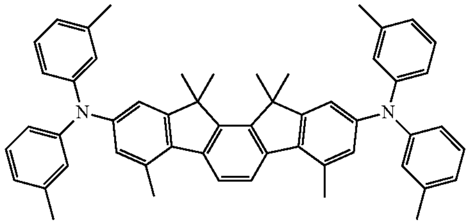
(181)
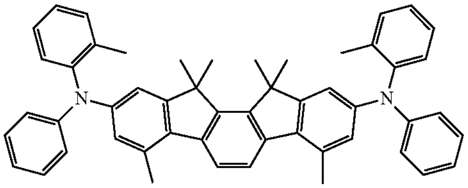
(182)
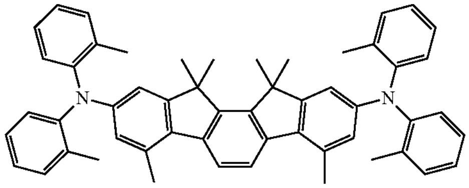
(183)
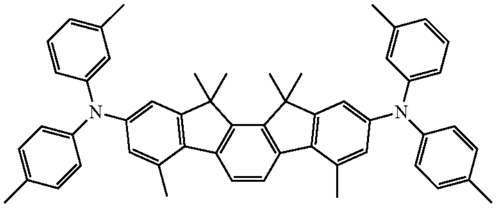
(184)
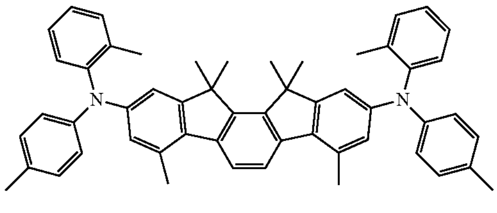
(185)
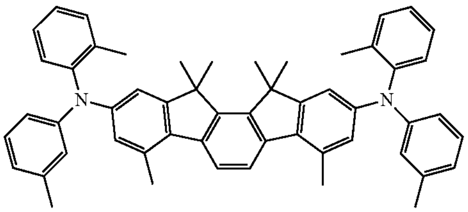
(186)
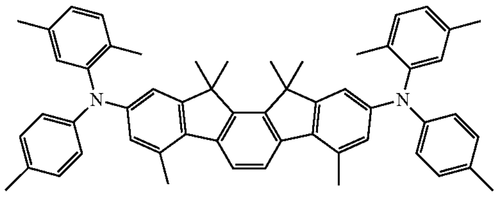
(187)
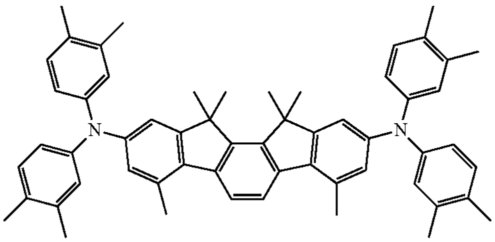

-continued
(188)
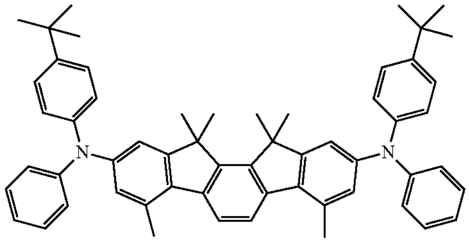
(189)
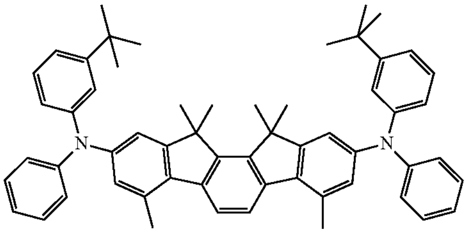
(190)
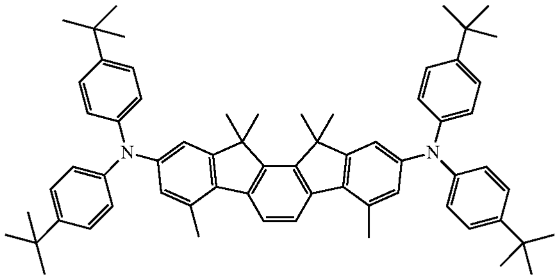
(191)
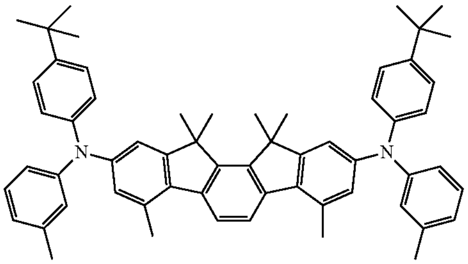
(192)
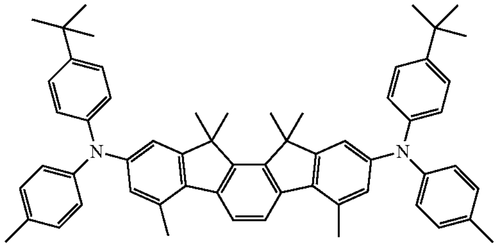
(193)
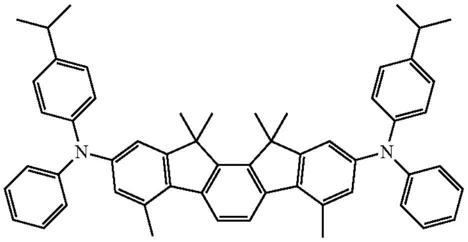
(194)
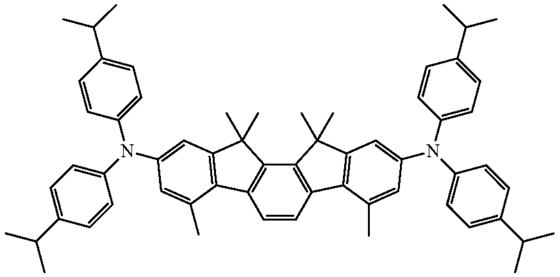
(195)
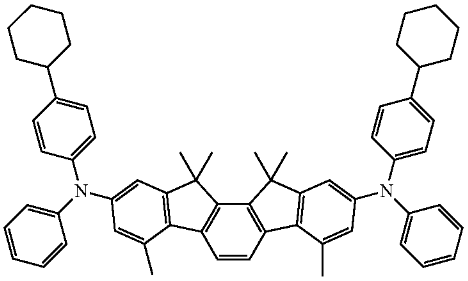
(196)
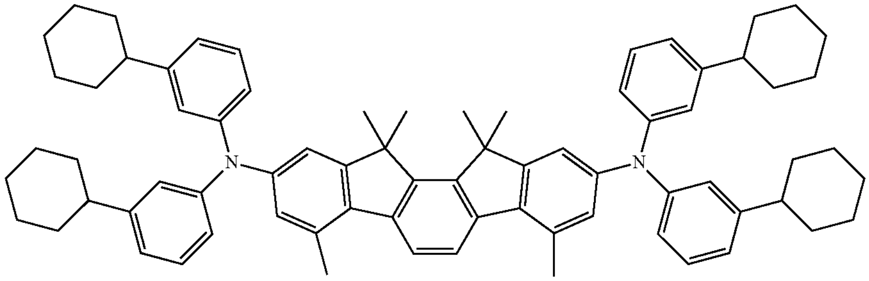

-continued
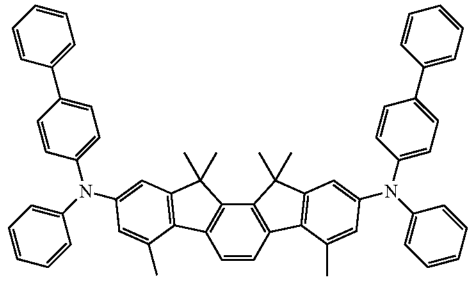
(197)
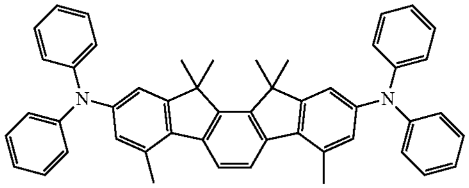
(198)
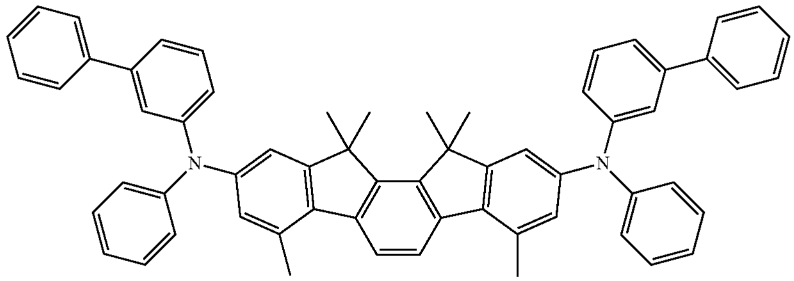
(199)
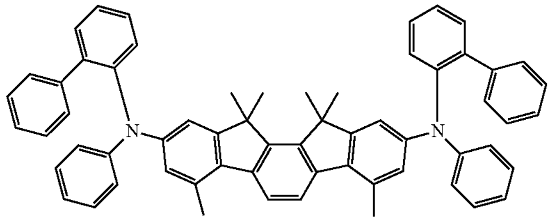
(200)
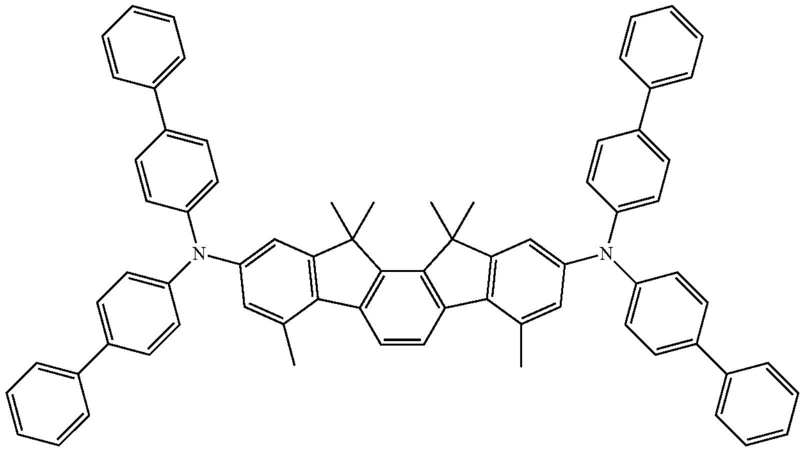
(201)

-continued
(202)
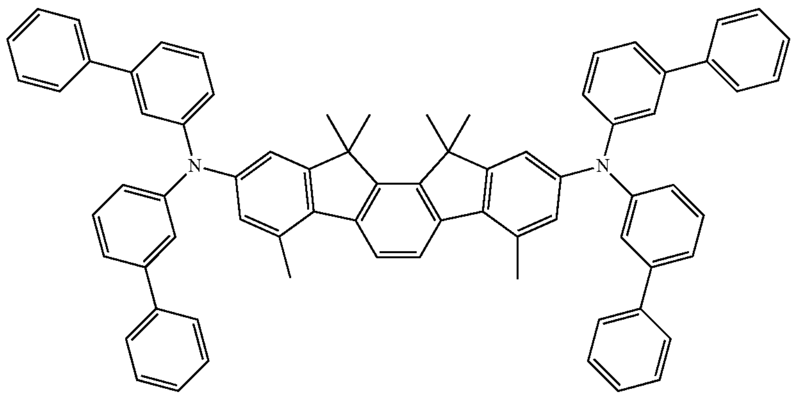
(203)
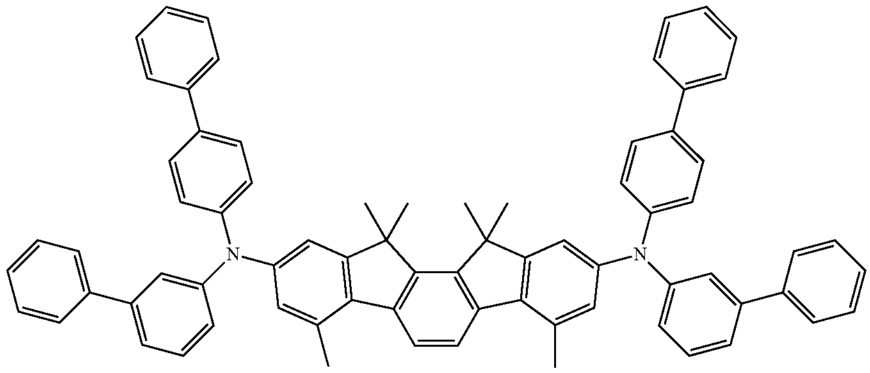
(204)
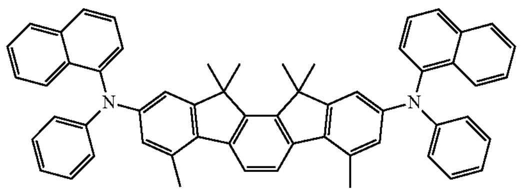
(205)
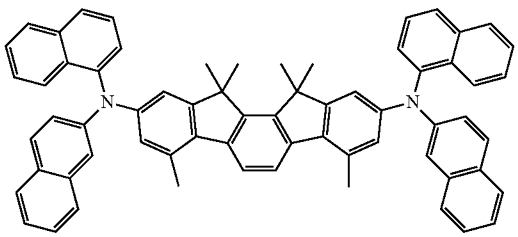
(206)
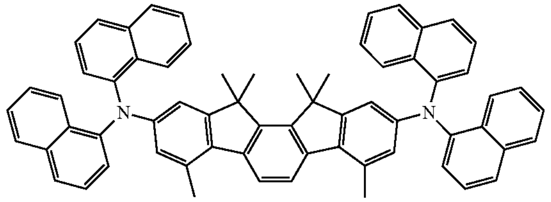
(207)
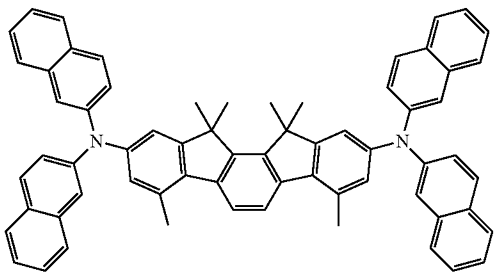

-continued
(208)
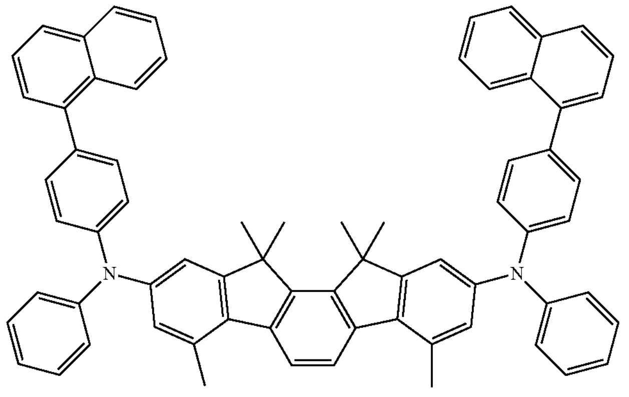
(209)
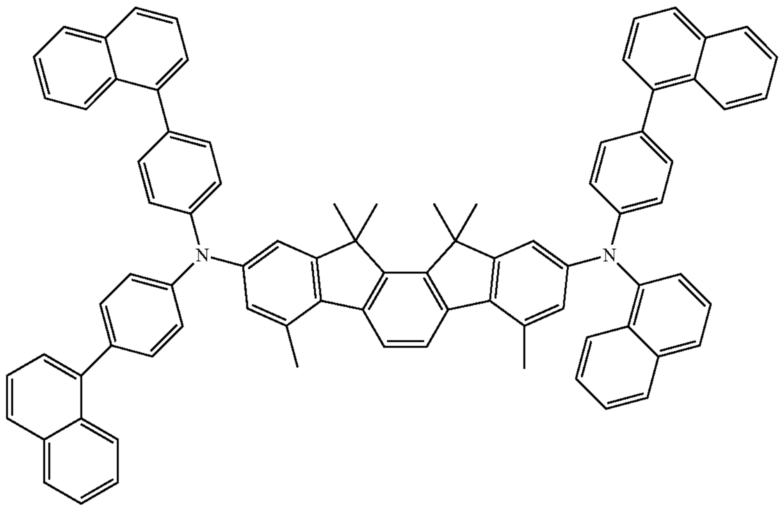
(210)
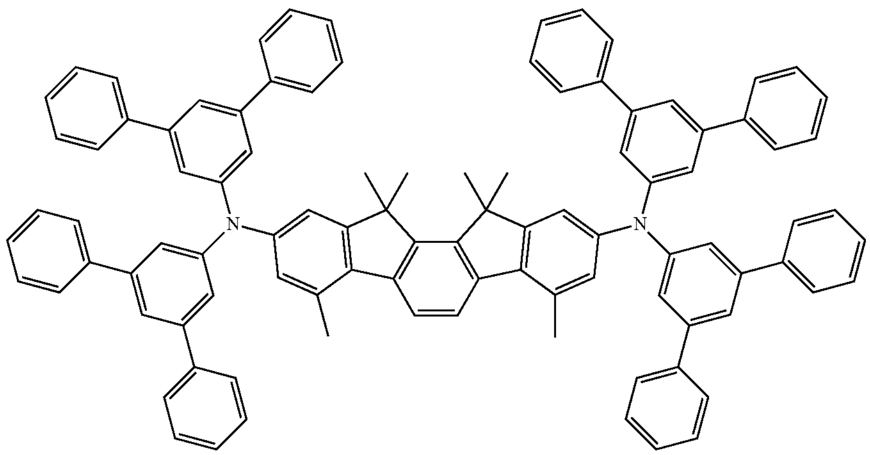

-continued
(211)
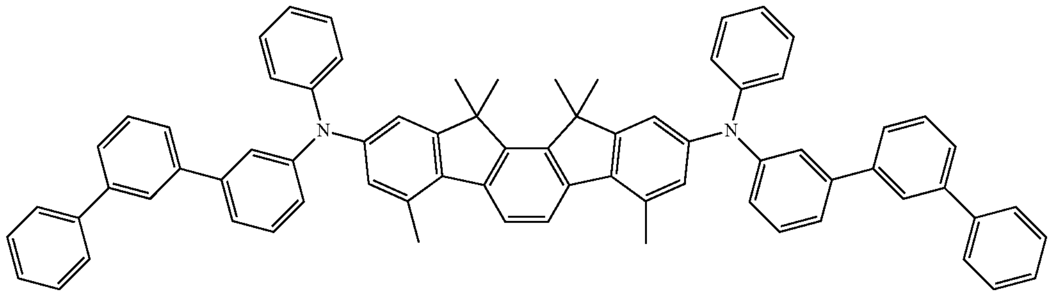
(212)
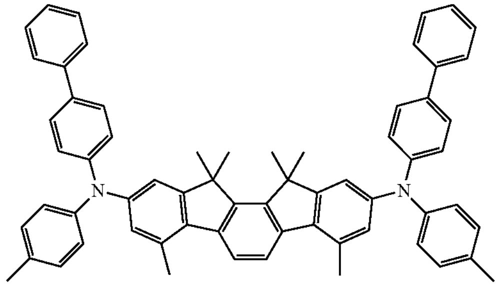
(213)
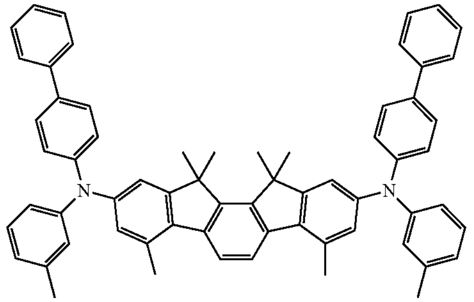
(214)
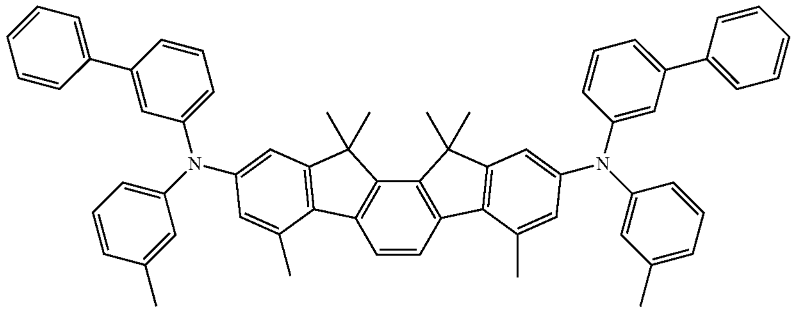
(215)
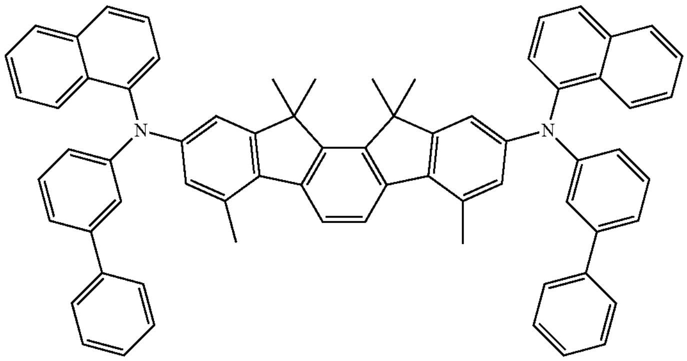

-continued
(216)
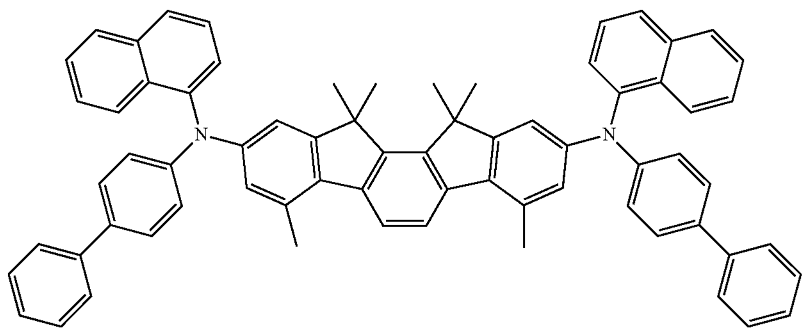
(217)
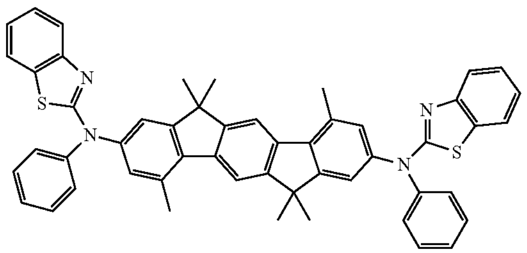
(218)
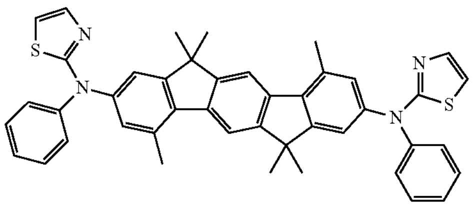
(219)
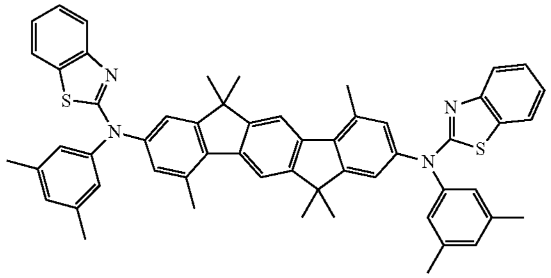
(220)
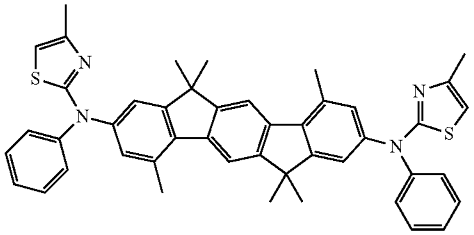
(221)
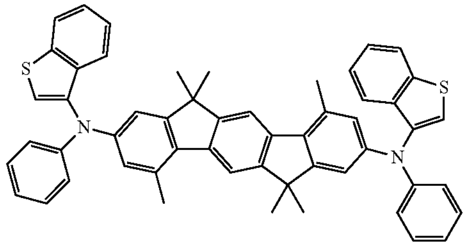
(222)
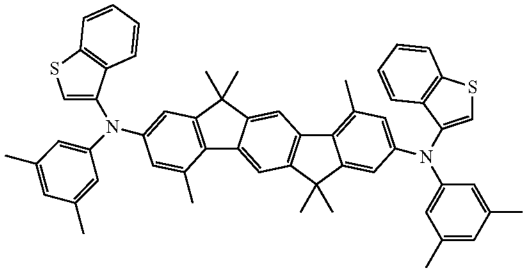
(223)
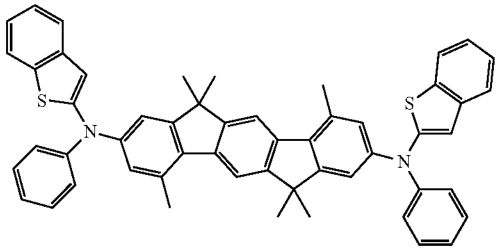
(224)
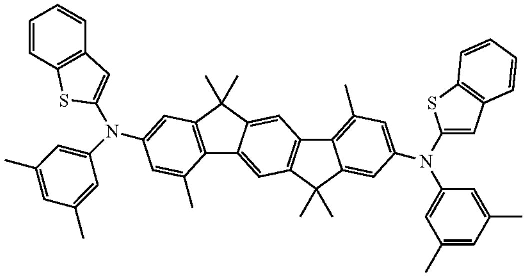

-continued
(225)
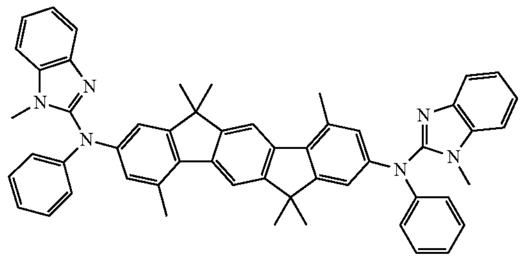
(226)
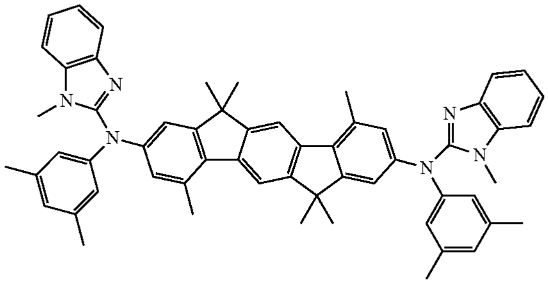
(227)
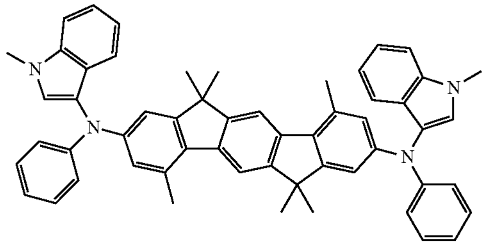
(228)
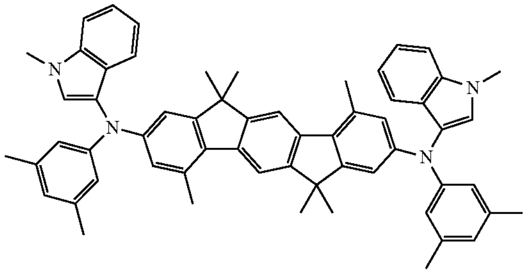
(229)
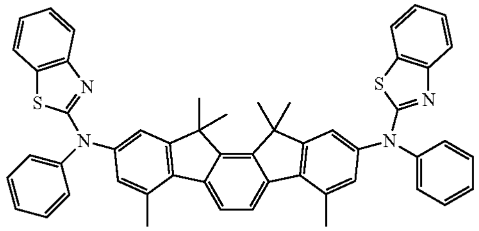
(230)
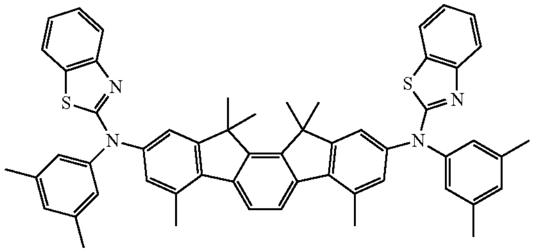
(231)
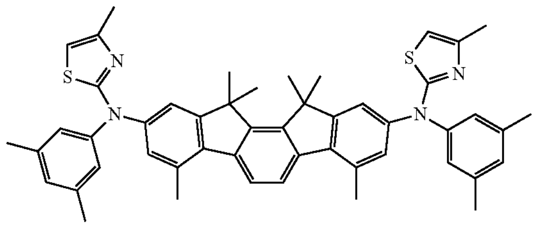
(232)
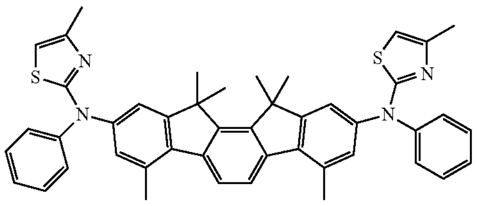
(233)
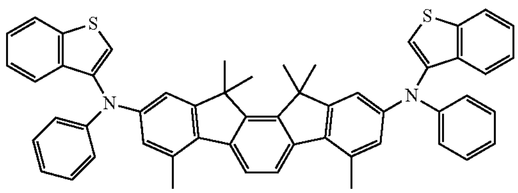
(234)
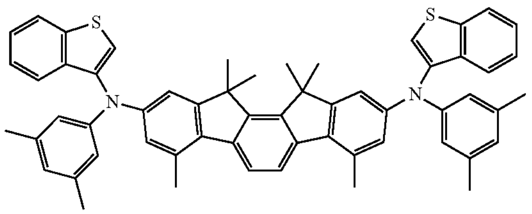
(235)
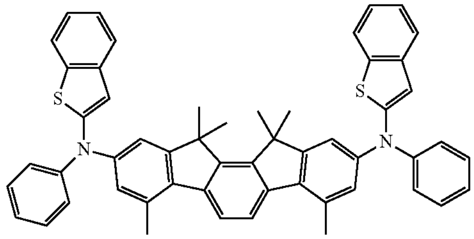
(236)
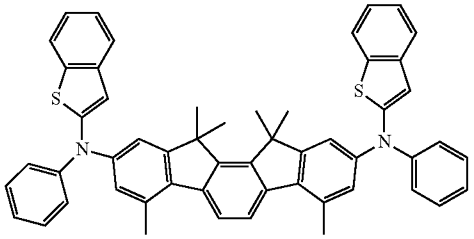

-continued
(237)
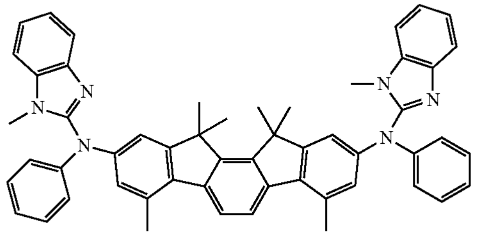
(238)
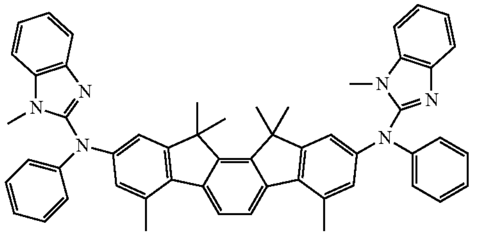
(239)
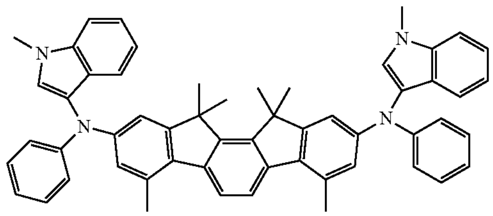
(240)
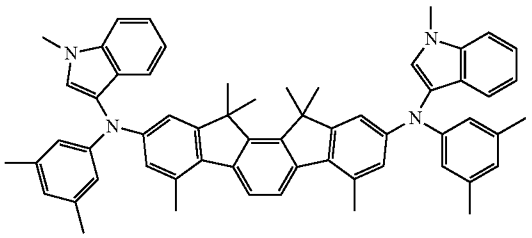
(241)
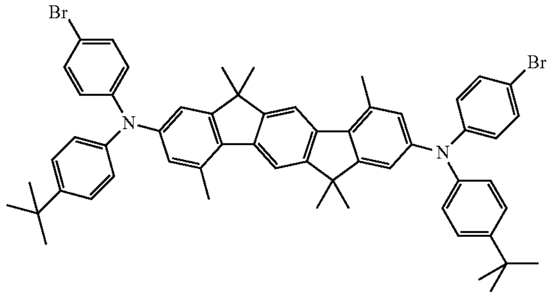
(242)
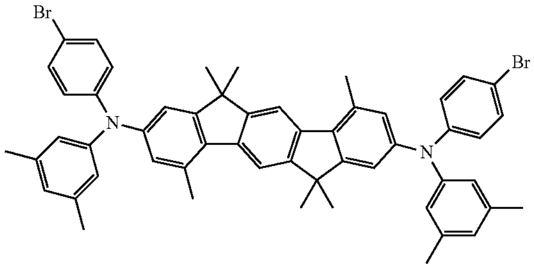
(243)
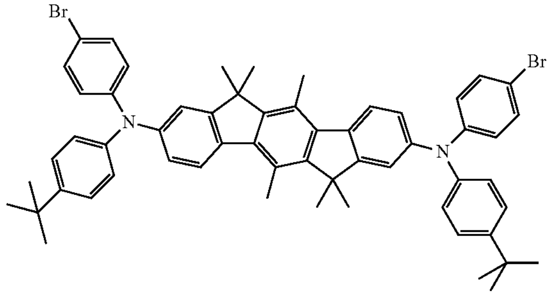
(244)
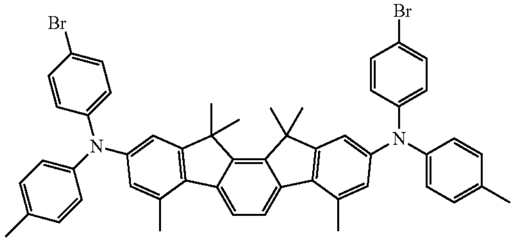
(245)
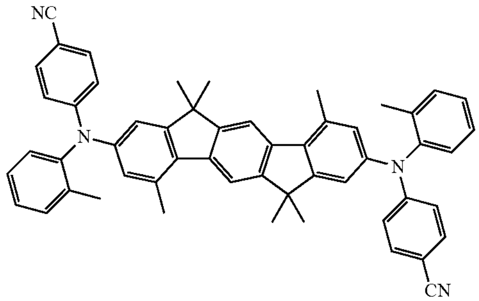
(246)
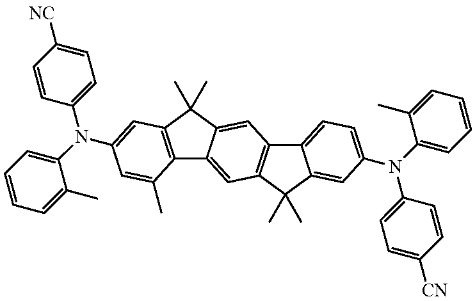

-continued
(247)
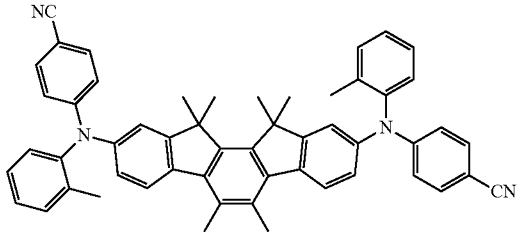
(248)
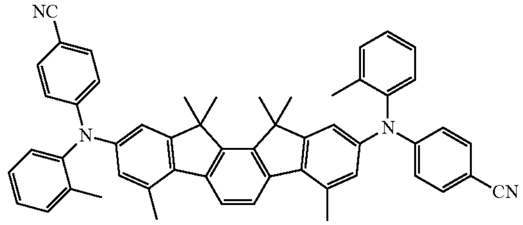
(249)
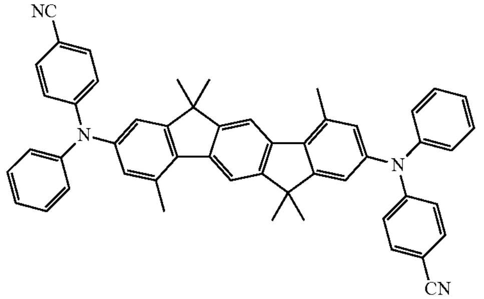
(250)
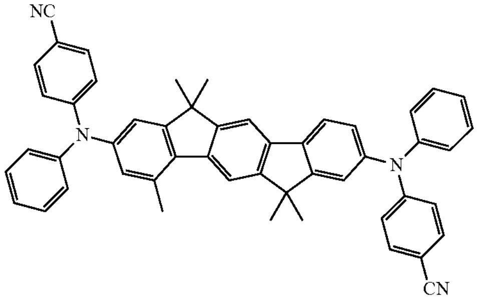
(251)
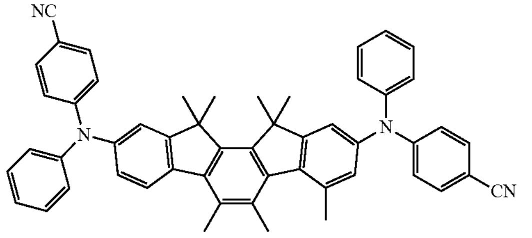
(252)
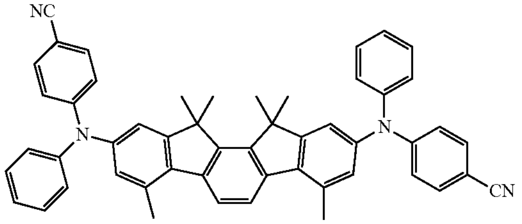
(253)
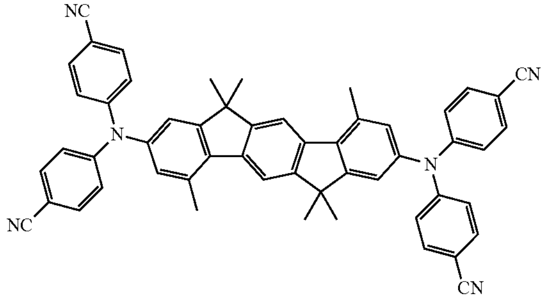
(254)
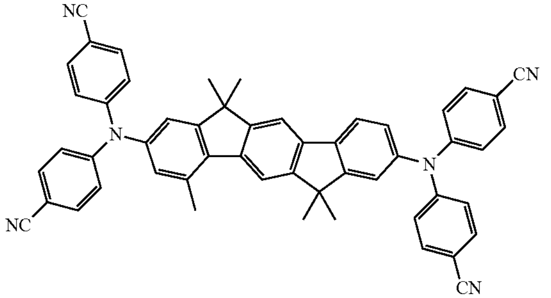
(255)
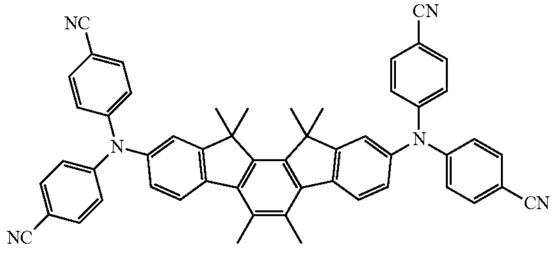
(256)
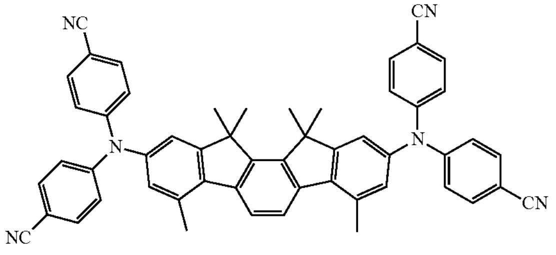

-continued
(257)
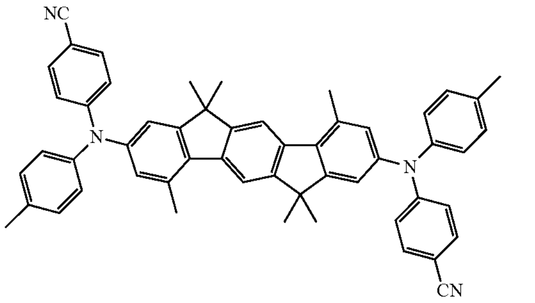
(258)
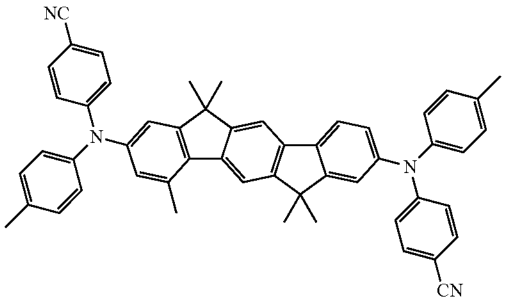
(259)
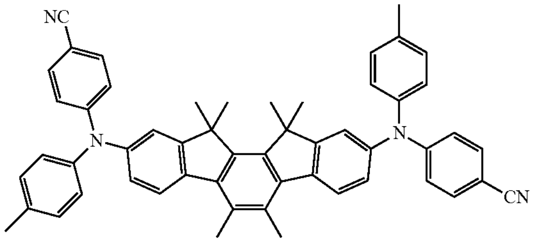
(260)
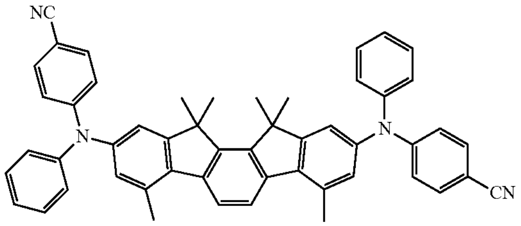
(261)
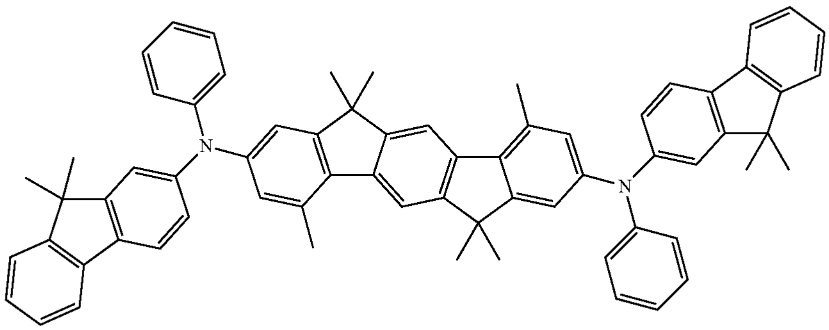
(262)
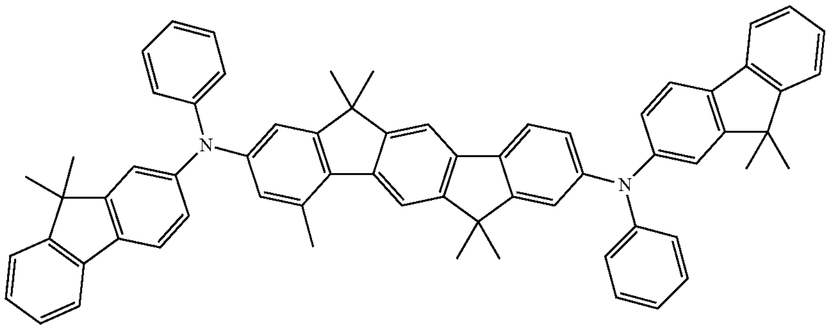
(263)
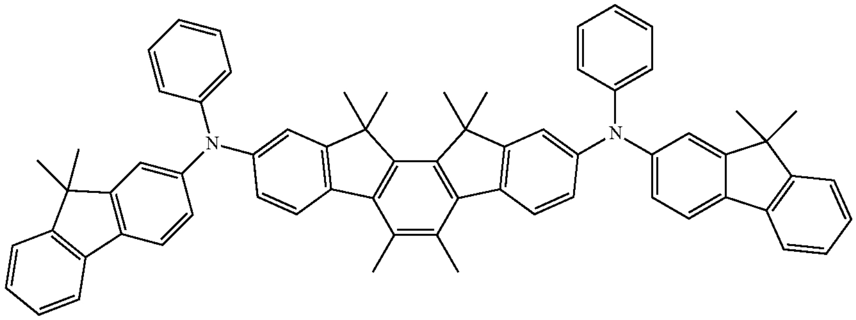

-continued
(264)
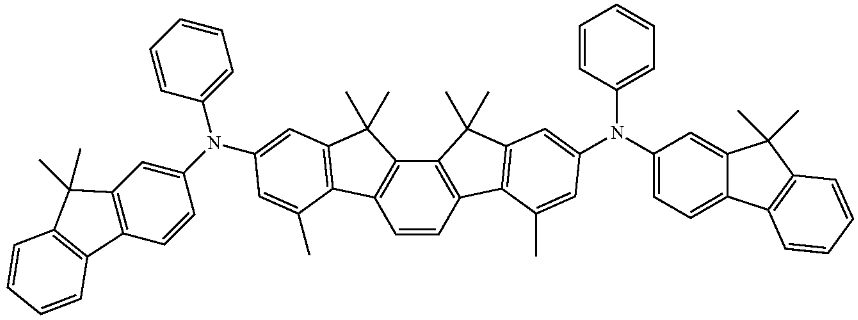
(265)
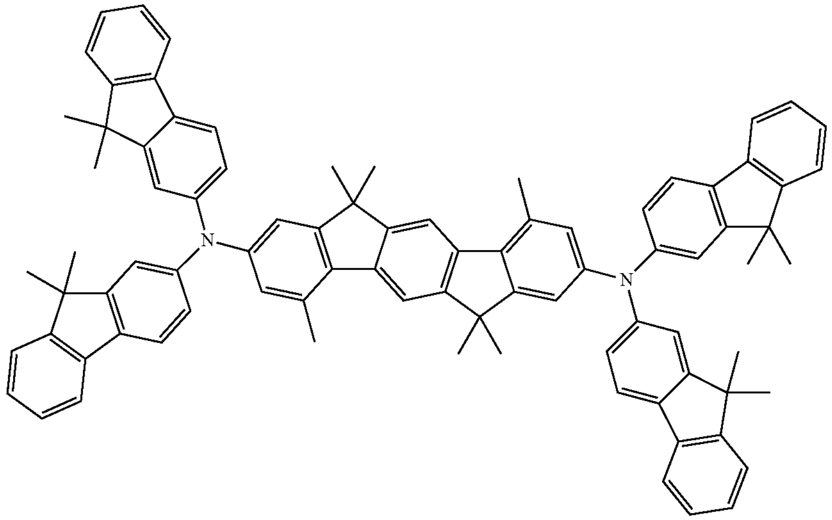
(266)
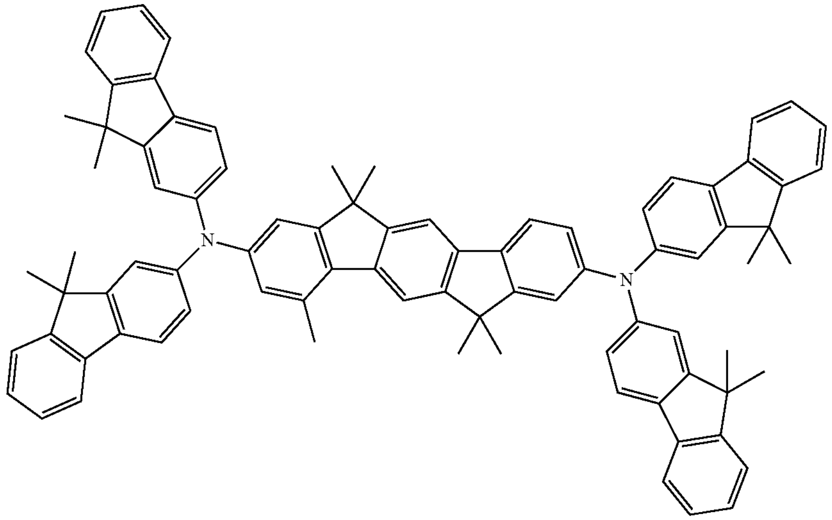

-continued
(267)
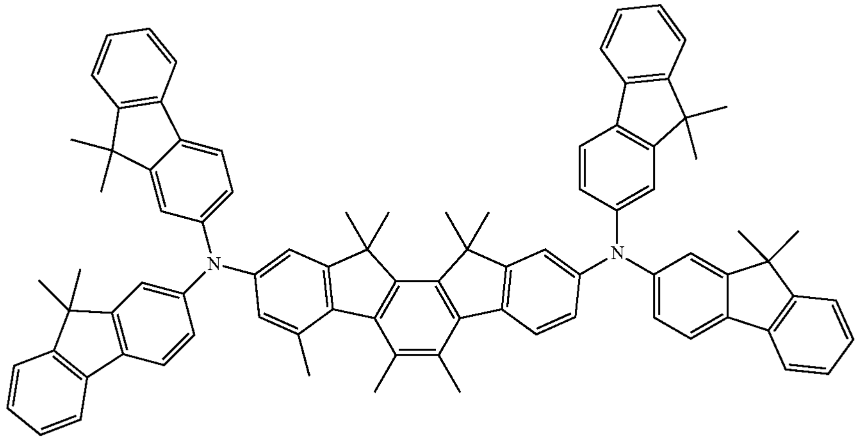
(268)
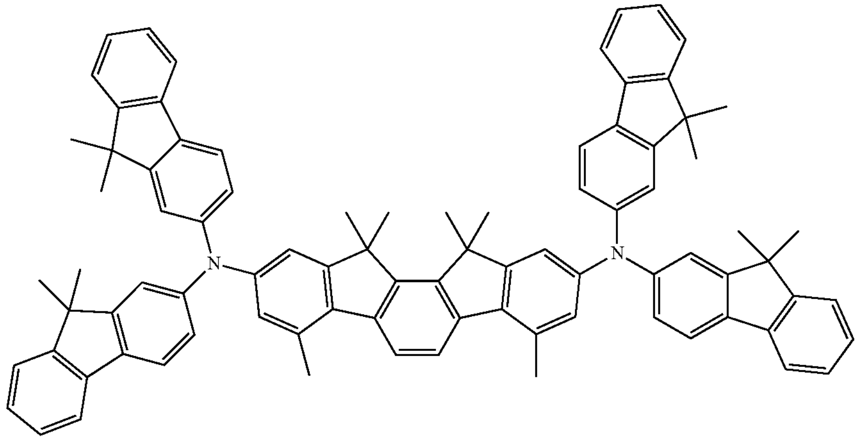
(269)
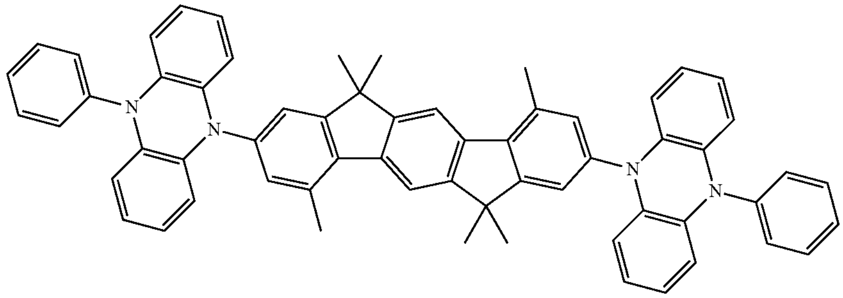
(270)
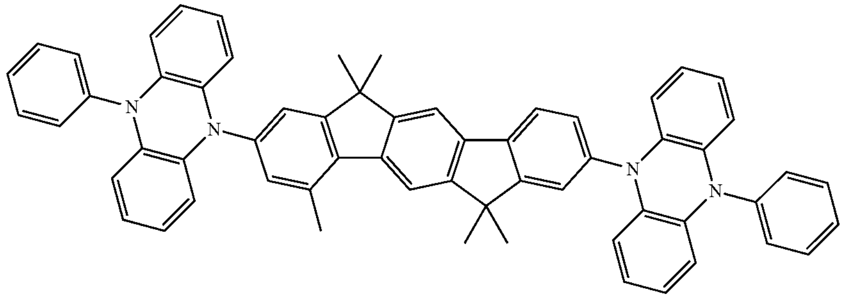

-continued
(271)
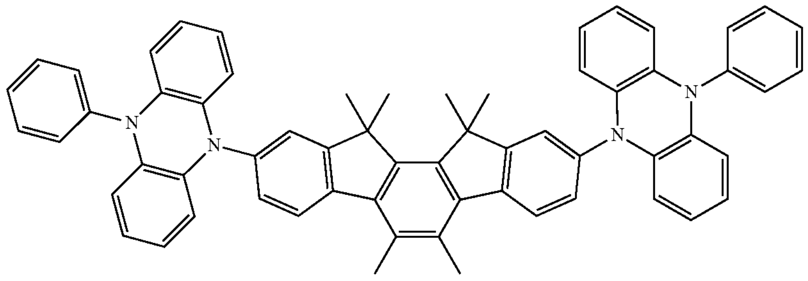
(272)
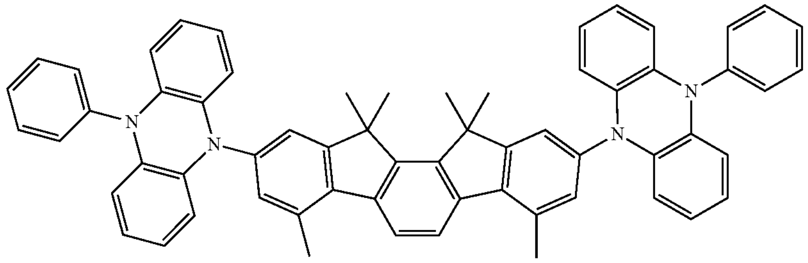
(273)
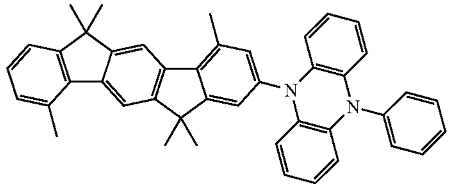
(274)
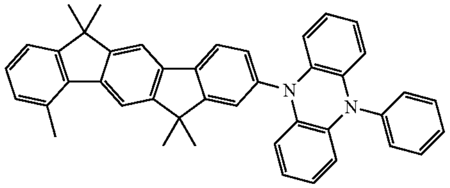
(275)
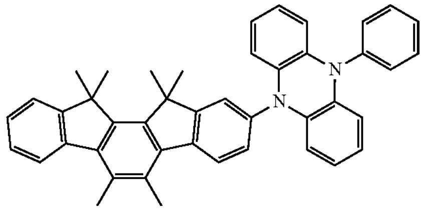
(276)
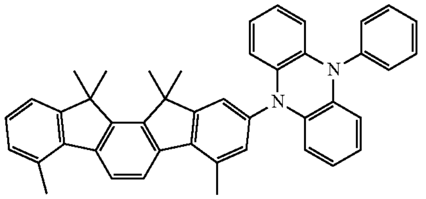
(277)
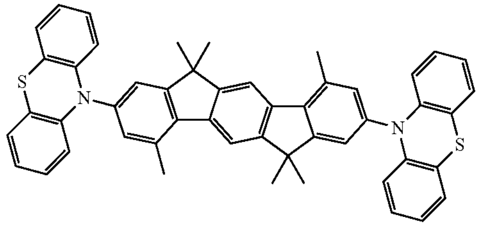
(278)
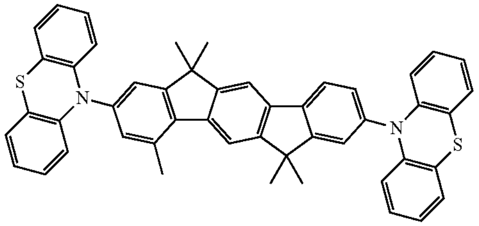
(279)
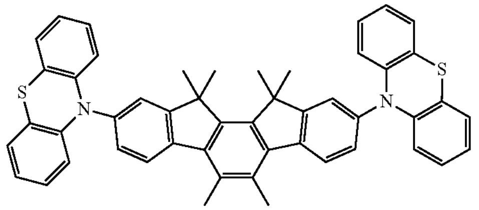
(280)
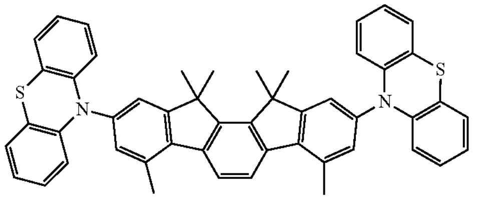

-continued
(281)
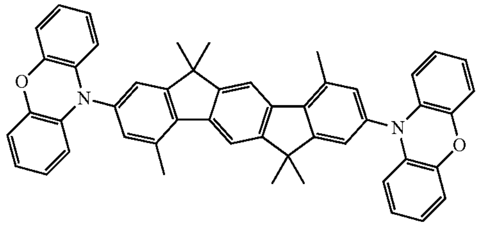
(282)
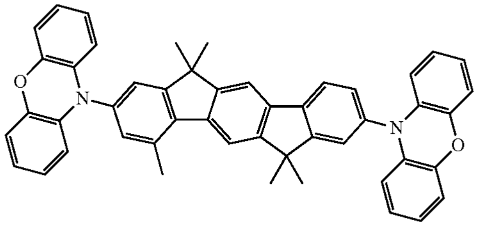
(283)
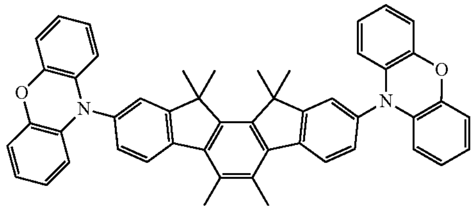
(284)
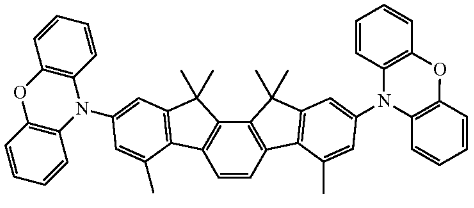
(285)
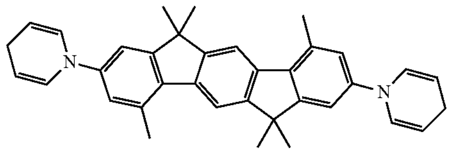
(286)
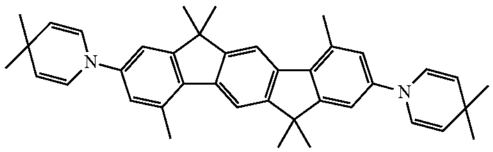
(287)
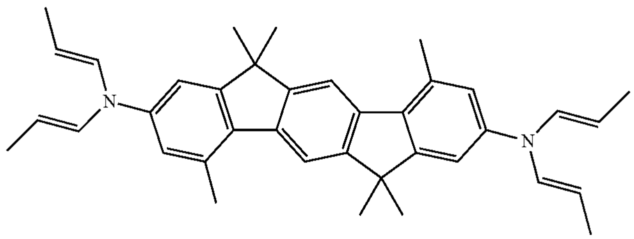
(288)
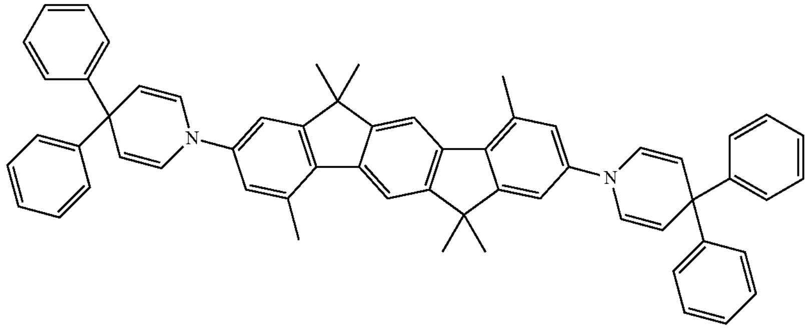
(289)
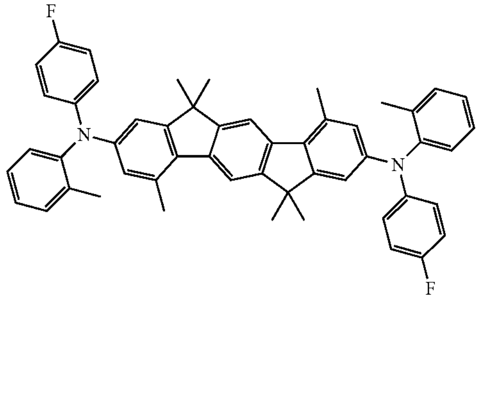
(290)
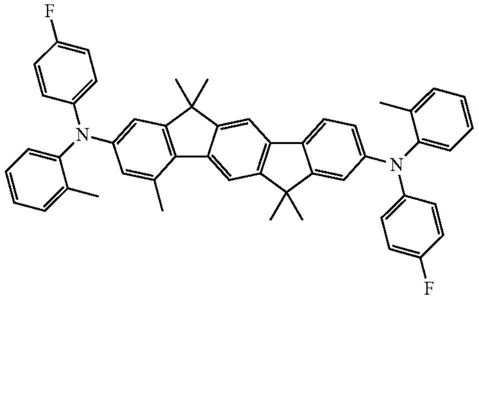

-continued
(291)
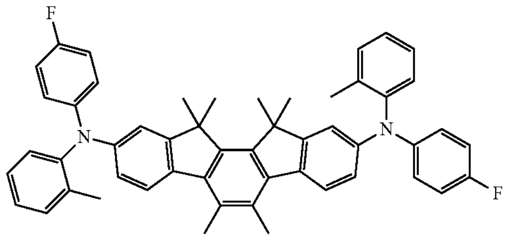
(292)
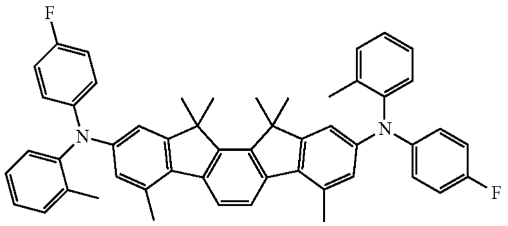
(293)
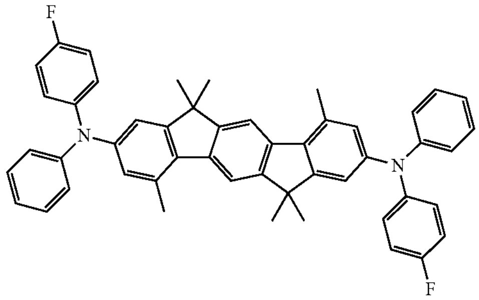
(294)
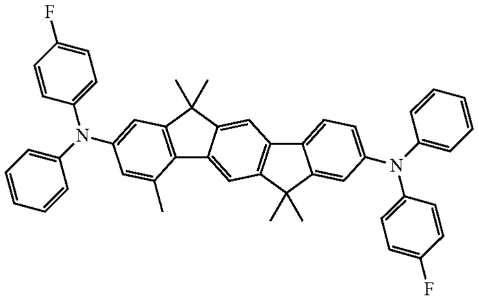
(295)
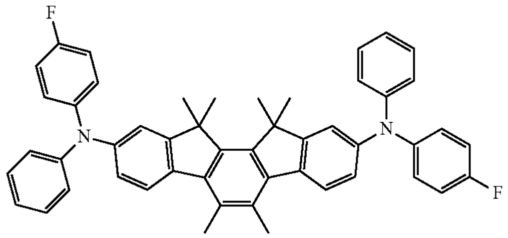
(296)
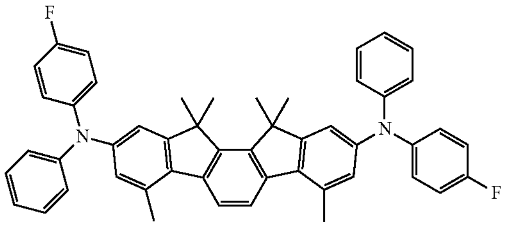
(297)
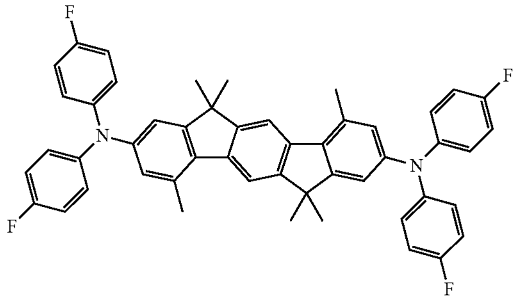
(298)
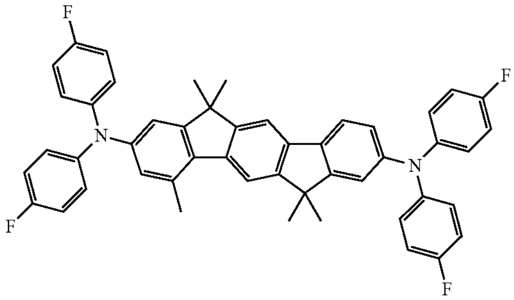
(299)
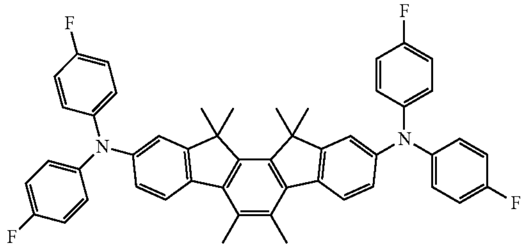
(300)
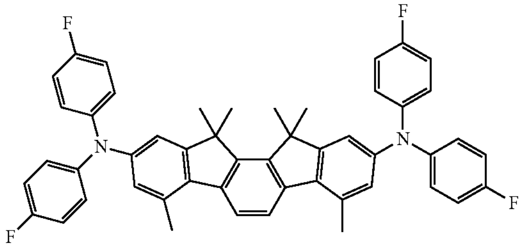

-continued
(301)
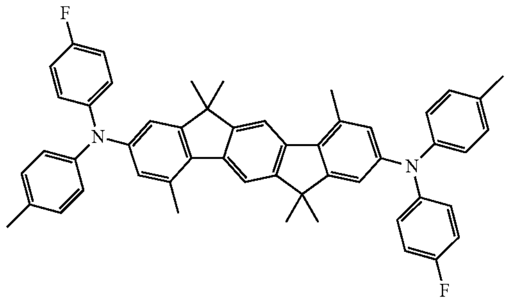
(302)
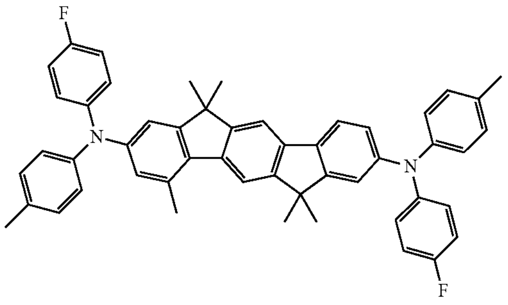
(303)
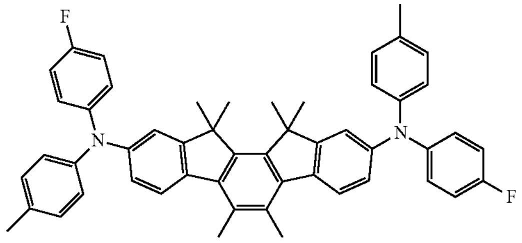
(304)
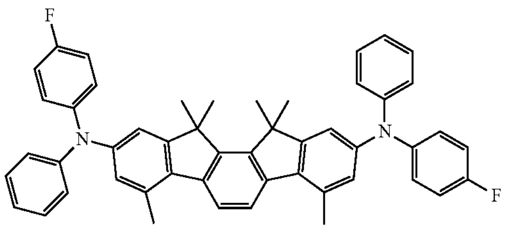
(305)
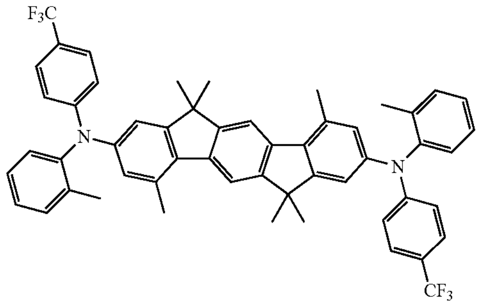
(306)
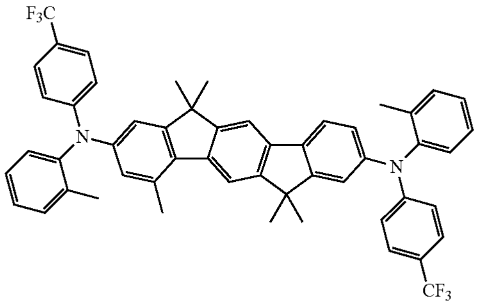
(307)
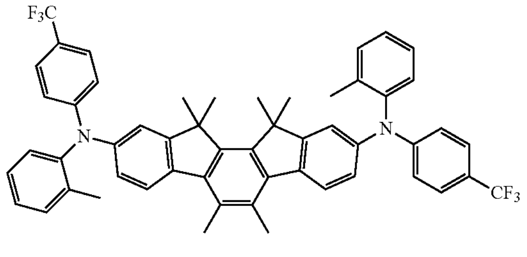
(308)
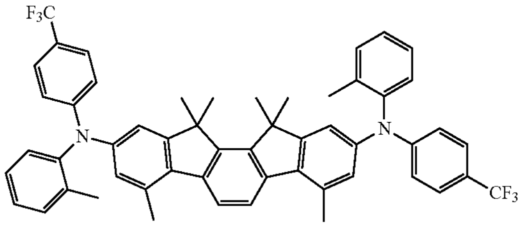
(309)
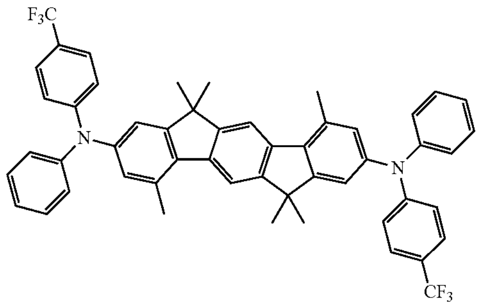
(310)
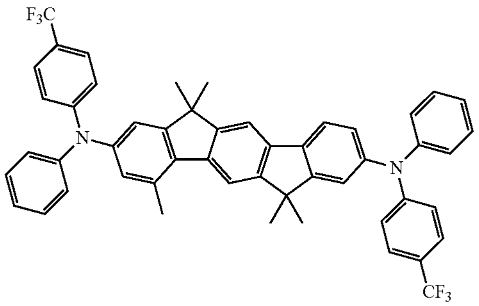

-continued (311)

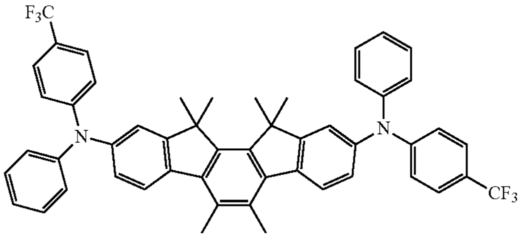

(312)

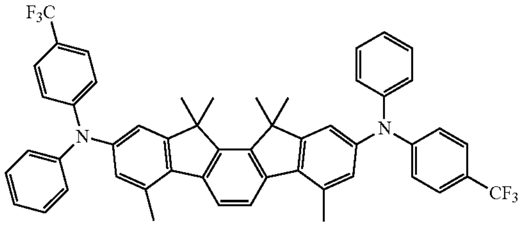

(313)

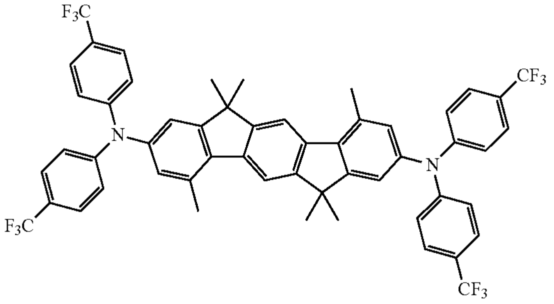

(314)

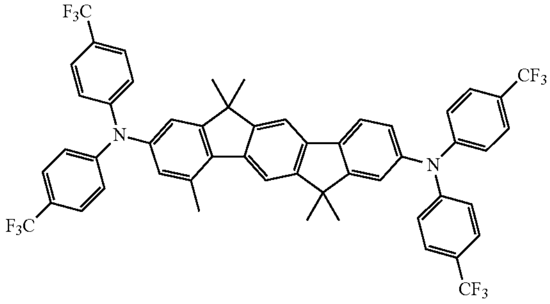

(315)

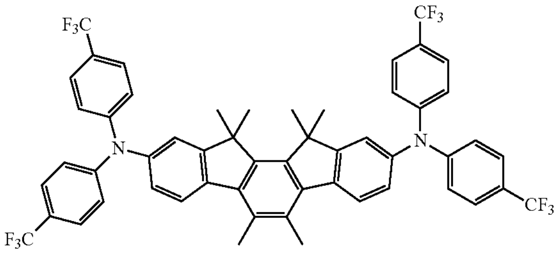

(316)

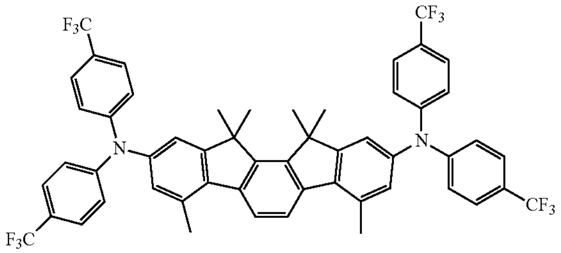

(317)

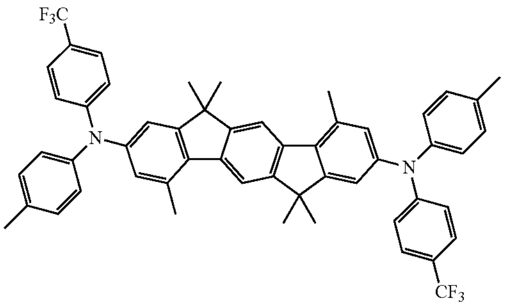

(318)

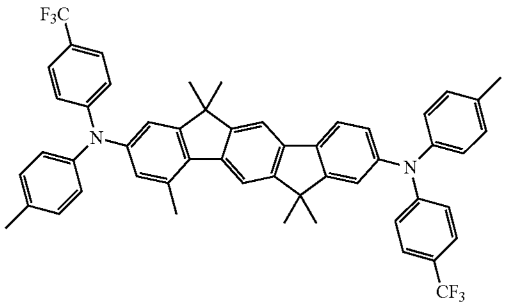

(319)

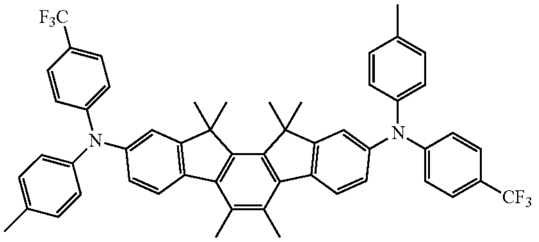

(320)

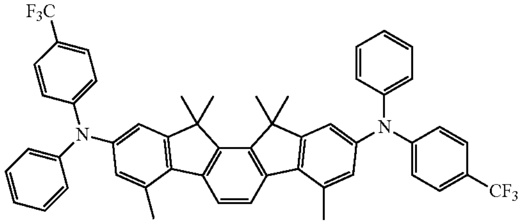

The compounds according to the invention can be prepared by synthetic steps known to the person skilled in the art, such as, for example, bromination, Suzuki coupling, Hartwig-Buchwald coupling, etc. Compounds of the formula (6a) can be prepared as shown in Synthesis Scheme 1. A correspondingly 2,3-substituted 1,4-benzenediboronic acid derivative is coupled to a 2-bromobenzoate with palladium catalysis. Other coupling reactions can likewise be used. After a cyclisation to give the indenofluorene, the latter can be brominated under standard conditions, as are known to the person skilled in the art of organic chemistry. The brominated compounds can be coupled to aromatic amines by a Buchwald coupling under standard conditions.

Synthesis Scheme 1:

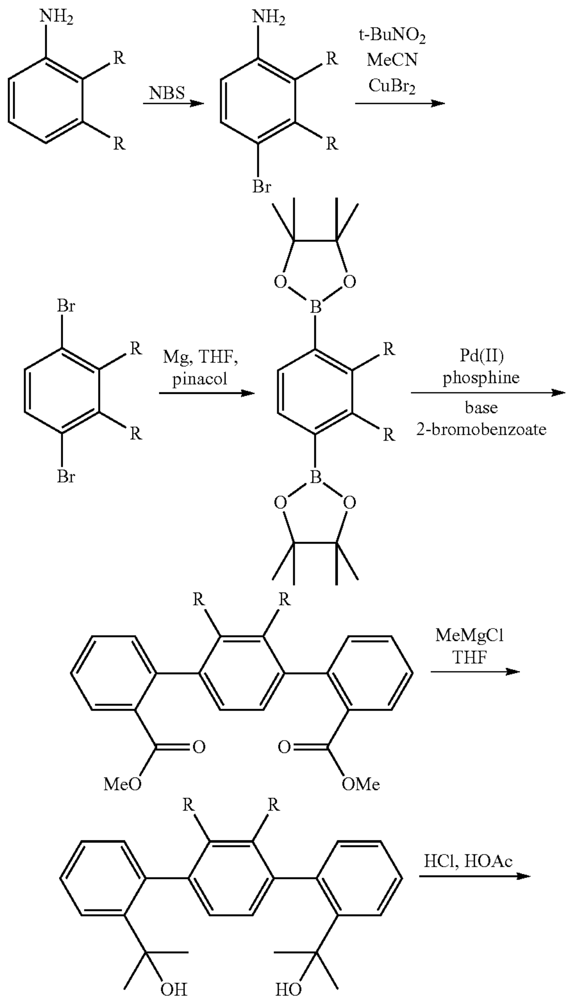

-continued

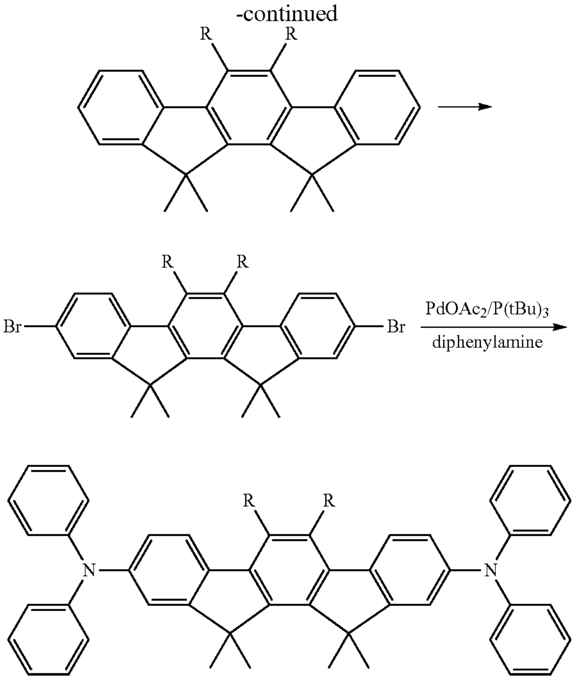

The synthesis of compounds of the formula (7a) is shown in Synthesis Scheme 2. The substituted cis-indenofluorene skeleton can be obtained by Diels-Alder reaction of a correspondingly substituted diphenylbutadiene derivative with an acetylenedicarboxylic acid derivative, followed by aromatisation, reduction of the ester groups and cyclisation to give the indenofluorene. The latter can, optionally after substitution of the indeno bridges, be brominated under standard conditions, as are known to the person skilled in the art of organic chemistry. The brominated compounds can be coupled to aromatic amines by a Buchwald coupling under standard conditions, as shown in Synthesis Scheme 3.

Synthesis Scheme 2:

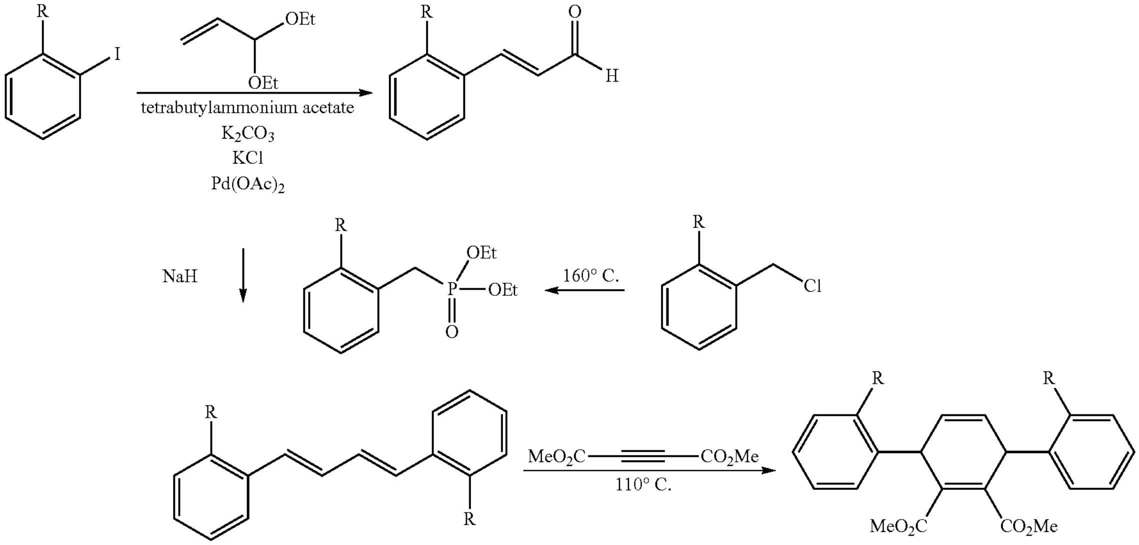

-continued

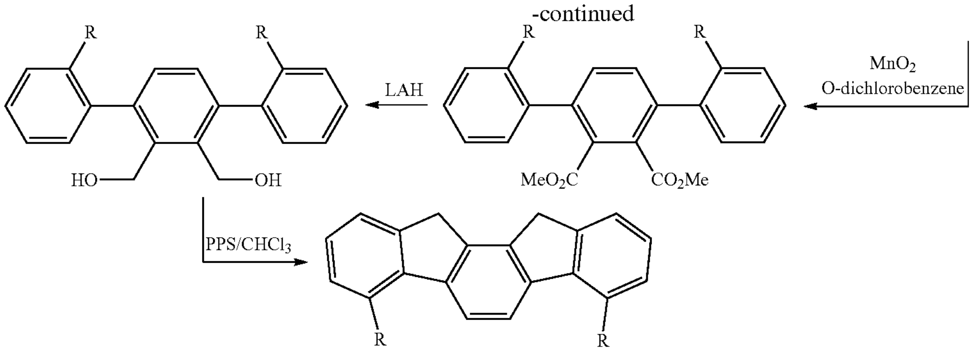

Synthesis Scheme 3:

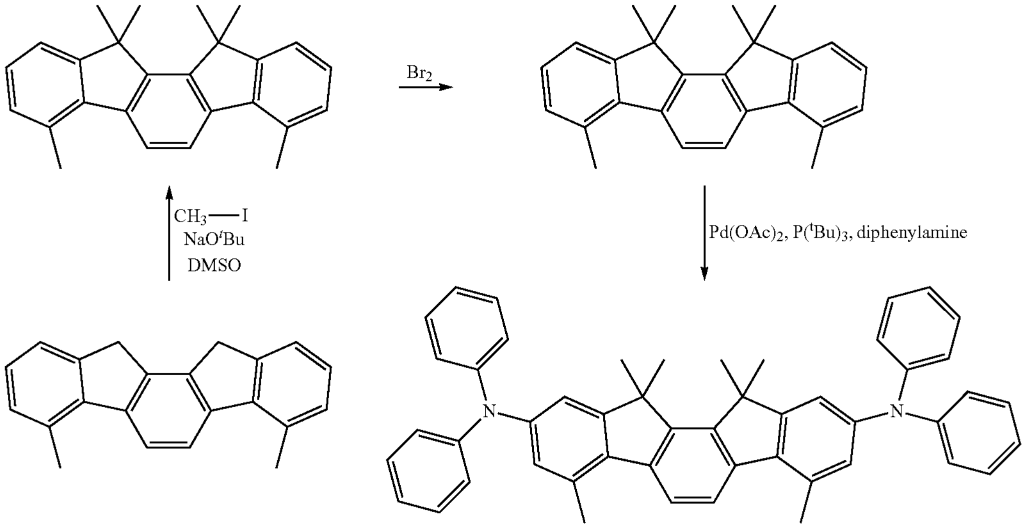

The brominated compounds are likewise suitable as intermediate for further derivatives according to the invention. Thus, the synthesis of corresponding phosphines can be carried out from the dibromoindenofluorene by lithiation and reaction with diarylchlorophosphines. Oxidation then gives the corresponding phosphine oxide. Other electrophiles, such as, for example, $AsCl_3$, aryl$PCl_2$, $SOCl_2$, $Ar_2S_2$, etc., can likewise be employed here. Further compounds according to the invention can easily be synthesised in accordance with these and similar synthesis schemes in the process known to the person skilled in the art of organic synthesis.

The present invention furthermore relates to a process for the preparation of the compounds according to the invention, comprising the reaction steps of:

a) synthesis of the indenofluorene skeleton or the corresponding heterocyclic derivative which carries hydrogen instead of the groups Y in these positions;
b) halogenation, giving an indenofluorene or a corresponding heterocyclic derivative which is substituted by halogen instead of the groups Y in these positions; and
c) reaction of the halogenated indenofluorene with a diarylamine or metallation and reaction with an electrophile.

The compounds of the formula (1) according to the invention are suitable for use in electronic devices, in particular in organic electroluminescent devices (OLEDs, PLEDs). Depending on the substitution, the compounds are employed in various functions and layers. The precise use of the compounds depends, in particular, on the choice of the groups Y, but also on the choice of the groups X.

The invention therefore furthermore relates to the use of the compounds of the formula (1) according to the invention in electronic devices, in particular in organic electroluminescent devices.

The invention still furthermore relates to organic electronic devices comprising at least one compound of the formula (1), in particular organic electroluminescent devices comprising anode, cathode and at least one emitting layer, characterised in that at least one organic layer, which may be an emitting layer or another layer, comprises at least one compound of the formula (1).

Apart from the cathode, anode and emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n transitions. However, it should be pointed out that each of these layers does not necessarily have to be present, and the choice of the layers always depends on the compounds used and in particular also on whether it is a fluorescent or phosphorescent electroluminescent device.

The organic electroluminescent device may also comprise a plurality of emitting layers, where at least one organic layer comprises at least one compound of the formula (1). These emission layers particularly preferably have in total a plurality of emission maxima between 380 nm and 750 nm, resulting overall in white emission, i.e. various emitting compounds which are able to fluoresce or phosphoresce and emit blue and yellow, orange or red light are used in the emitting layers. Particular preference is given to three-layer systems, i.e. systems having three emitting layers, where at least one of these layers comprises at least one compound of the formula (1) and where the three layers exhibit blue, green and orange or red emission (for the basic structure, see, for example, WO 05/011013). Emitters which have broad-band emission bands and thus exhibit white emission are likewise suitable for white emission.

It is particularly preferred for the compounds of the formula (1) to be employed as hole-transport material and/or as hole-injection material and/or as electron-blocking material. This applies, in particular, if the symbols Y and/or the symbols X stand for nitrogen. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which is between the hole-injection layer and the emission layer. If the compounds of the formula (1) are used as hole-transport or hole-injection material, it may be preferred for them to be doped with electron-acceptor compounds, for example with $F_4$-TCNQ or with compounds as described in EP 1476881 or EP 1596445. If the compound of the formula (1) is employed as hole-transport material in a hole-transport layer, a proportion of 100%, i.e. the use of this compound as pure material, may also be preferred.

It is furthermore preferred to employ the compounds of the formula (1) as electron-transport material and/or as hole-blocking material for fluorescent or phosphorescent OLEDs and/or as triplet matrix material for phosphorescent OLEDs. This applies, in particular, to compounds in which the groups Y stand for C═O, P═O or S═O.

Preference is furthermore given to an organic electroluminescent device, characterised in that one or more layers are coated by a sublimation process. In this, the materials are vapour-deposited in vacuum sublimation units at an initial pressure of usually below $10^{-5}$ mbar, preferably below $10^{-6}$ mbar. However, it is also possible for the initial pressure to be even lower, for example below $10^{-7}$ mbar.

Preference is likewise given to an organic electroluminescent device, characterised in that one or more layers are coated by the OVPD (organic vapour phase deposition) process or with the aid of carrier-gas sublimation. Here, the materials are applied at a pressure between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light-induced thermal imaging, thermal transfer printing) or ink-jet printing. Soluble compounds of the formula (1) are necessary for this purpose. High solubility can be achieved by suitable substitution of the compounds.

On use in organic electroluminescent devices, the compounds according to the invention have the following surprising advantages over the prior art:

1. On use of the compounds according to the invention as hole-transport material in a hole-transport and/or hole-injection layer, lower use voltages are required compared with compounds in accordance with the prior art which do not contain any substituents R in one of the positions as on the compounds according to the invention or which do not contain nitrogen in the indenofluorene skeleton.
2. On use of the compounds according to the invention as hole-transport material in a hole-transport and/or hole-injection layer, the operating voltage of the organic electroluminescent device is furthermore considerably lower than on use of compounds in accordance with the prior art. The use of the compounds according to the invention therefore results in significantly higher power efficiency of the OLED.
3. A further advantage on use of the compounds according to the invention as hole-transport material in a hole-transport and/or hole-injection layer is the reduced voltage difference between thin (for example 20 nm) and thick (for example 110 nm) hole-transport layers. This enables thicker hole-transport layers to be used with the compounds according to the invention without a significant loss in power efficiency. This is important since the optical coupling-out efficiency is controlled in a crucial manner by variation of the layer thickness of the hole-transport layer. Even improvements in the region of 0.1 V are regarded as a significant advance here.
4. The efficiency, lifetime and colour coordinates of corresponding devices are comparable with systems in accordance with the prior art.
5. The processability of the compounds according to the invention is clearly better compared with materials in accordance with the prior art which have a similar structure, but do not contain any substituents R other than hydrogen or deuterium. Thus, the compounds according to the invention do not exhibit crystallisation at the edge of the vapour-deposition source and thus clogging of the vapour-deposition source. The compounds according to the invention are therefore more suitable for mass production than materials in accordance with the prior art.

The present application text and also the examples following below are directed to the use of the compounds according to the invention in relation to OLEDs and the corresponding displays and illumination elements. In spite of this restriction of the description, it is possible for the person skilled in the art, without further inventive step, also to employ the compounds according to the invention for further uses in other electronic devices, for example for organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors or organic laser diodes (O-lasers), to mention but a few applications.

The present invention likewise relates to the use of the compounds according to the invention in the corresponding devices and to these devices themselves.

The invention is explained in greater detail by the following examples without thereby wishing to restrict it.

EXAMPLES

The following syntheses are carried out, unless indicated otherwise, in dried solvents under a protective-gas atmosphere. The starting materials can be purchased from ALDRICH.

Example 1

4,6,6,10,12,12-Hexamethyl-N,N,N',N'-tetraphenyl-6H,12H-indeno[1,2-b]fluorene-2,8-diamine)

a) Diethyl 2,2"-dimethyl[1,1';4',1"]terphenyl-2',5'-dicarboxylate

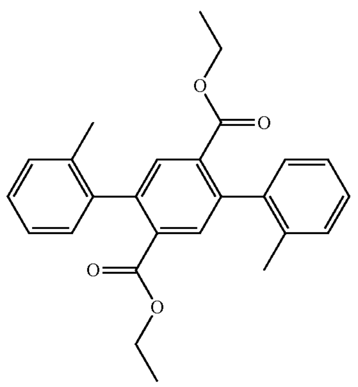 [SMILES: CCOC(=O)c1cc(-c2ccccc2C)c(C(=O)OCC)cc1-c1ccccc1C]

60 g (160 mmol) of diethyl dibromoterephthalate, 43 g (320 mmol) of o-tolylboronic acid, 365 mg (0.32 mmol) of $Pd(PPh_3)_4$ and 92 g (660 mmol) of $K_2CO_3$ are heated at the boil for 4 h in 300 ml of toluene and 300 ml of water. The mixture is subsequently partitioned between toluene and water, and the organic phase is washed three times with water and dried over $Na_2SO_4$. The residue remaining is recrystallised twice from heptane to give colourless crystals. The yield is 51 g (127 mmol, 81%).

b) 2-[5'-(1-Hydroxy-1-methylethyl)-2,2"-dimethyl[1,1';4',1"]terphenyl-2'-yl]propan-2-ol

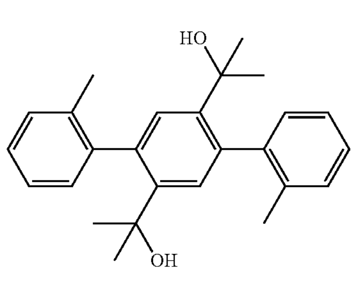 [SMILES: Cc1ccccc1-c1cc(C(C)(C)O)c(-c2ccccc2C)cc1C(C)(C)O]

39 g (97 mmol) of the diester are initially introduced in 500 ml of dried THF, 195 ml (580 mmol) of a 3 M methylmagnesium chloride solution in THF are added to the suspension at 5° C., and the mixture is stirred at 5° C. for 6 h. After this time, 200 ml of a saturated $NH_4Cl$ solution are added, the reaction mixture is partitioned between water and toluene, the aqueous phase is extracted three times with toluene, and the combined organic phases are dried over $Na_2SO_4$. Removal of the solvent in vacuo leaves 36 g (96 mmol, 99%) of a colourless solid which is homogeneous according to TLC and $^1H$-NMR and can be employed in the subsequent reaction without further purification.

c) 4,6,6,10,12,12-Hexamethyl-6,12-dihydroindeno[1,2-b]fluorene

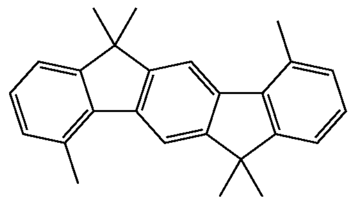 [SMILES: Cc1cccc2c1-c1cc3c(cc1C2(C)C)-c1c(C)cccc1C3(C)C]

33.7 g (90 mmol) of the diol are dissolved in 300 ml of dichloromethane, the solution is cooled to 5° C., and a mixture of 80 g of polyphosphoric acid in 55 ml of methanesulfonic acid is added. After 30 min at 5° C., 300 ml of EtOH are added, and the mixture is heated at the boil for 1 h. The colourless precipitate is filtered off, washed twice with EtOH and heptane and recrystallised once from chlorobenzene, giving the dimethylindenofluorene as a colourless solid (28.5 g, 84 mmol, 93%), which, according to RP-HPLC, has a purity of >99.8%.

d) 2,8-Dibromo-4,6,6,10,12,12-hexamethyl-6,12-dihydroindeno[1,2-b]-fluorene

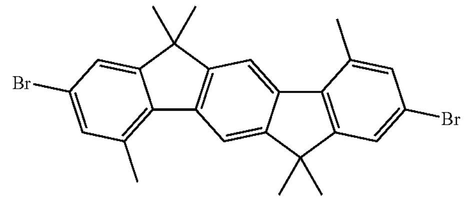 [SMILES: Cc1cc(Br)cc2c1-c1cc3c(cc1C2(C)C)-c1c(C)cc(Br)cc1C3(C)C]

33.8 g (100 mmol) of dimethylindenofluorene are dissolved in 1250 ml of dichloromethane, and the solution is cooled to 0° C. and mixed with a solution of 33 g (266 mmol) of $Na_2CO_3$ in 825 ml of water. After addition of 11.3 ml of bromine (220 mmol), the suspension is stirred at 5° C. for 6 h, and the colourless solid is filtered off, washed with water, EtOH and heptane and dried, leaving 38.3 g (77 mmol, 77%), purity >99.5% ($^1H$-NMR).

e) 4,6,6,10,12,12-Hexamethyl-N,N,N',N'-tetraphenyl-6H,12H-indeno-[1,2-b]fluorene-2,8-diamine

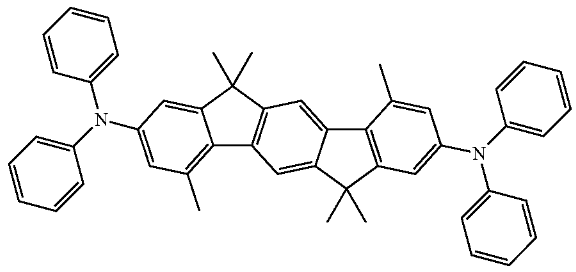 [SMILES: Cc1cc(N(c2ccccc2)c2ccccc2)cc2c1-c1cc3c(cc1C2(C)C)-c1c(C)cc(N(c2ccccc2)c2ccccc2)cc1C3(C)C]

38 g (77 mmol) of the dibromide are dissolved in 1400 ml of dry toluene, 31.1 g (183 mmol) of diphenylamine are added, and the mixture is saturated with Ar for 30 min. 23.5 g (245 mmol) of $NaO^tBu$, 3.9 ml (3.9 mmol) of a 1 M solution of tri-tert-butylphosphine in toluene, and 515 mg of $Pd(OAc)_2$ are subsequently added. The mixture is heated at the boil for 4 h, 500 ml of water, 50 ml of conc. HCl and 500 ml of EtOH are added to the suspension, and the precipitate is filtered off with suction, washed twice with water and MeOH and dried. The colourless solid is dissolved in boiling dichlorobenzene, filtered through a layer of silica gel and washed with boiling dichlorobenzene, and the solid precipitated in the filtrate is filtered off with suction and recrystallised three times from NMP. Sublimation twice in vacuo (360° C., $1\times10^{-5}$ mbar) gives the diamine (40.2 g, 60 mmol, 78%) in the form of a pale-yellow powder which has a purity, determined by RP-HPLC, of >99.9%.

Example 2

5,6,11,11,12,12-Hexamethyl-N,N,N',N'-tetraphenyl-11H,12H-indeno[2,1-a]fluorene-2,9-diamine a) 1,4-Dibromo-2,3-dimethylbenzene

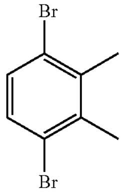

The compound is prepared in accordance with Cachia, Wahl, *Bull. Soc. Chim. Fr.* 1958, 1418-1420.

b) Pinacolyl 2,3-dimethylbenzene-1,4-bisboronate

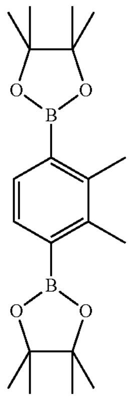

100 g (380 mmol) of 1,4-dibromo-2,3-dimethylbenzene are dissolved in 1500 ml of dry diethyl ether, 420 ml (840 mmol) of a 2 M solution of n-butyllithium in cyclohexane are added dropwise at −70° C., after 1 h 130 ml of trimethyl borate (1140 mmol) are added dropwise, the mixture is allowed to come to RT over the course of 1 h, the solvent is removed, 90 g (76 mmol) of pinacol and 1000 ml of toluene are added, the mixture is heated at the boil for 2 h, the solvent is removed again, and the residue, which is homogeneous according to $^1H$-NMR, is employed in the subsequent reaction without further purification.

c) Dimethyl 2',3'-dimethyl[1,1';4',1"]terphenyl-2,2"-dicarboxylate

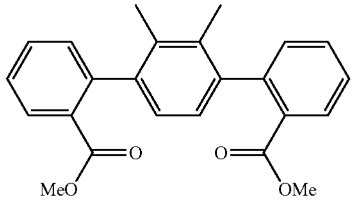 [SMILES: COC(=O)c1ccccc1-c1ccc(-c2ccccc2C(=O)OC)c(C)c1C]

57 g (160 mmol) of pinacolyl 2,3-dimethylbenzene-1,4-bisboronate are heated at the boil for 4 h in a mixture of 1150 ml of EtOH, 1150 ml of toluene, 600 ml of a 2 M $Na_2CO_3$ solution, 45 ml (320 mmol) of methyl 2-bromobenzoate and 7.5 g (7 mmol) of $Pd(PPh_3)_4$. The batch is subsequently poured into a mixture of ice-water/MeOH/HCl 1:1:1, and the colourless precipitate is filtered off with suction, washed with water and EtOH and dried. The solid is dissolved in boiling toluene, the solution is filtered through a layer of silica gel, heptane is added to the filtrate, and the precipitated product is filtered off with suction, giving 55.4 g (148 mmol, 92%) of the diester as a colourless powder.

d) 2-[2"-(1-Hydroxy-1-methylethyl)-2',3'-dimethyl [1,1;4',1"]terphenyl-2-yl]propan-2-ol

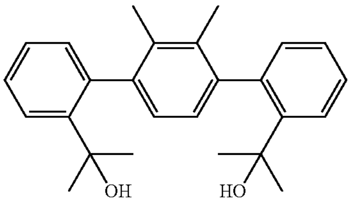 [SMILES: Cc1c(-c2ccccc2C(C)(C)O)ccc(-c2ccccc2C(C)(C)O)c1C]

55.4 g (148 mmol) of the diester are dissolved in 850 ml of THF, 300 ml (600 mmol) of a 2 M solution of methyllithium in diethyl ether are added at −75° C., and the mixture is stirred at −75° C. for 3 h. After warming to RT, the mixture is hydrolysed using $NH_4Cl$ solution, extracted with ethyl acetate, dried and freed from solvent in vacuo. The colourless solid remaining is recrystallised twice from toluene/EtOH, leaving 42.7 g (114 mmol, 77%) of the diol in the form of colourless crystals.

e) 5,6,11,11,12,12-Hexamethyl-11,12-dihydroindeno [2,1-a]fluorene

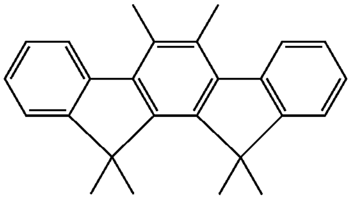 [SMILES: Cc1c(C)c2c(c3c1-c1ccccc1C3(C)C)C(C)(C)c1ccccc1-2]

41.2 g (110 mmol) of the diol are suspended in 500 ml of acetic acid, 1 ml of conc. HCl is added, and the mixture is heated at the boil for 4 h with vigorous stirring. After cooling to RT, the pale-yellow precipitate is filtered off with suction, washed with water, MeOH and heptane and recrystallised from chlorobenzene, giving 33.9 g (100 mmol, 91%) of cis-indenofluorene having a purity of >99% (RP-HPLC).

f) 2,9-Dibromo-5,6,11,11,12,12-hexamethyl-11,12-dihydroindeno-[2,1-a]fluorene

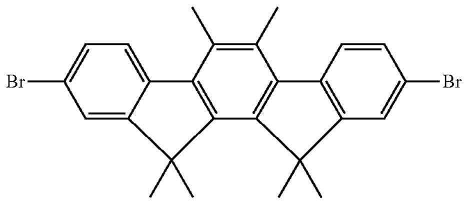 [SMILES: Cc1c(C)c2c(c3c1-c1ccc(Br)cc1C3(C)C)C(C)(C)c1cc(Br)ccc1-2]

26.9 g (79.4 mmol) of dimethyl-cis-indenofluorene are dissolved in 870 ml of dichloromethane, a solution of 23.6 g (190 mmol) of $Na_2CO_3$ hydrate in 580 ml of water is added, and 9 ml (176 mmol) of bromine in 40 ml of dichloromethane are added dropwise at 5° C. over the course of 15 min. The suspension is stirred at 5° C. for 6 h, and the colourless solid is filtered off, washed with water and MeOH and dried, giving 37.8 g (76.2 mmol, 96%) of the dibromide as a colourless powder having a purity, determined by $^1$H-NMR, of >99%.

g) 5,6,11,11,12,12-Hexamethyl-N,N,N',N'-tetraphenyl-11H,12H-indeno-[2,1-a]fluorene-2,9-diamine

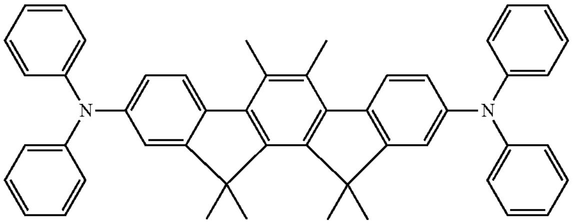 [SMILES: Cc1c(C)c2c(c3c1-c1ccc(N(c4ccccc4)c4ccccc4)cc1C3(C)C)C(C)(C)c1cc(N(c3ccccc3)c3ccccc3)ccc1-2]

28.5 g (57.4 mmol) of cis-indenofluorene dibromide are dissolved in 1000 ml of dry toluene, the solution is carefully saturated with Ar, and 23.3 g (137.83 mmol) of diphenylamine are added. After addition of 17.7 g of sodium tert-butoxide, 3 ml of a 1 M solution of tri-tert-butylphosphine in toluene and 385 mg of $Pd(OAc)_2$, the mixture is heated at the boil for 3 h, then cooled, 100 ml of water, 50 ml of conc. HCl and 500 ml of EtOH are added, the precipitate is filtered off with suction and dissolved in toluene, and the solution is filtered through silica gel and evaporated in vacuo. After recrystallisation six times from chlorobenzene, the colourless solid is sublimed in vacuo ($p=1\times10^{-5}$ mbar, T=375° C.). The colourless product obtained as a glass-like material (26.2 g, 68%) has a purity of >99.9%, determined by RP-HPLC.

Example 3

4,7,11,11,12,12-Hexamethyl-N,N,N',N'-tetraphenyl-11H,12H-indeno[2,1-a]fluorene-2,9-diamine

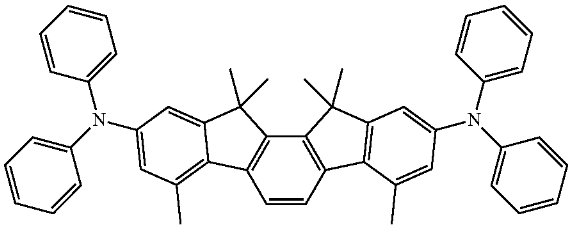 [SMILES: Cc1cc(N(c2ccccc2)c2ccccc2)cc2c1-c1ccc3c(c1C2(C)C)C(C)(C)c1cc(N(c2ccccc2)c2ccccc2)cc(C)c1-3]

a) O-methylcinnamaldehyde

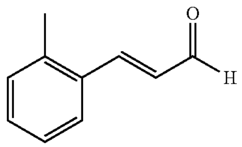

The compound can be synthesised in accordance with Battistuzzi et al., *Organic Letters* 2003, 5(5), 777-780.

b) Diethyl 2-methylbenzylphosphonate

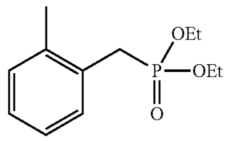 [SMILES: CCOP(=O)(Cc1ccccc1C)OCC]

The compound can be synthesised in accordance with de Meijere et al., *Eur. J. Org. Chem.* 1998, 2289-2299.

c) 2,2'-Dimethyl-trans-stilbene

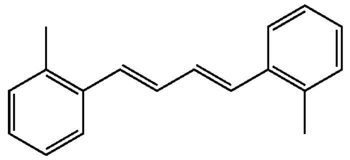 [SMILES: Cc1ccccc1/C=C/C=C/c1ccccc1C]

The compound can be synthesised in accordance with de Meijere et al., *Eur. J. Org. Chem.* 1998, 2289-2299.

5.99 g (149.9 mmol, 60% suspension in paraffin oil) of NaH are suspended in 250 ml of THF under an argon atmosphere. The mixture is cooled to 0° C., and 37.28 g (153.9 mmol) of diethyl 2-methylbenzylphosphonate in 20 ml of THF are added over the course of 15 min. 19.74 g (135.0 mmol) of o-cinnamaldehyde, dissolved in 20 ml of THF, are subsequently added. The reaction is subsequently stirred for several days at RT, giving 24.0 g (77%) of the product as a white solid.

d) 1,2-Dicarboxymethyl-3,6-di-o-tolyl-1,2,4,5-cyclohexadiene

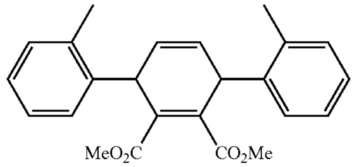

20.0 g (85.3 mmol) of 2,2'-dimethyl-trans-stilbene are stirred under reflux for 20 h with 11.5 ml (93.8 mmol) of dimethyl acetylenedicarboxylate in toluene, giving a solid, which is washed by stirring with hot heptane. The product is obtained as a pale-yellow solid in a yield of 87%.

e) 1,2-Dicarboxymethyl-3,6-di-o-tolylbenzene

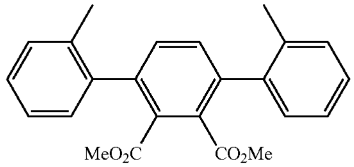

2.00 g (5.31 mmol) of 1,2-dicarboxymethyl-3,6-di-o-tolyl-1,2,4,5-cyclohexadiene are stirred for 20 h at 180° C. on a water separator with 9.23 g (10.62 mmol) of $MnO_2$ in 250 ml of o-dichlorobenzene. The mixture is filtered through Celite, giving 1.3 g (65%) of the product as a solid.

f) 1,2-Di[hydroxymethyl]-3,6-di-o-tolylbenzene

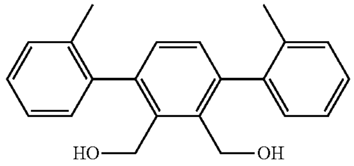 [SMILES: Cc1ccccc1-c1ccc(-c2ccccc2C)c(CO)c1CO]

250 ml of THF are slowly added to 10.13 g (267.3 mmol) of lithium aluminium hydride, then 71.5 g (190.9 mmol) of 1,2-dicarboxymethyl-3,6-di-o-tolylbenzene, dissolved in 450 ml of THF, are slowly added at such a rate that the temperature does not rise above 40° C. If necessary, the mixture is cooled using dry ice. When the addition is complete, the suspension is heated under reflux for 2 h. When the conversion is complete, a mixture of 120 ml of ethyl acetate and 340 ml of THF is slowly added with cooling at 0° C. (reaction of the excess lithium aluminium hydride with ethyl acetate). When quenching is complete, 300 ml of ethanol are carefully added, and the mixture is subjected to aqueous work-up. 200 ml of water are added, the precipitate is filtered off with suction, and the mother liquor is evaporated a little, extracted with ethyl acetate and dichloromethane, dried over $MgSO_4$ and evaporated, giving 61 g of crude product, which can be employed directly in the next transformation.

g) 4,7-Dimethylindeno[2,1-a]fluorene

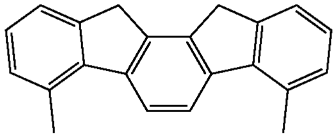 [SMILES: Cc1cccc2c1-c1ccc3c(c1C2)Cc1cccc(C)c1-3]

934 g of polyphosphoric acid are initially introduced, and 61.0 g (192 mmol) of 1,2-di[hydroxymethyl]-3,6-di-o-tolylbenzene, dissolved in 1500 ml of chloroform, are added. The mixture is subsequently heated under reflux for 2.5 h. The cooled reaction solution is introduced into ice-water, extracted with methylene chloride, dried and evaporated. The solid obtained is washed by stirring in boiling ethyl acetate, filtered off with suction and rinsed with heptane, giving 27 g (54%) of the product as a white solid.

h) 4,7,11,11,12,12-Hexamethyl-11,12-dihydroindeno [2,1-a]fluorene

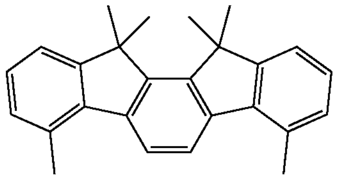 [SMILES: Cc1cccc2c1-c1ccc3c(c1C2(C)C)C(C)(C)c1cccc(C)c1-3]

30.0 g (63.74 mmol) of 4,7-dimethylindeno[2,1-a]fluorene are initially introduced in 700 ml of DMSO, and 36.76 g (382.47 mmol) of NaO$^t$Bu are added. The mixture is heated to an internal temperature of 65° C., and 23.8 ml (382.47 mmol) of iodomethane are then added dropwise at such a rate that the internal temperature doe not rise above 65° C. When conversion is complete, 100 ml of 26% $NH_3$ solution are added to the cooled reaction solution, and the mixture is stirred at room temperature for 16 h. The reaction product which precipitates out is filtered off with suction and dried azeotropically with toluene. The reaction product is purified by column chromatography (toluene/heptane 1:5), giving 18 g (83%) of the product as a white solid.

The bromination and Hartwig-Buchwald coupling of this compound are carried out analogously to Example 1f) and g).

Example 4

Production of OLEDs

OLEDs according to the invention are produced by a general process in accordance with WO 04/058911, which is adapted to the circumstances (layer-thickness variation, materials used) described here.

In Examples 5 to 18 below, the results for various OLEDs are presented. Glass platelets coated with structured ITO (indium tin oxide) form the substrates of the OLEDs. For improved processing, 20 nm of PEDOT (spincoated from water; purchased from H. C. Starck, Goslar, Germany; poly (3,4-ethylenedioxy-2,5-thiophene)) is applied to the substrate. The OLEDs consist of the following layer sequence: substrate/PEDOT 20 nm/HIL1 5 nm/hole-transport layer (HTM) 20 or 110 nm/NPB 20 nm/emission layer (EML) 30 nm/electron-transport layer (ETM) 20 nm and finally a cathode. The materials apart from the PEDOT are thermally vapour-deposited in a vacuum chamber. The emission layer here always consists of a matrix material (host) and a dopant, which is admixed with the host by co-evaporation. The cathode is formed by an LiF layer with a thickness of 1 nm and an Al layer with a thickness of 100 nm deposited on top. Table 1 shows the chemical structures of the materials used.

These OLEDs are characterised by standard methods; for this purpose, the electroluminescence spectra, the efficiency (measured in cd/A), the power efficiency (measured in lm/W) as a function of the luminance, calculated from current/voltage/luminance characteristic lines (IUL characteristic lines), and the lifetime are determined. The lifetime is defined as the time after which the initial luminance has dropped from 25,000 cd/m$^2$ to half. The use voltage is defined as the voltage at which the OLED achieves a luminance of 1 cd/m$^2$.

Table 2 shows the results for some OLEDs (Examples 5 to 18). The hole-transport materials according to the invention used are the compounds HTM3 (Synthesis Example 1), HTM4 (Synthesis Example 2) and HTM5 (Synthesis Example 3), as shown in Table 1. As comparison, compounds HTM1 and HTM2 in accordance with the closest prior art are used. Compounds HTM3, HTM4 and HTM5 are distinguished over the corresponding unsubstituted compounds HTM1 and HTM2 by a reduced use voltage, a reduced operating voltage and especially a reduced voltage difference between HTM layers with a thickness of 20 nm and a thickness of 110 nm at a luminance of 1000 cd/m$^2$. This is important in applications since the optical coupling-out efficiency is controlled in a crucial manner by variation of the layer thickness of the hole-transport layer. The lifetimes, efficiencies and colour coordinates on use of compounds HTM3, HTM4 and HTM5 according to the invention are, as expected, very similar to those on use of the corresponding reference materials HTM1 and HTM2.

TABLE 1

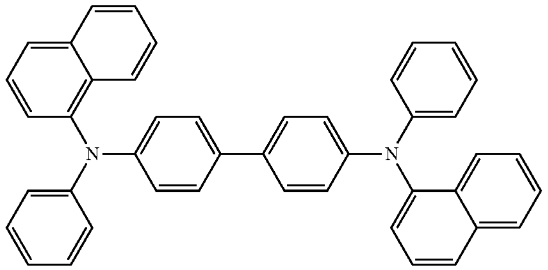 [SMILES: c1ccc(N(c2ccc(-c3ccc(N(c4ccccc4)c4cccc5ccccc45)cc3)cc2)c2cccc3ccccc23)cc1]

NPB

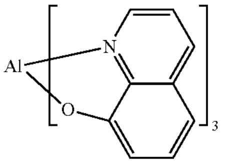

AlQ$_3$

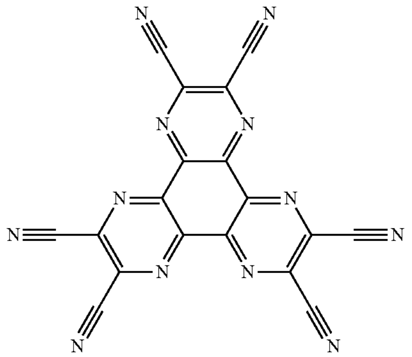 [SMILES: N#Cc1nc2c3nc(C#N)c(C#N)nc3c3nc(C#N)c(C#N)nc3c2nc1C#N]

HIL1

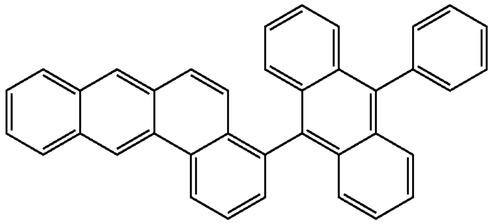 [SMILES: c1ccc(-c2c3ccccc3c(-c3cccc4c3ccc3cc5ccccc5cc34)c3ccccc23)cc1]

H1

TABLE 1-continued
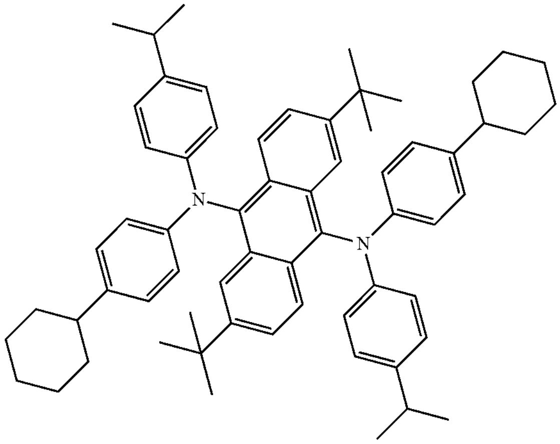 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
D1
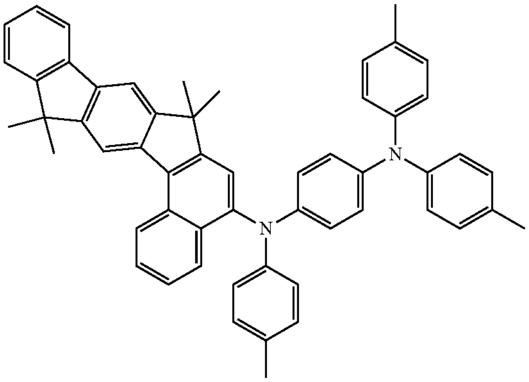 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
D2
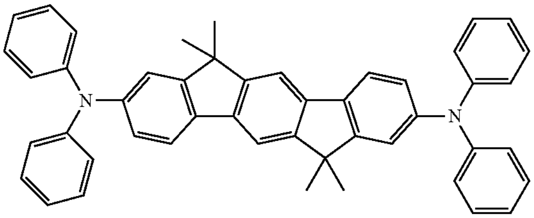 [SMILES: CC1(C)c2cc(N(c3ccccc3)c3ccccc3)ccc2-c2cc3c(cc21)-c1ccc(N(c2ccccc2)c2ccccc2)cc1C3(C)C]
HTM1
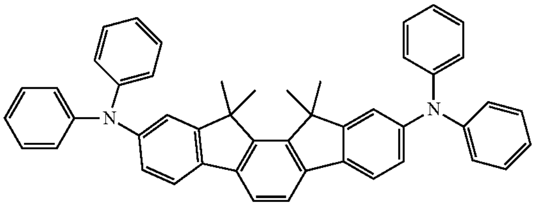 [SMILES: CC1(C)c2cc(N(c3ccccc3)c3ccccc3)ccc2-c2ccc3c(c21)C(C)(C)c1cc(N(c2ccccc2)c2ccccc2)ccc1-3]
HTM2
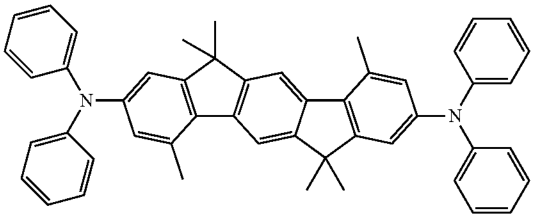 [SMILES: Cc1cc(N(c2ccccc2)c2ccccc2)cc2c1-c1cc3c(cc1C2(C)C)-c1c(C)cc(N(c2ccccc2)c2ccccc2)cc1C3(C)C]
HTM3 (Example 1)
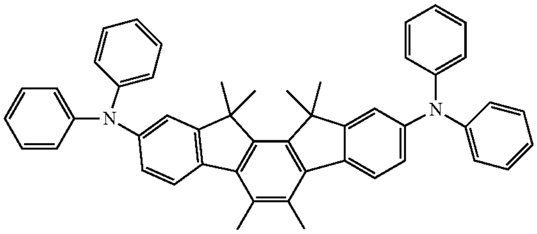 [SMILES: Cc1c(C)c2c(c3c1-c1ccc(N(c4ccccc4)c4ccccc4)cc1C3(C)C)C(C)(C)c1cc(N(c3ccccc3)c3ccccc3)ccc1-2]
HTM4 (Example 2)
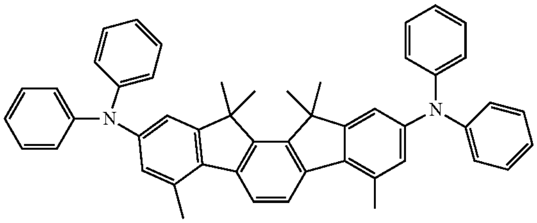 [SMILES: Cc1cc(N(c2ccccc2)c2ccccc2)cc2c1-c1ccc3c(c1C2(C)C)C(C)(C)c1cc(N(c2ccccc2)c2ccccc2)cc(C)c1-3]
HTM5 (Example 3)
TABLE 2
| Ex. | EML | HTM | Use voltage | Voltage for 1000 cd/$m^2$ | Efficiency at 1000 cd/$m^2$ | CIE x/y at 1000 cd/$m^2$ | Lifetime [h] |
|---|---|---|---|---|---|---|---|
| 5 (comp.) | H1 + 10% of D1 | HTM 1 20 nm | 2.8 V | 5.0 V | 17.1 cd/A | 0.34/0.62 | 355 |
| 6 (comp.) | H1 + 10% of D1 | HTM 1 110 nm | 3.2 V | 5.5 V | 21.4 cd/A | 0.31/0.65 | 277 |
| 7 | H1 + 10% of D1 | Ex. HTM3 20 nm | 2.8 V | 4.9 V | 16.7 cd/A | 0.34/0.61 | 348 |
| 8 | H1 + 10% of D1 | Ex. HTM3 110 nm | 3.1 V | 5.2 V | 21.9 cd/A | 0.32/0.65 | 291 |
| 9 (comp.) | H1 + 10% of D2 | HTM 1 20 nm | 2.8 V | 5.1 V | 14.4 cd/A | 0.32/0.58 | 361 |
| 10 (comp.) | H1 + 10% of D2 | HTM 1 110 nm | 2.9 V | 5.4 V | 15.1 cd/A | 0.28/0.62 | 294 |
| 11 | H1 + 10% of D2 | HTM3 20 nm | 2.8 V | 5.0 V | 14.9 cd/A | 0.32/0.58 | 365 |
| 12 | H1 + 10% of D2 | HTM3 110 nm | 2.9 V | 5.2 V | 15.3 cd/A | 0.28/0.62 | 285 |

TABLE 2-continued

| Ex. | EML | HTM | Use voltage | Voltage for 1000 cd/m$^2$ | Efficiency at 1000 cd/m$^2$ | CIE x/y at 1000 cd/m$^2$ | Lifetime [h] |
|---|---|---|---|---|---|---|---|
| 13 (comp.) | H1 + 10% of D2 | HTM 2 20 nm | 4.2 V | 6.2 V | 15.8 cd/A | 0.31/0.58 | 285 |
| 14 (comp.) | H1 + 10% of D2 | HTM 2 110 nm | 4.6 V | 6.5 V | 20.6 cd/A | 0.28/0.61 | 325 |
| 15 | H1 + 10% of D2 | HTM4 20 nm | 3.5 V | 5.4 V | 15.2 cd/A | 0.31/0.58 | 315 |
| 16 | H1 + 10% of D2 | HTM4 110 nm | 3.8 V | 5.6 V | 20.1 cd/A | 0.27/0.61 | 341 |
| 17 | H1 + 10% of D2 | HTM5 20 nm | 2.9 V | 5.1 V | 16.2 cd/A | 0.32/0.59 | 338 |
| 18 | H1 + 10% of D2 | HTM5 110 nm | 3.0 V | 5.2 V | 21.2 cd/A | 0.28/0.61 | 375 |

Example 19

Comparison of Processability

For the investigation of processability, HTM1 in accordance with the prior art and HTM3 as compound according to the invention are vapour-deposited at a rate of 0.1 nm/s under identical vapour-deposition conditions. During this process, the vapour-deposition source is investigated after vapour coating for 1 h and 2 h. After vapour deposition for only 1 h, clear crystallisation of HTM1 is evident at the edge of the vapour-deposition source, and after vapour-deposition for 2 h, the vapour-deposition source is completely clogged. With HTM3, by contrast, absolutely no crystallisation at the edge of the vapour-deposition source and thus absolutely no tendency to clog the vapour-deposition source is evident even after vapour deposition for 2 h. The same result is obtained with compounds HTM4 and HTM5 according to the invention. The compounds according to the invention are thus significantly more suitable for use in mass production than compound HTM1 in accordance with the prior art.

The invention claimed is:

1. A compound of formula (1)

formula (1)

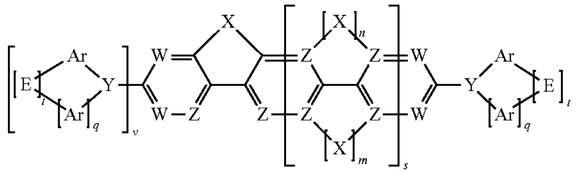

wherein

Y is on each occurrence, identically or differently, B, N, P, P═O, $PF_2$, C═O, O, S, S═O, or $SO_2$;

Ar is on each occurrence, identically or differently, an aromatic or heteroaromatic ring system having 5 to 40 aromatic ring atoms, optionally substituted by one or more radicals $R^1$;

X is on each occurrence, identically or differently, a group selected from $C(R^1)_2$ and C═O or a combination of these groups;

Z is C if a group X is bonded to the group Z, or is CR if no group X is bonded to the group Z;

W is CH;

R is on each occurrence, identically or differently, H, D, or $CH_3$;

E is on each occurrence, identically or differently, a single bond, $N(R^1)$, O, S, $C(R^1)_2$, $C(R^1)_2$-$C(R^1)_2$, $Si(R^1)_2$, or $B(R^1)$;

$R^1$ is on each occurrence, identically or differently, H, D, F, Cl, Br, I, CN, $NO_2$, $B(OR^2)_2$, $Si(R^2)_3$, a straight-chain alkyl, alkoxy, or thioalkoxy group having 1 to 40 C atoms or a straight-chain alkenyl or alkynyl group having 2 to 40 C atoms or a branched or cyclic alkyl, alkenyl, alkynyl, alkoxy, or thioalkoxy group having 3 to 40 C atoms, each of which is optionally substituted by one or more radicals $R^2$, and wherein one or more non-adjacent $CH_2$ groups are optionally replaced by —$R^2C$═$CR^2$—, —C≡C—, $Si(R^2)_2$, $Ge(R^2)_2$, $Sn(R^2)_2$, C═O, C═S, C═Se, C═$NR^2$, —O—, —S—, —COO— or —$CONR^2$—, and wherein one or more H atoms are optionally replaced by F, Cl, Br, I, CN or $NO_2$, or an aromatic or heteroaromatic ring system having 5 to 40 aromatic ring atoms, optionally substituted by one or more non-aromatic radicals $R^1$, or an aryloxy or heteroaryloxy group having 5 to 40 aromatic ring atoms, optionally substituted by one or more non-aromatic radicals $R^1$; and wherein two or more substituents $R^1$ optionally define a mono- or polycyclic ring system with one another;

$R^2$ is on each occurrence, identically or differently, H or an aliphatic or aromatic hydrocarbon radical having 1 to 20 C atoms;

m and n are 0 or 1, with the proviso that m+n=1;

q is on each occurrence 1 if the corresponding central atom of the group Y is an element from main group 3 or 5 and is on each occurrence 0 if the corresponding central atom of the group Y is an element from main group 4 or 6;

s is 1;

t is on each occurrence, identically or differently, 0 or 1, wherein when t is 0, radicals $R^1$ are bonded instead of the group E and q is 0;

v is 0 or 1, where when v is 0, hydrogen or a group R may be bonded instead of the group Y; and wherein at least one radical R represents a substituent other than H or D.

2. The compound of claim 1, wherein Y is, identically or differently, N, C═O, P, or P═O.

3. The compound of claim 2, wherein Y is N.

4. The compound of claim 1, wherein Ar is, identically or differently on each occurrence, an aromatic or heteroaromatic ring system having 5 to 16 aromatic ring atoms, a triarylamine, or a spirobifluorene, each of which is optionally substituted by one or more radicals $R^1$.

5. The compound of claim 1, wherein Ar is, identically or differently on each occurrence an aromatic or heteroaromatic ring system selected from benzene, ortho- biphenyl, meta-biphenyl, para-biphenyl, fluorene, naphthalene, anthracene, phenanthrene, benzanthracene, pyridine, pyrene, thiophene, triphenylamine, diphenyl-1-naphthylamine, diphenyl-2-naphthylamine, phenyldi(1-naphthyl)amine, and phenyldi(2-naphthyl)amine, each of which is optionally substituted by $R^1$.

6. The compound of claim 1, wherein (1) t is 0 or (2) t is 1 and E is a single bond, $C(R^1)_2$, S, or $N(R^1)$.

7. The compound of claim 1, wherein said compound is selected from compounds of formulae (6), (7), (8), and (9)

formula (6)

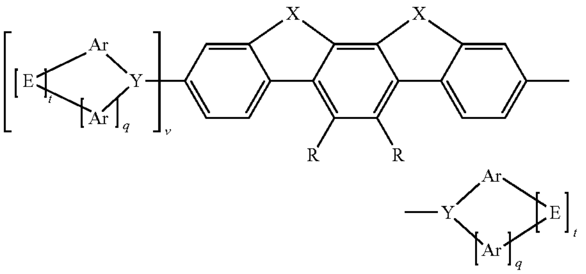

formula (7)

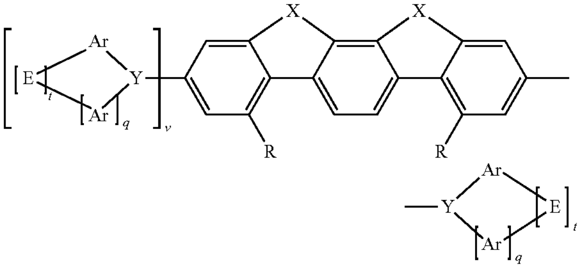

formula (8)

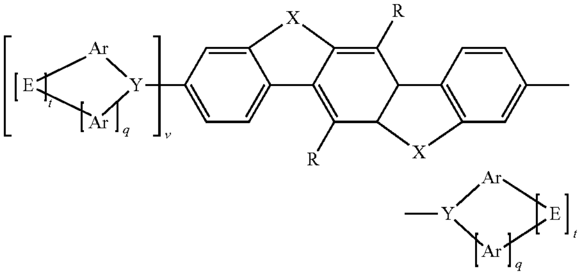

formula (9)

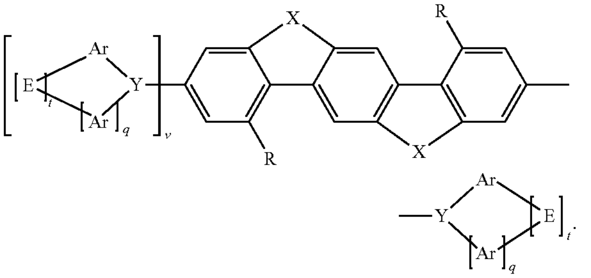

8. The compound of claim 1, wherein said compound is selected from compounds of formulae (6a), (7a), (8a), and (9a)

formula (6a)

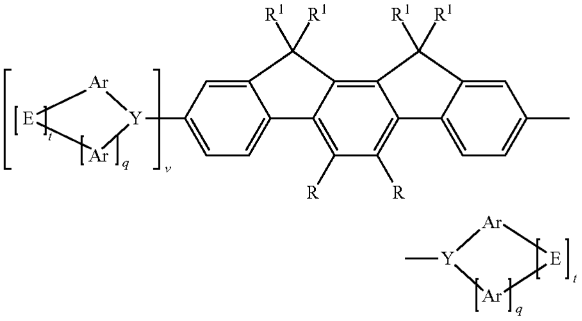

formula (7a)

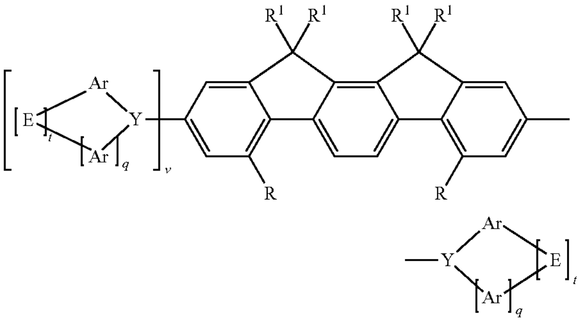

formula (8a)

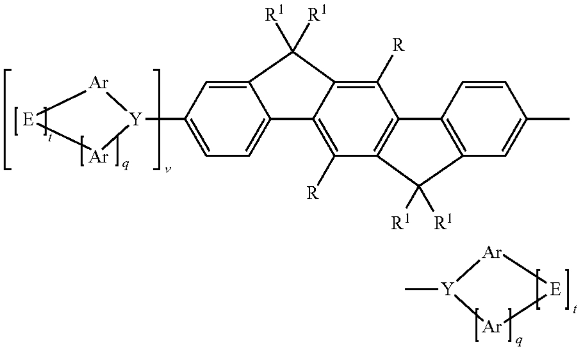

formula (9a)

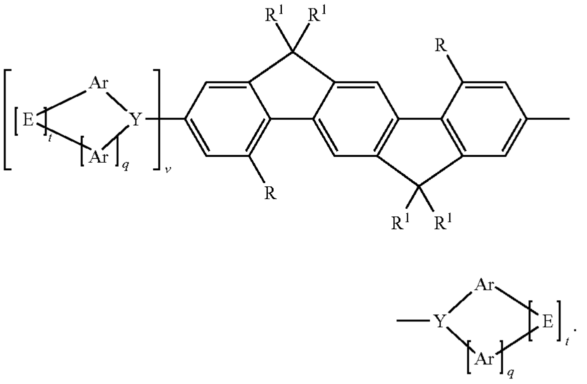

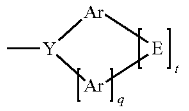

9. The compound of claim 1, wherein said compound is selected from compounds of formula (2) and formula (3)
formula (2)
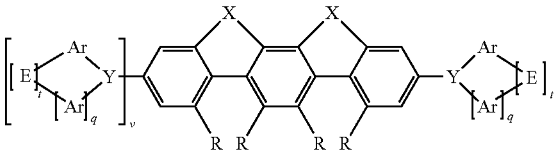
-continued
formula (3)
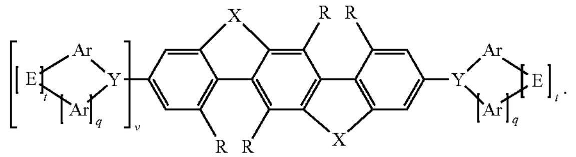
10. The compound of claim 1, wherein radicals R other than hydrogen are on each occurrence, identically or differently, methyl.
11. The compound according to claim 1, wherein the compound is
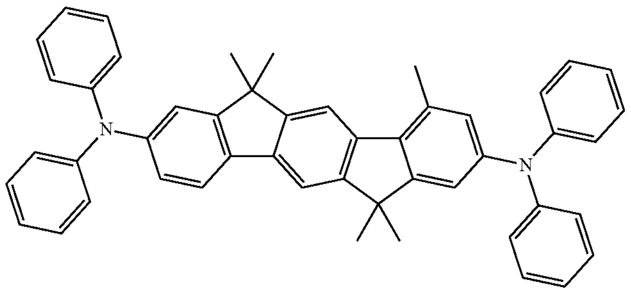 [SMILES: Cc1cc(N(c2ccccc2)c2ccccc2)cc2c1-c1cc3c(cc1C2(C)C)-c1ccc(N(c2ccccc2)c2ccccc2)cc1C3(C)C]
(1)
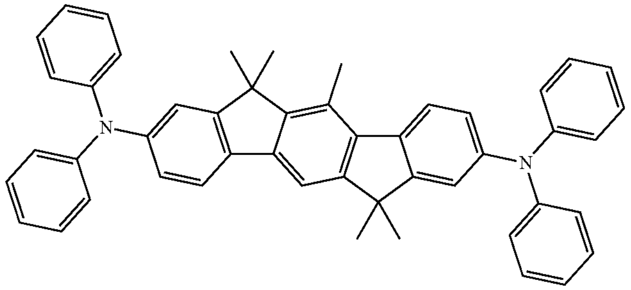
(2)
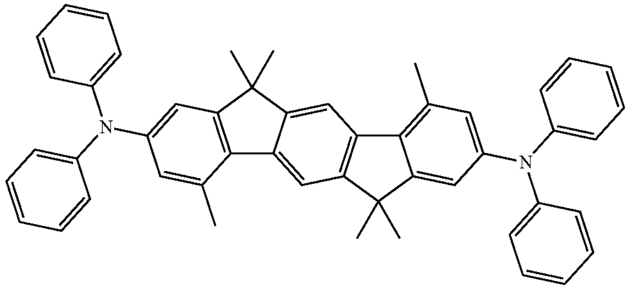 [SMILES: Cc1cc(N(c2ccccc2)c2ccccc2)cc2c1-c1cc3c(cc1C2(C)C)-c1c(C)cc(N(c2ccccc2)c2ccccc2)cc1C3(C)C]
(3)
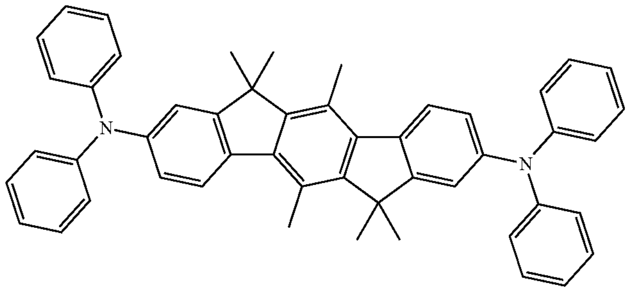 [SMILES: Cc1c2c(c(C)c3c1C(C)(C)c1cc(N(c4ccccc4)c4ccccc4)ccc1-3)C(C)(C)c1cc(N(c3ccccc3)c3ccccc3)ccc1-2]
(4)

-continued
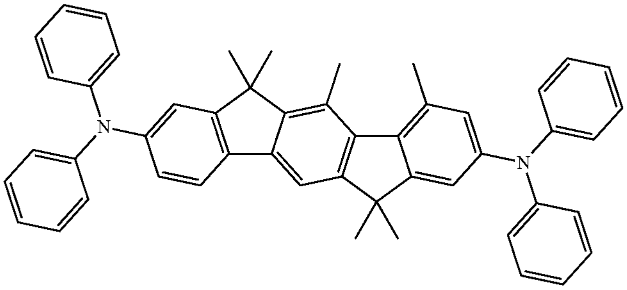 [SMILES: Cc1cc(N(c2ccccc2)c2ccccc2)cc2c1-c1c(cc3c(c1C)C(C)(C)c1cc(N(c4ccccc4)c4ccccc4)ccc1-3)C2(C)C]
(5)
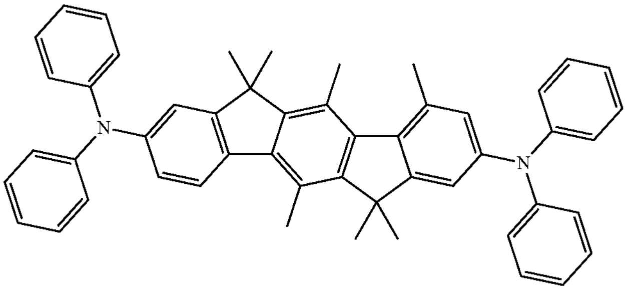 [SMILES: Cc1cc(N(c2ccccc2)c2ccccc2)cc2c1-c1c(C)c3c(c(C)c1C2(C)C)-c1ccc(N(c2ccccc2)c2ccccc2)cc1C3(C)C]
(6)
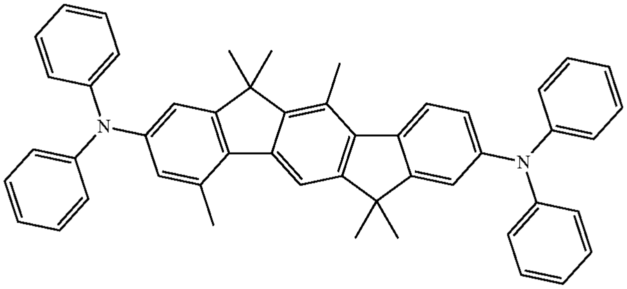 [SMILES: Cc1cc(N(c2ccccc2)c2ccccc2)cc2c1-c1cc3c(c(C)c1C2(C)C)-c1ccc(N(c2ccccc2)c2ccccc2)cc1C3(C)C]
(7)
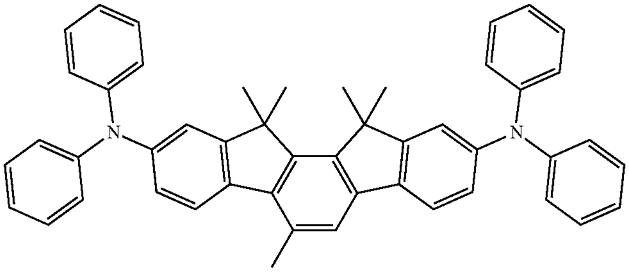 [SMILES: Cc1cc2c(c3c1-c1ccc(N(c4ccccc4)c4ccccc4)cc1C3(C)C)C(C)(C)c1cc(N(c3ccccc3)c3ccccc3)ccc1-2]
(25)
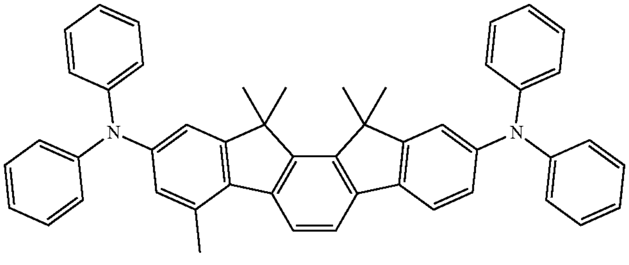 [SMILES: Cc1cc(N(c2ccccc2)c2ccccc2)cc2c1-c1ccc3c(c1C2(C)C)C(C)(C)c1cc(N(c2ccccc2)c2ccccc2)ccc1-3]
(26)

-continued
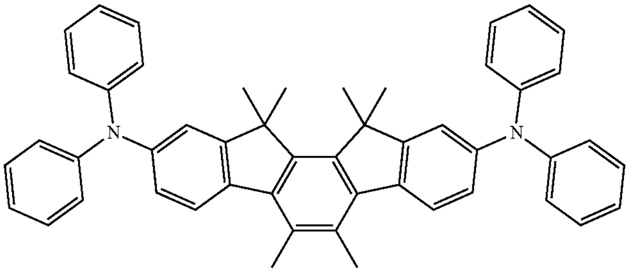 [SMILES: Cc1c(C)c2c(c3c1-c1ccc(N(c4ccccc4)c4ccccc4)cc1C3(C)C)C(C)(C)c1cc(N(c3ccccc3)c3ccccc3)ccc1-2]
(27)
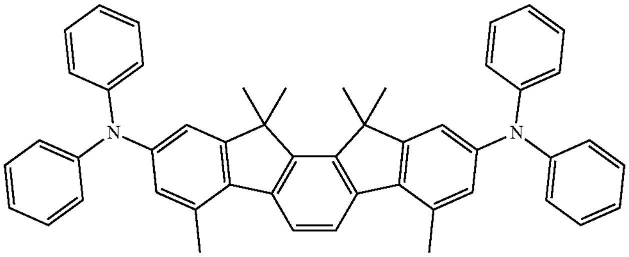 [SMILES: Cc1cc(N(c2ccccc2)c2ccccc2)cc2c1-c1ccc3c(c1C2(C)C)C(C)(C)c1cc(N(c2ccccc2)c2ccccc2)cc(C)c1-3]
(28)
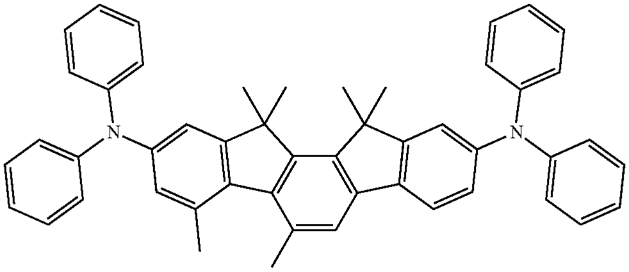 [SMILES: Cc1cc(N(c2ccccc2)c2ccccc2)cc2c1-c1c(C)cc3c(c1C2(C)C)C(C)(C)c1cc(N(c2ccccc2)c2ccccc2)ccc1-3]
(29)
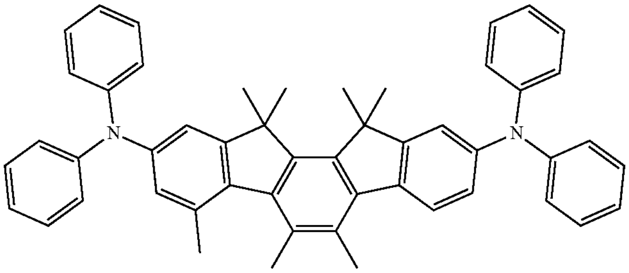 [SMILES: Cc1cc(N(c2ccccc2)c2ccccc2)cc2c1-c1c(C)c(C)c3c(c1C2(C)C)C(C)(C)c1cc(N(c2ccccc2)c2ccccc2)ccc1-3]
(30)
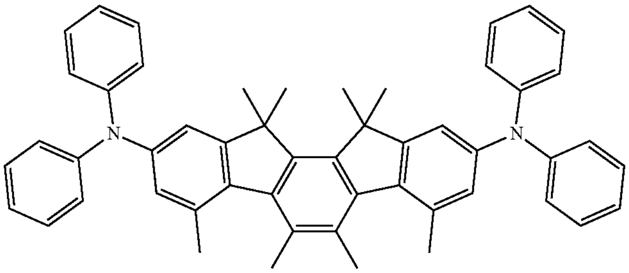 [SMILES: Cc1cc(N(c2ccccc2)c2ccccc2)cc2c1-c1c(C)c(C)c3c(c1C2(C)C)C(C)(C)c1cc(N(c2ccccc2)c2ccccc2)cc(C)c1-3]
(31)

-continued
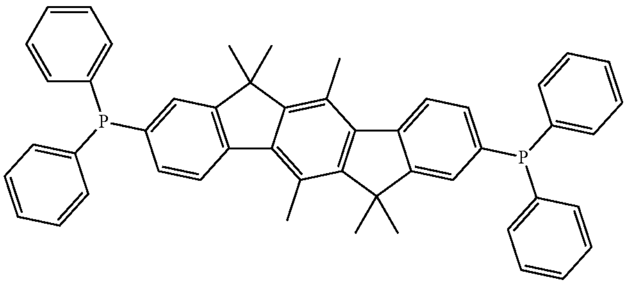 [SMILES: Cc1c2c(c(C)c3c1C(C)(C)c1cc(P(c4ccccc4)c4ccccc4)ccc1-3)C(C)(C)c1cc(P(c3ccccc3)c3ccccc3)ccc1-2]
(75)
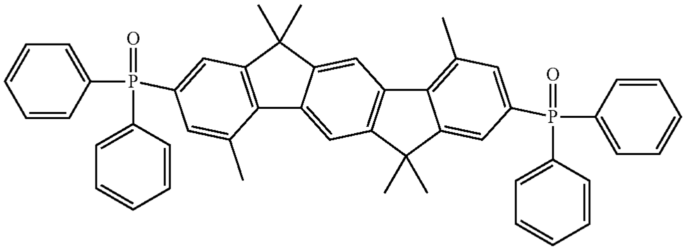 [SMILES: Cc1cc(P(=O)(c2ccccc2)c2ccccc2)cc2c1-c1cc3c(cc1C2(C)C)-c1c(C)cc(P(=O)(c2ccccc2)c2ccccc2)cc1C3(C)C]
(79)
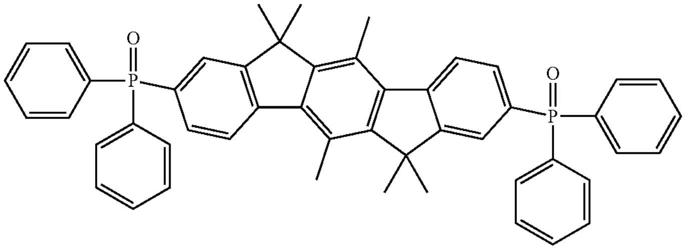 [SMILES: Cc1c2c(c(C)c3c1C(C)(C)c1cc(P(=O)(c4ccccc4)c4ccccc4)ccc1-3)C(C)(C)c1cc(P(=O)(c3ccccc3)c3ccccc3)ccc1-2]
(80)
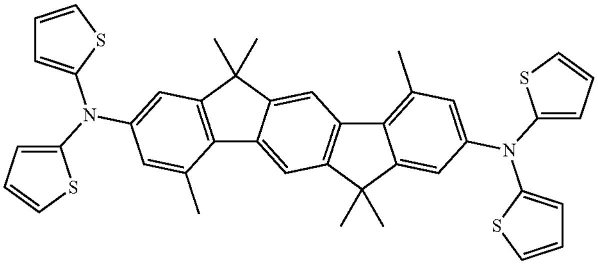 [SMILES: Cc1cc(N(c2cccs2)c2cccs2)cc2c1-c1cc3c(cc1C2(C)C)-c1c(C)cc(N(c2cccs2)c2cccs2)cc1C3(C)C]
(81)
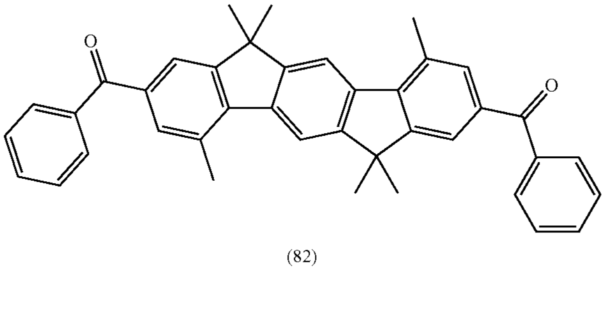
(82)

-continued
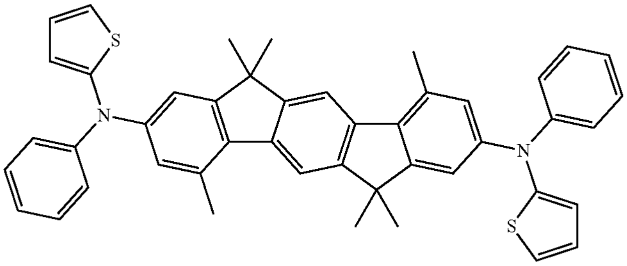 [SMILES: Cc1cc(N(c2ccccc2)c2cccs2)cc2c1-c1cc3c(cc1C2(C)C)-c1c(C)cc(N(c2ccccc2)c2cccs2)cc1C3(C)C]
(84)
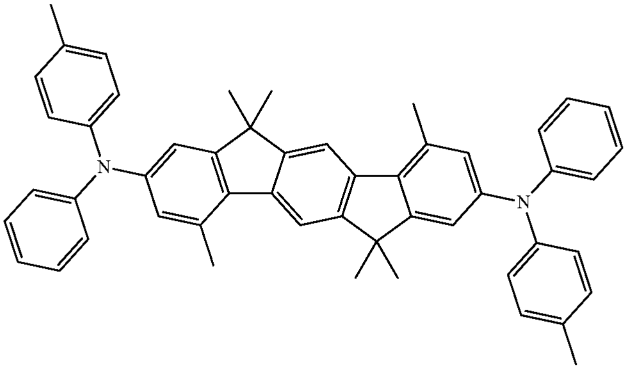 [SMILES: Cc1ccc(N(c2ccccc2)c2cc(C)c3c(c2)C(C)(C)c2cc4c(cc2-3)C(C)(C)c2cc(N(c3ccccc3)c3ccc(C)cc3)cc(C)c2-4)cc1]
(107)
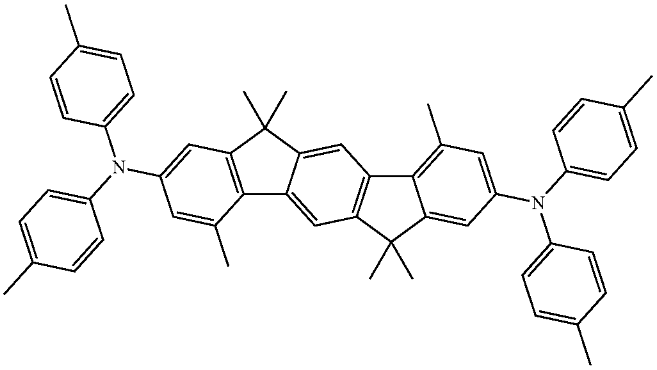
(108)
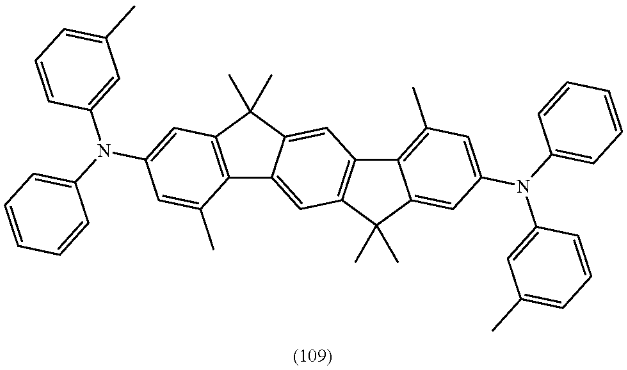
(109)

-continued
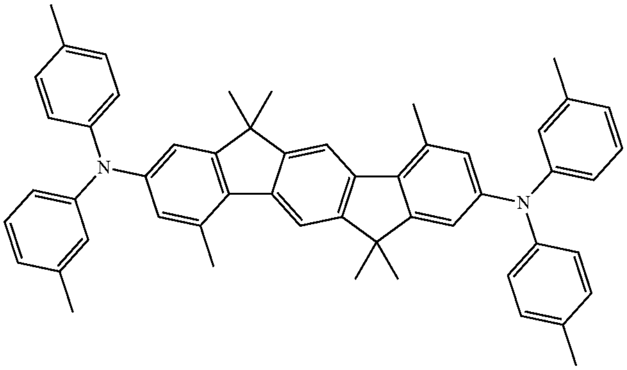 [SMILES: Cc1ccc(N(c2cccc(C)c2)c2cc(C)c3c(c2)C(C)(C)c2cc4c(cc2-3)C(C)(C)c2cc(N(c3ccc(C)cc3)c3cccc(C)c3)cc(C)c2-4)cc1]
(110)
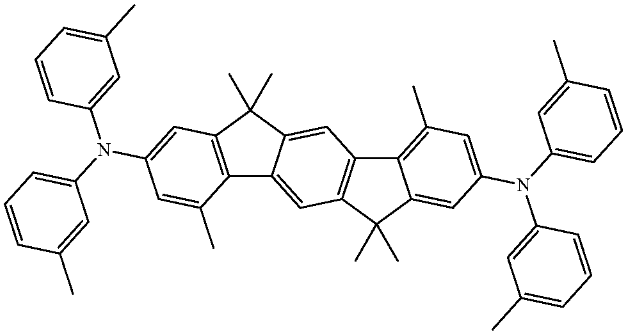 [SMILES: Cc1cccc(N(c2cccc(C)c2)c2cc(C)c3c(c2)C(C)(C)c2cc4c(cc2-3)C(C)(C)c2cc(N(c3cccc(C)c3)c3cccc(C)c3)cc(C)c2-4)c1]
(111)
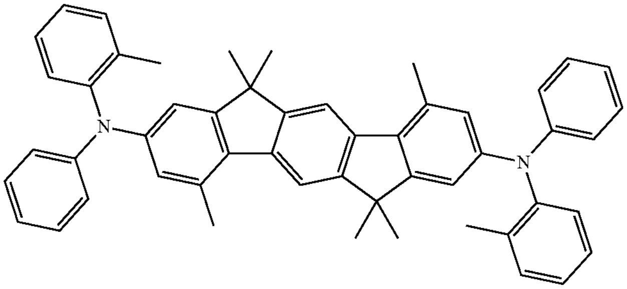 [SMILES: Cc1ccccc1N(c1ccccc1)c1cc(C)c2c(c1)C(C)(C)c1cc3c(cc1-2)C(C)(C)c1cc(N(c2ccccc2)c2ccccc2C)cc(C)c1-3]
(112)
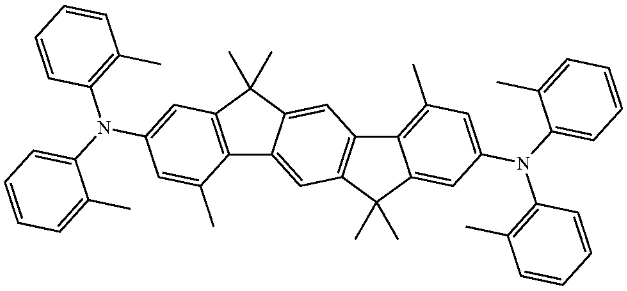 [SMILES: Cc1ccccc1N(c1cc(C)c2c(c1)C(C)(C)c1cc3c(cc1-2)C(C)(C)c1cc(N(c2ccccc2C)c2ccccc2C)cc(C)c1-3)c1ccccc1C]
(113)

-continued
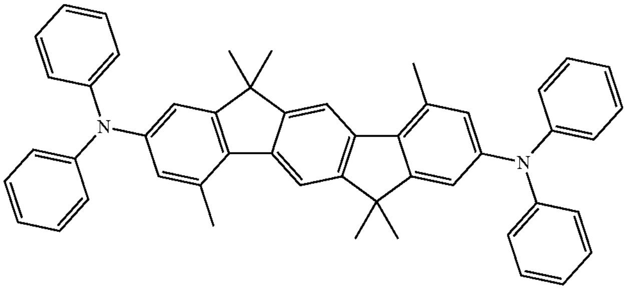 [SMILES: Cc1cc(N(c2ccccc2)c2ccccc2)cc2c1-c1cc3c(cc1C2(C)C)-c1c(C)cc(N(c2ccccc2)c2ccccc2)cc1C3(C)C]
(114)
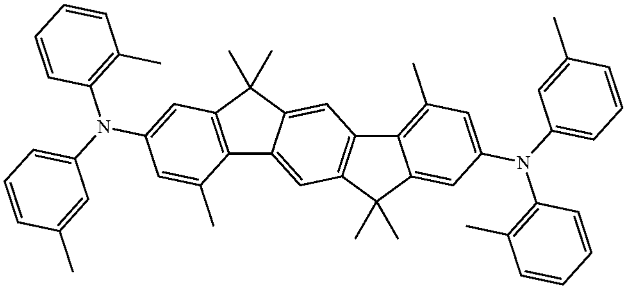 [SMILES: Cc1cccc(N(c2cc(C)c3c(c2)C(C)(C)c2cc4c(cc2-3)C(C)(C)c2cc(N(c3cccc(C)c3)c3ccccc3C)cc(C)c2-4)c2ccccc2C)c1]
(115)
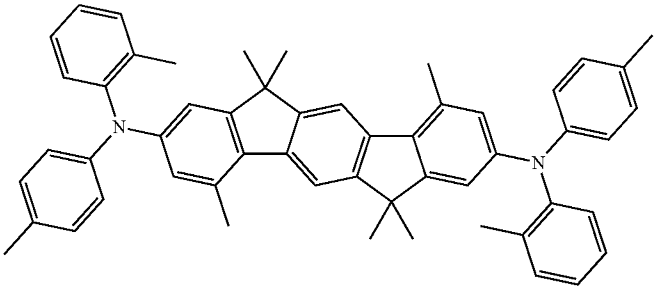
(116)
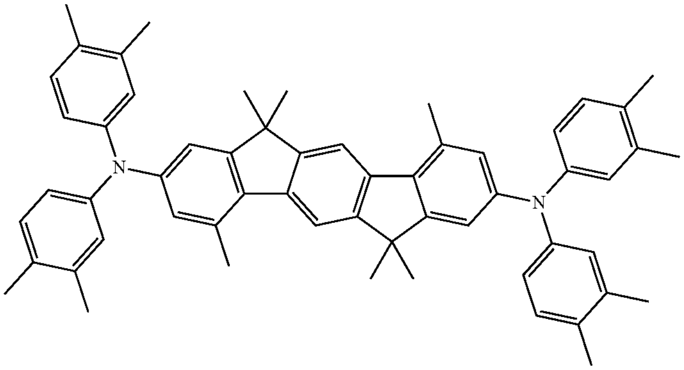
(117)

-continued
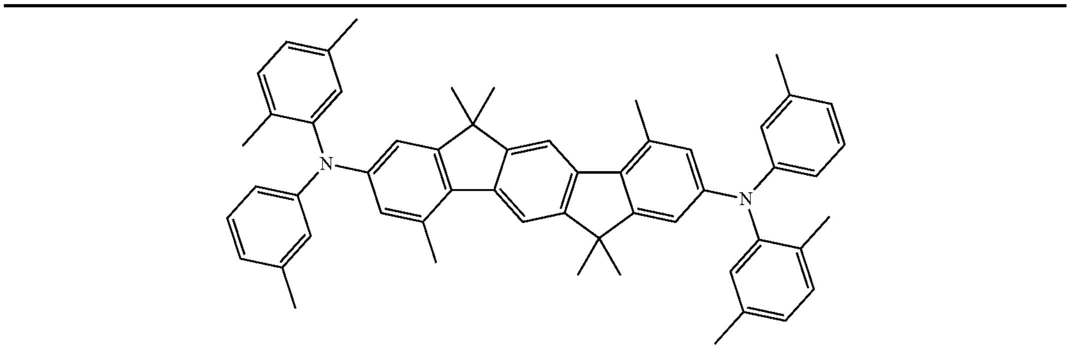
(118)
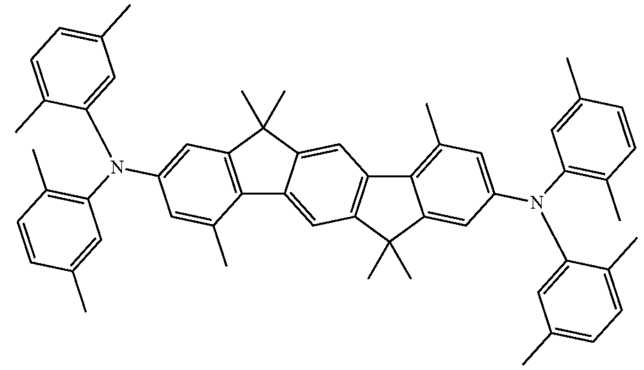
(119)
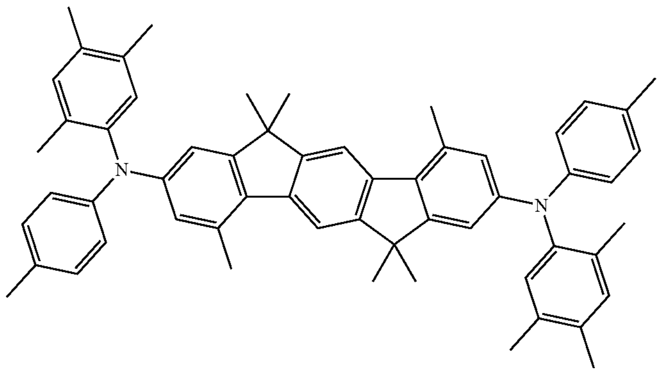
(120)
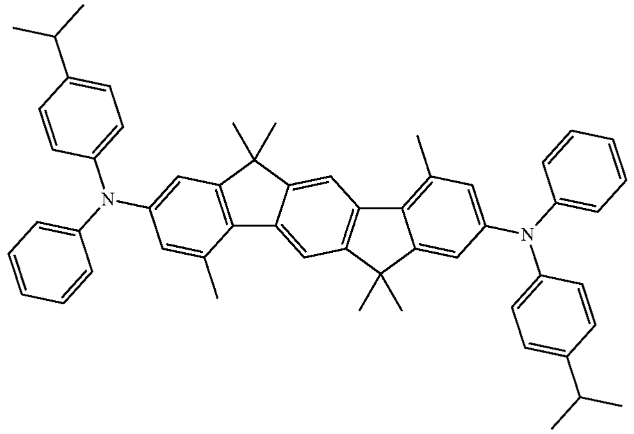 [SMILES: Cc1cc(N(c2ccccc2)c2ccc(C(C)C)cc2)cc2c1-c1cc3c(cc1C2(C)C)-c1c(C)cc(N(c2ccccc2)c2ccc(C(C)C)cc2)cc1C3(C)C]
(121)

-continued
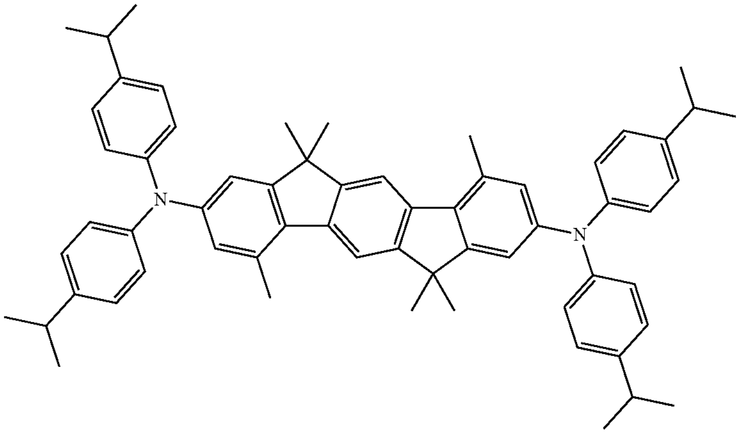 [SMILES: Cc1cc(N(c2ccc(C(C)C)cc2)c2ccc(C(C)C)cc2)cc2c1-c1cc3c(cc1C2(C)C)-c1c(C)cc(N(c2ccc(C(C)C)cc2)c2ccc(C(C)C)cc2)cc1C3(C)C]
(122)
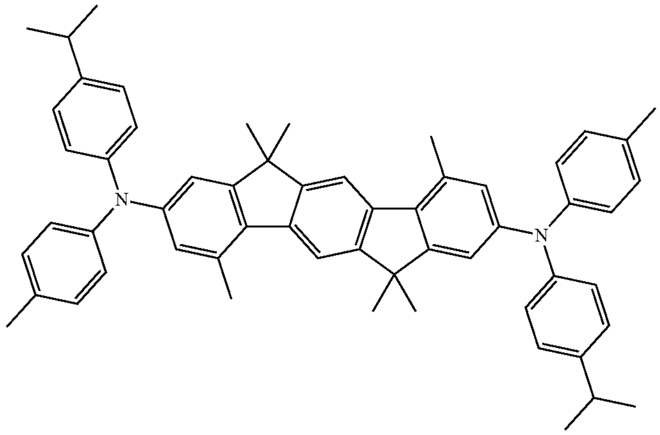
(123)
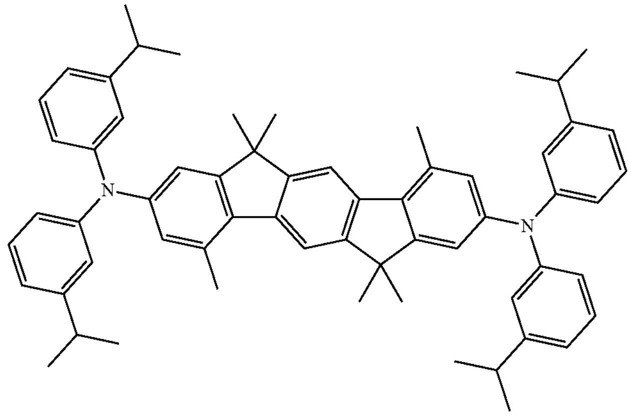 [SMILES: Cc1cc(N(c2cccc(C(C)C)c2)c2cccc(C(C)C)c2)cc2c1-c1cc3c(cc1C2(C)C)-c1c(C)cc(N(c2cccc(C(C)C)c2)c2cccc(C(C)C)c2)cc1C3(C)C]
(124)

-continued
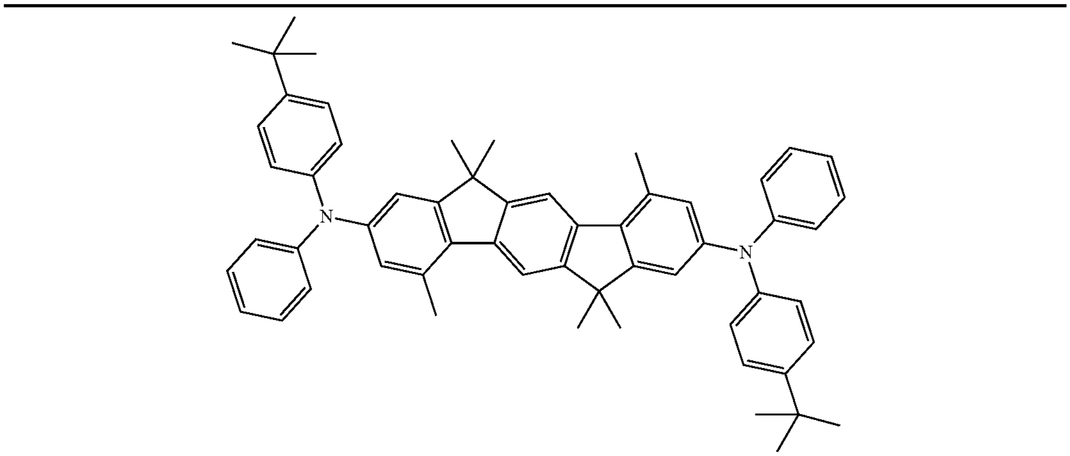
(125)
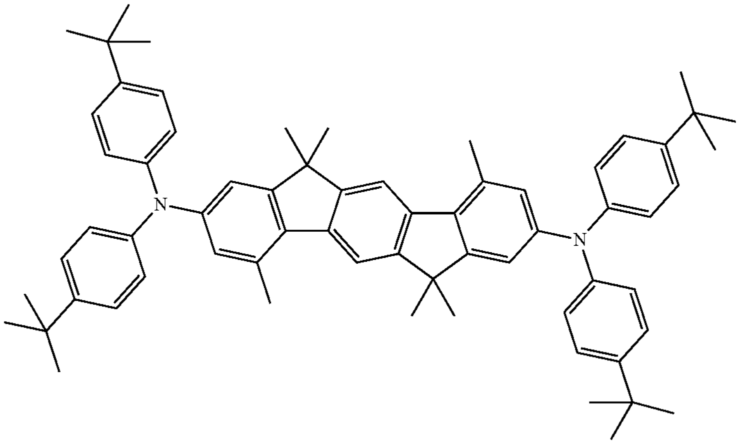 [SMILES: Cc1cc(N(c2ccc(C(C)(C)C)cc2)c2ccc(C(C)(C)C)cc2)cc2c1-c1cc3c(cc1C2(C)C)-c1c(C)cc(N(c2ccc(C(C)(C)C)cc2)c2ccc(C(C)(C)C)cc2)cc1C3(C)C]
(126)
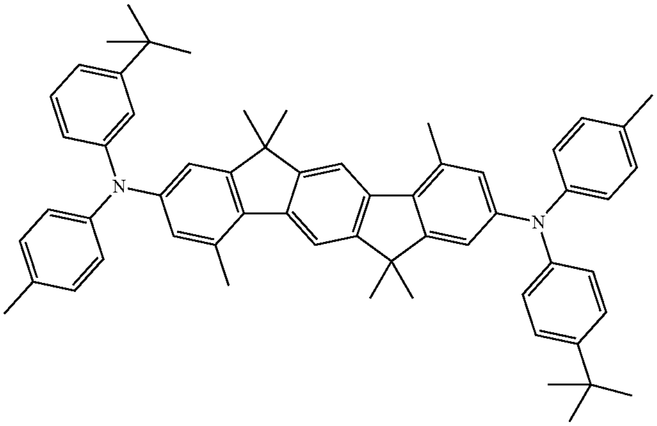
(127)

-continued
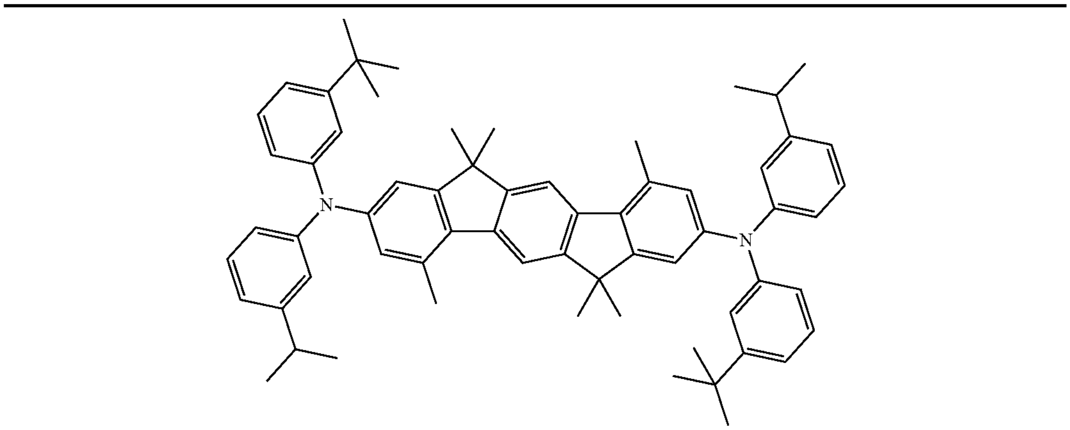
(128)
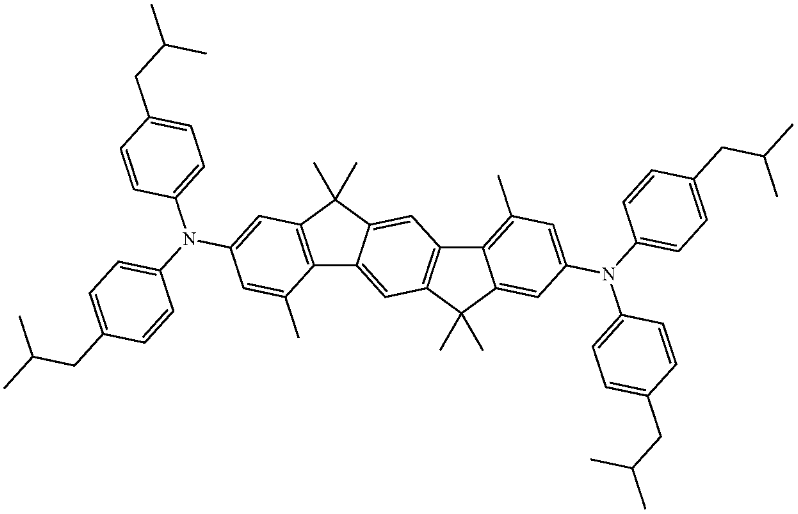 [SMILES: Cc1cc(N(c2ccc(CC(C)C)cc2)c2ccc(CC(C)C)cc2)cc2c1-c1cc3c(cc1C2(C)C)-c1c(C)cc(N(c2ccc(CC(C)C)cc2)c2ccc(CC(C)C)cc2)cc1C3(C)C]
(129)
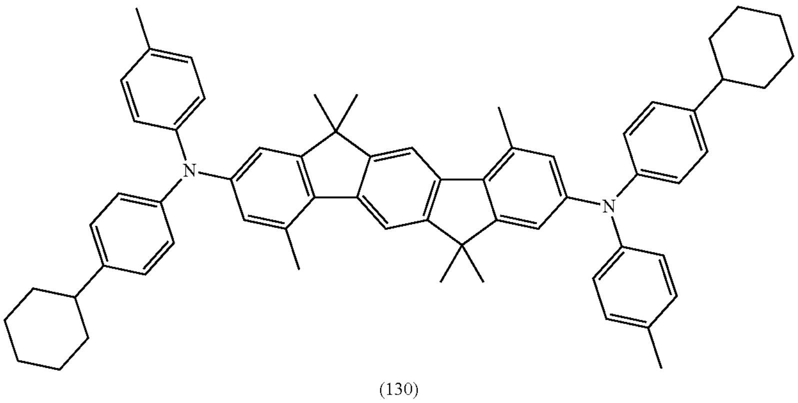
(130)

-continued
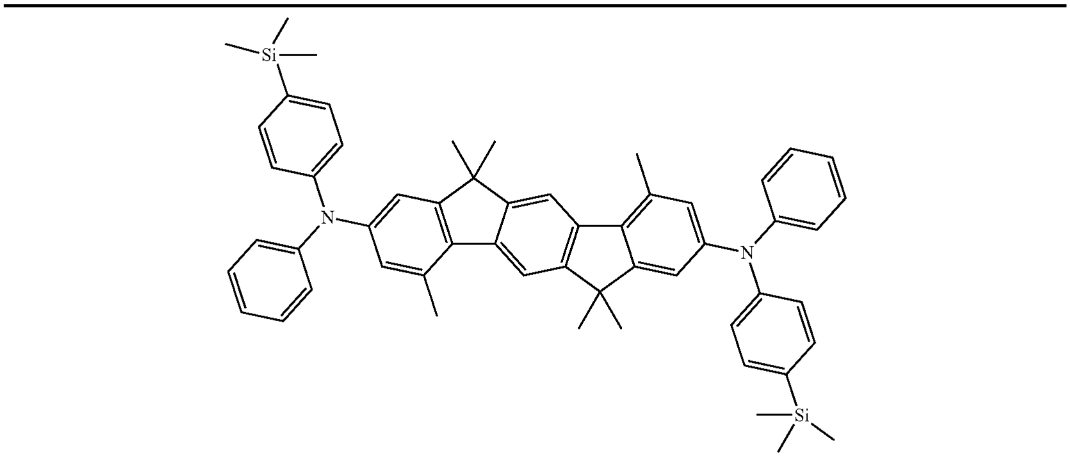
(131)
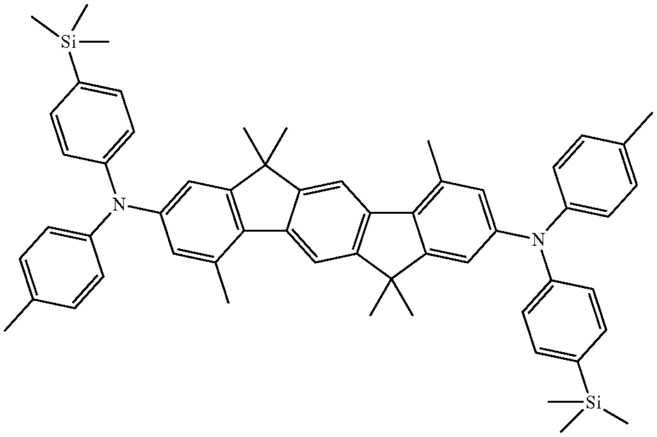
(132)
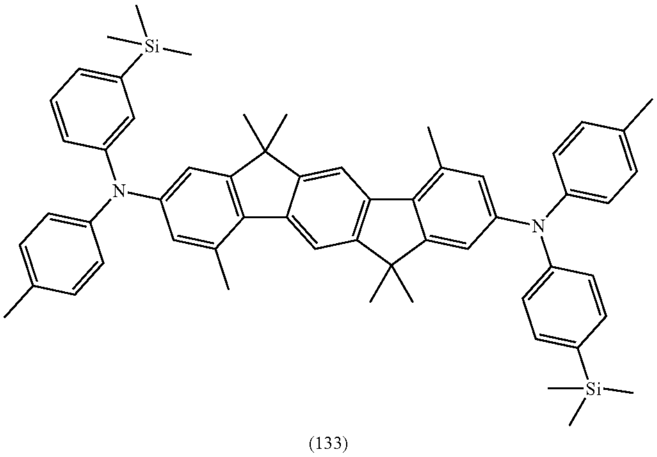
(133)

-continued
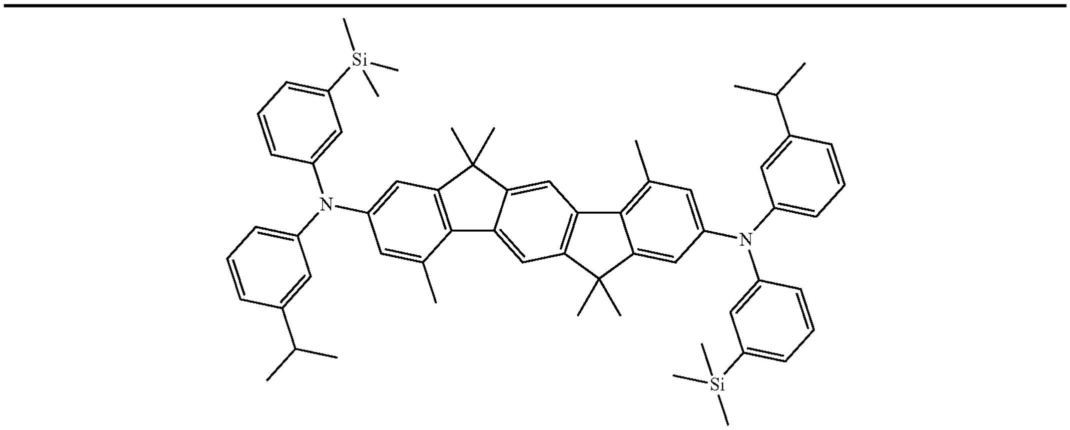
(134)
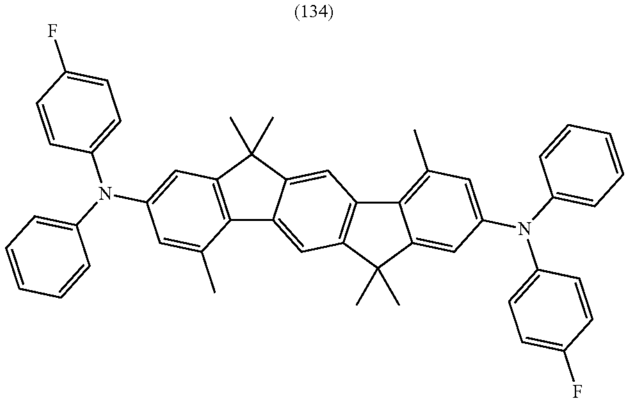
(135)
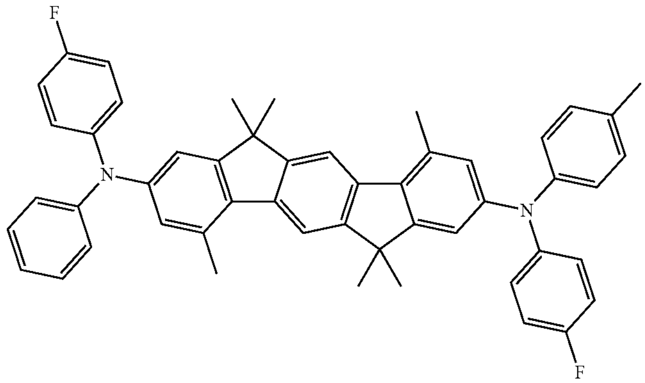 [SMILES: Cc1ccc(N(c2ccc(F)cc2)c2cc(C)c3c(c2)C(C)(C)c2cc4c(cc2-3)C(C)(C)c2cc(N(c3ccccc3)c3ccc(F)cc3)cc(C)c2-4)cc1]
(136)
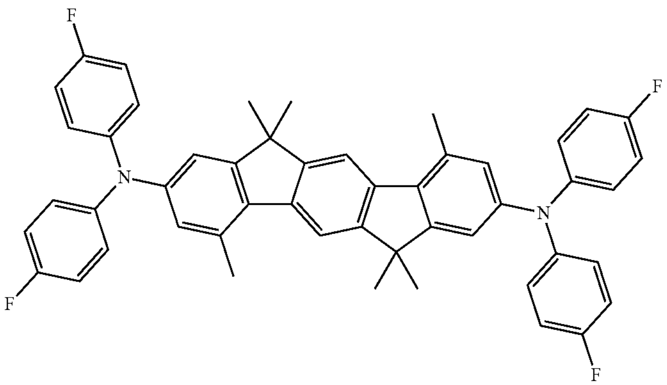 [SMILES: Cc1cc(N(c2ccc(F)cc2)c2ccc(F)cc2)cc2c1-c1cc3c(cc1C2(C)C)-c1c(C)cc(N(c2ccc(F)cc2)c2ccc(F)cc2)cc1C3(C)C]
(137)

-continued
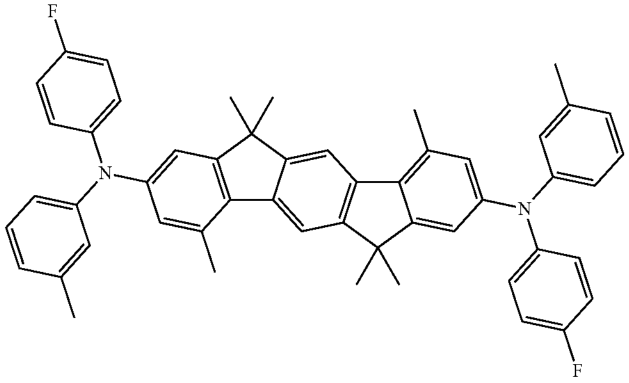 [SMILES: Cc1cccc(N(c2ccc(F)cc2)c2cc(C)c3c(c2)C(C)(C)c2cc4c(cc2-3)C(C)(C)c2cc(N(c3ccc(F)cc3)c3cccc(C)c3)cc(C)c2-4)c1]
(138)
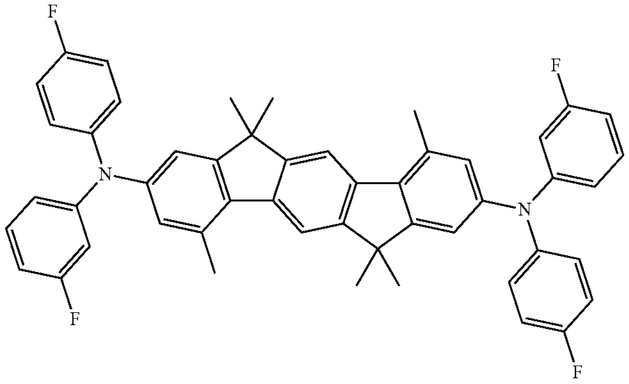
(139)
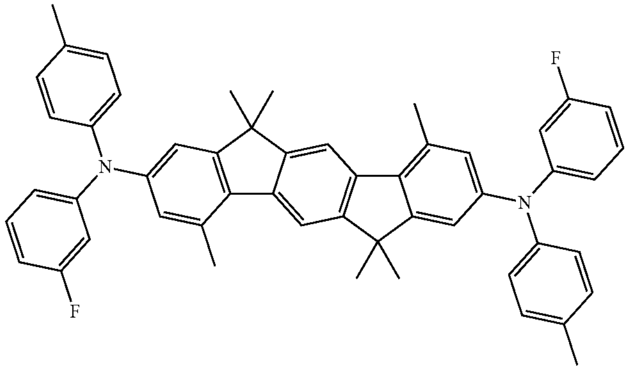
(140)
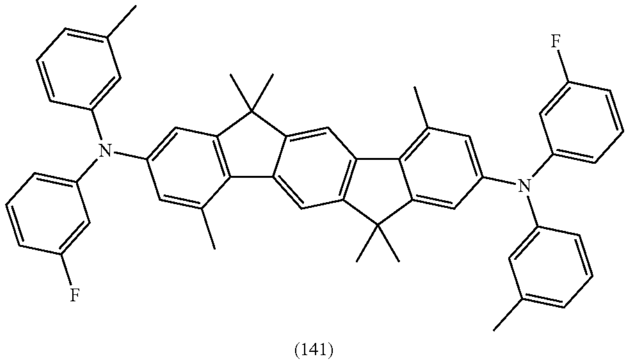
(141)

-continued
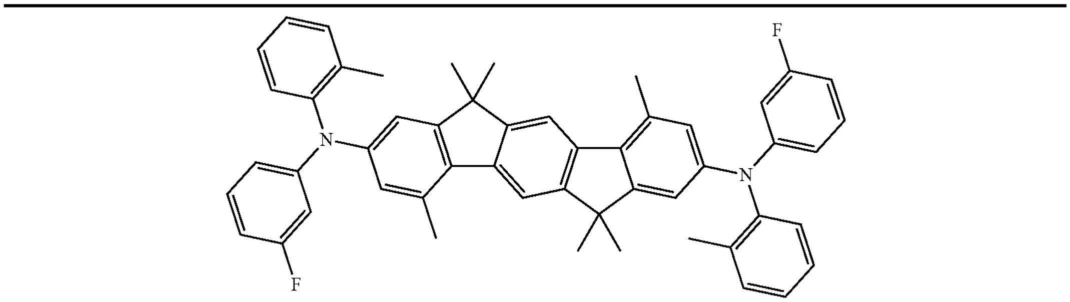
(142)
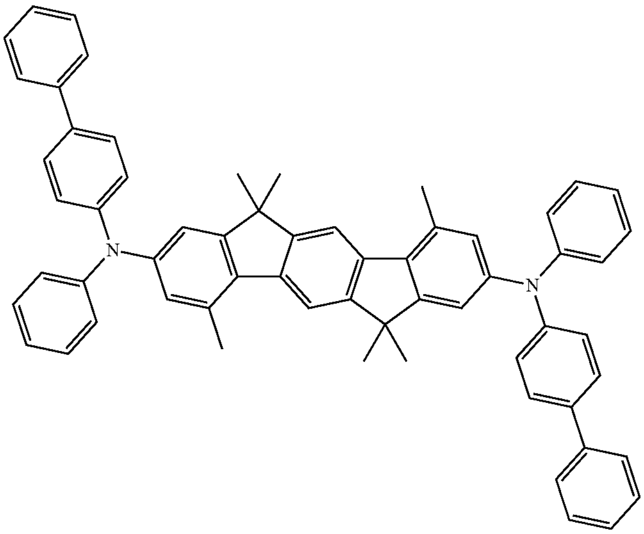 [SMILES: Cc1cc(N(c2ccccc2)c2ccc(-c3ccccc3)cc2)cc2c1-c1cc3c(cc1C2(C)C)-c1c(C)cc(N(c2ccccc2)c2ccc(-c4ccccc4)cc2)cc1C3(C)C]
(143)
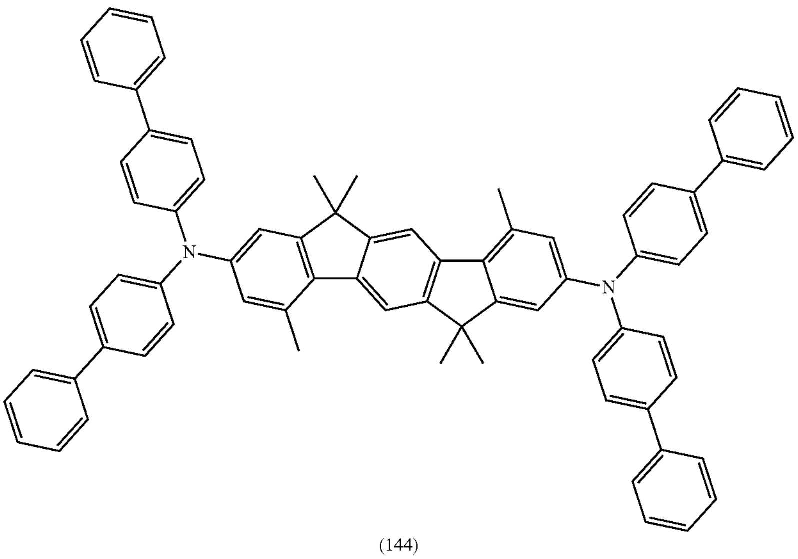
(144)

-continued
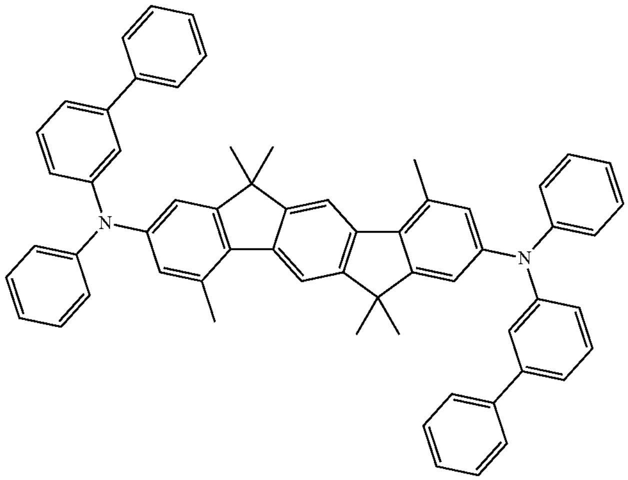 [SMILES: Cc1cc(N(c2ccccc2)c2cccc(-c3ccccc3)c2)cc2c1-c1cc3c(cc1C2(C)C)-c1c(C)cc(N(c2ccccc2)c2cccc(-c4ccccc4)c2)cc1C3(C)C]
(145)
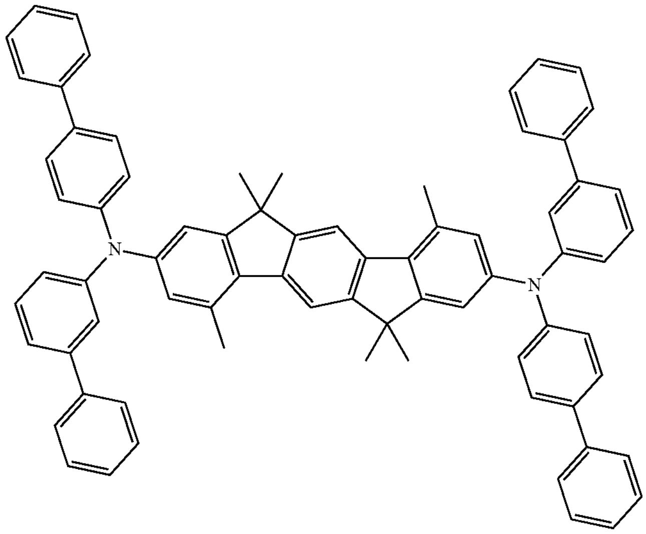 [SMILES: Cc1cc(N(c2ccc(-c3ccccc3)cc2)c2cccc(-c3ccccc3)c2)cc2c1-c1cc3c(cc1C2(C)C)-c1c(C)cc(N(c2ccc(-c4ccccc4)cc2)c2cccc(-c4ccccc4)c2)cc1C3(C)C]
(146)
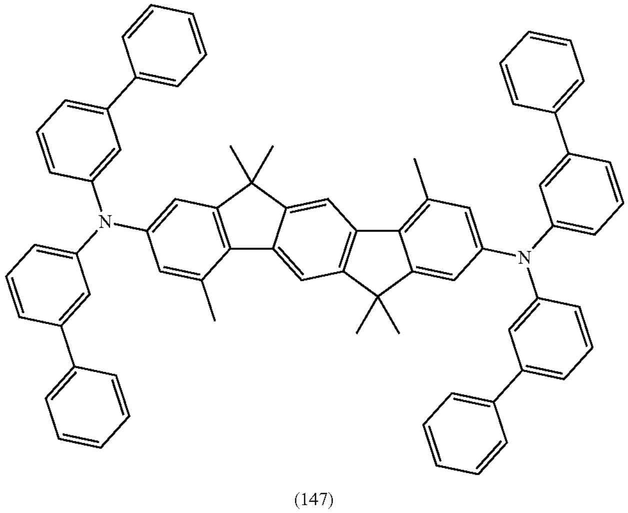
(147)

-continued
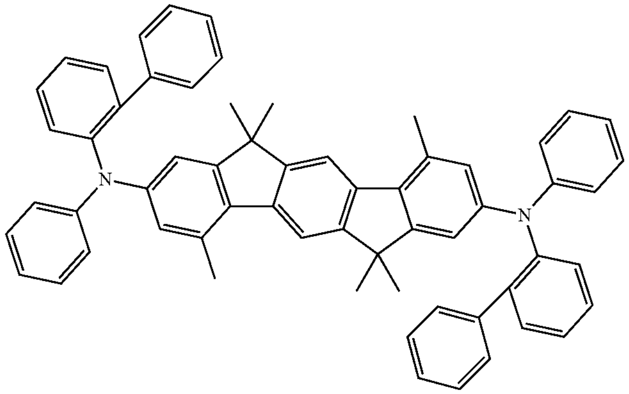 [SMILES: Cc1cc(N(c2ccccc2)c2ccccc2-c2ccccc2)cc2c1-c1cc3c(cc1C2(C)C)-c1c(C)cc(N(c2ccccc2)c2ccccc2-c2ccccc2)cc1C3(C)C]
(148)
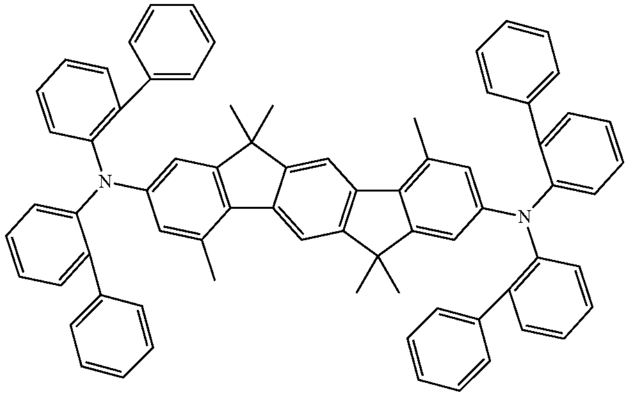 [SMILES: Cc1cc(N(c2ccccc2-c2ccccc2)c2ccccc2-c2ccccc2)cc2c1-c1cc3c(cc1C2(C)C)-c1c(C)cc(N(c2ccccc2-c2ccccc2)c2ccccc2-c2ccccc2)cc1C3(C)C]
(149)
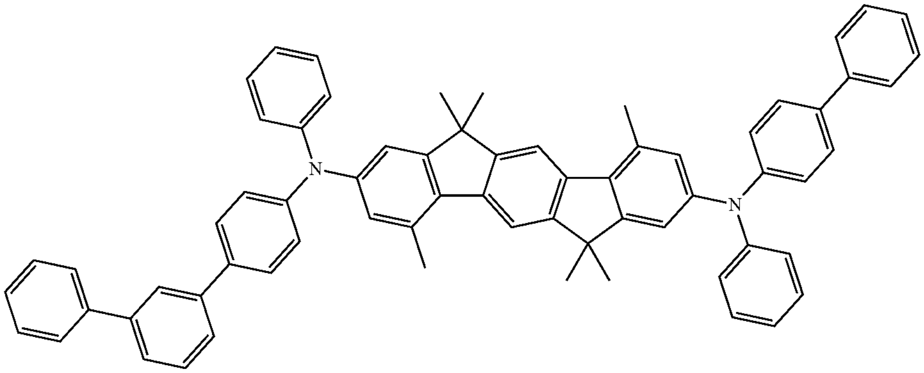 [SMILES: Cc1cc(N(c2ccccc2)c2ccc(-c3ccccc3)cc2)cc2c1-c1cc3c(cc1C2(C)C)-c1c(C)cc(N(c2ccccc2)c2ccc(-c4cccc(-c5ccccc5)c4)cc2)cc1C3(C)C]
(150)

-continued
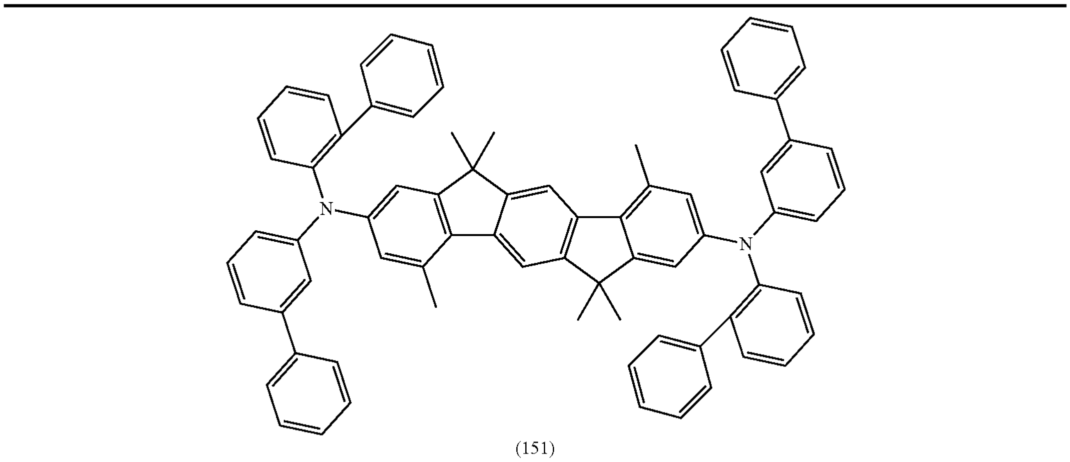
(151)
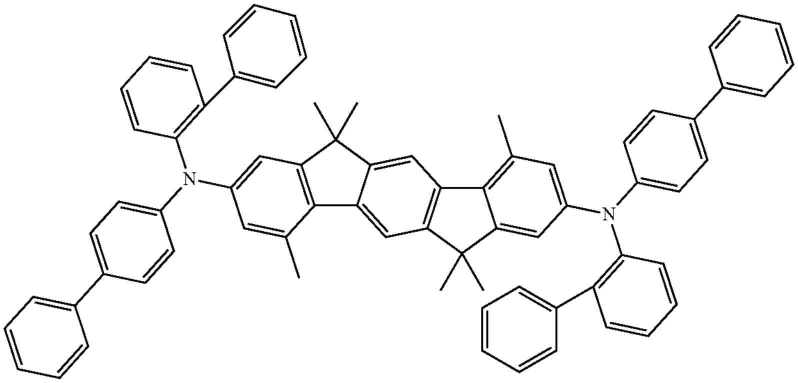 [SMILES: Cc1cc(N(c2ccc(-c3ccccc3)cc2)c2ccccc2-c2ccccc2)cc2c1-c1cc3c(cc1C2(C)C)-c1c(C)cc(N(c2ccc(-c4ccccc4)cc2)c2ccccc2-c2ccccc2)cc1C3(C)C]
(152)
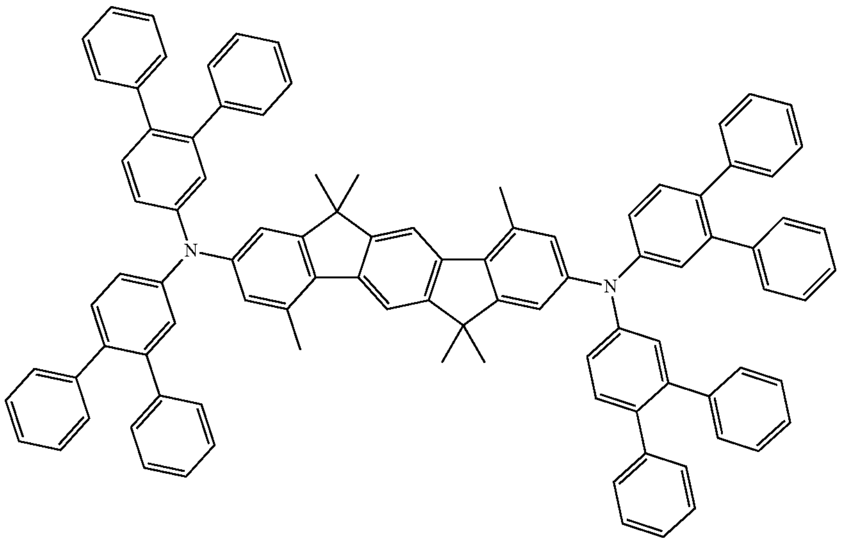 [SMILES: Cc1cc(N(c2ccc(-c3ccccc3)c(-c3ccccc3)c2)c2ccc(-c3ccccc3)c(-c3ccccc3)c2)cc2c1-c1cc3c(cc1C2(C)C)-c1c(C)cc(N(c2ccc(-c4ccccc4)c(-c4ccccc4)c2)c2ccc(-c4ccccc4)c(-c4ccccc4)c2)cc1C3(C)C]
(153)

-continued
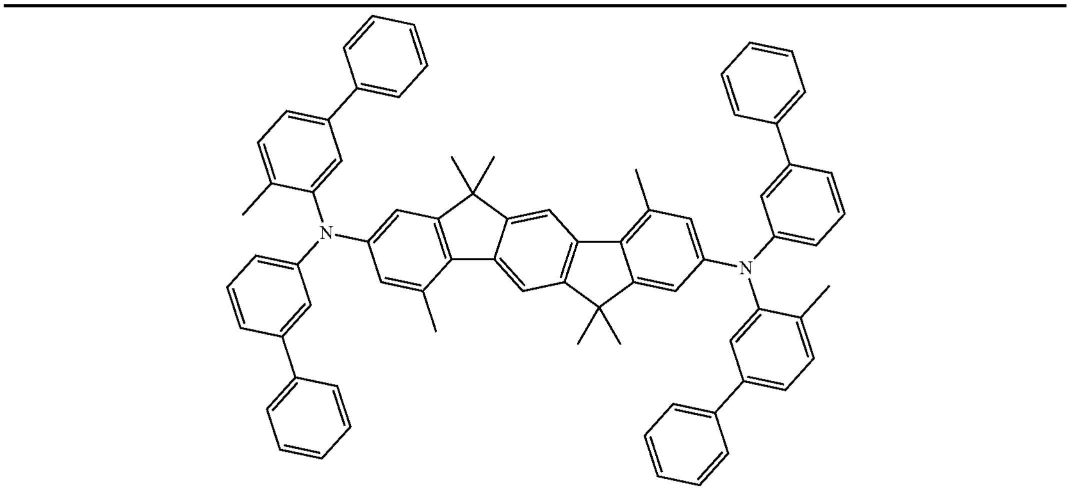
(154)
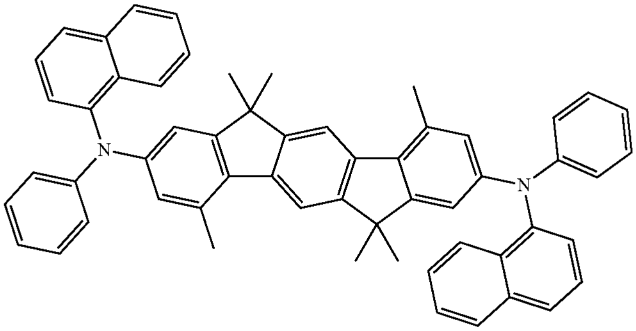 [SMILES: Cc1cc(N(c2ccccc2)c2cccc3ccccc23)cc2c1-c1cc3c(cc1C2(C)C)-c1c(C)cc(N(c2ccccc2)c2cccc4ccccc24)cc1C3(C)C]
(155)
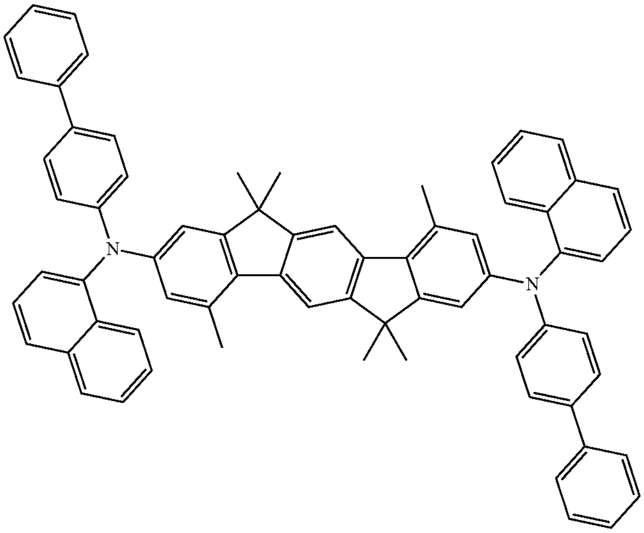 [SMILES: Cc1cc(N(c2ccc(-c3ccccc3)cc2)c2cccc3ccccc23)cc2c1-c1cc3c(cc1C2(C)C)-c1c(C)cc(N(c2ccc(-c4ccccc4)cc2)c2cccc4ccccc24)cc1C3(C)C]
(156)

-continued
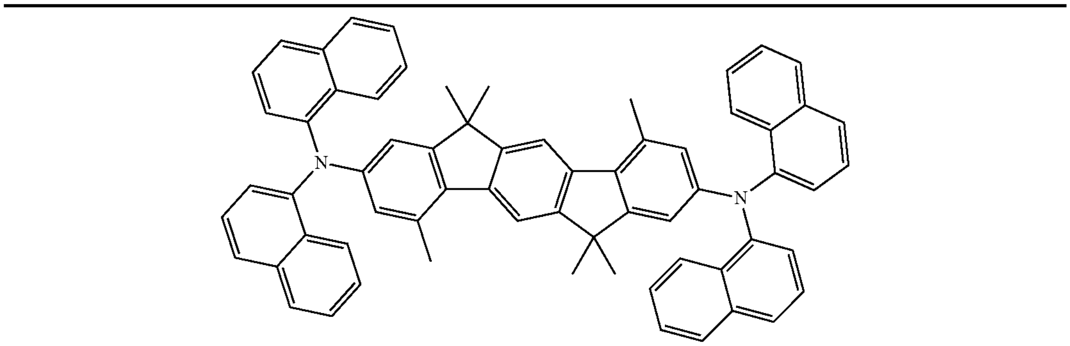
(157)
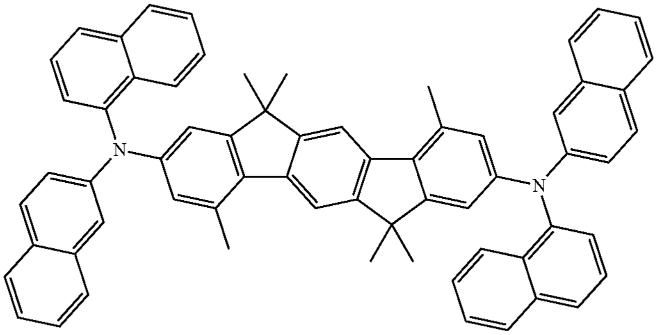 [SMILES: Cc1cc(N(c2ccc3ccccc3c2)c2cccc3ccccc23)cc2c1-c1cc3c(cc1C2(C)C)-c1c(C)cc(N(c2ccc4ccccc4c2)c2cccc4ccccc24)cc1C3(C)C]
(158)
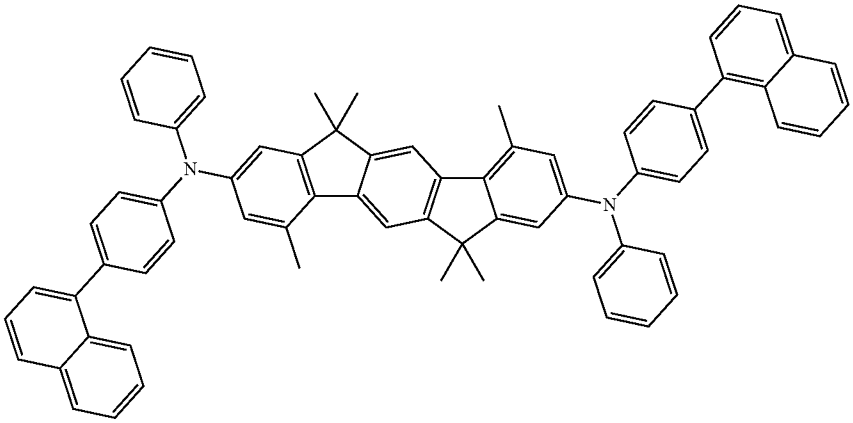 [SMILES: Cc1cc(N(c2ccccc2)c2ccc(-c3cccc4ccccc34)cc2)cc2c1-c1cc3c(cc1C2(C)C)-c1c(C)cc(N(c2ccccc2)c2ccc(-c4cccc5ccccc45)cc2)cc1C3(C)C]
(159)
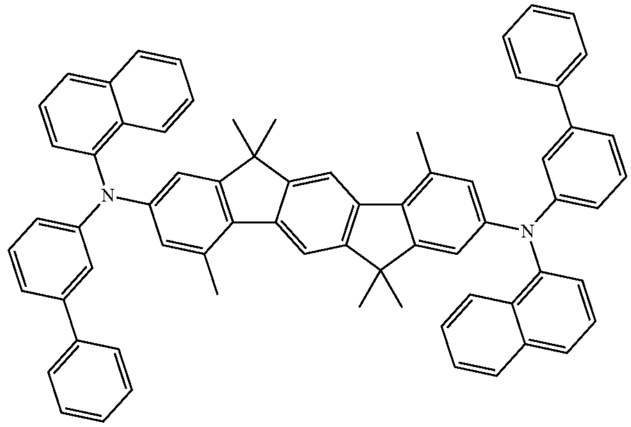 [SMILES: Cc1cc(N(c2cccc(-c3ccccc3)c2)c2cccc3ccccc23)cc2c1-c1cc3c(cc1C2(C)C)-c1c(C)cc(N(c2cccc(-c4ccccc4)c2)c2cccc4ccccc24)cc1C3(C)C]
(160)

-continued
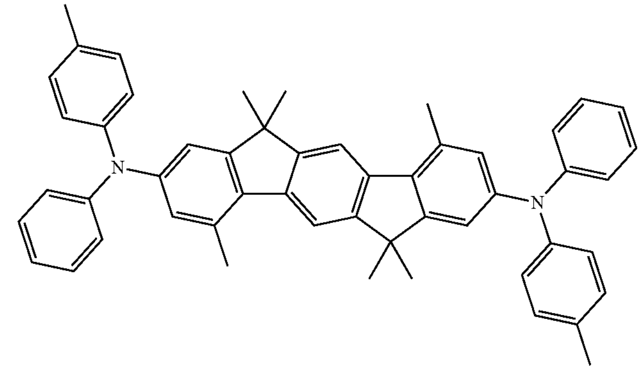 [SMILES: Cc1ccc(N(c2ccccc2)c2cc(C)c3c(c2)C(C)(C)c2cc4c(cc2-3)C(C)(C)c2cc(N(c3ccccc3)c3ccc(C)cc3)cc(C)c2-4)cc1]
(161)
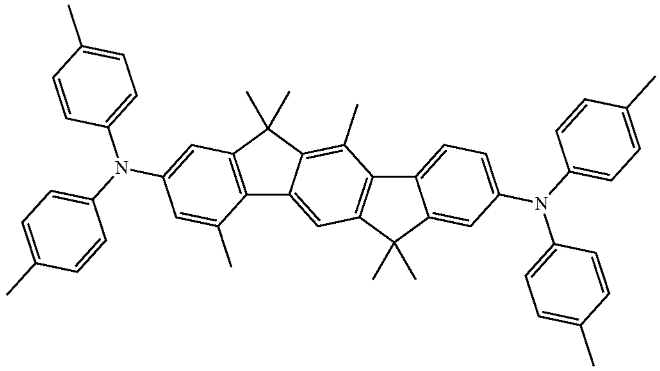
(162)
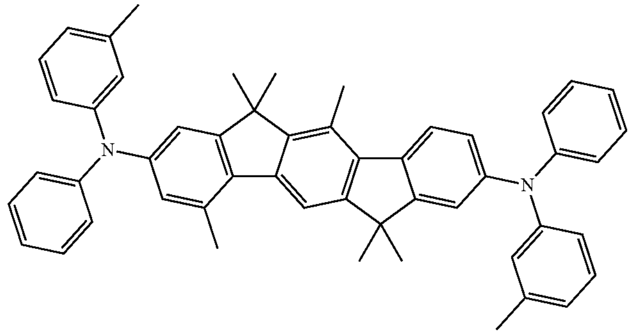 [SMILES: Cc1cccc(N(c2ccccc2)c2ccc3c(c2)C(C)(C)c2cc4c(c(C)c2-3)C(C)(C)c2cc(N(c3ccccc3)c3cccc(C)c3)cc(C)c2-4)c1]
(163)
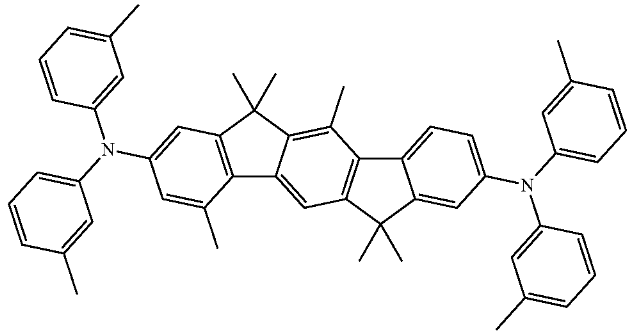 [SMILES: Cc1cccc(N(c2cccc(C)c2)c2ccc3c(c2)C(C)(C)c2cc4c(c(C)c2-3)C(C)(C)c2cc(N(c3cccc(C)c3)c3cccc(C)c3)cc(C)c2-4)c1]
(164)

-continued
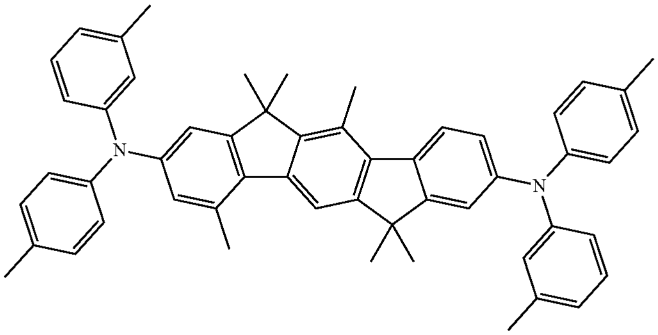
(165)
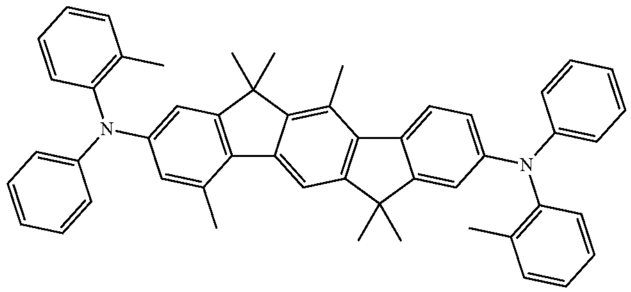 [SMILES: Cc1ccccc1N(c1ccccc1)c1ccc2c(c1)C(C)(C)c1cc3c(c(C)c1-2)C(C)(C)c1cc(N(c2ccccc2)c2ccccc2C)cc(C)c1-3]
(166)
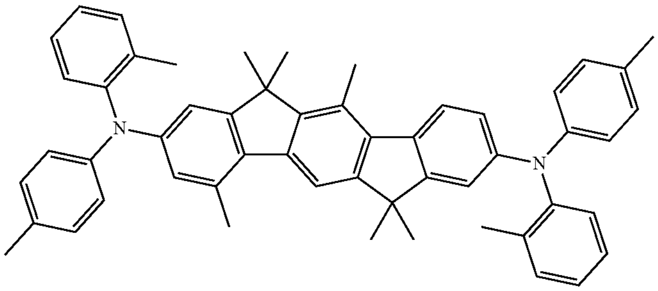
(167)
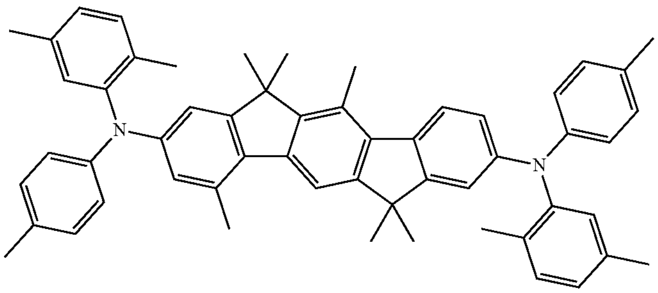
(168)

-continued
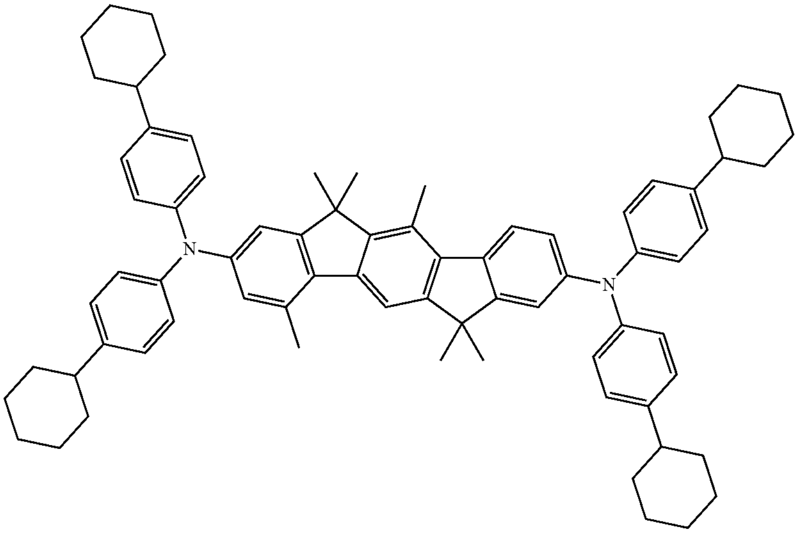 [SMILES: Cc1cc(N(c2ccc(C3CCCCC3)cc2)c2ccc(C3CCCCC3)cc2)cc2c1-c1cc3c(c(C)c1C2(C)C)-c1ccc(N(c2ccc(C4CCCCC4)cc2)c2ccc(C4CCCCC4)cc2)cc1C3(C)C]
(169)
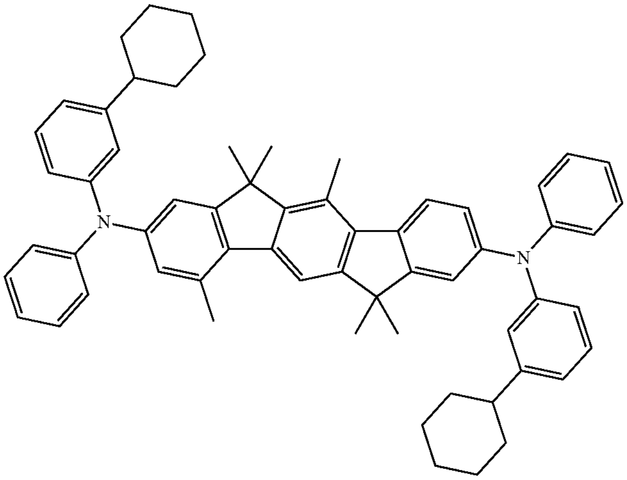 [SMILES: Cc1cc(N(c2ccccc2)c2cccc(C3CCCCC3)c2)cc2c1-c1cc3c(c(C)c1C2(C)C)-c1ccc(N(c2ccccc2)c2cccc(C4CCCCC4)c2)cc1C3(C)C]
(170)
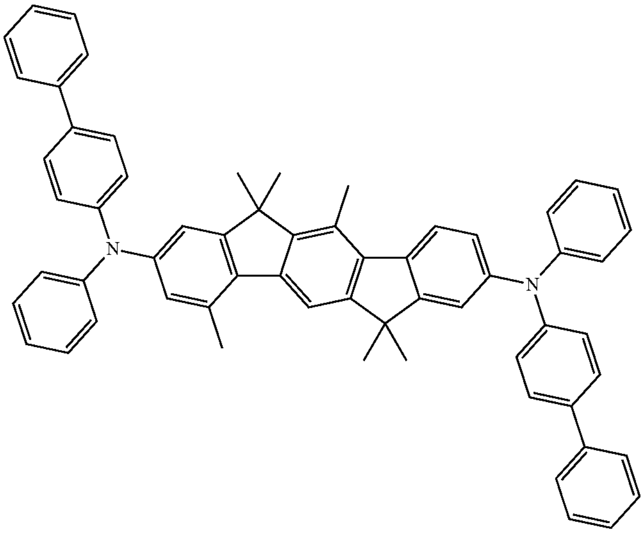 [SMILES: Cc1cc(N(c2ccccc2)c2ccc(-c3ccccc3)cc2)cc2c1-c1cc3c(c(C)c1C2(C)C)-c1ccc(N(c2ccccc2)c2ccc(-c4ccccc4)cc2)cc1C3(C)C]
(171)

-continued
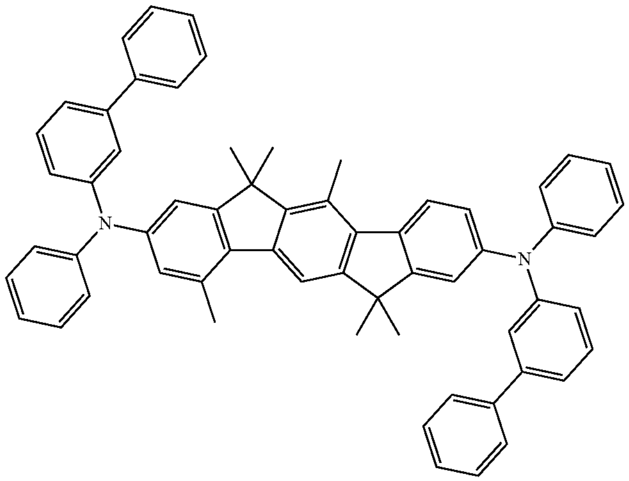 [SMILES: Cc1cc(N(c2ccccc2)c2cccc(-c3ccccc3)c2)cc2c1-c1cc3c(c(C)c1C2(C)C)-c1ccc(N(c2ccccc2)c2cccc(-c4ccccc4)c2)cc1C3(C)C]
(172)
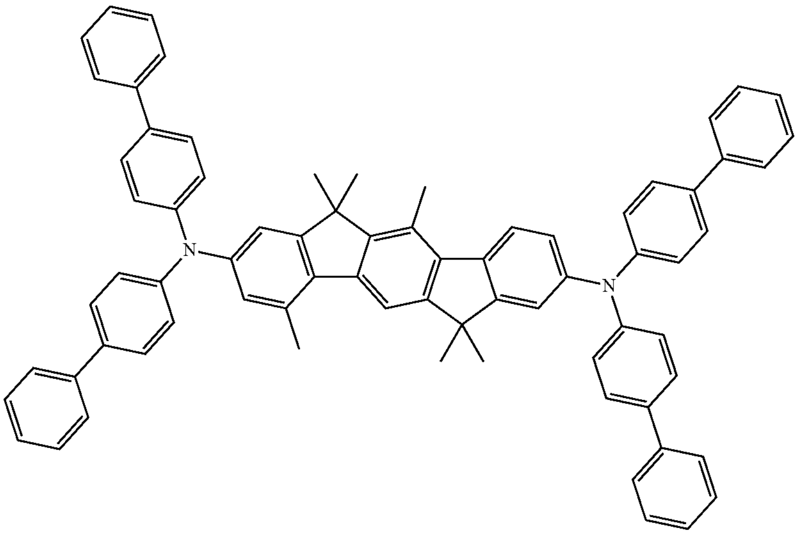 [SMILES: Cc1cc(N(c2ccc(-c3ccccc3)cc2)c2ccc(-c3ccccc3)cc2)cc2c1-c1cc3c(c(C)c1C2(C)C)-c1ccc(N(c2ccc(-c4ccccc4)cc2)c2ccc(-c4ccccc4)cc2)cc1C3(C)C]
(173)
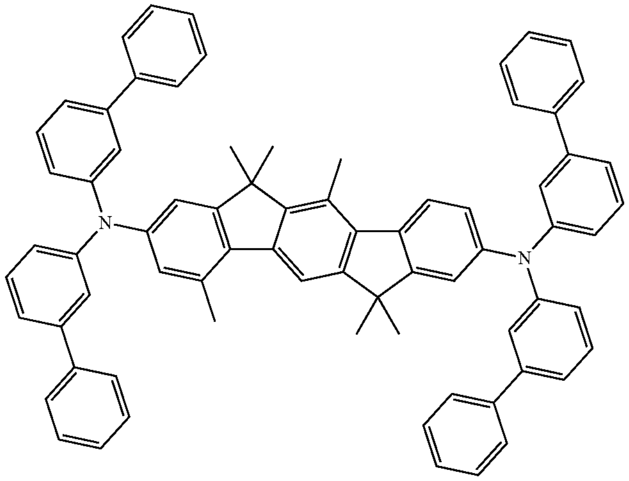 [SMILES: Cc1cc(N(c2cccc(-c3ccccc3)c2)c2cccc(-c3ccccc3)c2)cc2c1-c1cc3c(c(C)c1C2(C)C)-c1ccc(N(c2cccc(-c4ccccc4)c2)c2cccc(-c4ccccc4)c2)cc1C3(C)C]
(174)

-continued
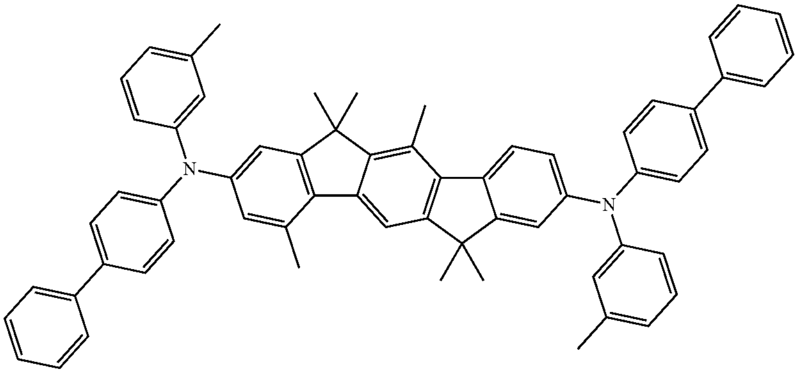 [SMILES: Cc1cccc(N(c2ccc(-c3ccccc3)cc2)c2ccc3c(c2)C(C)(C)c2cc4c(c(C)c2-3)C(C)(C)c2cc(N(c3ccc(-c5ccccc5)cc3)c3cccc(C)c3)cc(C)c2-4)c1]
(175)
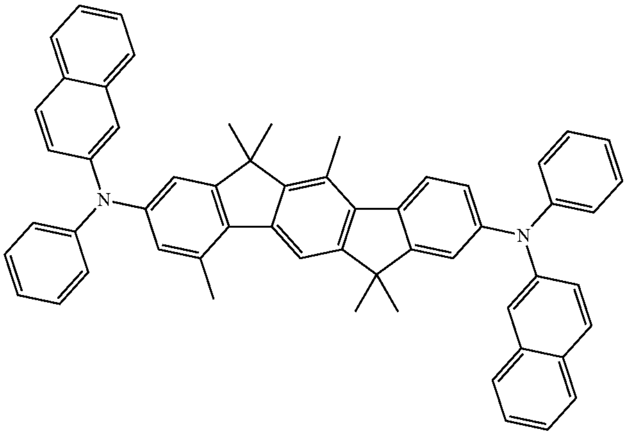 [SMILES: Cc1cc(N(c2ccccc2)c2ccc3ccccc3c2)cc2c1-c1cc3c(c(C)c1C2(C)C)-c1ccc(N(c2ccccc2)c2ccc4ccccc4c2)cc1C3(C)C]
(176)
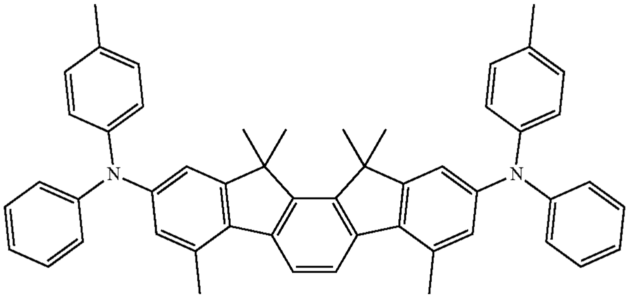 [SMILES: Cc1ccc(N(c2ccccc2)c2cc(C)c3c(c2)C(C)(C)c2c-3ccc3c2C(C)(C)c2cc(N(c4ccccc4)c4ccc(C)cc4)cc(C)c2-3)cc1]
(177)
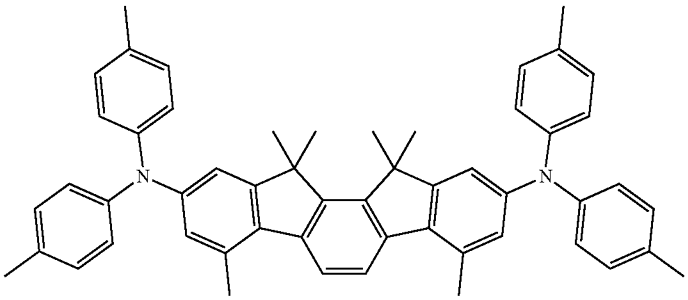
(178)

-continued
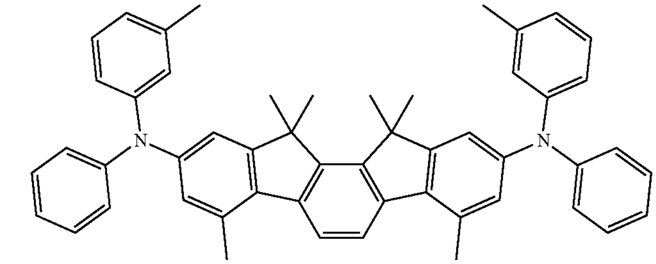 [SMILES: Cc1cccc(N(c2ccccc2)c2cc(C)c3c(c2)C(C)(C)c2c-3ccc3c2C(C)(C)c2cc(N(c4ccccc4)c4cccc(C)c4)cc(C)c2-3)c1]
(179)
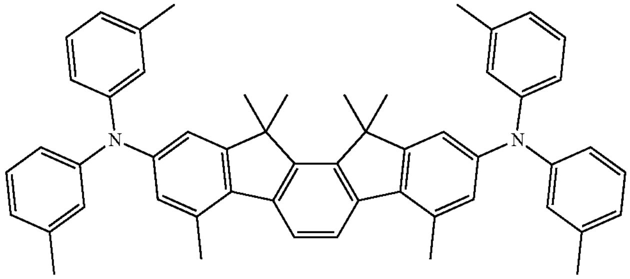 [SMILES: Cc1cccc(N(c2cccc(C)c2)c2cc(C)c3c(c2)C(C)(C)c2c-3ccc3c2C(C)(C)c2cc(N(c4cccc(C)c4)c4cccc(C)c4)cc(C)c2-3)c1]
(180)
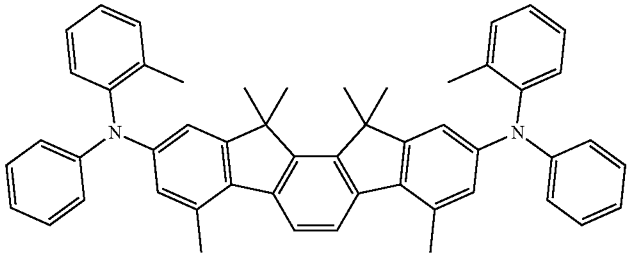 [SMILES: Cc1ccccc1N(c1ccccc1)c1cc(C)c2c(c1)C(C)(C)c1c-2ccc2c1C(C)(C)c1cc(N(c3ccccc3)c3ccccc3C)cc(C)c1-2]
(181)
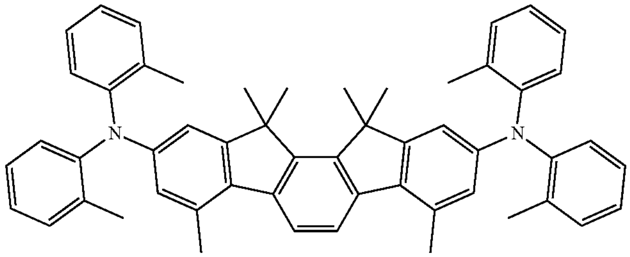 [SMILES: Cc1ccccc1N(c1cc(C)c2c(c1)C(C)(C)c1c-2ccc2c1C(C)(C)c1cc(N(c3ccccc3C)c3ccccc3C)cc(C)c1-2)c1ccccc1C]
(182)
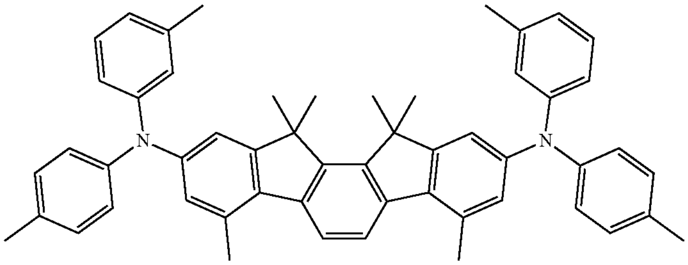
(183)

-continued
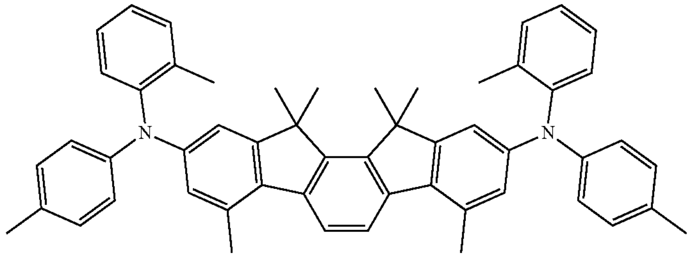
(184)
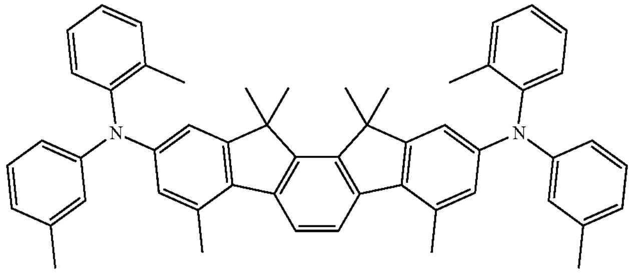 [SMILES: Cc1cccc(N(c2cc(C)c3c(c2)C(C)(C)c2c-3ccc3c2C(C)(C)c2cc(N(c4cccc(C)c4)c4ccccc4C)cc(C)c2-3)c2ccccc2C)c1]
(185)
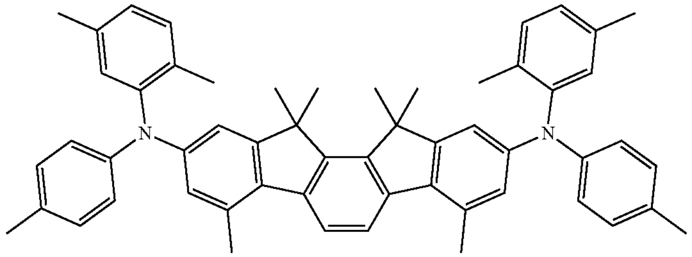
(186)
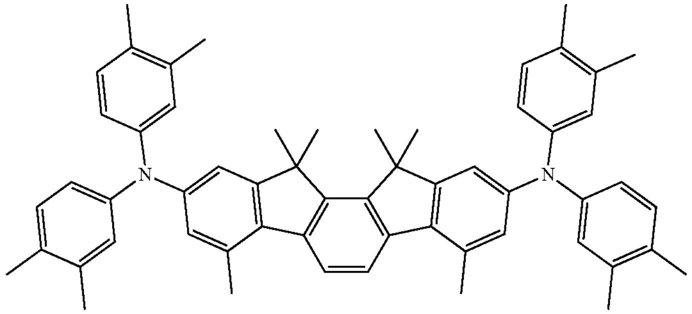
(187)
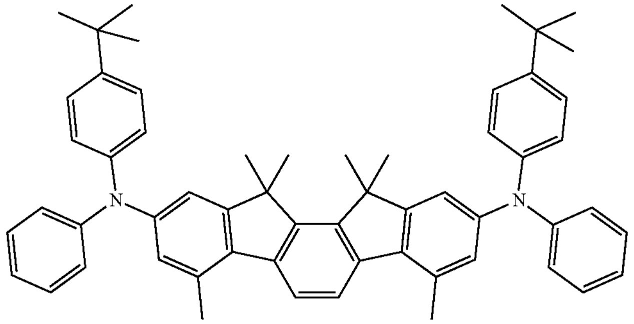 [SMILES: Cc1cc(N(c2ccccc2)c2ccc(C(C)(C)C)cc2)cc2c1-c1ccc3c(c1C2(C)C)C(C)(C)c1cc(N(c2ccccc2)c2ccc(C(C)(C)C)cc2)cc(C)c1-3]
(188)

-continued
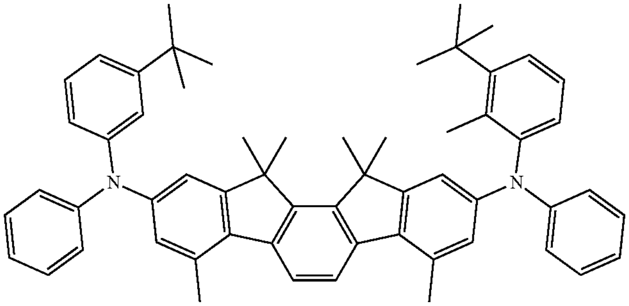 [SMILES: Cc1cc(N(c2ccccc2)c2cccc(C(C)(C)C)c2)cc2c1-c1ccc3c(c1C2(C)C)C(C)(C)c1cc(N(c2ccccc2)c2cccc(C(C)(C)C)c2C)cc(C)c1-3]
(189)
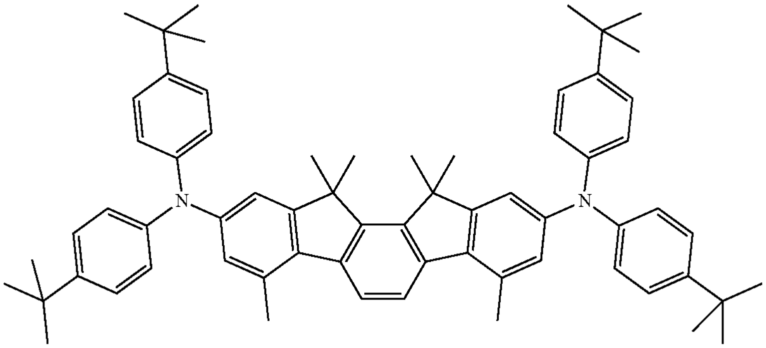 [SMILES: Cc1cc(N(c2ccc(C(C)(C)C)cc2)c2ccc(C(C)(C)C)cc2)cc2c1-c1ccc3c(c1C2(C)C)C(C)(C)c1cc(N(c2ccc(C(C)(C)C)cc2)c2ccc(C(C)(C)C)cc2)cc(C)c1-3]
(190)
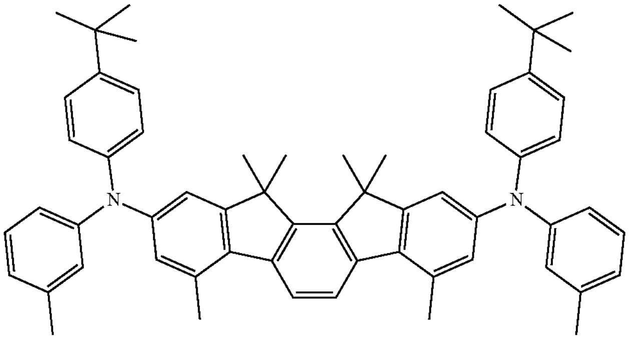 [SMILES: Cc1cccc(N(c2ccc(C(C)(C)C)cc2)c2cc(C)c3c(c2)C(C)(C)c2c-3ccc3c2C(C)(C)c2cc(N(c4ccc(C(C)(C)C)cc4)c4cccc(C)c4)cc(C)c2-3)c1]
(191)
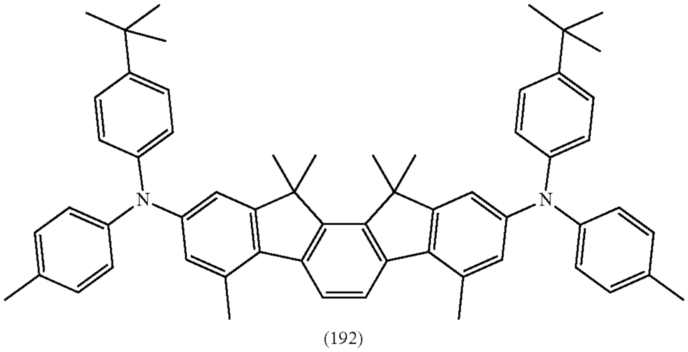
(192)

-continued
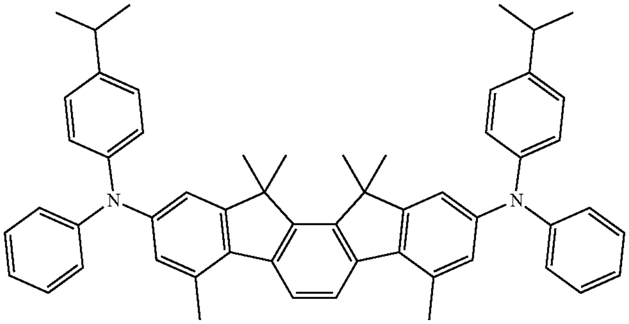 [SMILES: Cc1cc(N(c2ccccc2)c2ccc(C(C)C)cc2)cc2c1-c1ccc3c(c1C2(C)C)C(C)(C)c1cc(N(c2ccccc2)c2ccc(C(C)C)cc2)cc(C)c1-3]
(193)
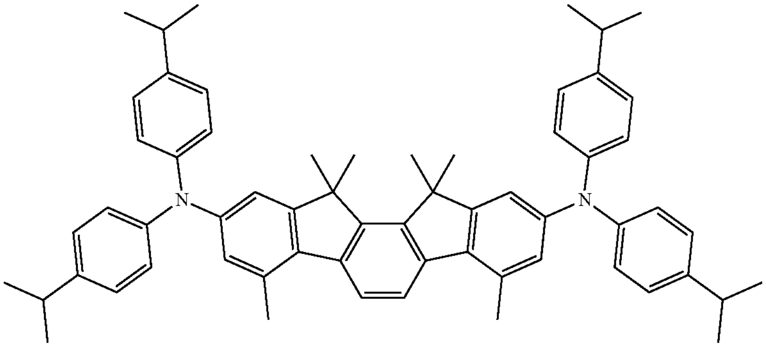 [SMILES: Cc1cc(N(c2ccc(C(C)C)cc2)c2ccc(C(C)C)cc2)cc2c1-c1ccc3c(c1C2(C)C)C(C)(C)c1cc(N(c2ccc(C(C)C)cc2)c2ccc(C(C)C)cc2)cc(C)c1-3]
(194)
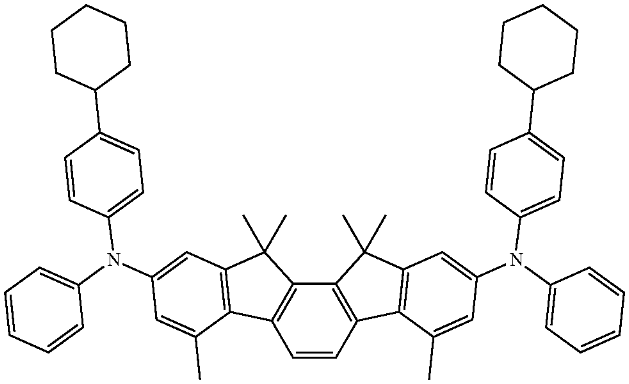 [SMILES: Cc1cc(N(c2ccccc2)c2ccc(C3CCCCC3)cc2)cc2c1-c1ccc3c(c1C2(C)C)C(C)(C)c1cc(N(c2ccccc2)c2ccc(C4CCCCC4)cc2)cc(C)c1-3]
(195)
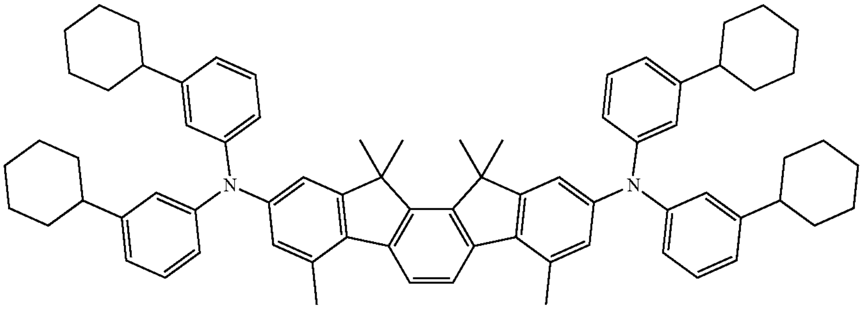 [SMILES: Cc1cc(N(c2cccc(C3CCCCC3)c2)c2cccc(C3CCCCC3)c2)cc2c1-c1ccc3c(c1C2(C)C)C(C)(C)c1cc(N(c2cccc(C4CCCCC4)c2)c2cccc(C4CCCCC4)c2)cc(C)c1-3]
(196)

-continued
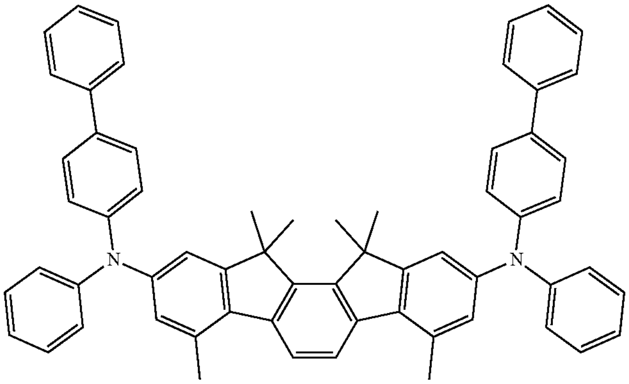 [SMILES: Cc1cc(N(c2ccccc2)c2ccc(-c3ccccc3)cc2)cc2c1-c1ccc3c(c1C2(C)C)C(C)(C)c1cc(N(c2ccccc2)c2ccc(-c4ccccc4)cc2)cc(C)c1-3]
(197)
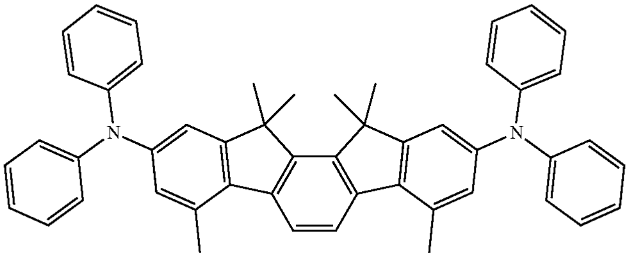 [SMILES: Cc1cc(N(c2ccccc2)c2ccccc2)cc2c1-c1ccc3c(c1C2(C)C)C(C)(C)c1cc(N(c2ccccc2)c2ccccc2)cc(C)c1-3]
(198)
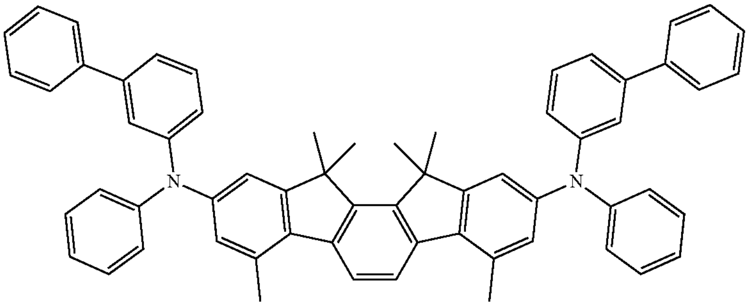 [SMILES: Cc1cc(N(c2ccccc2)c2cccc(-c3ccccc3)c2)cc2c1-c1ccc3c(c1C2(C)C)C(C)(C)c1cc(N(c2ccccc2)c2cccc(-c4ccccc4)c2)cc(C)c1-3]
(199)
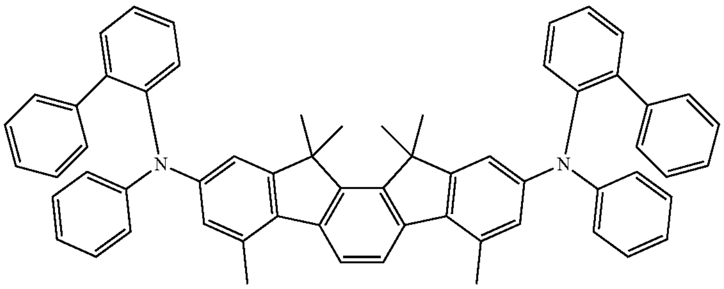 [SMILES: Cc1cc(N(c2ccccc2)c2ccccc2-c2ccccc2)cc2c1-c1ccc3c(c1C2(C)C)C(C)(C)c1cc(N(c2ccccc2)c2ccccc2-c2ccccc2)cc(C)c1-3]
(200)

-continued
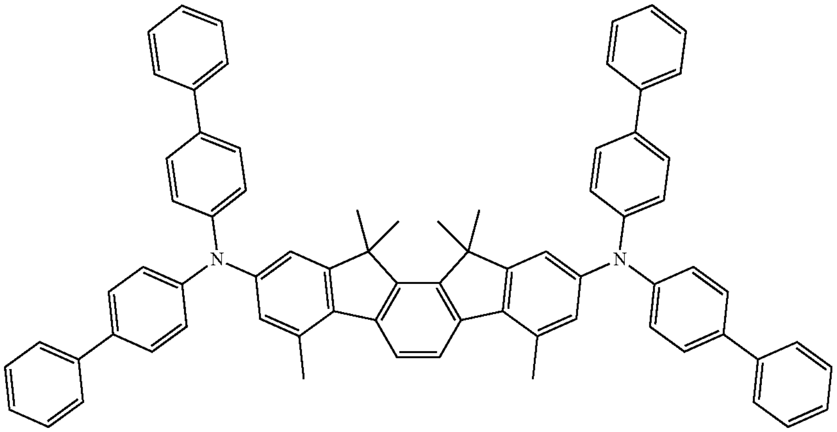 [SMILES: Cc1cc(N(c2ccc(-c3ccccc3)cc2)c2ccc(-c3ccccc3)cc2)cc2c1-c1ccc3c(c1C2(C)C)C(C)(C)c1cc(N(c2ccc(-c4ccccc4)cc2)c2ccc(-c4ccccc4)cc2)cc(C)c1-3]
(201)
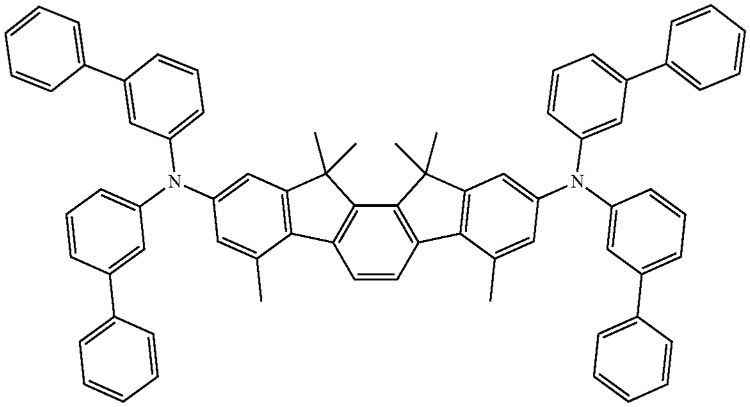 [SMILES: Cc1cc(N(c2cccc(-c3ccccc3)c2)c2cccc(-c3ccccc3)c2)cc2c1-c1ccc3c(c1C2(C)C)C(C)(C)c1cc(N(c2cccc(-c4ccccc4)c2)c2cccc(-c4ccccc4)c2)cc(C)c1-3]
(202)
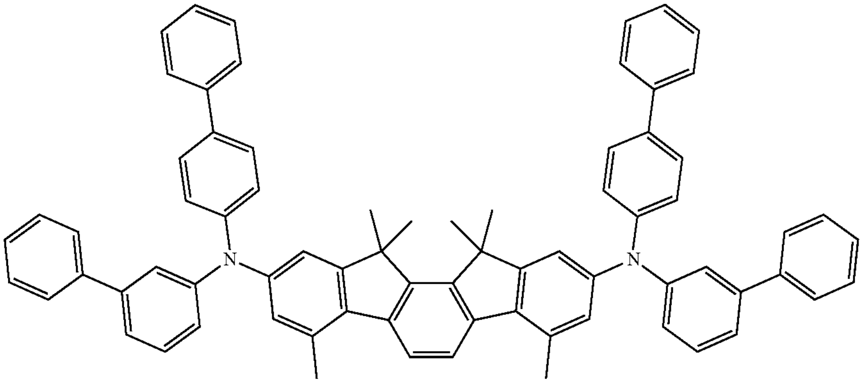 [SMILES: Cc1cc(N(c2ccc(-c3ccccc3)cc2)c2cccc(-c3ccccc3)c2)cc2c1-c1ccc3c(c1C2(C)C)C(C)(C)c1cc(N(c2ccc(-c4ccccc4)cc2)c2cccc(-c4ccccc4)c2)cc(C)c1-3]
(203)
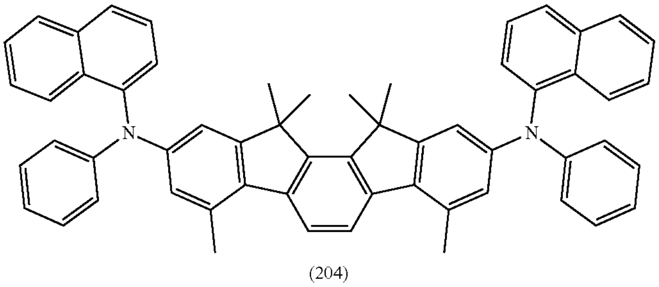
(204)

-continued
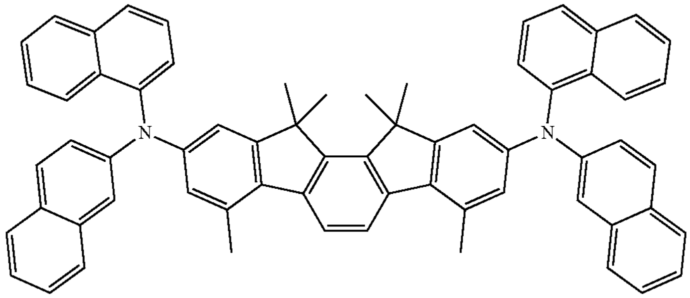 [SMILES: Cc1cc(N(c2ccc3ccccc3c2)c2cccc3ccccc23)cc2c1-c1ccc3c(c1C2(C)C)C(C)(C)c1cc(N(c2ccc4ccccc4c2)c2cccc4ccccc24)cc(C)c1-3]
(205)
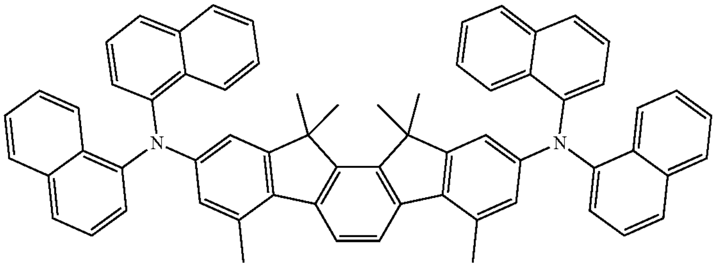 [SMILES: Cc1cc(N(c2cccc3ccccc23)c2cccc3ccccc23)cc2c1-c1ccc3c(c1C2(C)C)C(C)(C)c1cc(N(c2cccc4ccccc24)c2cccc4ccccc24)cc(C)c1-3]
(206)
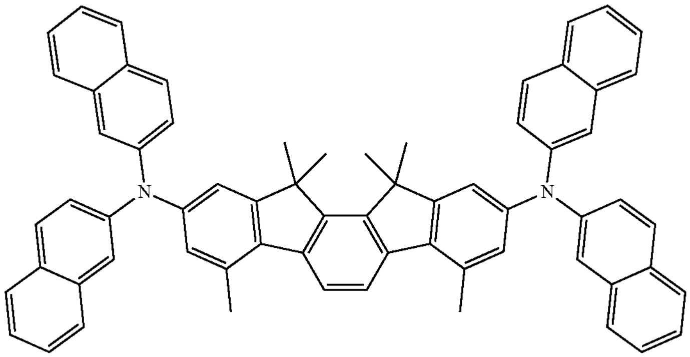 [SMILES: Cc1cc(N(c2ccc3ccccc3c2)c2ccc3ccccc3c2)cc2c1-c1ccc3c(c1C2(C)C)C(C)(C)c1cc(N(c2ccc4ccccc4c2)c2ccc4ccccc4c2)cc(C)c1-3]
(207)
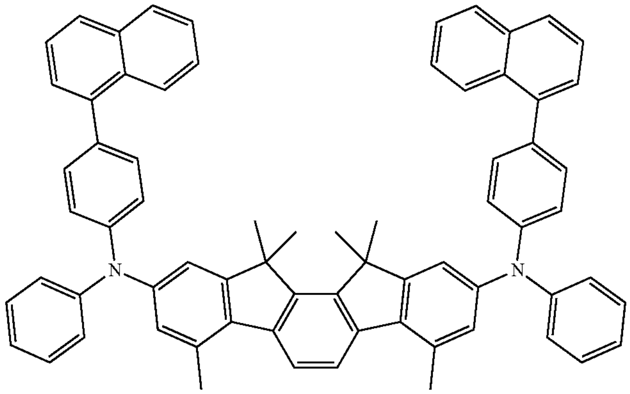 [SMILES: Cc1cc(N(c2ccccc2)c2ccc(-c3cccc4ccccc34)cc2)cc2c1-c1ccc3c(c1C2(C)C)C(C)(C)c1cc(N(c2ccccc2)c2ccc(-c4cccc5ccccc45)cc2)cc(C)c1-3]
(208)

-continued
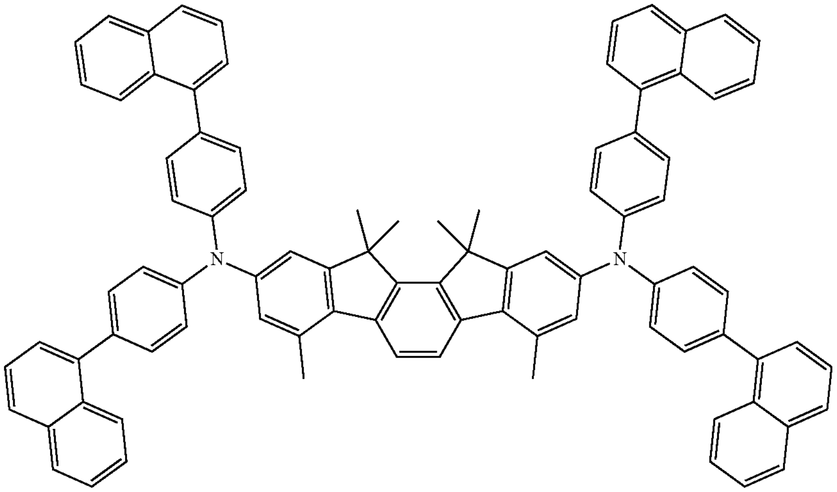 [SMILES: Cc1cc(N(c2ccc(-c3cccc4ccccc34)cc2)c2ccc(-c3cccc4ccccc34)cc2)cc2c1-c1ccc3c(c1C2(C)C)C(C)(C)c1cc(N(c2ccc(-c4cccc5ccccc45)cc2)c2ccc(-c4cccc5ccccc45)cc2)cc(C)c1-3]
(209)
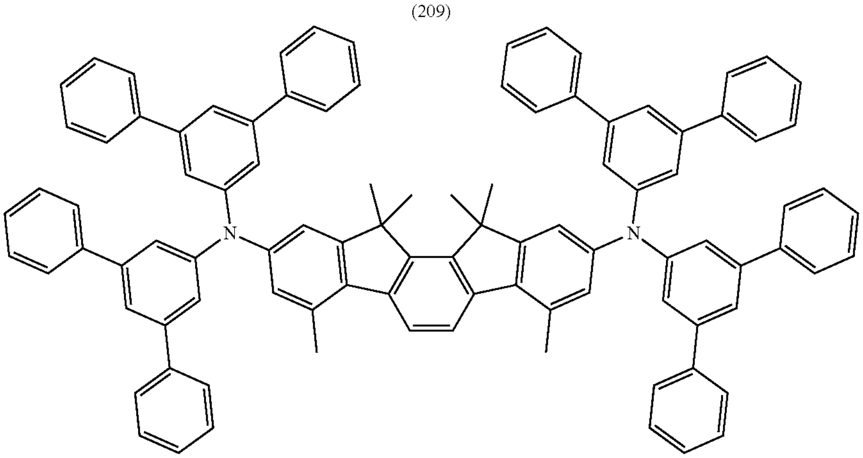
(210)
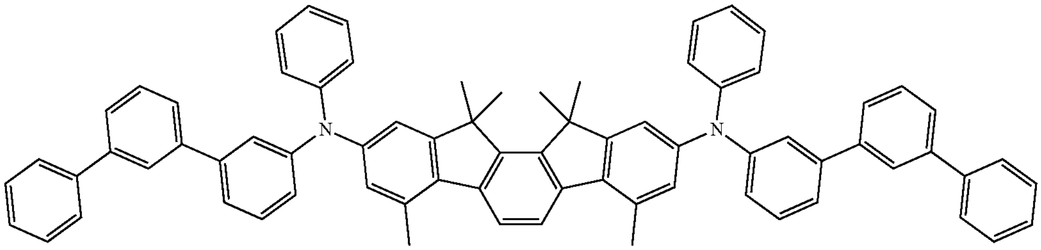 [SMILES: Cc1cc(N(c2ccccc2)c2cccc(-c3cccc(-c4ccccc4)c3)c2)cc2c1-c1ccc3c(c1C2(C)C)C(C)(C)c1cc(N(c2ccccc2)c2cccc(-c4cccc(-c5ccccc5)c4)c2)cc(C)c1-3]
(211)
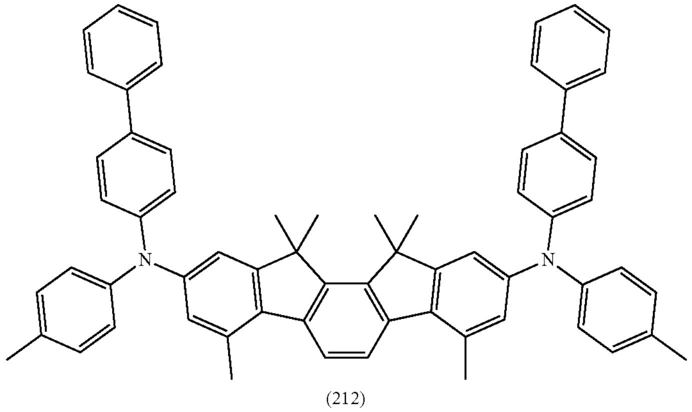
(212)

-continued
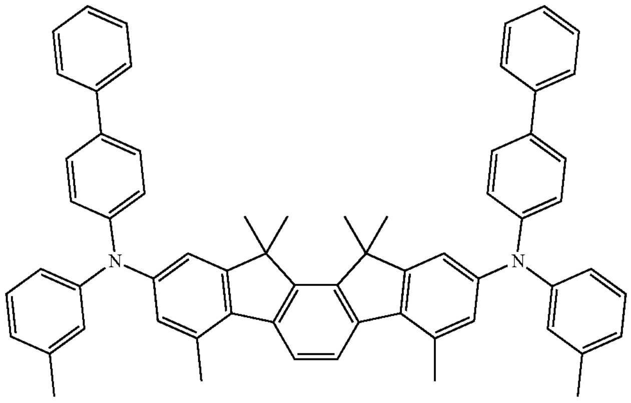 [SMILES: Cc1cccc(N(c2ccc(-c3ccccc3)cc2)c2cc(C)c3c(c2)C(C)(C)c2c-3ccc3c2C(C)(C)c2cc(N(c4ccc(-c5ccccc5)cc4)c4cccc(C)c4)cc(C)c2-3)c1]
(213)
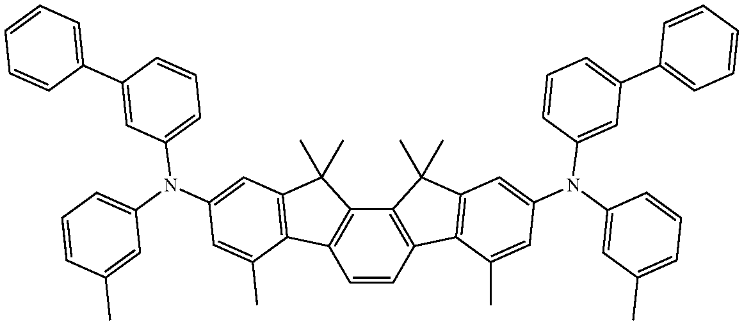 [SMILES: Cc1cccc(N(c2cccc(-c3ccccc3)c2)c2cc(C)c3c(c2)C(C)(C)c2c-3ccc3c2C(C)(C)c2cc(N(c4cccc(C)c4)c4cccc(-c5ccccc5)c4)cc(C)c2-3)c1]
(214)
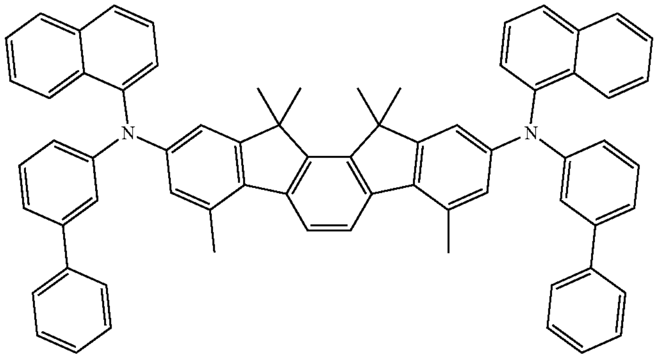 [SMILES: Cc1cc(N(c2cccc(-c3ccccc3)c2)c2cccc3ccccc23)cc2c1-c1ccc3c(c1C2(C)C)C(C)(C)c1cc(N(c2cccc(-c4ccccc4)c2)c2cccc4ccccc24)cc(C)c1-3]
(215)
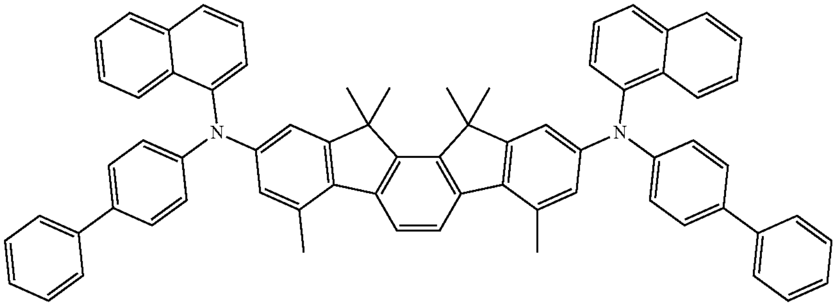 [SMILES: Cc1cc(N(c2ccc(-c3ccccc3)cc2)c2cccc3ccccc23)cc2c1-c1ccc3c(c1C2(C)C)C(C)(C)c1cc(N(c2ccc(-c4ccccc4)cc2)c2cccc4ccccc24)cc(C)c1-3]
(216)

-continued
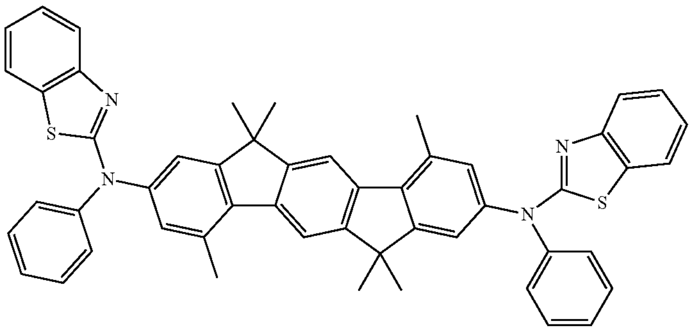 [SMILES: Cc1cc(N(c2ccccc2)c2nc3ccccc3s2)cc2c1-c1cc3c(cc1C2(C)C)-c1c(C)cc(N(c2ccccc2)c2nc4ccccc4s2)cc1C3(C)C]
(217)
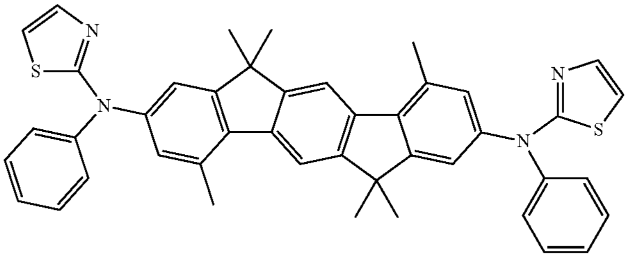 [SMILES: Cc1cc(N(c2ccccc2)c2nccs2)cc2c1-c1cc3c(cc1C2(C)C)-c1c(C)cc(N(c2ccccc2)c2nccs2)cc1C3(C)C]
(218)
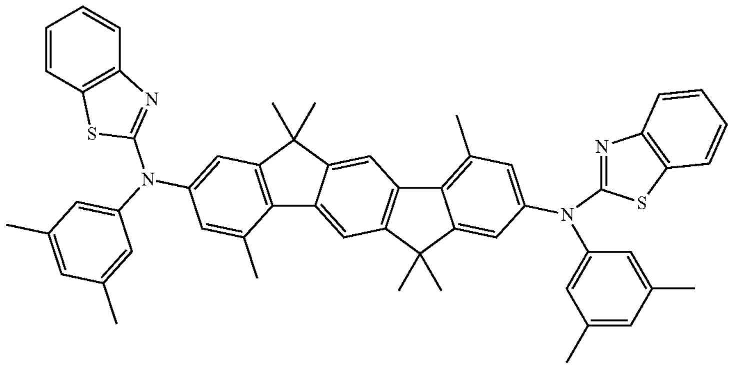 [SMILES: Cc1cc(C)cc(N(c2cc(C)c3c(c2)C(C)(C)c2cc4c(cc2-3)C(C)(C)c2cc(N(c3cc(C)cc(C)c3)c3nc5ccccc5s3)cc(C)c2-4)c2nc3ccccc3s2)c1]
(219)
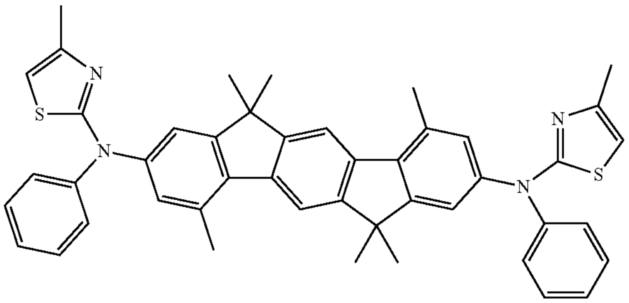 [SMILES: Cc1csc(N(c2ccccc2)c2cc(C)c3c(c2)C(C)(C)c2cc4c(cc2-3)C(C)(C)c2cc(N(c3ccccc3)c3nc(C)cs3)cc(C)c2-4)n1]
(220)

-continued
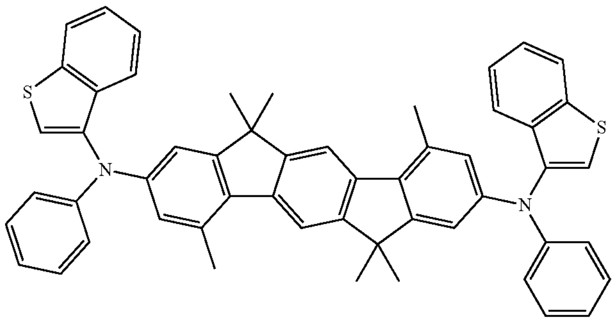 [SMILES: Cc1cc(N(c2ccccc2)c2csc3ccccc23)cc2c1-c1cc3c(cc1C2(C)C)-c1c(C)cc(N(c2ccccc2)c2csc4ccccc24)cc1C3(C)C]
(221)
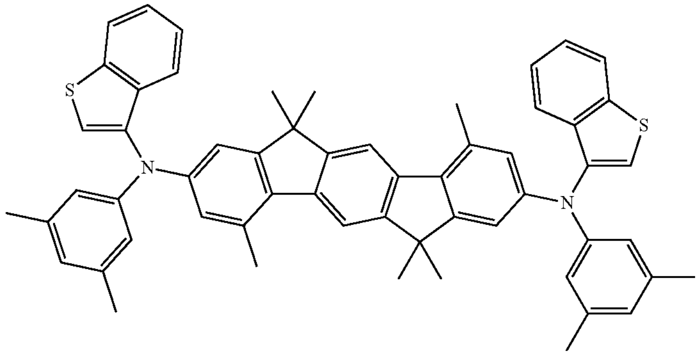
(222)
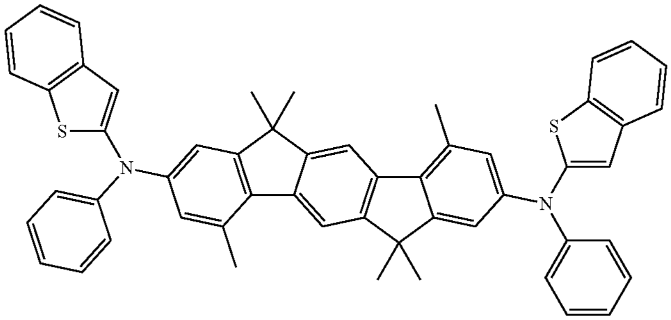 [SMILES: Cc1cc(N(c2ccccc2)c2cc3ccccc3s2)cc2c1-c1cc3c(cc1C2(C)C)-c1c(C)cc(N(c2ccccc2)c2cc4ccccc4s2)cc1C3(C)C]
(223)
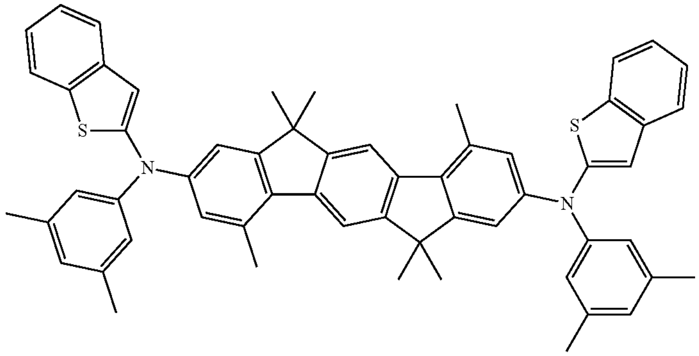
(224)

-continued
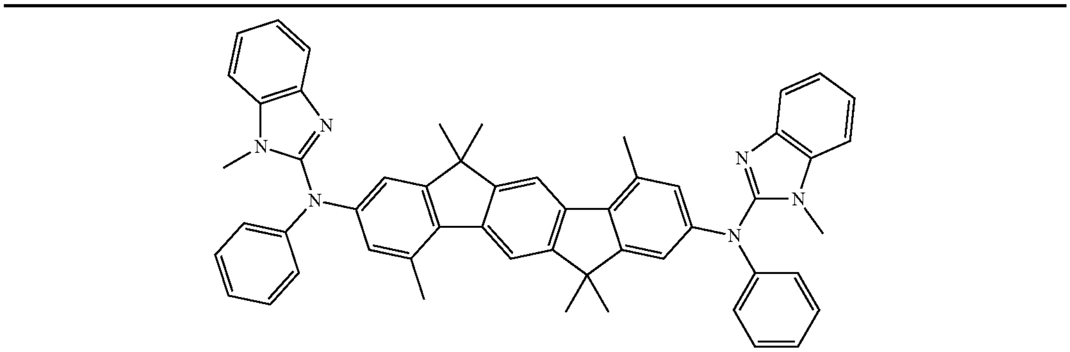
(225)
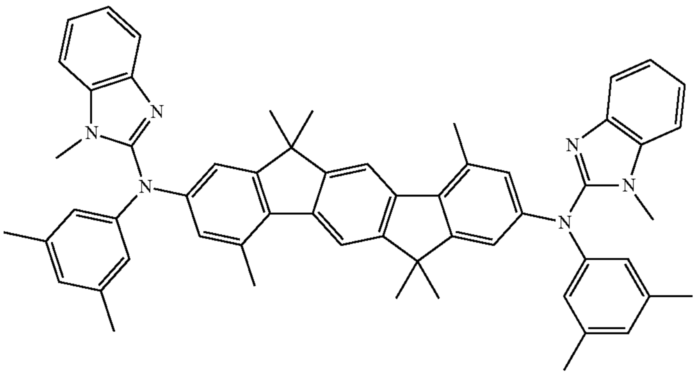
(226)
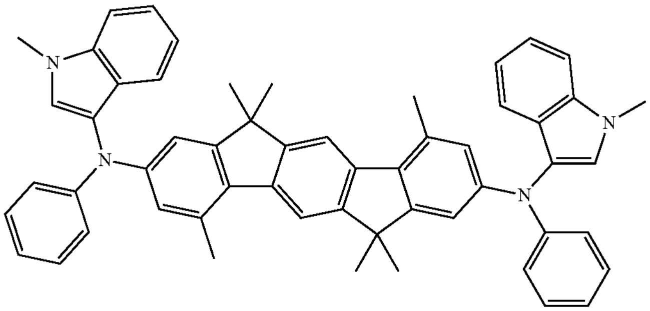 [SMILES: Cc1cc(N(c2ccccc2)c2cn(C)c3ccccc23)cc2c1-c1cc3c(cc1C2(C)C)-c1c(C)cc(N(c2ccccc2)c2cn(C)c4ccccc24)cc1C3(C)C]
(227)
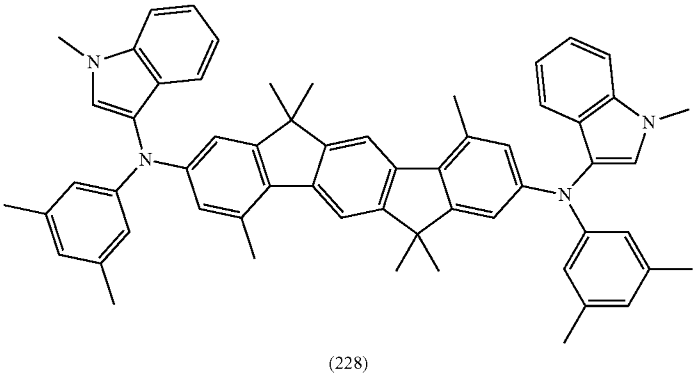
(228)

-continued
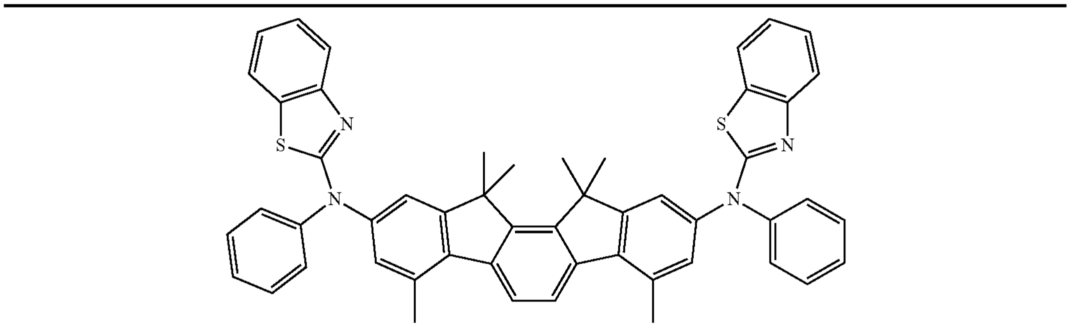
(229)
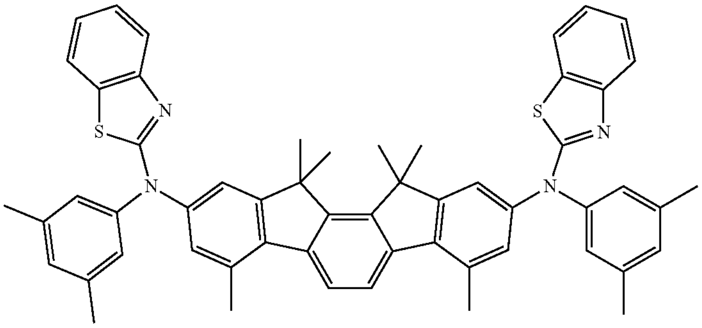
(230)
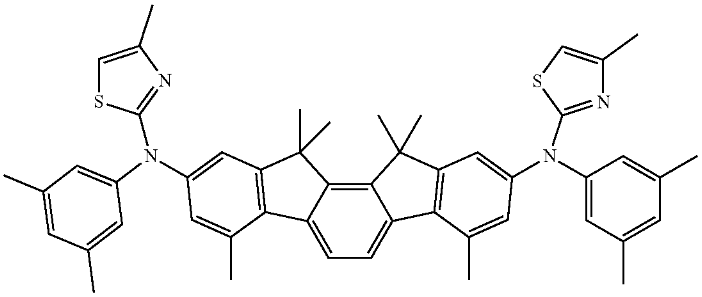
(231)
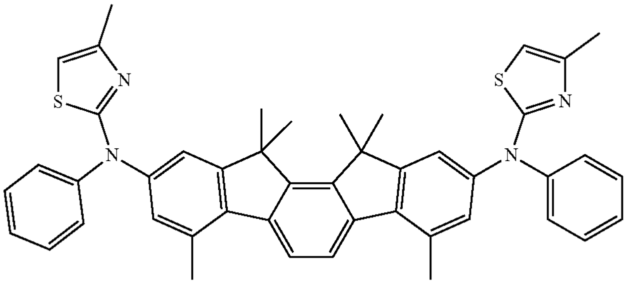 [SMILES: Cc1csc(N(c2ccccc2)c2cc(C)c3c(c2)C(C)(C)c2c-3ccc3c2C(C)(C)c2cc(N(c4ccccc4)c4nc(C)cs4)cc(C)c2-3)n1]
(232)
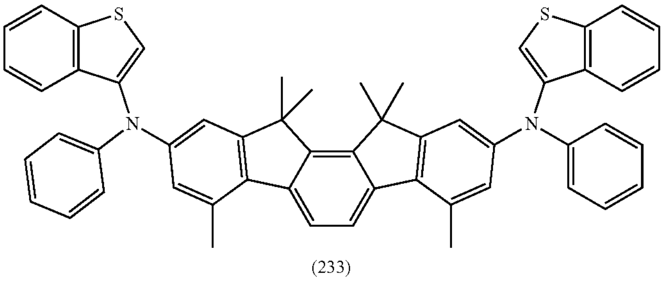
(233)

-continued
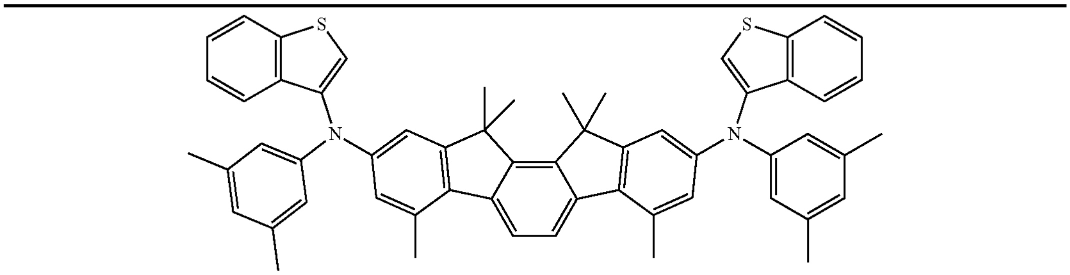
(234)
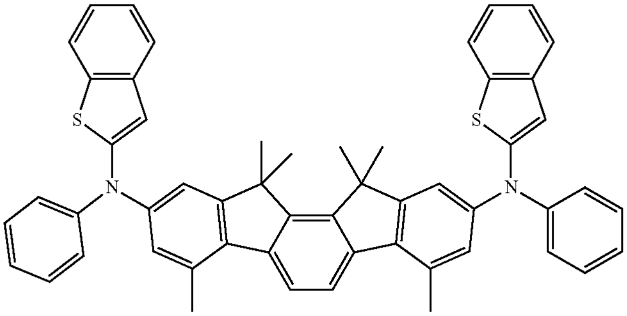 [SMILES: Cc1cc(N(c2ccccc2)c2cc3ccccc3s2)cc2c1-c1ccc3c(c1C2(C)C)C(C)(C)c1cc(N(c2ccccc2)c2cc4ccccc4s2)cc(C)c1-3]
(235)
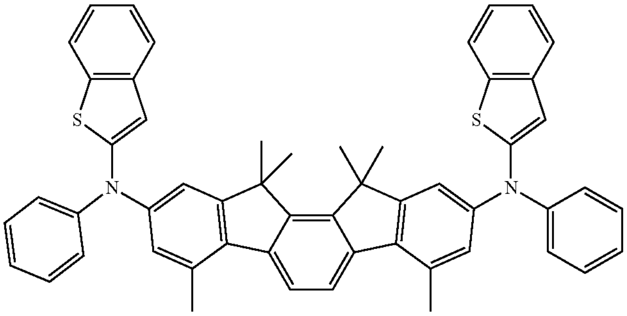 [SMILES: Cc1cc(N(c2ccccc2)c2cc3ccccc3s2)cc2c1-c1ccc3c(c1C2(C)C)C(C)(C)c1cc(N(c2ccccc2)c2cc4ccccc4s2)cc(C)c1-3]
(236)
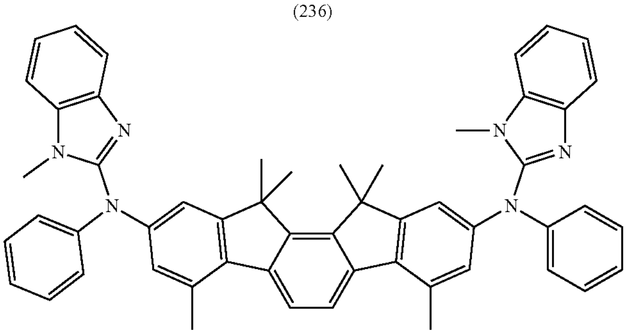
(237)
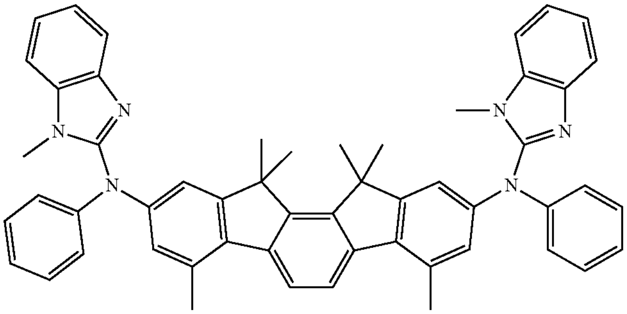 [SMILES: Cc1cc(N(c2ccccc2)c2nc3ccccc3n2C)cc2c1-c1ccc3c(c1C2(C)C)C(C)(C)c1cc(N(c2ccccc2)c2nc4ccccc4n2C)cc(C)c1-3]
(238)

-continued
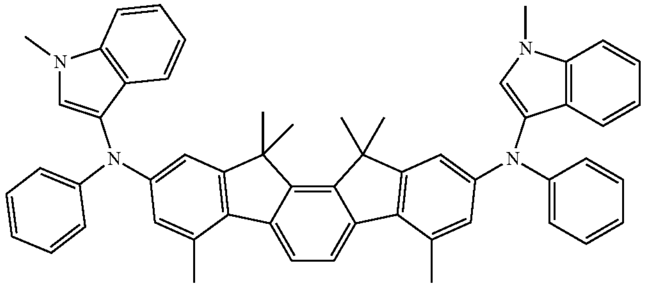 [SMILES: Cc1cc(N(c2ccccc2)c2cn(C)c3ccccc23)cc2c1-c1ccc3c(c1C2(C)C)C(C)(C)c1cc(N(c2ccccc2)c2cn(C)c4ccccc24)cc(C)c1-3]
(239)
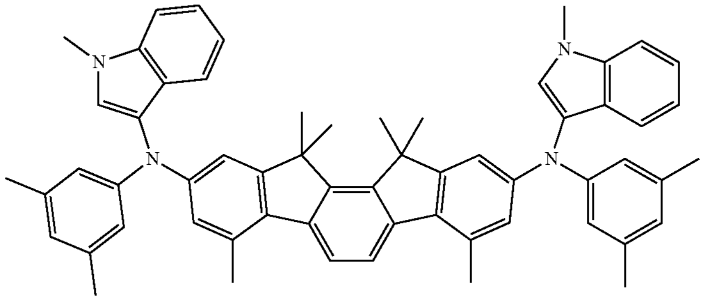
(240)
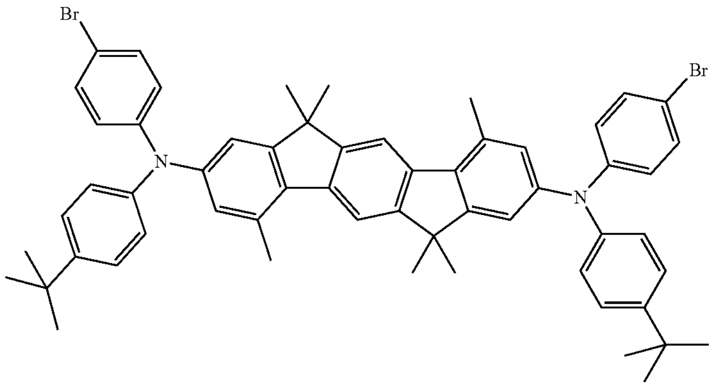 [SMILES: Cc1cc(N(c2ccc(Br)cc2)c2ccc(C(C)(C)C)cc2)cc2c1-c1cc3c(cc1C2(C)C)-c1c(C)cc(N(c2ccc(Br)cc2)c2ccc(C(C)(C)C)cc2)cc1C3(C)C]
(241)
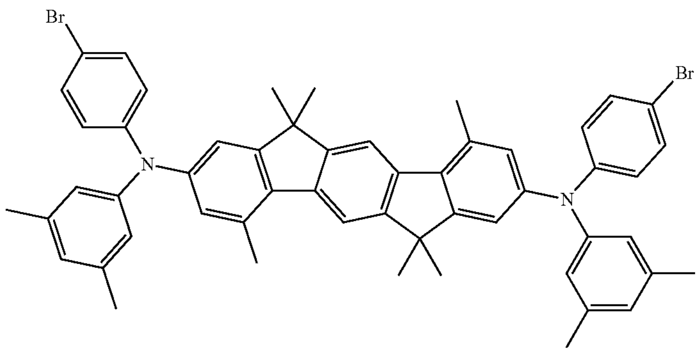
(242)

-continued
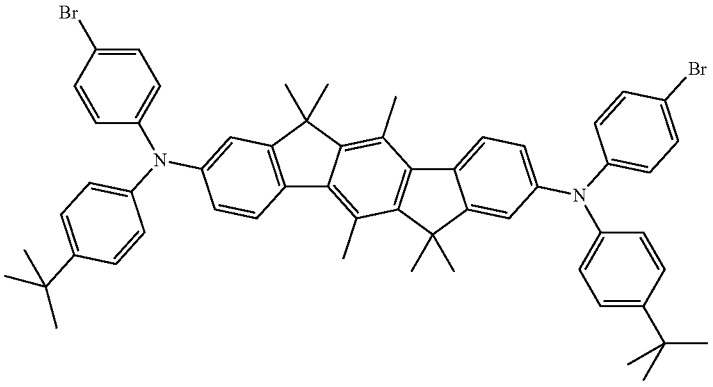 [SMILES: Cc1c2c(c(C)c3c1C(C)(C)c1cc(N(c4ccc(Br)cc4)c4ccc(C(C)(C)C)cc4)ccc1-3)C(C)(C)c1cc(N(c3ccc(Br)cc3)c3ccc(C(C)(C)C)cc3)ccc1-2]
(243)
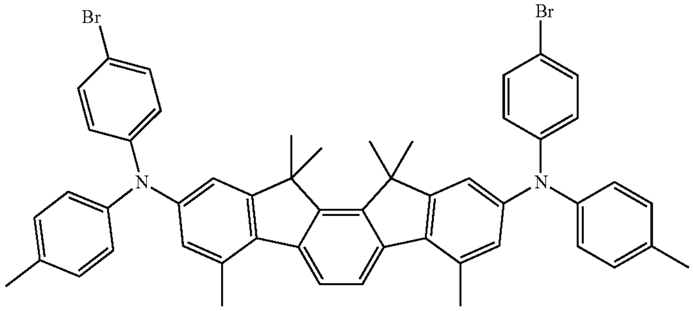
(244)
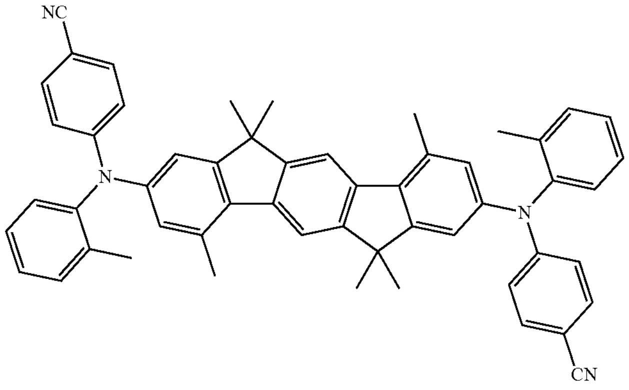 [SMILES: Cc1ccccc1N(c1ccc(C#N)cc1)c1cc(C)c2c(c1)C(C)(C)c1cc3c(cc1-2)C(C)(C)c1cc(N(c2ccc(C#N)cc2)c2ccccc2C)cc(C)c1-3]
(245)
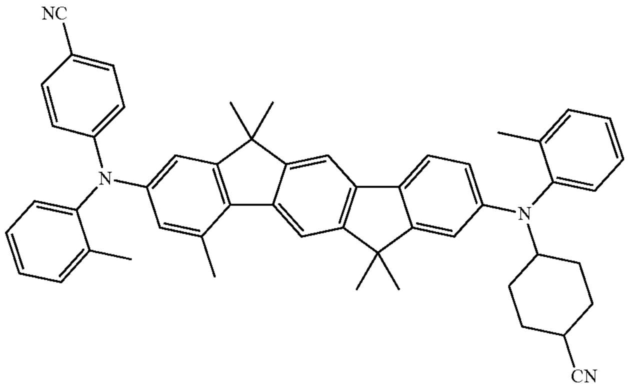 [SMILES: Cc1ccccc1N(c1ccc(C#N)cc1)c1cc(C)c2c(c1)C(C)(C)c1cc3c(cc1-2)C(C)(C)c1cc(N(c2ccccc2C)C2CCC(C#N)CC2)ccc1-3]
(246)

-continued
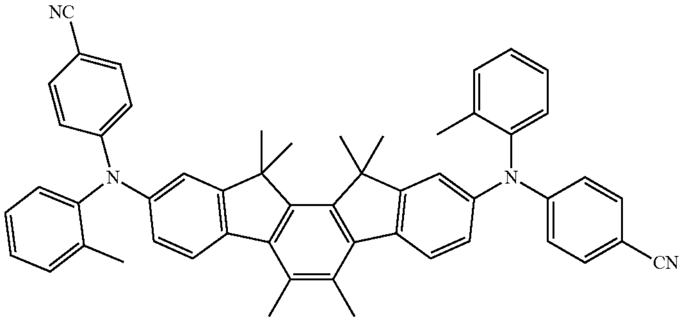 [SMILES: Cc1ccccc1N(c1ccc(C#N)cc1)c1ccc2c(c1)C(C)(C)c1c-2c(C)c(C)c2c1C(C)(C)c1cc(N(c3ccc(C#N)cc3)c3ccccc3C)ccc1-2]
(247)
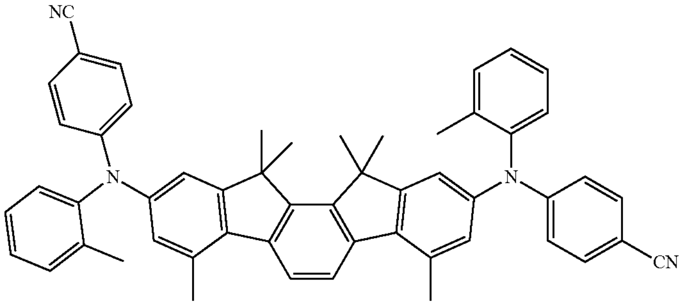 [SMILES: Cc1ccccc1N(c1ccc(C#N)cc1)c1cc(C)c2c(c1)C(C)(C)c1c-2ccc2c1C(C)(C)c1cc(N(c3ccc(C#N)cc3)c3ccccc3C)cc(C)c1-2]
(248)
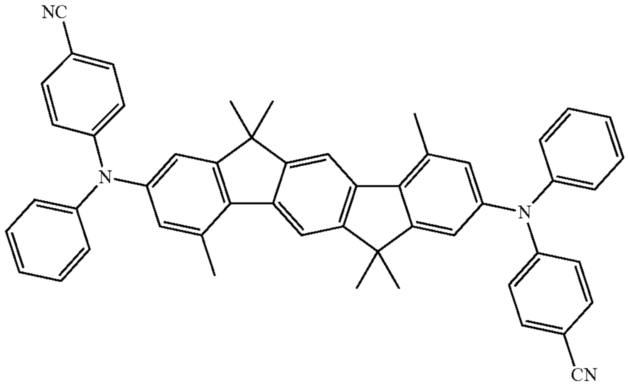 [SMILES: Cc1cc(N(c2ccccc2)c2ccc(C#N)cc2)cc2c1-c1cc3c(cc1C2(C)C)-c1c(C)cc(N(c2ccccc2)c2ccc(C#N)cc2)cc1C3(C)C]
(249)
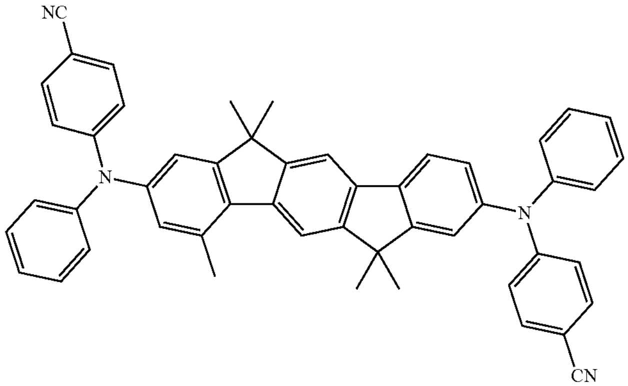 [SMILES: Cc1cc(N(c2ccccc2)c2ccc(C#N)cc2)cc2c1-c1cc3c(cc1C2(C)C)-c1ccc(N(c2ccccc2)c2ccc(C#N)cc2)cc1C3(C)C]
(250)

-continued
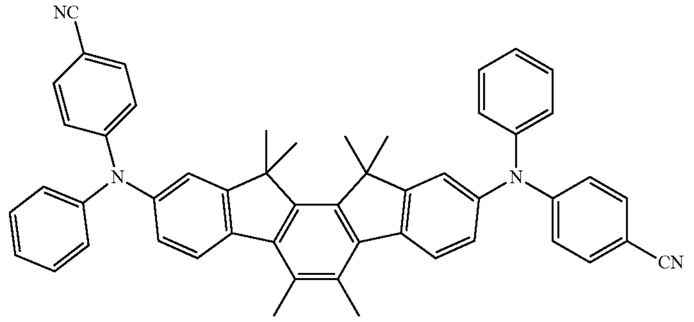 [SMILES: Cc1c(C)c2c(c3c1-c1ccc(N(c4ccccc4)c4ccc(C#N)cc4)cc1C3(C)C)C(C)(C)c1cc(N(c3ccccc3)c3ccc(C#N)cc3)ccc1-2]
(251)
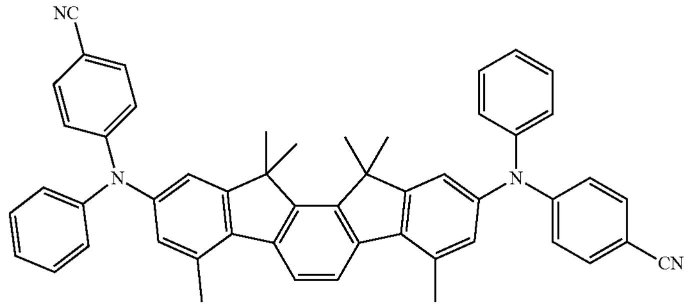 [SMILES: Cc1cc(N(c2ccccc2)c2ccc(C#N)cc2)cc2c1-c1ccc3c(c1C2(C)C)C(C)(C)c1cc(N(c2ccccc2)c2ccc(C#N)cc2)cc(C)c1-3]
(252)
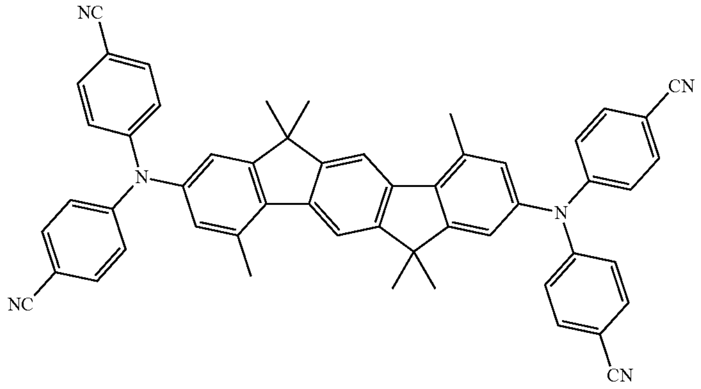 [SMILES: Cc1cc(N(c2ccc(C#N)cc2)c2ccc(C#N)cc2)cc2c1-c1cc3c(cc1C2(C)C)-c1c(C)cc(N(c2ccc(C#N)cc2)c2ccc(C#N)cc2)cc1C3(C)C]
(253)
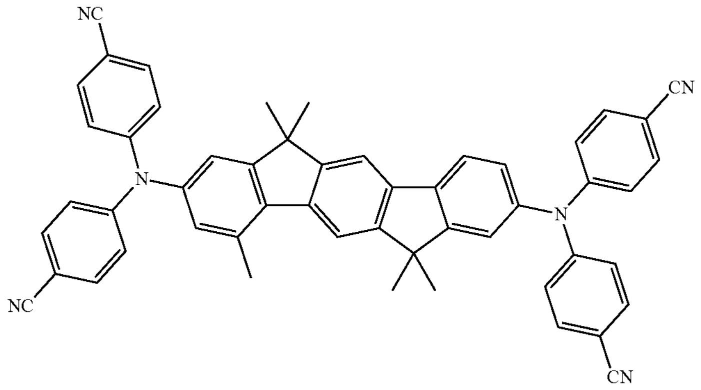 [SMILES: Cc1cc(N(c2ccc(C#N)cc2)c2ccc(C#N)cc2)cc2c1-c1cc3c(cc1C2(C)C)-c1ccc(N(c2ccc(C#N)cc2)c2ccc(C#N)cc2)cc1C3(C)C]
(254)

-continued
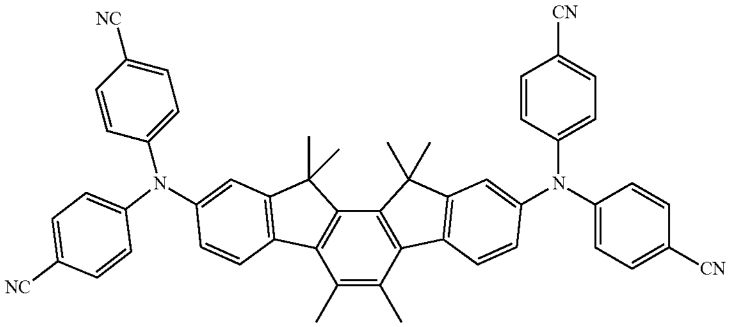 [SMILES: Cc1c(C)c2c(c3c1-c1ccc(N(c4ccc(C#N)cc4)c4ccc(C#N)cc4)cc1C3(C)C)C(C)(C)c1cc(N(c3ccc(C#N)cc3)c3ccc(C#N)cc3)ccc1-2]
(255)
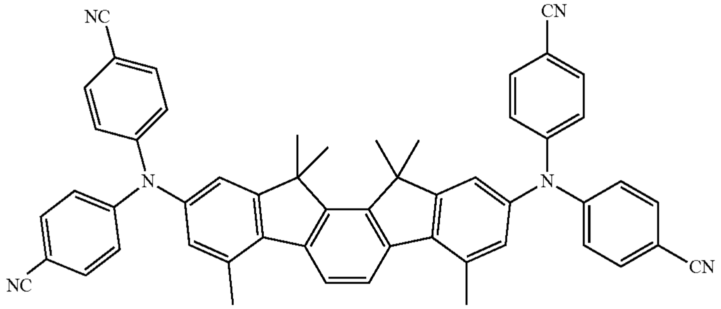
(256)
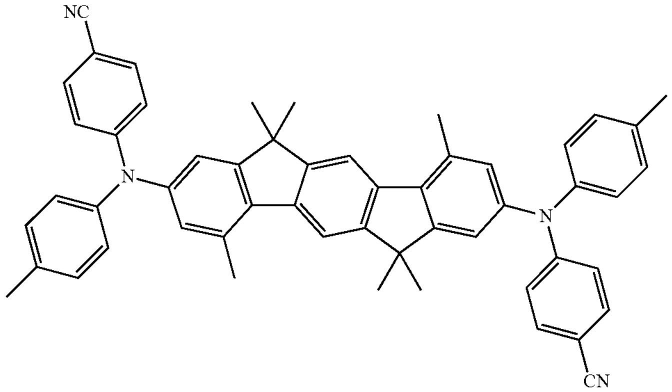
(257)
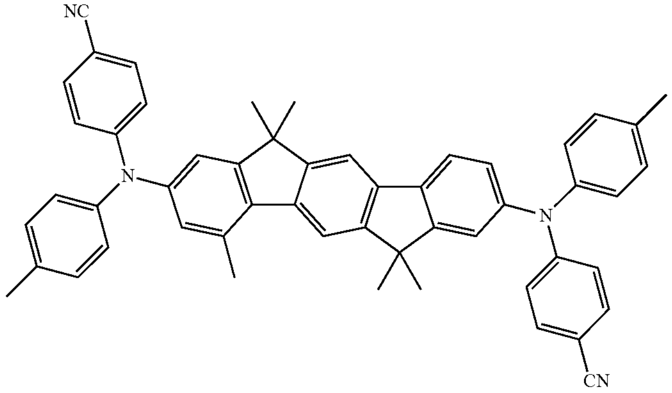
(258)

-continued
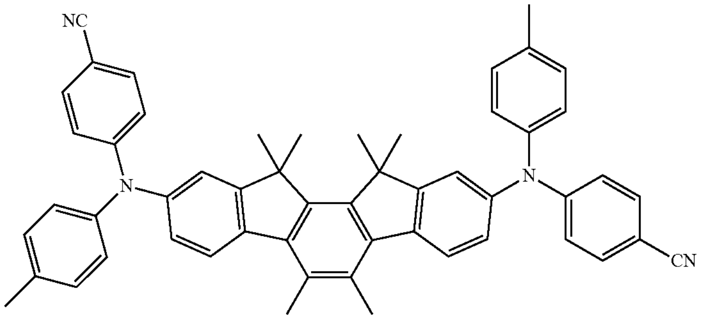 [SMILES: Cc1ccc(N(c2ccc(C#N)cc2)c2ccc3c(c2)C(C)(C)c2c-3c(C)c(C)c3c2C(C)(C)c2cc(N(c4ccc(C)cc4)c4ccc(C#N)cc4)ccc2-3)cc1]
(259)
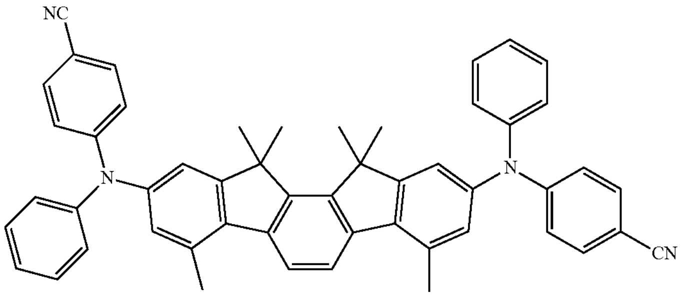 [SMILES: Cc1cc(N(c2ccccc2)c2ccc(C#N)cc2)cc2c1-c1ccc3c(c1C2(C)C)C(C)(C)c1cc(N(c2ccccc2)c2ccc(C#N)cc2)cc(C)c1-3]
(260)
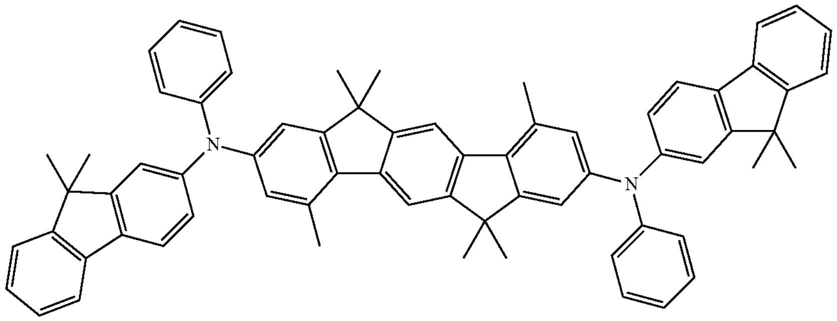 [SMILES: Cc1cc(N(c2ccccc2)c2ccc3c(c2)C(C)(C)c2ccccc2-3)cc2c1-c1cc3c(cc1C2(C)C)-c1c(C)cc(N(c2ccccc2)c2ccc4c(c2)C(C)(C)c2ccccc2-4)cc1C3(C)C]
(261)
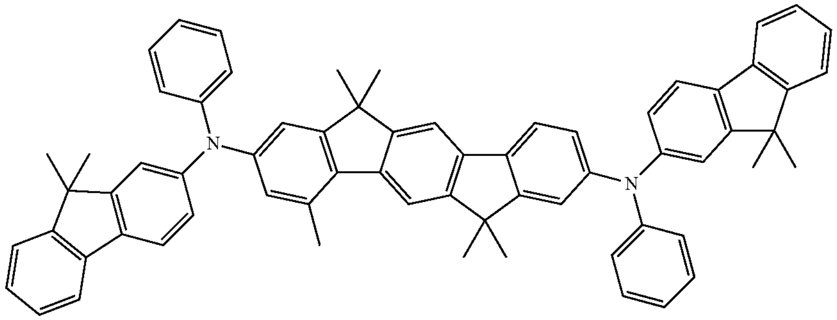 [SMILES: Cc1cc(N(c2ccccc2)c2ccc3c(c2)C(C)(C)c2ccccc2-3)cc2c1-c1cc3c(cc1C2(C)C)-c1ccc(N(c2ccccc2)c2ccc4c(c2)C(C)(C)c2ccccc2-4)cc1C3(C)C]
(262)

-continued
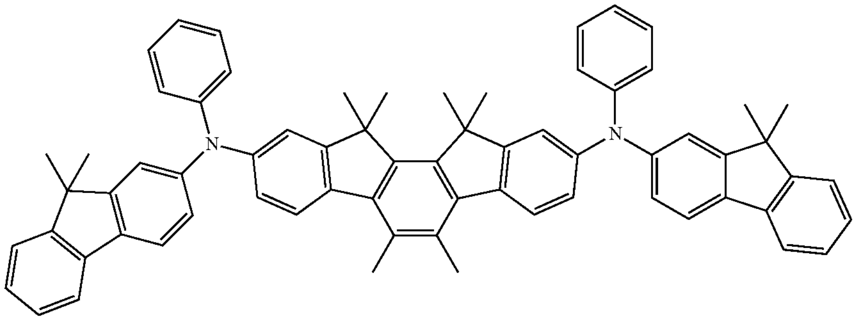 [SMILES: Cc1c(C)c2c(c3c1-c1ccc(N(c4ccccc4)c4ccc5c(c4)C(C)(C)c4ccccc4-5)cc1C3(C)C)C(C)(C)c1cc(N(c3ccccc3)c3ccc4c(c3)C(C)(C)c3ccccc3-4)ccc1-2]
(263)
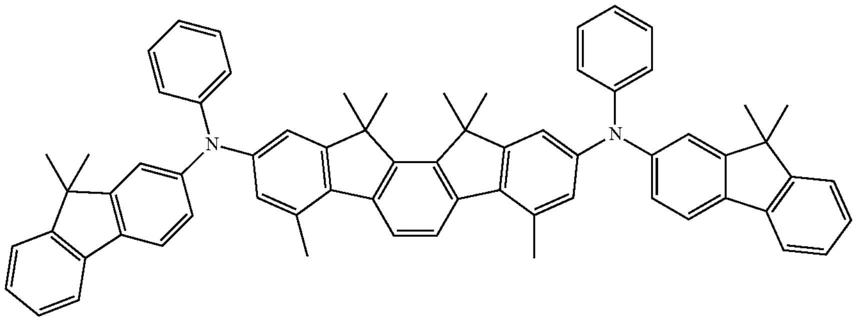 [SMILES: Cc1cc(N(c2ccccc2)c2ccc3c(c2)C(C)(C)c2ccccc2-3)cc2c1-c1ccc3c(c1C2(C)C)C(C)(C)c1cc(N(c2ccccc2)c2ccc4c(c2)C(C)(C)c2ccccc2-4)cc(C)c1-3]
(264)
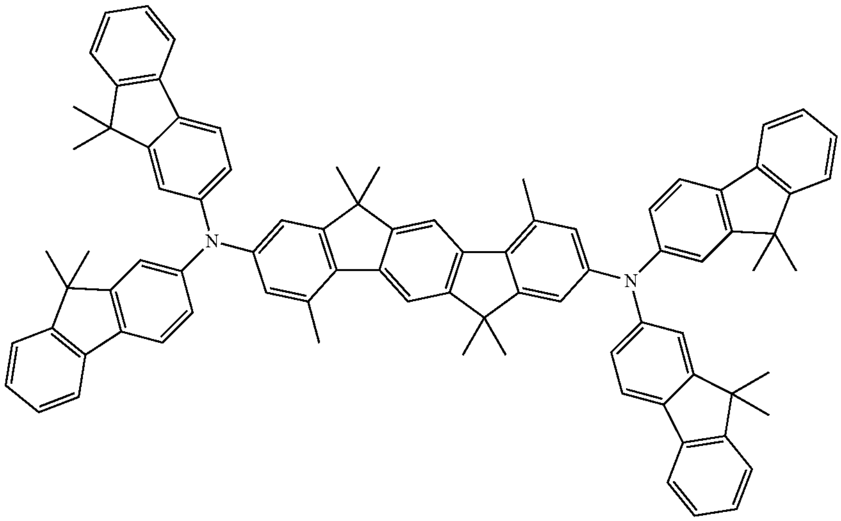 [SMILES: Cc1cc(N(c2ccc3c(c2)C(C)(C)c2ccccc2-3)c2ccc3c(c2)C(C)(C)c2ccccc2-3)cc2c1-c1cc3c(cc1C2(C)C)-c1c(C)cc(N(c2ccc4c(c2)C(C)(C)c2ccccc2-4)c2ccc4c(c2)C(C)(C)c2ccccc2-4)cc1C3(C)C]
(265)

-continued
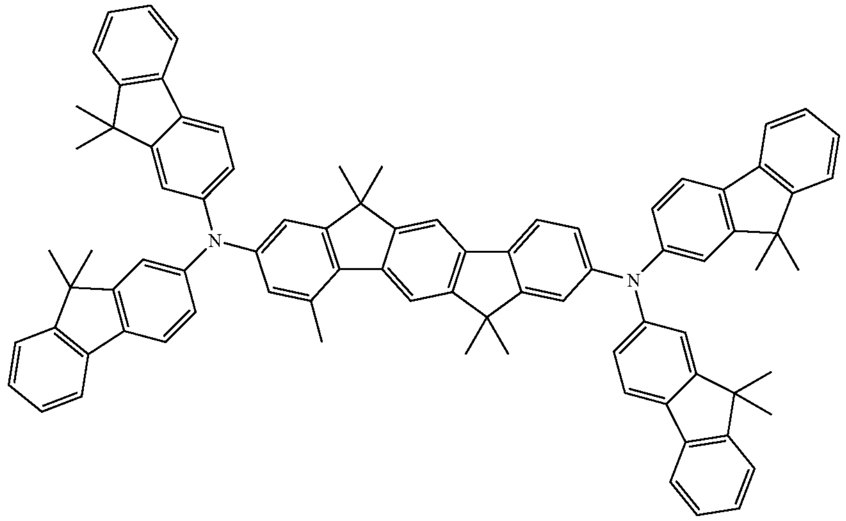 [SMILES: Cc1cc(N(c2ccc3c(c2)C(C)(C)c2ccccc2-3)c2ccc3c(c2)C(C)(C)c2ccccc2-3)cc2c1-c1cc3c(cc1C2(C)C)-c1ccc(N(c2ccc4c(c2)C(C)(C)c2ccccc2-4)c2ccc4c(c2)C(C)(C)c2ccccc2-4)cc1C3(C)C]
(266)
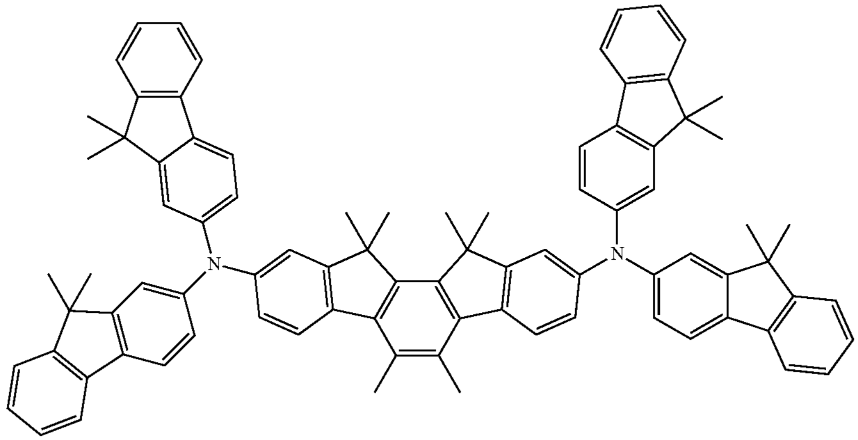 [SMILES: Cc1c(C)c2c(c3c1-c1ccc(N(c4ccc5c(c4)C(C)(C)c4ccccc4-5)c4ccc5c(c4)C(C)(C)c4ccccc4-5)cc1C3(C)C)C(C)(C)c1cc(N(c3ccc4c(c3)C(C)(C)c3ccccc3-4)c3ccc4c(c3)C(C)(C)c3ccccc3-4)ccc1-2]
(267)
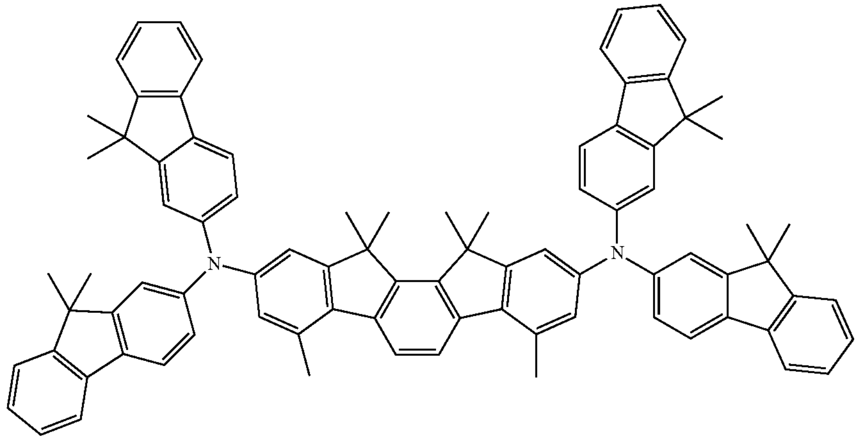 [SMILES: Cc1cc(N(c2ccc3c(c2)C(C)(C)c2ccccc2-3)c2ccc3c(c2)C(C)(C)c2ccccc2-3)cc2c1-c1ccc3c(c1C2(C)C)C(C)(C)c1cc(N(c2ccc4c(c2)C(C)(C)c2ccccc2-4)c2ccc4c(c2)C(C)(C)c2ccccc2-4)cc(C)c1-3]
(268)

-continued
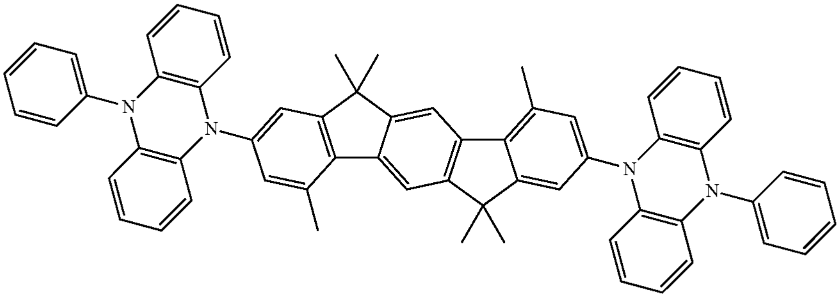 [SMILES: Cc1cc(N2c3ccccc3N(c3ccccc3)c3ccccc32)cc2c1-c1cc3c(cc1C2(C)C)-c1c(C)cc(N2c4ccccc4N(c4ccccc4)c4ccccc42)cc1C3(C)C]
(269)
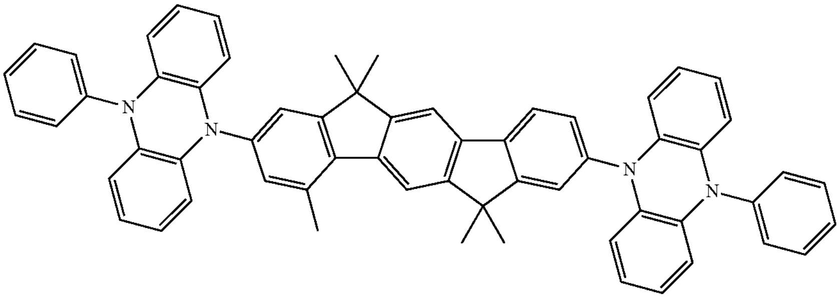 [SMILES: Cc1cc(N2c3ccccc3N(c3ccccc3)c3ccccc32)cc2c1-c1cc3c(cc1C2(C)C)-c1ccc(N2c4ccccc4N(c4ccccc4)c4ccccc42)cc1C3(C)C]
(270)
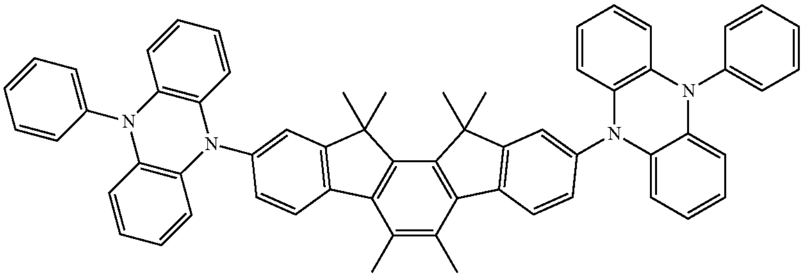 [SMILES: Cc1c(C)c2c(c3c1-c1ccc(N4c5ccccc5N(c5ccccc5)c5ccccc54)cc1C3(C)C)C(C)(C)c1cc(N3c4ccccc4N(c4ccccc4)c4ccccc43)ccc1-2]
(271)
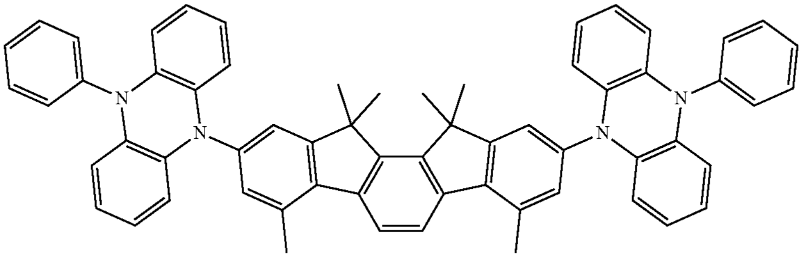 [SMILES: Cc1cc(N2c3ccccc3N(c3ccccc3)c3ccccc32)cc2c1-c1ccc3c(c1C2(C)C)C(C)(C)c1cc(N2c4ccccc4N(c4ccccc4)c4ccccc42)cc(C)c1-3]
(272)
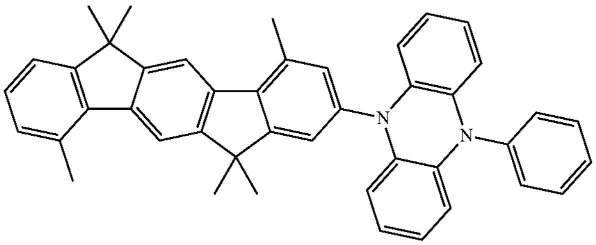 [SMILES: Cc1cccc2c1-c1cc3c(cc1C2(C)C)-c1c(C)cc(N2c4ccccc4N(c4ccccc4)c4ccccc42)cc1C3(C)C]
(273)

-continued
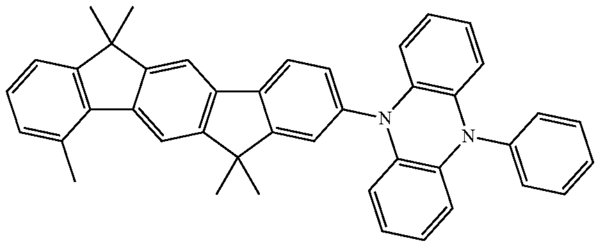 [SMILES: Cc1cccc2c1-c1cc3c(cc1C2(C)C)-c1ccc(N2c4ccccc4N(c4ccccc4)c4ccccc42)cc1C3(C)C]
(274)
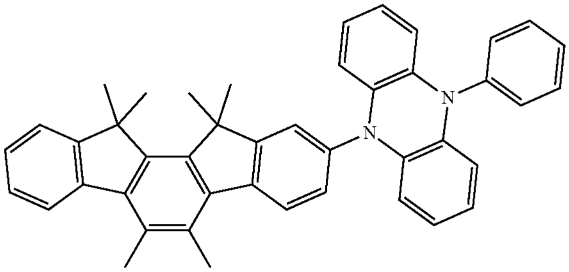 [SMILES: Cc1c(C)c2c(c3c1-c1ccccc1C3(C)C)C(C)(C)c1cc(N3c4ccccc4N(c4ccccc4)c4ccccc43)ccc1-2]
(275)
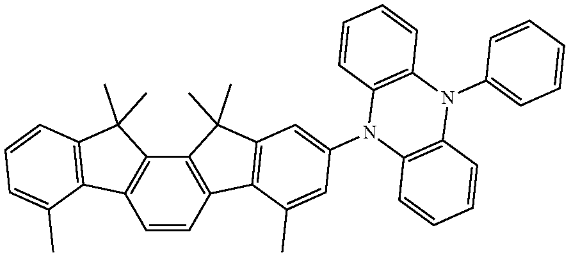 [SMILES: Cc1cccc2c1-c1ccc3c(c1C2(C)C)C(C)(C)c1cc(N2c4ccccc4N(c4ccccc4)c4ccccc42)cc(C)c1-3]
(276)
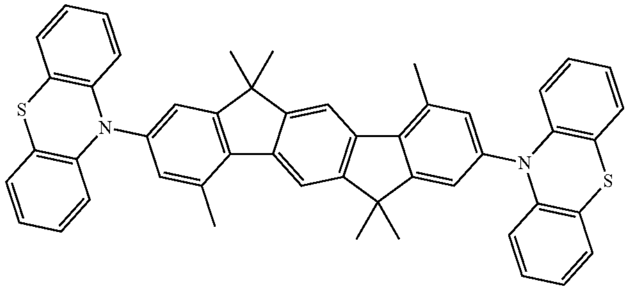
(277)
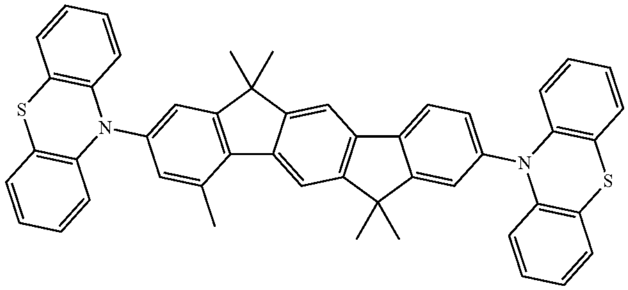 [SMILES: Cc1cc(N2c3ccccc3Sc3ccccc32)cc2c1-c1cc3c(cc1C2(C)C)-c1ccc(N2c4ccccc4Sc4ccccc42)cc1C3(C)C]
(278)

-continued
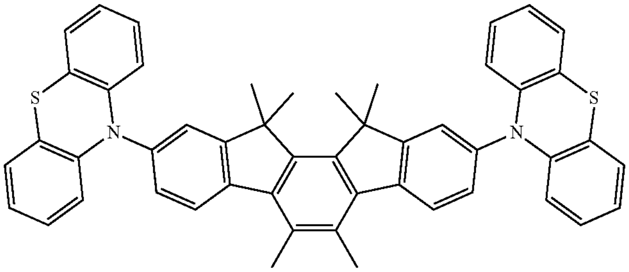 [SMILES: Cc1c(C)c2c(c3c1-c1ccc(N4c5ccccc5Sc5ccccc54)cc1C3(C)C)C(C)(C)c1cc(N3c4ccccc4Sc4ccccc43)ccc1-2]
(279)
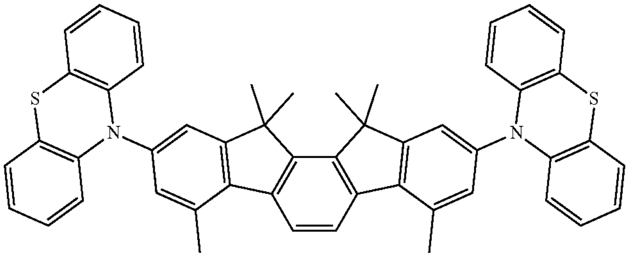 [SMILES: Cc1cc(N2c3ccccc3Sc3ccccc32)cc2c1-c1ccc3c(c1C2(C)C)C(C)(C)c1cc(N2c4ccccc4Sc4ccccc42)cc(C)c1-3]
(280)
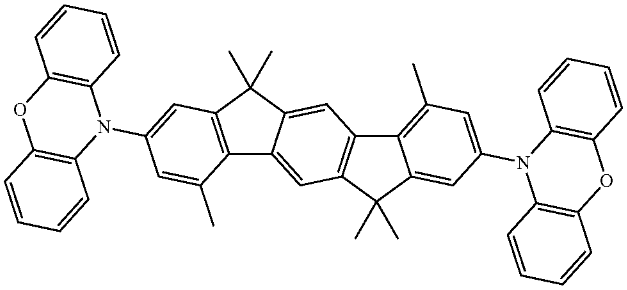 [SMILES: Cc1cc(N2c3ccccc3Oc3ccccc32)cc2c1-c1cc3c(cc1C2(C)C)-c1c(C)cc(N2c4ccccc4Oc4ccccc42)cc1C3(C)C]
(281)
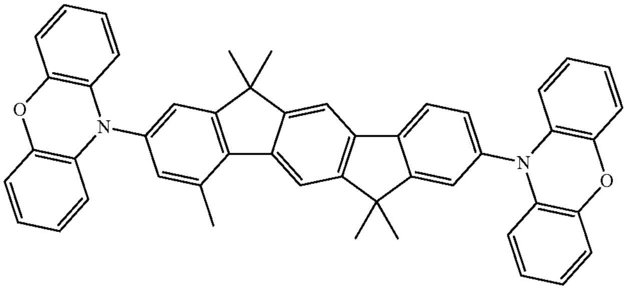 [SMILES: Cc1cc(N2c3ccccc3Oc3ccccc32)cc2c1-c1cc3c(cc1C2(C)C)-c1ccc(N2c4ccccc4Oc4ccccc42)cc1C3(C)C]
(282)
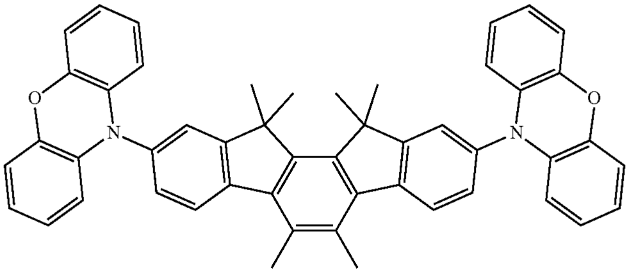
(283)

-continued
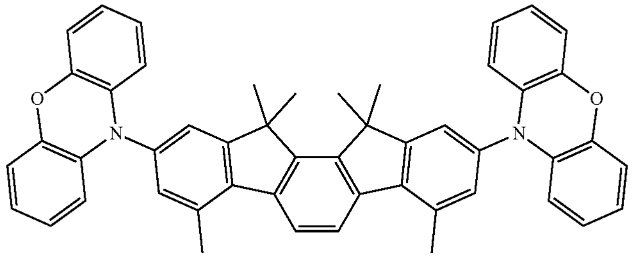 [SMILES: Cc1cc(N2c3ccccc3Oc3ccccc32)cc2c1-c1ccc3c(c1C2(C)C)C(C)(C)c1cc(N2c4ccccc4Oc4ccccc42)cc(C)c1-3]
(284)
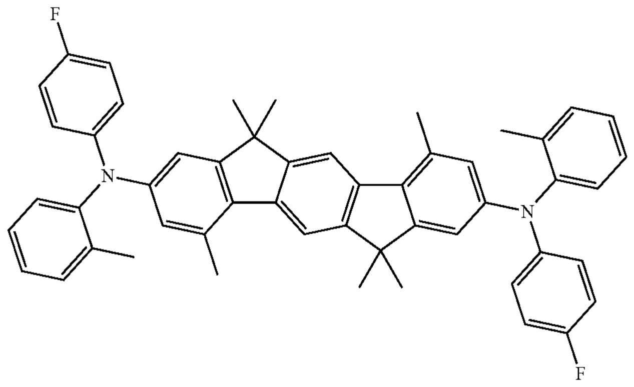 [SMILES: Cc1ccccc1N(c1ccc(F)cc1)c1cc(C)c2c(c1)C(C)(C)c1cc3c(cc1-2)C(C)(C)c1cc(N(c2ccc(F)cc2)c2ccccc2C)cc(C)c1-3]
(289)
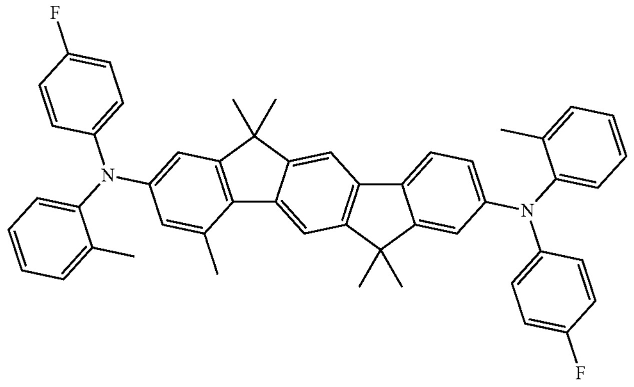 [SMILES: Cc1ccccc1N(c1ccc(F)cc1)c1ccc2c(c1)C(C)(C)c1cc3c(cc1-2)C(C)(C)c1cc(N(c2ccc(F)cc2)c2ccccc2C)cc(C)c1-3]
(290)
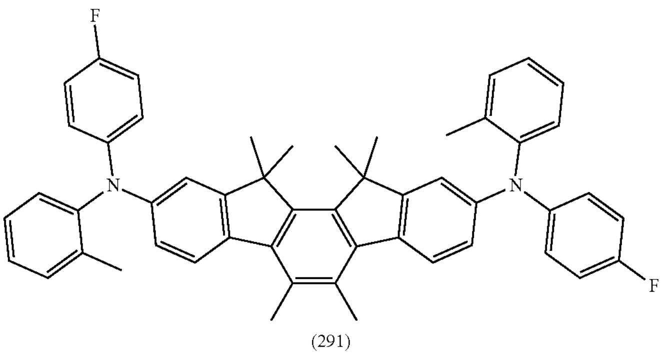
(291)

-continued
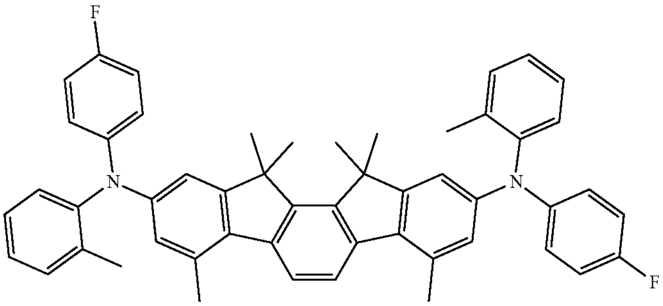 [SMILES: Cc1ccccc1N(c1ccc(F)cc1)c1cc(C)c2c(c1)C(C)(C)c1c-2ccc2c1C(C)(C)c1cc(N(c3ccc(F)cc3)c3ccccc3C)cc(C)c1-2]
(292)
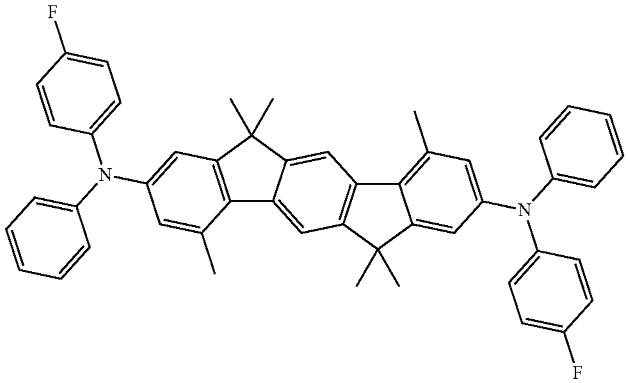 [SMILES: Cc1cc(N(c2ccccc2)c2ccc(F)cc2)cc2c1-c1cc3c(cc1C2(C)C)-c1c(C)cc(N(c2ccccc2)c2ccc(F)cc2)cc1C3(C)C]
(293)
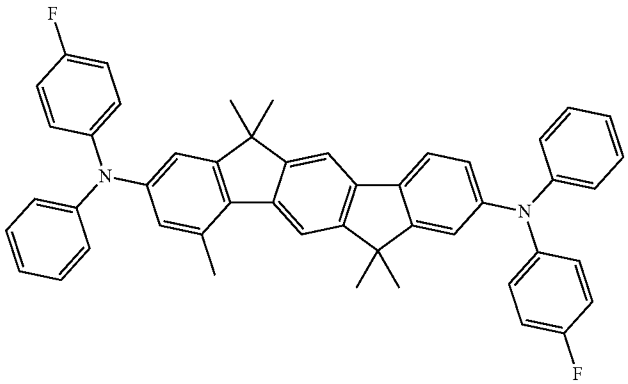 [SMILES: Cc1cc(N(c2ccccc2)c2ccc(F)cc2)cc2c1-c1cc3c(cc1C2(C)C)-c1ccc(N(c2ccccc2)c2ccc(F)cc2)cc1C3(C)C]
(294)
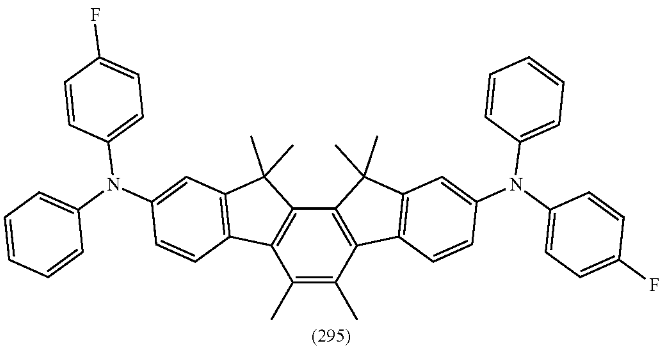
(295)

-continued
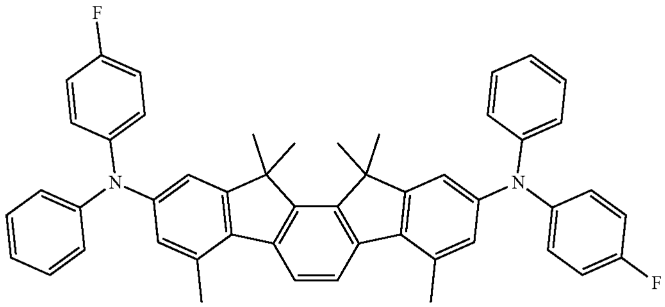 [SMILES: Cc1cc(N(c2ccccc2)c2ccc(F)cc2)cc2c1-c1ccc3c(c1C2(C)C)C(C)(C)c1cc(N(c2ccccc2)c2ccc(F)cc2)cc(C)c1-3]
(296)
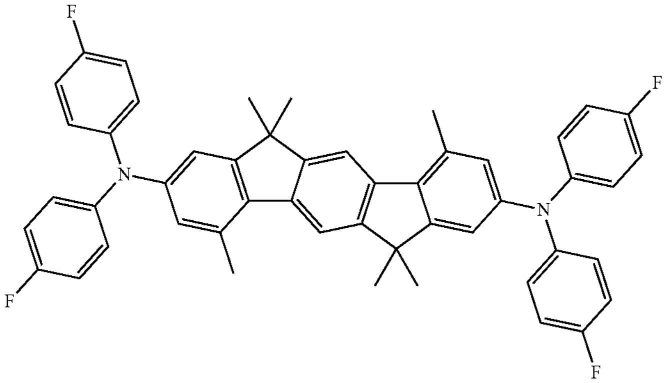 [SMILES: Cc1cc(N(c2ccc(F)cc2)c2ccc(F)cc2)cc2c1-c1cc3c(cc1C2(C)C)-c1c(C)cc(N(c2ccc(F)cc2)c2ccc(F)cc2)cc1C3(C)C]
(297)
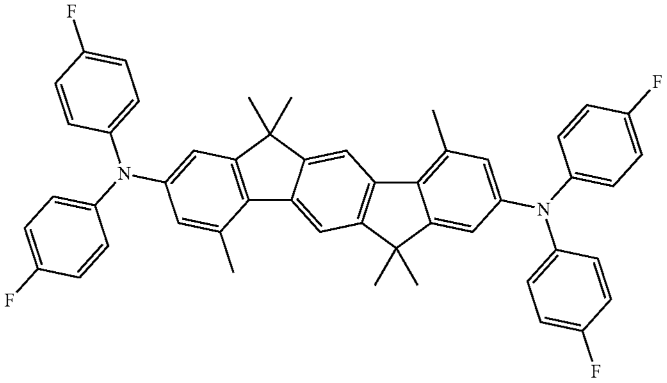 [SMILES: Cc1cc(N(c2ccc(F)cc2)c2ccc(F)cc2)cc2c1-c1cc3c(cc1C2(C)C)-c1c(C)cc(N(c2ccc(F)cc2)c2ccc(F)cc2)cc1C3(C)C]
(298)
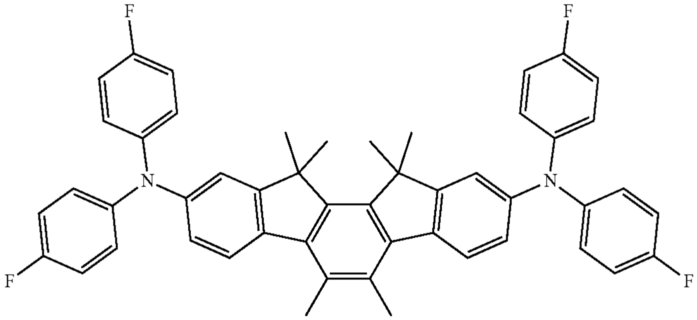 [SMILES: Cc1c(C)c2c(c3c1-c1ccc(N(c4ccc(F)cc4)c4ccc(F)cc4)cc1C3(C)C)C(C)(C)c1cc(N(c3ccc(F)cc3)c3ccc(F)cc3)ccc1-2]
(299)

-continued
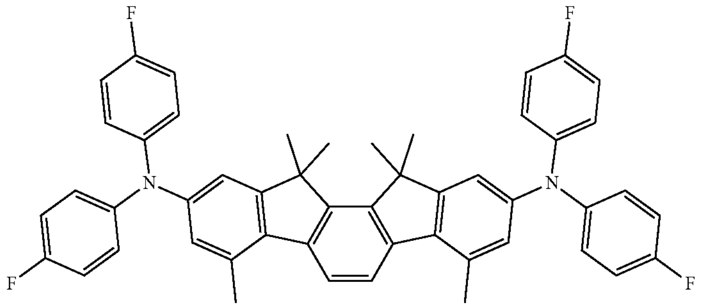 [SMILES: Cc1cc(N(c2ccc(F)cc2)c2ccc(F)cc2)cc2c1-c1ccc3c(c1C2(C)C)C(C)(C)c1cc(N(c2ccc(F)cc2)c2ccc(F)cc2)cc(C)c1-3]
(300)
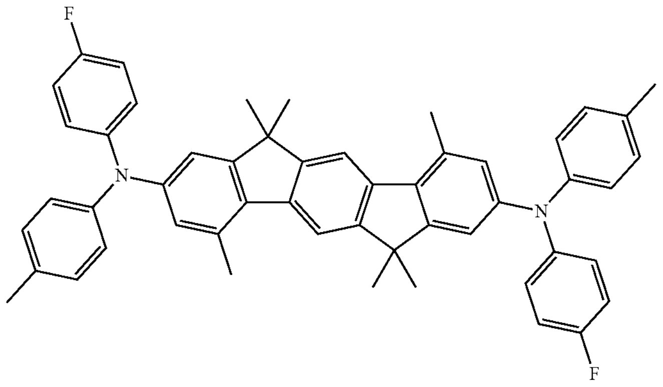
(301)
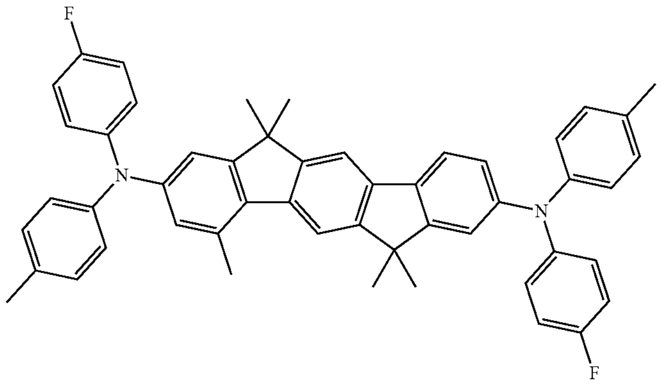
(302)
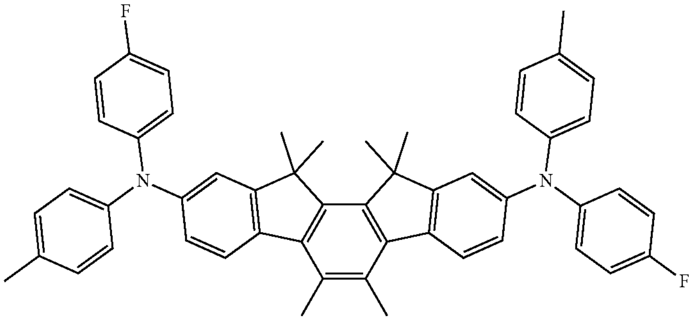 [SMILES: Cc1ccc(N(c2ccc(F)cc2)c2ccc3c(c2)C(C)(C)c2c-3c(C)c(C)c3c2C(C)(C)c2cc(N(c4ccc(C)cc4)c4ccc(F)cc4)ccc2-3)cc1]
(303)

-continued
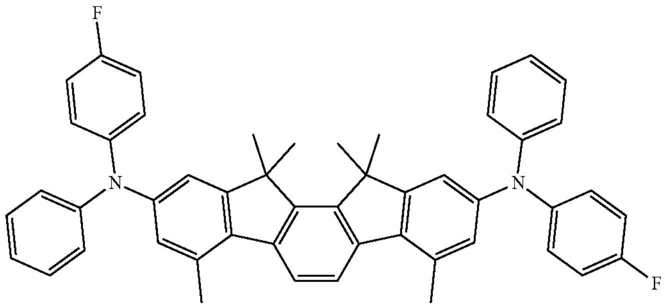 [SMILES: Cc1cc(N(c2ccccc2)c2ccc(F)cc2)cc2c1-c1ccc3c(c1C2(C)C)C(C)(C)c1cc(N(c2ccccc2)c2ccc(F)cc2)cc(C)c1-3]
(304)
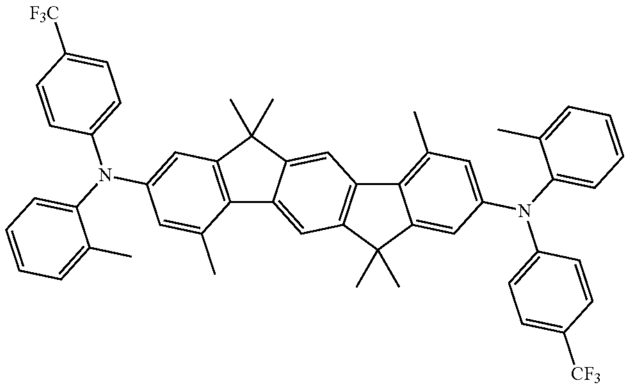 [SMILES: Cc1ccccc1N(c1ccc(C(F)(F)F)cc1)c1cc(C)c2c(c1)C(C)(C)c1cc3c(cc1-2)C(C)(C)c1cc(N(c2ccc(C(F)(F)F)cc2)c2ccccc2C)cc(C)c1-3]
(305)
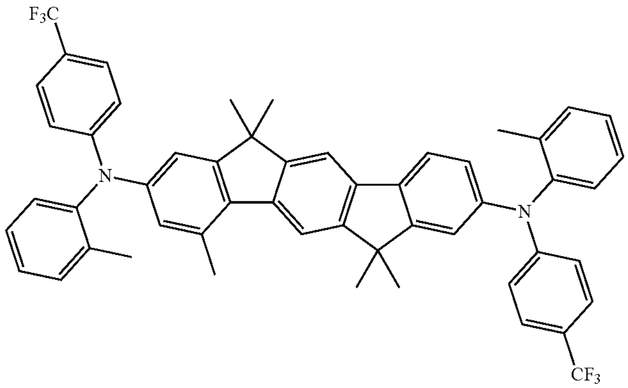 [SMILES: Cc1ccccc1N(c1ccc(C(F)(F)F)cc1)c1ccc2c(c1)C(C)(C)c1cc3c(cc1-2)C(C)(C)c1cc(N(c2ccc(C(F)(F)F)cc2)c2ccccc2C)cc(C)c1-3]
(306)
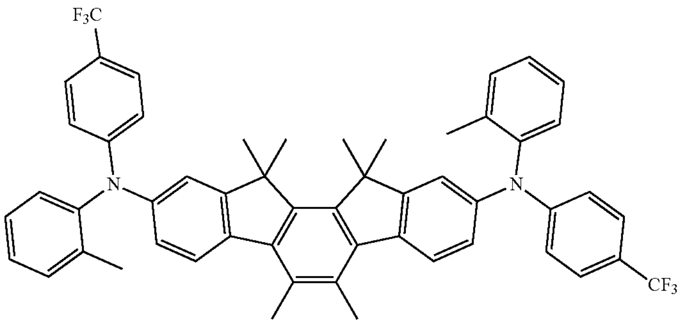 [SMILES: Cc1ccccc1N(c1ccc(C(F)(F)F)cc1)c1ccc2c(c1)C(C)(C)c1c-2c(C)c(C)c2c1C(C)(C)c1cc(N(c3ccc(C(F)(F)F)cc3)c3ccccc3C)ccc1-2]
(307)

-continued
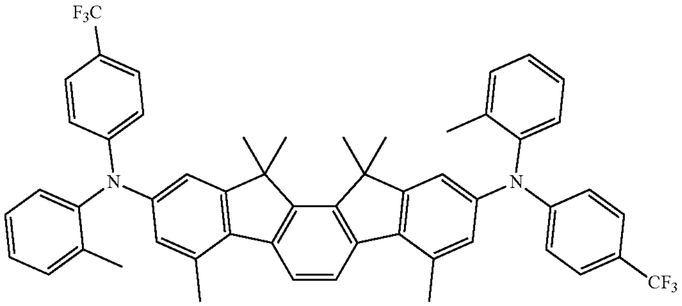 [SMILES: Cc1ccccc1N(c1ccc(C(F)(F)F)cc1)c1cc(C)c2c(c1)C(C)(C)c1c-2ccc2c1C(C)(C)c1cc(N(c3ccc(C(F)(F)F)cc3)c3ccccc3C)cc(C)c1-2]
(308)
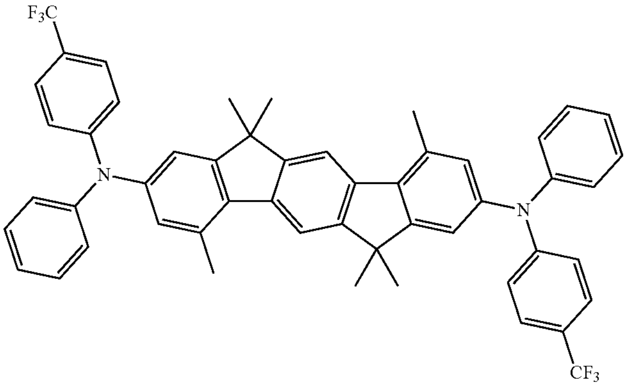 [SMILES: Cc1cc(N(c2ccccc2)c2ccc(C(F)(F)F)cc2)cc2c1-c1cc3c(cc1C2(C)C)-c1c(C)cc(N(c2ccccc2)c2ccc(C(F)(F)F)cc2)cc1C3(C)C]
(309)
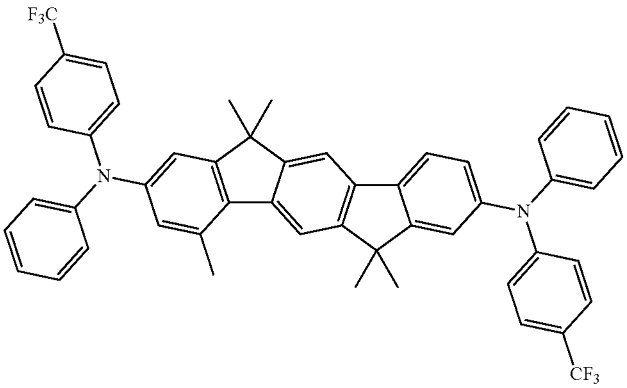 [SMILES: Cc1cc(N(c2ccccc2)c2ccc(C(F)(F)F)cc2)cc2c1-c1cc3c(cc1C2(C)C)-c1ccc(N(c2ccccc2)c2ccc(C(F)(F)F)cc2)cc1C3(C)C]
(310)
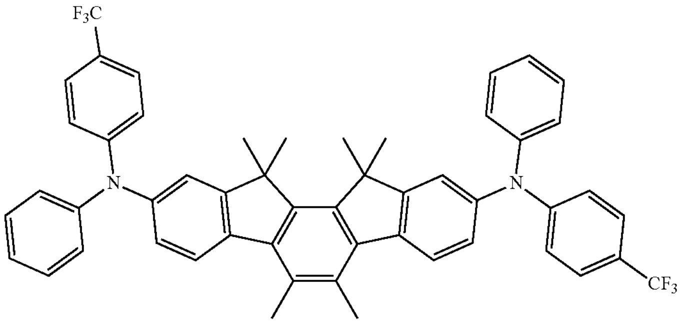 [SMILES: Cc1c(C)c2c(c3c1-c1ccc(N(c4ccccc4)c4ccc(C(F)(F)F)cc4)cc1C3(C)C)C(C)(C)c1cc(N(c3ccccc3)c3ccc(C(F)(F)F)cc3)ccc1-2]
(311)

-continued
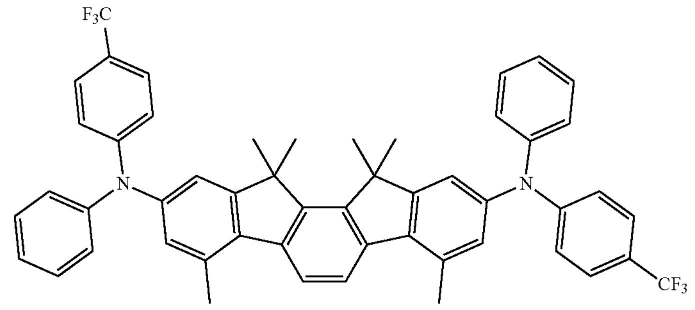 [SMILES: Cc1cc(N(c2ccccc2)c2ccc(C(F)(F)F)cc2)cc2c1-c1ccc3c(c1C2(C)C)C(C)(C)c1cc(N(c2ccccc2)c2ccc(C(F)(F)F)cc2)cc(C)c1-3]
(312)
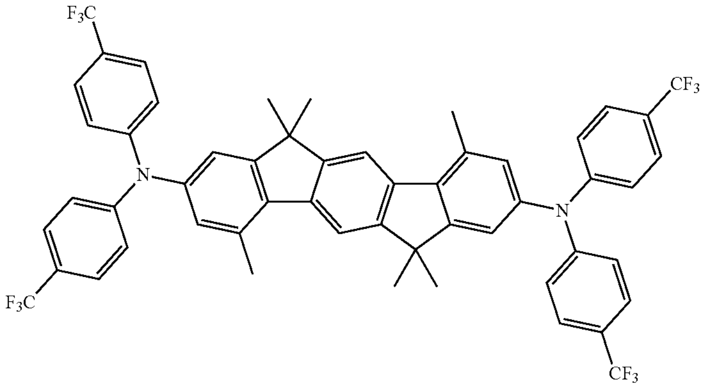 [SMILES: Cc1cc(N(c2ccc(C(F)(F)F)cc2)c2ccc(C(F)(F)F)cc2)cc2c1-c1cc3c(cc1C2(C)C)-c1c(C)cc(N(c2ccc(C(F)(F)F)cc2)c2ccc(C(F)(F)F)cc2)cc1C3(C)C]
(313)
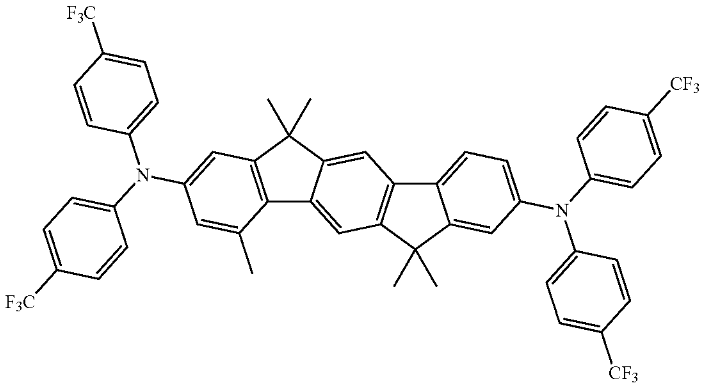
(314)
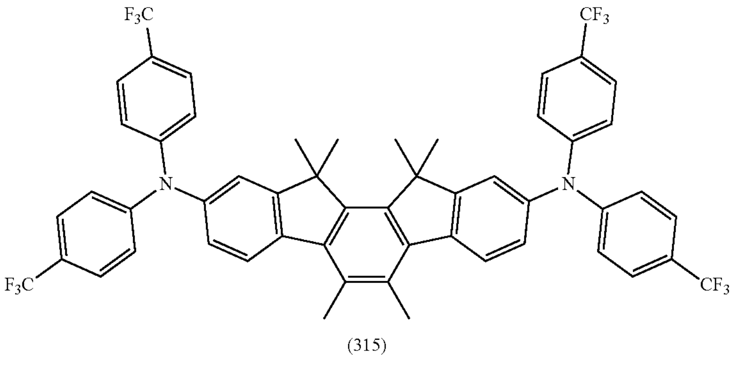
(315)

-continued
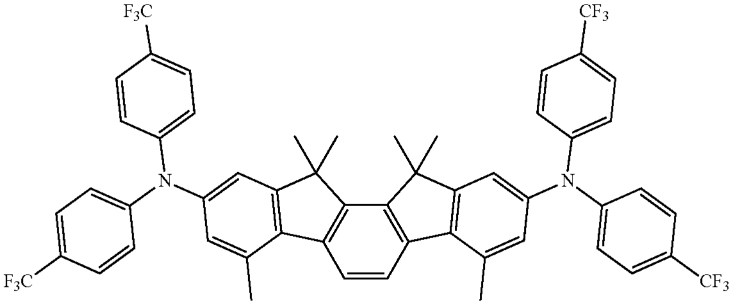 [SMILES: Cc1cc(N(c2ccc(C(F)(F)F)cc2)c2ccc(C(F)(F)F)cc2)cc2c1-c1ccc3c(c1C2(C)C)C(C)(C)c1cc(N(c2ccc(C(F)(F)F)cc2)c2ccc(C(F)(F)F)cc2)cc(C)c1-3]
(316)
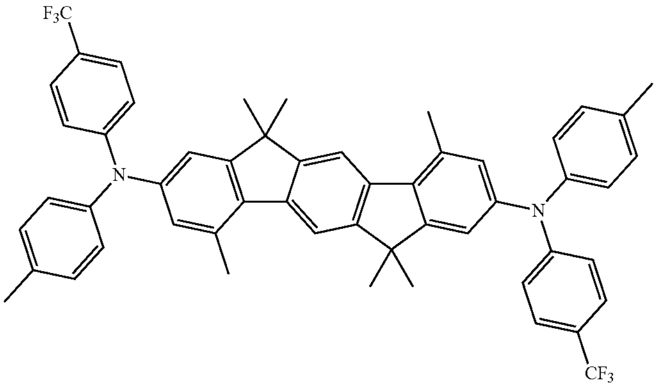
(317)
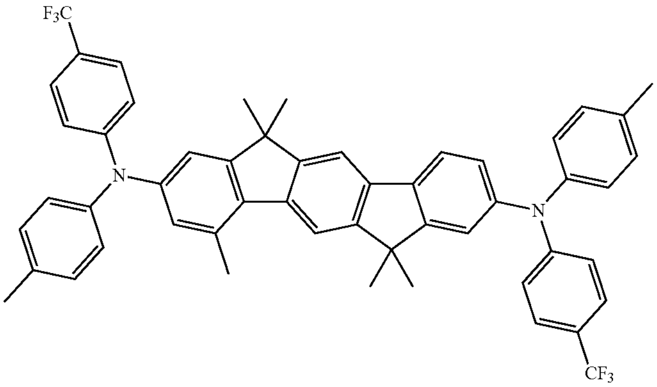
(318)
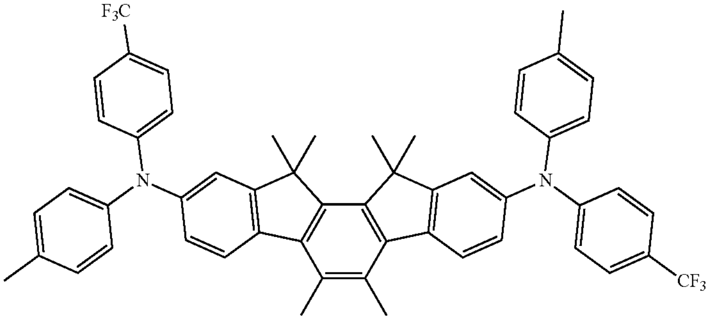 [SMILES: Cc1ccc(N(c2ccc(C(F)(F)F)cc2)c2ccc3c(c2)C(C)(C)c2c-3c(C)c(C)c3c2C(C)(C)c2cc(N(c4ccc(C)cc4)c4ccc(C(F)(F)F)cc4)ccc2-3)cc1]
(319)

-continued
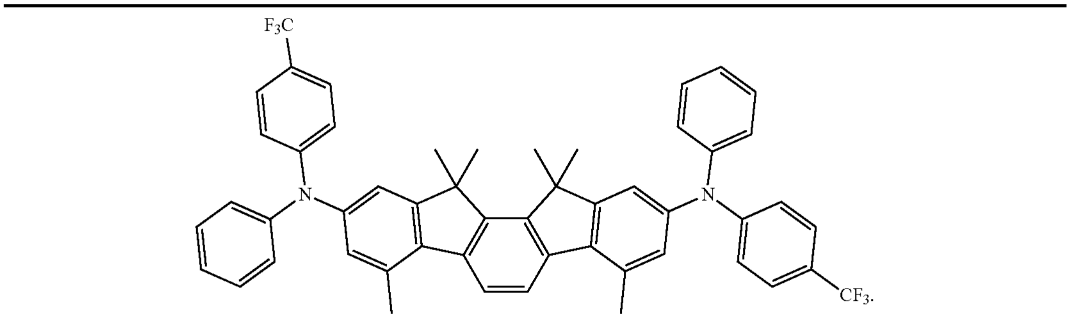
(320)
* * * * *